(12) United States Patent
Caldarelli et al.

(10) Patent No.: US 8,916,577 B2
(45) Date of Patent: Dec. 23, 2014

(54) TRICYCLIC DERIVATIVES, PROCESS FOR THEIR PREPARATION AND THEIR USE AS KINASE INHIBITORS

(75) Inventors: Marina Caldarelli, Milan (IT);
Francesco Casuscelli, Dairago (MI) (IT); Daniele Donati, Nerviano (MI) (IT); Danilo Mirizzi, Nerviano (MI) (IT); Francesca Quartieri, Arona (NO) (IT); Marco Silvagni, Segrate (MI) (IT)

(73) Assignee: Nerviano Medical Sciences S.R.L., Nerviano (MI) (IT)

( * ) Notice: Subject to any disclaimer, the term of this patent is extended or adjusted under 35 U.S.C. 154(b) by 0 days.

(21) Appl. No.: 13/980,182

(22) PCT Filed: Jan. 19, 2012

(86) PCT No.: PCT/EP2012/050765
§ 371 (c)(1),
(2), (4) Date: Jul. 17, 2013

(87) PCT Pub. No.: WO2012/101029
PCT Pub. Date: Aug. 2, 2012

(65) Prior Publication Data
US 2013/0302416 A1 Nov. 14, 2013

(30) Foreign Application Priority Data
Jan. 26, 2011 (EP) .................................. 11152189

(51) Int. Cl.
*A61K 45/06* (2006.01)
*A61K 31/551* (2006.01)
*C07D 498/14* (2006.01)
*C07D 498/04* (2006.01)
*C07D 487/04* (2006.01)
*A61K 31/519* (2006.01)
*A61K 31/5377* (2006.01)
*A61K 31/5383* (2006.01)

(52) U.S. Cl.
CPC ............ *C07D 487/04* (2013.01); *C07D 498/14* (2013.01); *A61K 31/5377* (2013.01); *A61K 31/5383* (2013.01); *C07D 498/04* (2013.01); *A61K 45/06* (2013.01); *A61K 31/519* (2013.01); *A61K 31/551* (2013.01)
USPC ............................ 514/267; 544/250; 544/251

(58) Field of Classification Search
CPC ... A61K 31/519; A61K 31/55; C07D 487/04; C07D 498/04; C07D 498/14
USPC .................... 514/267; 544/250, 251
See application file for complete search history.

(56) References Cited

FOREIGN PATENT DOCUMENTS

| WO | WO 2005/037843 A1 | 4/2005 |
| WO | WO 2008/074788 A1 | 6/2008 |
| WO | WO 2009/089305 * | 7/2009 | ............ A01N 43/58 |
| WO | WO 2009/089305 A1 | 7/2009 |

OTHER PUBLICATIONS

International Search Report dated Aug. 3, 2012 issued in PCT/EP2012/050765.
Alsina J. et al., "Solid-Phase Synthesis With Tris(Alkoxy)Benzyl Backbone Amide Linkage (BAL)", Chem. Eur. J. 5 (10):2787-2795 (1999).
Amaravadi R. et al., "The Survival Kinases Akt and Pim as Potential Pharmacological Targets", The Journal of Clinical Investigation 115(10):2618-2624 (Oct. 2005).
Bertheau P. et al., "Exquisite Sensitivity of TP53 Mutant and Basal Breast Cancers to a Dose-Dense Epirubicin-Cyclophosphamide Regimen", PLoS Medicine 4(3):0585-0594 (Mar. 2007).
Brault L. et al., "PIM Serine/Threonine Kinases in the Pathogenesis and Therapy of Hematologic Malignancies and Solid Cancers", Haematologica 95(6):1004-1015 (2010).
Carre M-C et al., "Arynic Condensation of Ketone Enolates. Efficient Access to a New Series of Benzocyclobutenols", J. Org. Chem. 49:2050-2052 (1984).
Carter S.L. et al., "A Signature of Chromosomal Instability Inferred from Gene Expression Profiles Predicts Clinical Outcome in Multiple Human Cancers", Nature Genetics 38(9):1043-1048 (Sep. 2006).
Choudhary C. et al., "Mislocalized Activation of Oncogenic RTKs Switches Downstream Signaling Outcomes", Molecular Cell 36:326-339 (Oct. 23, 2009).
Cohen A.M. et al., "Increased Expression of the hPim-2 Gene in Human Chronic Lymphocytic Leukemia and Non-Hodgkin Lymphoma", Leukemia & Lymphoma 45(5):951-955 (May 2004).
Cohen P., "The Development and Therapeutic Potential of Protein Kinase Inhibitors", Current Opinion in Chemical Biology 3:459-465 (1999).

(Continued)

*Primary Examiner* — Erich A Leeser
(74) *Attorney, Agent, or Firm* — Scully, Scott, Murphy & Presser, P.C.

(57) ABSTRACT

New substituted tricyclic compounds of formula (I) are described, wherein R1, R2, X, Y, Z are herein defined, having protein kinase inhibiting activity. The invention includes methods to prepare the compounds of formula (I), pharmaceutical compositions containing them, and their use in therapy, in particular for the treatment of diseases caused by and/or associated with dysregulated activity of protein kinase.

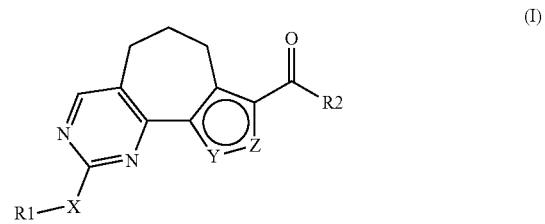

21 Claims, 3 Drawing Sheets

(56) References Cited

OTHER PUBLICATIONS

Colombo M. et al., "A Fully Automated Method for Accurate Mass Determination Using High-Performance Liquid Chromatography with a Quadrupole/Orthogonal Acceleration Time-of-Flight Mass Spectrometer", Rapid Communications in Mass Spectrometry 18:511-517 (2004).
De Carcer G. et al., "Targeting Cell Cycle Kinases for Cancer Therapy", Current Medicinal Chemistry 14:969-985 (2007).
Fivush A.M. et al., "AMEBA: An Acid Sensitive Aldehyde Resin for Solid Phase Synthesis", Tetrahedron Letters 38 (41):7151-7154 (1997).
Huttmann A. et al., "Gene Expression Signatures Separate B-Cell Chronic Lymphocytic Leukaemia Prognostic Subgroups Defined by ZAP-70 and CD38 Expression Status", Leukemia 20:1774-1782 (2006).
Jelluma N. et al., "Chromosomal Instability by Inefficient Mps1 Auto-Activation Due to a Weakened Mitotic Checkpoint and Lagging Chromosomes", PLoS One 3(6):e2415 (8 pages) (Jun. 2008).
Jelluma N. et al., "Mps1 Phosphorylates Borealin to Control Aurora B Activity and Chromosomes Alignment", Cell 132:233-246 (Jan. 25, 2008).
Jensen K.J. et al., "Backbone Amide Linker (BAL) Strategy for Solid-Phase Synthesis of C-Terminal-Modified and Cyclic Peptides", J. Am. Chem. Soc. 120:5441-5452 (1998).
Jones M.H. et al., "Chemical Genetics Reveals a Role for Mps1 Kinase in Kinetochore Attachment During Mitosis", Current Biology 15:160-165 (Jan. 26, 2005).
Kim K-T et al., "Pim-1 is Up-Regulated by Constitutively Activated FLT3 and Plays a Role in FLT3-Mediated Cell Survival", Blood 105(4):1759-1767 (Feb. 15, 2005).
Kops G.J.P.L. et al., "On the Road to Cancer: Aneuploidy and the Mitotic Checkpoint", Nature Reviews-Cancer 5:773-785 (Oct. 2005).
Kumar A. et al., "Crystal Structures of Proto-Oncogene Kinase Pim1: A Target of Aberrant Somatic Hypermutations in Diffuse Large Cell Lymphoma", J. Mol. Biol. 348:183-193 (2005).
Lackey K. et al., "The Discovery of Potent cRaf1 Kinase Inhibitors", Bioorganic & Medicinal Chemistry Letters 10:223-226 (2000).
Musacchio A. et al., "The Spindle-Assembly Checkpoint in Space and Time", Nature Reviews-Molecular Cell Biology 8:379-393 (May 2007).
Palmer B.D. et al., "Structure-Activity Relationship for 5-Substituted 1-Phenylbenzimidazoles as Selective Inhibitors of the Platelet-Derived Growth Factor Receptor", J. Med. Chem. 42:2373-2382 (1999).
Schmidt M. et al., "Ablation of the Spindle Assembly Checkpoint by a Compound Targeting Mps1", European Molecular Biology Organization Reports 6(9):866-872 (2005).
Shah N. et al., "Potential Roles for the PIMI1 Kinase in Human Cancer-A Molecular and Therapeutic Appraisal", European Journal of Cancer 44:2144-2151 (2008).
Stucke V.M. et al., "Human Mps1 Kinase is Required for the Spindle Assembly Checkpoint But Not for Centrosome Duplication", The European Molecular Biology Organization 21(7):1723-1732 (2002).
Tamburini J. et al., "Protein Synthesis is Resistant to Rapamycin and Constitutes a Promising Therapeutic Target in Acute Myeloid Leukemia", Blood 114(8):1618-1627 (Aug. 20, 2009).
Tighe A. et al., "Mps 1 Kinase Activity Restrains Anaphase During an Unperturbed Mitosis and Targets Mad2 to Kinetochores", J. Cell Biol. 181(6):893-901 (2008).
Velculescu V.E., "Defining the Blueprint of the Cancer Genome", Carcinogensis 29(6):1087-1091 (2008).
Weaver B.A.A. et al., "Aneuploidy Acts Both Oncogenically and as Tumor Suppressor", Cancer Cell 11:25-36 (Jan. 2007).
Weiss E. et al., "The *Saccharomyces cerevisiae* Spindle Pole Body Duplication Gene MPS1 is Part of a Mitotic Checkpoint", The Journal of Cell Biology 132(1&2):111-123 (Jan. 1996).
Winey M. et al., "MPS1 and MPS2: Novel Yeast Genes Defining Distinct Steps of Spindle Pole Body Duplication", The Journal of Cell Biology 114(4):745-754 (Aug. 1991).
Yuan B. et al., "Increased Expression of Mitotic Checkpoint Genes in Breast Cancer Cells With Chromosomal Instability", Clin Cancer Research 12(2):405-410 (Jan. 15, 2006).

\* cited by examiner

TRICYCLIC DERIVATIVES, PROCESS FOR THEIR PREPARATION AND THEIR USE AS KINASE INHIBITORS

TECHNICAL FIELD

The present invention relates to tricyclic derivatives, to a process for their preparation, to pharmaceutical compositions comprising them, and to their use as therapeutic agents, particularly in the treatment of cancer and cell proliferation disorders.

The compounds of this invention are therefore useful in treating diseases caused by dysregulated protein kinase activity. The present invention also provides methods for preparing these compounds, pharmaceutical compositions comprising these compounds, and methods of treating diseases utilizing pharmaceutical compositions comprising these compounds.

BACKGROUND ART

The malfunctioning of protein kinases (PKs) is the hallmark of numerous diseases. A large share of the oncogenes and proto-oncogenes involved in human cancers encode for PKs. The enhanced activities of PKs are also implicated in many non-malignant diseases, such as benign prostate hyperplasia, familial adenomatosis, polyposis, neurofibromatosis, psoriasis, vascular smooth cell proliferation associated with atherosclerosis, pulmonary fibrosis, arthritis glomerulonephritis and post-surgical stenosis and restenosis.

PKs are also implicated in inflammatory conditions and in the multiplication of viruses and parasites. PKs may also play a major role in the pathogenesis and development of neurodegenerative disorders.

For a general reference to PKs malfunctioning or deregulation see, for instance, Current Opinion in Chemical Biology 1999, 3, 459-465 and Carcinogenesis 2008, 29, 1087-1091.

The use of mitotic inhibitors in cancer therapy is a widely accepted clinical strategy for the treatment of a broad range of human cancers. Taxanes (paclitaxel and docetaxel) and vinca alkaloids (e.g. vincristine and vinblastine) work by either stabilizing or destabilizing microtubules with catastrophic consequences in cells progressing through mitosis. They are first line therapeutics for several tumour types and second line in cisplatin-refractory ovarian, breast, lung, bladder and esophagus cancers (taxanes). However, due to the role of microtubules in processes such as cell movement, phagocytosis and axonal transport certain toxicities such as peripheral neuropathy are frequently observed with these agents. Progression through mitosis is a requirement of all proliferating cells and hence cancer therapies that have targets in mitosis are generally applicable to a wide range of tumour types.

Several protein kinases play key roles in the orchestration of the cell cycle and some of them are already subject to targeted therapies in the oncology setting including Cdk-2 and Aurora-A. The fidelity of mitosis is of paramount importance and several "checkpoints" exist in normal cells to maintain chromosome integrity during the cell cycle.

The Spindle Assembly Checkpoint (SAC) is specifically required for proper chromosomal segregation into the two daughter cells upon cellular division. It ensures that sister chromatids aligned at the metaphase plate do not separate prior to the bipolar attachment of all duplicated chromosomes to the mitotic spindle (Reviewed in Musacchio A. and Salmon D. Nat Rev Mol Cell Biol, May; 8(5): 379-93, 2007).

Even a single un-aligned chromosome is sufficient to trigger the SAC signal, it is a tightly regulated pathway that ultimately results into the inhibition of the anaphase promoting complex/cyclosome (APC/C)-mediated polyubiquitylation and degradation of two key mitotic components: cyclin B1 and Securin. Securin specifically is required to get sister chromatids separation and anaphase transition, instead cyclin B1 inactivates the master mitotic kinase CDK1 promoting mitotic exit. (Reviewed in Musacchio A. and Salmon D. Nat Rev Mol Cell Biol, May; 8(5): 379-93, 2007).

A large group of proteins has been already identified to play a role in SAC functions: human MPS1 (monopolar spindle 1) kinase, also known as TTK, has certainly a major role. MPS1 is a dual Tyrosine and Serine/Threonine kinase highly conserved from yeast to mammals. The human genome encodes for just one MPS1 gene family member, which does not have high sequence similarities with other protein kinases.

MPS1 is a cell cycle regulating enzyme that is upregulated and activated in mitosis upon phosphorylation (Stucke V M, et al., Embo J. 21 (7): 1723, 002).

In *Saccharomyces cerevisiae*, MPS1 controls spindle-pole body duplication (Winey M. et al., J. Cell Biol 114:745, 1991), spindle assembly (Jones, M. H. et al., Curr. Biol. 15: 160, 2005) and the spindle assembly checkpoint (Weiss and Winey, J. Cell. Biol 132:111, 1996). Instead, in higher eukaryotes the MPS1 kinase activity is mainly involved in SAC regulation and functions (Jelluma, N. et al., Cell 132: 233, 2008).

RNA interference experiments indicate that in the absence of MPS1 the SAC functions are compromised: mitotic length is reduced and cells divide rapidly without metaphase plate alignment, which ultimately causes aberrant aneuploidization, mitotic catastrophe and is not anymore compatible with cellular survival (Jelluma N. et al., Cell 132: 233, 2008; Tighe A. et al., J Cell Biol 2008; Jelluma N. et al., Plos ONE 3 (6): e2415, 2008). Moreover, to support these results, a small molecule ATP-competitor MPS1 inhibitor was described and despite its not clean selectivity profile, it was shown to be capable to inactivate SAC functions, inactivate nocodazole and taxol mediated mitotic arrest and promote cell death mainly in tumorigenic cell lines (Schmidt et al., EMBO Rep, 6(9): 866, 2005).

Despite that most of the tumors are aneuploid, MPS1 was never found to be mutated in cancer, instead, it has been found unregulated in a number of tumors of different origins like bladder, anaplastic thyroid, breast and prostate cancer (Yuan B. et al, Clin Cancer Res, 12(2): 405-410 2006). Moreover it was found in the signature of the top 25 genes over-expressed in CIN and aneuploid tumors which predict clinical outcome in breast and lung cancer, medulloblastoma, glioma, mesothelioma and lymphoma (Carter S L et al., Nat Genet. 38 (9): 1043, 2006). Finally, it is highly elevated in metastatic tumors and it was found to be over-expressed in p53-mutated breast cancers (Bertheau P. et al., Plos Med 4(3):e90, 2007).

Together with the fact that also other SAC components like MAD2, BUBR1 or BUB1 have been found up-regulated in different tumors (deCarcer G. et al., Curr Med Chem 14(9): 969, 2007), it seems that SAC functions could be required and essential to keep tumoral highly aneuploidy cells capable to segregate and tumoral selectivity of SAC inhibitors is foreseen in particular for highly aneuploid tumors like colon, lung and breast carcinomas (Kops G. J. et al., Nat. Rev Cancer, 5:773, 2005).

Finally, massive aneuploidy induction and SAC deregulation have been shown to reduce tumorigenesis in tumour prone mice sustaining the hypothesis that SAC inhibition could confer tumour growth inhibition (Weaver et al., Cancer Cell 11(1): 25, 2007). Thus, for these reasons, pharmacological attenuation of MPS1 function may have a therapeutic benefit in the treatment of several diverse cancers.

Originally identified as activated genes by proviral mutagenesis in a lymphoma mouse model, PIMs (PIM1, PIM2 and/or PIM3 throughout this application) are protein-serine/threonine kinases. PIM kinases are poorly expressed in normal tissues, and overexpressed or even mutated in a discrete number of human cancers, including lymphoma, leukaemia, prostate, pancreas and gastric cancers [Shah et al. *Eur. J. Cancer,* 44, 2144-51, (2008)].

PIM kinases are constitutively active and their activity supports in vitro and in vivo tumor cell growth and survival through modification of an increasing number of common as well as isoform-specific substrates including several cell cycle regulators and apoptosis mediators. PIM1 but not PIM2 seems also to mediate homing and migration of normal and malignant hematopoietic cells by regulating chemokine receptor surface expression [Brault et al. *Haematologica* 95 1004-1015 (2010)].

There is increasing evidence that PIM1 and PIM2 kinases may be involved in mediating the oncogenic effects of some acute myelogenous leukemias (AML)-associated oncogenes. In particular, the oncogenic role of FLT3-mutations (ITD and KD mut., present in 30% of AMLs) and/or translocations involving the MLL gene (occurring in 20% of AMLs), [Kumar, et al. *J. Mol. Biol.* 348, 183-193, (2005)]. PIM1 is more expressed in FLT3-ITD-transformed AML cells than in WT bone marrow cells. Data suggest that PIM1 as well as PIM2 inhibition may mediate FLT3-ITD-dependent death of AML cells. Interestingly, cells transformed by FLT3 mutations that confer resistance to small-molecule tyrosine kinase inhibitors were still sensitive to knockdown of PIM2, or PIM1 and PIM2 by RNAi, [Kim et al., *Blood* 105, 1759-67, (2005)].

Moreover, PIM2 has been reported being over-expressed and associated with progression of several malignancies that originate from the B-cell lineage such as chronic lymphocytic (CLL), diffuse large B-cell lymphoma (DLBCL), mantle cell lymphoma (MCL) or myeloma [Cohen et al., *Leukemia & Lymphoma* 45(5) 951-955 (2004), Huttmann et al. *Leukemia* 20 1774 (2006)].

Interestingly, PIMs and AKT/PKB seem to play partly redundant roles in mediating growth and survival of hematopoietic cells most probably due to overlapping substrates like BAD, p21 $^{WAF1/CIP1}$, p27$^{KIP1}$, or Cot/Tpl-2 [Choudhary et al., *Mol. Cell.* 36 326-39 (2009)].

PIM kinases have been shown to control mTOR inhibition (rapamycin) resistant, proliferation and survival. Therefore, a combination of small molecule inhibitors targeting several survival kinases might be essential for a powerful cancer therapeutic platform [Amaravadi R., et al. J. Clin. Invest. 2005, 115 (10) 2618-24]. Oncogenic protein synthesis through eIF4E binding protein 1 (4E-BP1) seems to be mTOR-independent and controlled by PIM-2. This observations suggest that the oncogenic eIF4F translation-initiating complex could be blocked with small molecules PIM2 inhibitors [Tamburini J. et al. Blood 2009, 114 (8), 1618-27 and; Brault L. et al. Haematologica 2010, 95 (6), 1004-1015].

Tetrahydrobenzocycloheptene derivatives known in the art as immunosuppressive agents and for treating and preventing inflammatory conditions, allergic disorders and immune disorders are disclosed in WO2009/089305.

Tetrahydrocycloheptapyrimidine derivatives known in the art as protein kinase inhibitors are disclosed in WO2005/037843.

Despite these developments, there is still need for effective agents for said diseases.

BRIEF DESCRIPTION OF THE DRAWINGS

The present disclosure will be better understood by reference to the following drawings of which.

DESCRIPTION OF THE INVENTION

Figure 1:
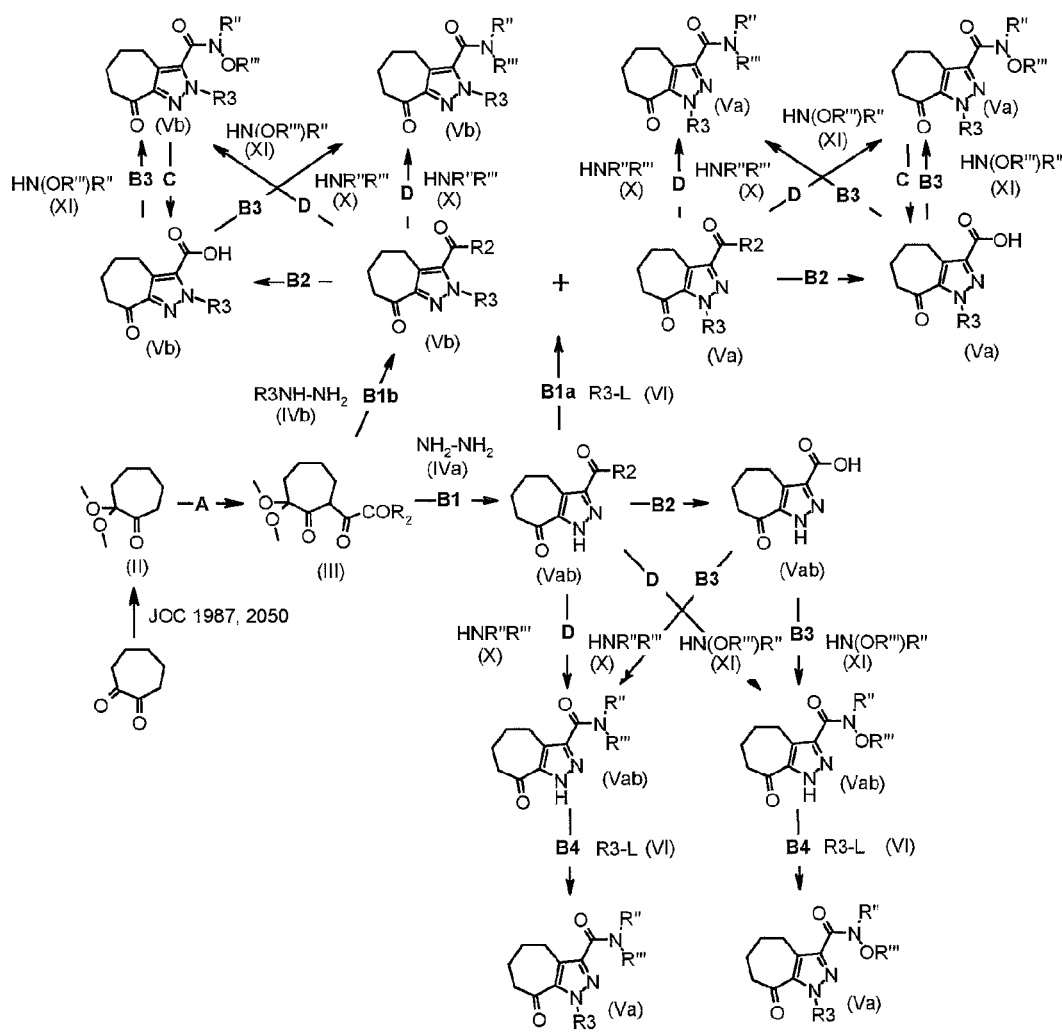
FIG. 1 illustrates the preparation of compounds of formula (Vab), (Va) and (Vb) that are intermediates for the preparation of a compound of formula (I) wherein one of Y and Z is nitrogen and the other is N—R3 wherein R3 is as defined in formula (I)

The present inventors have now discovered that compounds of formula (I), described below, are kinase inhibitors and are thus useful in therapy as antitumor agents and lack, in terms of both toxicity and side effects, the aforementioned drawbacks associated with currently available antitumor drugs.

Accordingly, a first object of the present invention is to provide a substituted tricyclic compound of formula (I)

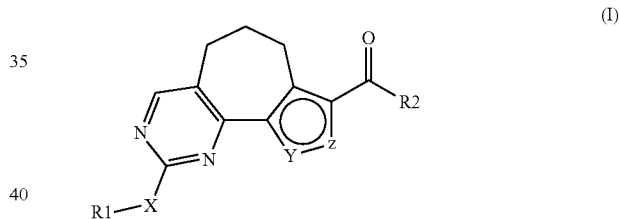

(I)

wherein:

R1 is hydrogen, halogen or an optionally substituted group selected from amino, straight or branched $C_1$-$C_6$ alkyl, $C_3$-$C_7$ cycloalkyl, cycloalkyl-alkyl, aryl, arylalkyl, heterocyclyl and heterocyclylalkyl;

X is a single bond or a divalent radical selected from —NR'—, —CONR'—, —NH—CO—NH—, —O—, —S—, —SO$_2$—, and —OSO$_2$—, wherein R' is hydrogen or an optionally substituted group selected from straight or branched $C_1$-$C_6$ alkyl, $C_3$-$C_7$ cycloalkyl, cycloalkyl-alkyl, aryl, arylalkyl, heterocyclyl and heterocyclylalkyl; one of Y and Z is nitrogen and the other is N—R3 wherein R3 is hydrogen or an optionally substituted group selected from straight or branched $C_1$-$C_6$ alkyl, $C_3$-$C_7$ cycloalkyl, cycloalkyl-alkyl, aryl, arylalkyl, heterocyclyl and heterocyclylalkyl or is a group —(CH$_2$)$_n$—, wherein n is 2 or 3, forming a ring with R2, or Y is oxygen and Z is nitrogen, or Y is nitrogen and Z is oxygen;

R2 is a group selected from —NR"R'", —N(OR'")R" and OR", wherein R" and R'" are, each independently, hydrogen or an optionally substituted group selected from straight or branched $C_1$-$C_6$ alkyl, $C_3$-$C_7$ cycloalkyl, cycloalkyl-alkyl, aryl, arylalkyl, heterocyclyl and heterocyclylalkyl or, together with the nitrogen atom to which they are bonded, R"

and R''' may form a 5 to 6 membered heteroaryl or heterocyclyl group, optionally containing one additional heteroatom selected among N, O and S;

or a pharmaceutically acceptable salt thereof.

The present invention also provides methods of synthesizing the substituted tricyclic derivatives, represented by formula (I), prepared through a process consisting of standard synthetic transformations and isomers, tautomers, hydrates, solvates, complexes, metabolites, prodrugs, carriers, N-oxides.

The present invention also provides a method for treating diseases caused by and/or associated with dysregulated protein kinase activity, particularly ABL, ACK1, AKT1, ALK, AUR1, AUR2, BRK, BUB1, CDC7/DBF4, CDK2/CYCA, CHK1, CK2, EEF2K, EGFR1, EphA2, EphB4, ERK2, FAK, FGFR1, FLT3, GSK3beta, Haspin, IGFR1, IKK2, IR, JAK1, JAK2, JAK3, KIT, LCK, LYN, MAPKAPK2, MELK, MET, MNK2, MPS1, MST4, NEK6, NIM1, P38alpha, PAK4, PDGFR, PDK1, PERK, PIM1, PIM2, PIM3, PKAalpha, PKCbeta, PLK1, RET, ROS1, SULU1, Syk, TLK2, TRKA, TYK, VEGFR2, VEGFR3, ZAP70, more particularly MPS1, PIM1, PIM2, PIM3.

A preferred method of the present invention is to treat a disease caused by and/or associated with dysregulated protein kinase activity selected from the group consisting of cancer, cell proliferative disorders, viral infections, autoimmune and neurodegenerative disorders.

Another preferred method of the present invention is to treat specific types of cancer including but not limited to: carcinoma, such as bladder, breast, colon, kidney, liver, lung, including small cell lung cancer, esophagus, gall-bladder, ovary, pancreas, stomach, cervix, thyroid, prostate, and skin, including squamous cell carcinoma; hematopoietic tumors of lymphoid lineage, including leukaemia, acute lymphocitic leukaemia, acute lymphoblastic leukaemia, B-cell lymphoma, T-cell-lymphoma, Hodgkin's lymphoma, non-Hodgkin's lymphoma, hairy cell lymphoma and Burkett's lymphoma; hematopoietic tumors of myeloid lineage, including acute and chronic myelogenous leukemias, myelodysplastic syndrome and promyelocytic leukaemia; tumors of mesenchymal origin, including fibrosarcoma and rhabdomyosarcoma; tumors of the central and peripheral nervous system, including astrocytoma, neuroblastoma, glioma and schwannomas; other tumors, including melanoma, seminoma, teratocarcinoma, osteosarcoma, xeroderma pigmentosum, keratoxanthoma, thyroid follicular cancer, Kaposi's sarcoma and mesothelioma, highly aneuploid tumors and tumors which do overexpress mitotic checkpoint.

Another preferred method of the present invention is to treat specific cellular proliferation disorders such as, for example, benign prostate hyperplasia, familial adenomatous polyposis, neurofibromatosis, psoriasis, vascular smooth cell proliferation associated with atherosclerosis, pulmonary fibrosis, arthritis, glomerulonephritis and post-surgical stenosis and restenosis.

Another preferred method of the present invention is to treat immune cell-associated diseases and disorders, such as inflammatory and autoimmune diseases, for examples multiple sclerosis, systemic lupus erythematosis, inflammatory bowel diseases (IBD), Crohn's disease, irritable bowel syndrome, pancreatitis, ulcerative colitis, diverticulosis, myasthenia gravis, vasculitis, psoriasis, scleroderma, asthma, allergy, systemic sclerosis, vitiligo, arthritis such as osteoarthritis, juvenile rheumatoid arthritis, ankylosing spondylitis.

Another preferred method of the present invention is to treat viral infections, in particular the prevention of AIDS development in HIV-infected individuals.

Another preferred method of the present invention is to treat neurodegenerative disorders, such as Alzheimer's disease, Parkinson's disease and Huntington's disease.

In addition, the method of the present invention also provides tumor angiogenesis and metastasis inhibition as well as the treatment of organ transplant rejection and host versus graft disease.

The present invention also provides a pharmaceutical composition comprising a therapeutically effective amount of a compound of formula (I), as defined above, and one or more pharmaceutically acceptable excipient, carrier and/or diluent.

The present invention further provides a pharmaceutical composition comprising a compound of formula (I) in combination with known anticancer treatments such as radiation therapy or chemotherapy regimen in combination with cytostatic or cytotoxic agents, antibiotic-type agents, alkylating agents, antimetabolite agents, hormonal agents, immunological agents, interferon-type agents, cyclooxygenase inhibitors (e.g. COX-2 inhibitors), matrixmetalloprotease inhibitors, telomerase inhibitors, tyrosine kinase inhibitors, anti-growth factor receptor agents, anti-HER agents, anti-EGFR agents, anti-angiogenesis agents (e.g. angiogenesis inhibitors), farnesyl transferase inhibitors, ras-raf signal transduction pathway inhibitors, cell cycle inhibitors, other cdks inhibitors, tubulin binding agents, topoisomerase I inhibitors, topoisomerase II inhibitors, and the like.

The present invention further provides an in vitro method for inhibiting protein kinase activity which comprises contacting the kinase with an effective amount of a compound of formula (I) as defined above.

Additionally, the invention provides a product or kit comprising a compound of formula (I) or a pharmaceutically acceptable salt thereof, as defined above, or pharmaceutical compositions thereof and one or more chemotherapeutic agents, as a combined preparation for simultaneous, separate or sequential use in anticancer therapy.

In another aspect the invention provides a compound of formula (I) or a pharmaceutically acceptable salt thereof, as defined above, for use as a medicament.

Moreover the invention provides the use of a compound of formula (I) or a pharmaceutically acceptable salt thereof, as defined above, in the manufacture of a medicament with anticancer activity.

Finally, the invention provides a compound of formula (I) or a pharmaceutically acceptable salt thereof, as defined above, for use in a method of treating cancer.

Unless otherwise specified, when referring to the compounds of formula (I) per se as well as to any pharmaceutical composition thereof or to any therapeutic treatment comprising them, the present invention includes all of the hydrates, solvates, complexes, metabolites, prodrugs, carriers, N-oxides and pharmaceutically acceptable salts of the compounds of this invention.

In other words, if easily obtainable from the compounds of formula (I) as defined above, also their isomers, tautomers, hydrates, solvates, complexes, metabolites, prodrugs, carriers and N-oxides are object of the present invention.

A metabolite of a compound of formula (I) is any compound into which this same compound of formula (I) is converted in vivo, for instance upon administration to a mammal in need thereof. Typically, without however representing a limiting example, upon administration of a compound of formula (I), this same derivative may be converted into a variety of compounds, for instance including more soluble derivatives like hydroxylated derivatives, which are easily excreted. Hence, depending upon the metabolic pathway thus occurring, any of these hydroxylated derivatives may be regarded as a metabolite of the compounds of formula (I).

Prodrugs are any covalently bonded compounds, which release in vivo the active parent drug according to formula (I).

N-oxides are compounds of formula (I) wherein nitrogen and oxygen are tethered through a dative bond.

If a stereogenic center or another form of an isomeric center is present in a compound of the present invention, all forms of such isomer or isomers, including enantiomers and diastereomers, are intended to be covered herein. Compounds containing a stereogenic center may be used as a racemic mixture, an enantiomerically enriched mixture, or the racemic mixture may be separated using well-known techniques and an individual enantiomer may be used alone. In cases in which compounds have unsaturated carbon-carbon double bonds, both the cis (Z) and trans (E) isomers are within the scope of this invention.

In cases wherein compounds may exist in tautomeric forms, such as keto-enol tautomers, each tautomeric form is contemplated as being included within this invention whether existing in equilibrium or predominantly in one form.

In case wherein Y is N—R3 and Z is N, the compound of the present invention has the general formula (Ia); in case wherein Y is N and Z is N—R3, the compound of the present invention has the general formula (Ib); in case wherein Y is O and Z is N, the compound of the present invention has the general formula (Ic); in case wherein Y is N and Z is O, the compound of the present invention has the general formula (Id), here below:

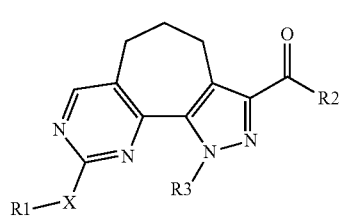
(Ia)

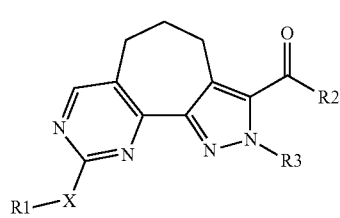
(Ib)

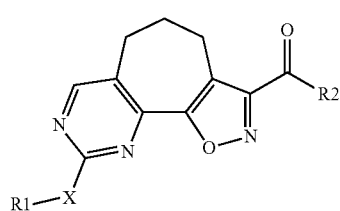
(Ic)

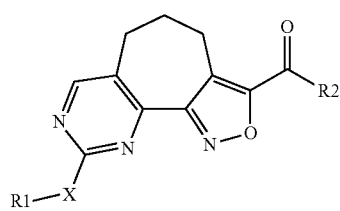
(Id)

wherein R1, X, R2 and R3 are as defined above.

Unless otherwise provided, when in compounds of formula (Ia) or (Ib) R3 is hydrogen, only one of the tautomeric forms is indicated, the remaining one has still to be intended as comprised within the scope of the invention:

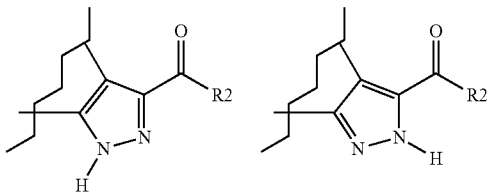

The term "aryl" includes carbocyclic or heterocyclic hydrocarbons with from 1 to 2 ring moieties, either fused or linked to each other by single bonds, wherein at least one of the rings is aromatic; if present, any aromatic heterocyclic hydrocarbon also referred to as heteroaryl group, comprises a 5 to 6 membered ring with from 1 to 3 heteroatoms selected from N, O and S.

Examples of aryl groups according to the invention are, for instance, phenyl, biphenyl, α- or β-naphthyl, dihydronaphthyl, thienyl, benzothienyl, furyl, benzofuranyl, pyrrolyl, imidazolyl, pyrazolyl, thiazolyl, isothiazolyl, oxazolyl, isoxazolyl, pyridyl, pyrazinyl, pyrimidinyl, pyridazinyl, indolyl, isoindolyl, purinyl, quinolyl, isoquinolyl, dihydroquinolinyl, quinoxalinyl, benzodioxolyl, indanyl, indenyl, triazolyl, and the like.

With the term "heterocyclyl" (also known as "heterocycloalkyl") we intend a 3- to 7-membered, saturated or partially unsaturated carbocyclic ring where one or more carbon atoms are replaced by heteroatoms such as nitrogen, oxygen and sulfur. Non limiting examples of heterocyclyl groups are, for instance, pyrane, pyrrolidine, pyrroline, imidazoline, imidazolidine, pyrazolidine, pyrazoline, thiazoline, thiazolidine, dihydrofuran, tetrahydrofuran, 1,3-dioxolane, piperidine, piperazine, morpholine and the like.

With the term "$C_3$-$C_7$ cycloalkyl" we intend, unless otherwise provided, 3- to 7-membered all-carbon monocyclic ring, which may contain one or more double bonds but does not have a completely conjugated π-electron system. Examples of cycloalkyl groups, without limitation, are cyclopropane, cyclobutane, cyclopentane, cyclopentene, cyclohexane, cyclohexene, cyclohexadiene, cycloeptane, cycloeptene, cycloeptadiene.

With the term "straight or branched $C_1$-$C_6$ alkyl", hence comprehensive of $C_1$-$C_4$ alkyl, we intend any of the groups such as, for instance, methyl, ethyl, n-propyl, isopropyl, n-butyl, isobutyl, tert-butyl, sec-butyl, n-pentyl, n-hexyl, and the like.

With the term "straight or branched $C_2$-$C_6$ alkenyl" we intend any of the groups such as, for instance, vinyl, allyl, 1-propenyl, isopropenyl, 1-butenyl, 2-butenyl, 3-butenyl, 2-pentenyl, 1-hexenyl, and the like.

With the term "straight or branched $C_2$-$C_6$ alkynyl" we intend any of the groups such as, for instance, ethynyl, 2-propynyl, 4-pentynyl, and the like.

According to the present invention and unless otherwise provided, any of the above R1, R2, R3, R', R" and R'" groups may be optionally substituted, in any of their free positions, by one or more groups, for instance 1 to 6 groups, independently selected from: halogen, nitro, oxo (═O), cyano, $C_1$-$C_6$ alkyl, polyfluorinated alkyl, polyfluorinated alkoxy, alkenyl, alkynyl, hydroxyalkyl, aryl, arylalkyl, heterocyclyl, $C_3$-$C_7$ cycloalkyl, hydroxy, alkoxy, aryloxy, heterocyclyloxy, methylenedioxy, alkylcarbonyloxy, arylcarbonyloxy, cycloalkenyloxy, heterocyclylcarbonyloxy, alkylideneaminooxy, carboxy, alkoxycarbonyl, aryloxycarbonyl, cycloalkyloxycarbonyl, heterocyclyloxycarbonyl, amino, ureido, alkylamino, dialkylamino, arylamino, diarylamino, heterocyclylamino, formylamino, alkylcarbonylamino, arylcarbonylamino, heterocyclylcarbonylamino, aminocarbonyl, alkylaminocarbonyl, dialkylaminocarbonyl, arylaminocarbonyl, heterocyclylaminocarbonyl, alkoxycarbonylamino, hydroxyaminocarbonyl alkoxyimino, alkylsulfonylamino, arylsulfonylamino, heterocyclylsulfonylamino, formyl, alkylcarbonyl, arylcarbonyl, cycloalkylcarbonyl, heterocyclylcarbonyl, heterocyclylsulfonyl, alkylsulfonyl, arylsulfonyl, aminosulfonyl, alkylaminosulfonyl, dialkylaminosulfonyl, arylaminosulfonyl, heterocyclylaminosulfonyl, arylthio, alkylthio, phosphonate and alkylphosphonate.

In their turn, whenever appropriate, each of the above substituent may be further substituted by one or more of the aforementioned groups.

In this respect, with the term "halogen" we intend a fluorine, chlorine, bromine or iodine atom.

With the term "cyano" we intend a —CN residue.

With the term "nitro" we intend a —$NO_2$ group.

With the term "alkenyl" or "alkynyl" we intend any of the aforementioned straight or branched $C_2$-$C_6$ alkyl groups further bearing a double or triple bond. Non limiting examples of alkenyl or alkynyl groups of the invention are, for instance, vinyl, allyl, 1-propenyl, isopropenyl, 1-butenyl, 2-butenyl, 3-butenyl, 2-pentenyl, 1-hexenyl, ethynyl, 2-propynyl, 4-pentynyl, and the like.

With the term "polyfluorinated alkyl" or "polyfluorinated alkoxy" we intend any of the above straight or branched $C_1$-$C_6$ alkyl or alkoxy groups which are substituted by more than one fluorine atom such as, for instance, trifluoromethyl, trifluoroethyl, 1,1,1,3,3,3-hexafluoropropyl, trifluoromethoxy and the like.

With the term "alkoxy", "aryloxy", "heterocyclyloxy" and derivatives thereof we intend any of the above $C_1$-$C_6$ alkyl, aryl or heterocyclyl groups linked to the rest of the molecule through an oxygen atom (—O—).

From all of the above, it is clear to the skilled person that any group which name is a composite name such as, for instance, arylamino, has to be intended as conventionally construed by the parts from which it derives, e.g. by an amino group which is further substituted by aryl, wherein aryl is as above defined.

Likewise, any of the terms such as, for instance, alkylthio, alkylamino, dialkylamino, alkoxycarbonyl, alkoxycarbonylamino, heterocyclylcarbonyl, heterocyclylcarbonylamino, cycloalkyloxycarbonyl and the like, include groups wherein the alkyl, alkoxy, aryl, $C_3$-$C_7$ cycloalkyl and heterocyclyl moieties are as above defined.

Pharmaceutically acceptable salts of the compounds of formula (I) include the acid addition salts with inorganic or organic acids, e.g., nitric, hydrochloric, hydrobromic, sulfuric, perchloric, phosphoric, acetic, trifluoroacetic, propionic, glycolic, fumaric, lactic, oxalic, malonic, malic, maleic, tartaric, citric, benzoic, cinnamic, mandelic, methanesulphonic, isethionic and salicylic acid. Preferably, the acid addition salt of the compounds of the invention is selected between the hydrochloride or mesylate salts.

Pharmaceutically acceptable salts of the compounds of formula (I) also include the salts with inorganic or organic bases, e.g., alkali or alkaline-earth metals, especially sodium, potassium, calcium ammonium or magnesium hydroxides, carbonates or bicarbonates, acyclic or cyclic amines, preferably methylamine, ethylamine, diethylamine, triethylamine, piperidine and the like.

Preferred compounds of formula (I) are the compounds wherein:

X is a group —NH— and R2 is a group selected from —NHR", —N(OR''')R" and —OR", wherein R" is hydrogen or an optionally substituted group selected from straight or branched $C_1$-$C_6$ alkyl, $C_3$-$C_7$ cycloalkyl, cycloalkyl-alkyl, aryl, arylalkyl, heterocyclyl and heterocyclylalkyl; and R''', Y, Z, R1 and R3 are as above defined.

Other preferred compounds are the compounds of formula (I) wherein X is a group —O— and R2 is a group selected from —NHR", —N(OR''')R" and —OR", wherein R" is hydrogen or an optionally substituted group selected from straight or branched $C_1$-$C_6$ alkyl, $C_3$-$C_7$ cycloalkyl, cycloalkyl-alkyl, aryl, arylalkyl, heterocyclyl and heterocyclylalkyl; and R''', Y, Z, R1 and R3 are as above defined.

Other preferred compounds are the compounds of formula (I) wherein X is a group —S— and R2 is a group selected from —NHR", —N(OR''')R" and —OR", wherein R" is hydrogen or an optionally substituted group selected from straight or branched $C_1$-$C_6$ alkyl, $C_3$-$C_7$ cycloalkyl, cycloalkyl-alkyl, aryl, arylalkyl, heterocyclyl and heterocyclylalkyl; and R''', Y, Z, R1 and R3 are as above defined.

Other preferred compounds are the compounds of formula (I) wherein X is a bond and R2 is a group selected from —NHR", —N(OR''')R" and —OR", wherein R" is hydrogen or an optionally substituted group selected from straight or branched $C_1$-$C_6$ alkyl, $C_3$-$C_7$ cycloalkyl, cycloalkyl-alkyl, aryl, arylalkyl, heterocyclyl and heterocyclylalkyl; and R''', Y, Z, R1 and R3 are as above defined.

Other preferred compounds are the compounds of formula (I) wherein X is a group —NH— and R2 is a group —NHR" or —N(OR''')R" wherein R" is hydrogen or an optionally substituted group selected from straight or branched $C_1$-$C_4$ alkyl and aryl; and R''', Y, Z, R1 and R3 are as above defined.

Other preferred compounds are the compounds of formula (I) wherein X is a group —O— and R2 is a group —NHR" or —N(OR''')R" wherein R" is hydrogen or an optionally substituted group selected from straight or branched $C_1$-$C_4$ alkyl and aryl; and R''', Y, Z, R1, R3 are as above defined.

Other preferred compounds are the compounds of formula (I) wherein X is a group —S— and R2 is a group —NHR" or —N(OR''')R" wherein R" is hydrogen or an optionally substituted group selected from straight or branched $C_1$-$C_4$ alkyl and aryl; and R''', Y, Z, R1 and R3 are as above defined.

Other preferred compounds are the compounds of formula (I) wherein X is a bond and R2 is a group —NHR" or —N(OR''')R" wherein R" is hydrogen or an optionally substituted group selected from straight or branched $C_1$-$C_4$ alkyl and aryl; and R''', Y, Z, R1, R3 are as above defined.

Other preferred compounds are the compounds of formula (I) wherein R2 is NH and R3 is a group —$(CH_2)_n$—, wherein n is 2 or 3, that is compounds of formula (Ib1) and (Ib2):

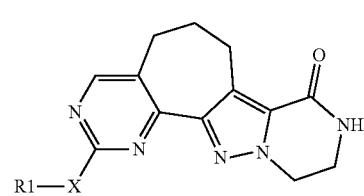

(Ib1)

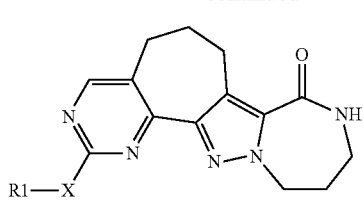
(Ib2)

wherein
X and R1 have any of the meanings defined in formula (I).
Other preferred compounds are the compounds of formula (I) wherein R2 is O and R3 is a group —(CH$_2$)$_n$—, wherein n is 2 or 3, that is compounds of formula (Ib3) and (Ib4):

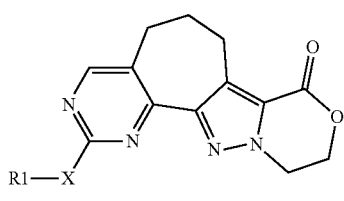
(Ib3)

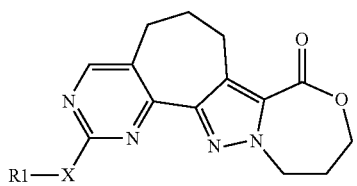
(Ib4)

wherein
X and R1 have any of the meanings defined in formula (I).
Preferred specific compounds of formula (I) are the compounds listed below:
1) 9-[(4-bromo-2-methoxyphenyl)amino]-1-methyl-1,4,5,6-tetrahydropyrazolo[4',3':6,7]cyclohepta[1,2-d]pyrimidine-3-carboxamide
2) 9-[(4-bromo-2-methoxyphenyl)amino]-N-(2,6-diethylphenyl)-1-methyl-1,4,5,6-tetrahydropyrazolo[4',3':6,7]cyclohepta[1,2-d]pyrimidine-3-carboxamide
3) 9-{[2-methoxy-4-(4-methylpiperazin-1-yl)phenyl]amino}-1-methyl-1,4,5,6-tetrahydropyrazolo[4',3':6,7]cyclohepta[1,2-d]pyrimidine-3-carboxamide
4) N-(2,6-diethylphenyl)-9-{[2-methoxy-4-(4-methylpiperazin-1-yl)phenyl]amino}-1-methyl-1,4,5,6-tetrahydropyrazolo[4',3':6,7]cyclohepta[1,2-d]pyrimidine-3-carboxamide
5) N-[(1S)-2-amino-1-phenylethyl]-9-({2-methoxy-4-[(1-methylpiperidin-4-yl)carbamoyl]phenyl}amino)-1-methyl-1,4,5,6-tetrahydropyrazolo[4',3':6,7]cyclohepta[1,2-d]pyrimidine-3-carboxamide
6) ethyl 9-{[2-methoxy-4-(4-methylpiperazin-1-yl)phenyl]amino}-1,4,5,6-tetrahydropyrazolo[4',3':6,7]cyclohepta[1,2-d]pyrimidine-3-carboxylate
7) N-benzyl-9-{[2-methoxy-4-(4-methylpiperazin-1-yl)phenyl]amino}-1-methyl-1,4,5,6-tetrahydropyrazolo[4',3':6,7]cyclohepta[1,2-d]pyrimidine-3-carboxamide
8) 9-{[2-methoxy-4-(4-methylpiperazin-1-yl)phenyl]amino}-1-methyl-N-phenyl-1,4,5,6-tetrahydropyrazolo[4',3':6,7]cyclohepta[1,2-d]pyrimidine-3-carboxamide
9) N-(2,6-diethylphenyl)-9-({4-[(4-hydroxycyclohexyl)amino]-2-methoxyphenyl}amino)-1-methyl-1,4,5,6-tetrahydropyrazolo[4',3':6,7]cyclohepta[1,2-d]pyrimidine-3-carboxamide
10) N-(2,6-diethylphenyl)-9-[(4-{[3-(dimethylamino)propyl](methyl)amino}-2-methoxyphenyl)amino]-1-methyl-1,4,5,6-tetrahydropyrazolo[4',3':6,7]cyclohepta[1,2-d]pyrimidine-3-carboxamide
11) N-(2,6-diethylphenyl)-9-({2-methoxy-4-[4-(pyrrolidin-1-yl)piperidin-1-yl]phenyl}amino)-1-methyl-1,4,5,6-tetrahydropyrazolo[4',3':6,7]cyclohepta[1,2-d]pyrimidine-3-carboxamide
12) N-(2,6-diethylphenyl)-9-({4-[(3R)-3-(dimethylamino)pyrrolidin-1-yl]-2-methoxyphenyl}amino)-1-methyl-1,4,5,6-tetrahydropyrazolo[4',3':6,7]cyclohepta[1,2-d]pyrimidine-3-carboxamide
13) N-(2,6-diethylphenyl)-9-[(4-{[2-(dimethylamino)ethyl](methyl)amino}-2-methoxyphenyl)amino]-1-methyl-1,4,5,6-tetrahydropyrazolo[4',3':6,7]cyclohepta[1,2-d]pyrimidine-3-carboxamide
14) N-(2,6-diethylphenyl)-9-({4-[4-(2-hydroxyethyl)piperazin-1-yl]-2-methoxyphenyl}amino)-1-methyl-1,4,5,6-tetrahydropyrazolo[4',3':6,7]cyclohepta[1,2-d]pyrimidine-3-carboxamide
15) N-(2-ethylphenyl)-9-{[2-methoxy-4-(4-methylpiperazin-1-yl)phenyl]amino}-1-methyl-1,4,5,6-tetrahydropyrazolo[4',3':6,7]cyclohepta[1,2-d]pyrimidine-3-carboxamide
16) 9-[(4-bromo-2-methoxyphenyl)amino]-1-methyl-N-[(1S)-2-(morpholin-4-yl)-1-phenylethyl]-1,4,5,6-tetrahydropyrazolo[4',3':6,7]cyclohepta[1,2-d]pyrimidine-3-carboxamide
17) 9-[(4-bromo-2-methoxyphenyl)amino]-N-(2,6-dimethylphenyl)-1-methyl-1,4,5,6-tetrahydropyrazolo[4',3':6,7]cyclohepta[1,2-d]pyrimidine-3-carboxamide
18) 9-{[2-methoxy-4-(4-methylpiperazin-1-yl)phenyl]amino}-1-methyl-N-[(1S)-2-(morpholin-4-yl)-1-phenylethyl]-1,4,5,6-tetrahydropyrazolo[4',3':6,7]cyclohepta[1,2-d]pyrimidine-3-carboxamide
19) 9-[(4-bromo-2-methoxyphenyl)amino]-N-(2-ethyl-6-methylphenyl)-1-methyl-1,4,5,6-tetrahydropyrazolo[4',3':6,7]cyclohepta[1,2-d]pyrimidine-3-carboxamide
20) N-(2,6-dimethylphenyl)-9-{[2-methoxy-4-(4-methylpiperazin-1-yl)phenyl]amino}-1-methyl-1,4,5,6-tetrahydropyrazolo[4',3':6,7]cyclohepta[1,2-d]pyrimidine-3-carboxamide
21) 9-{[4-(dimethylamino)-2-methoxyphenyl]amino}-N-(2,6-dimethylphenyl)-1-methyl-1,4,5,6-tetrahydropyrazolo[4',3':6,7]cyclohepta[1,2-d]pyrimidine-3-carboxamide
22) N-(2,6-diethylphenyl)-9-({4-[4-(dimethylamino)piperidin-1-yl]-2-methoxyphenyl}amino)-1-methyl-1,4,5,6-tetrahydropyrazolo[4',3':6,7]cyclohepta[1,2-d]pyrimidine-3-carboxamide
23) N-(2,6-diethylphenyl)-9-{[2-methoxy-4-(4-methyl-1,4-diazepan-1-yl)phenyl]amino}-1-methyl-1,4,5,6-tetrahydropyrazolo[4',3':6,7]cyclohepta[1,2-d]pyrimidine-3-carboxamide
24) N-(2,6-diethylphenyl)-9-[(2-methoxyphenyl)amino]-1-methyl-1,4,5,6-tetrahydropyrazolo[4',3':6,7]cyclohepta[1,2-d]pyrimidine-3-carboxamide
25) N-(2,6-diethylphenyl)-9-({2-methoxy-4-[(1-methylpiperidin-4-yl)amino]phenyl}amino)-1-methyl-1,4,5,6-tetrahydropyrazolo[4',3':6,7]cyclohepta[1,2-d]pyrimidine-3-carboxamide
26) 9-{[4-(1-azabicyclo[2.2.2]oct-3-ylamino)-2-methoxyphenyl]amino}-N-(2,6-diethylphenyl)-1-methyl-1,4,5,6-tetrahydropyrazolo[4',3':6,7]cyclohepta[1,2-d]pyrimidine-3-carboxamide 27) N-(2-ethyl-6-methylphenyl)-9-{[2-methoxy-4-(4-methylpiperazin-1-yl)phenyl]amino}-1-methyl-1,4,5,6-tetrahydropyrazolo[4',3':6,7]cyclohepta[1,2-d]pyrimidine-3-carboxamide 28) N-cyclohexyl-9-{[2-methoxy-4-(4-methylpiperazin-1-yl)phenyl]amino}-1-methyl-1,4,5,6-tetrahydropyrazolo[4',3':6,7]cyclohepta[1,2-d]pyrimidine-3-carboxamide 29) N-(2,6-diethylphenyl)-1-methyl-9-{[4-(4-methylpiperazin-1-yl)phenyl]amino}-1,4,5,6-tetrahydropyrazolo[4',3':6,7]cyclohepta[1,2-d]pyrimidine-3-carboxamide 30) 9-amino-N-(2,6-diethylphenyl)-1-methyl-1,4,5,6-tetrahydropyrazolo[4',3':6,7]cyclohepta[1,2-d]pyrimidine-3-carboxamide 31) 1-[3-(dimethylamino)propyl]-9-(methylsulfanyl)-1,4,5,6-tetrahydropyrazolo[4',3':6,7]cyclohepta[1,2-d]pyrimidine-3-carboxamide 32) 9-[(4-bromo-2-methoxyphenyl)amino]-N,1-dimethyl-1,4,5,6-tetrahydropyrazolo[4',3':6,7]cyclohepta[1,2-d]pyrimidine-3-carboxamide 33) 4-({3-[(2,6-diethylphenyl)carbamoyl]-1-methyl-1,4,5,6-tetrahydropyrazolo[4',3':6,7]cyclohepta[1,2-d]pyrimidin-9-yl}amino)-3-methoxybenzoic 34) 4-({3-[(2,6-diethylphenyl)carbamoyl]-1-methyl-1,4,5,6-tetrahydropyrazolo[4',3':6,7]cyclohepta[1,2-d]pyrimidin-9-yl}amino)-3-(trifluoromethoxy)benzoic acid 35) N-(2,6-diethylphenyl)-9-({2-methoxy-4-[(1-methylpiperidin-4-yl)carbamoyl]phenyl}amino)-1-methyl-1,4,5,6-tetrahydropyrazolo[4',3':6,7]cyclohepta[1,2-d]pyrimidine-3-carboxamide 36) N-(2,6-diethylphenyl)-9-[(2-methoxy-4-{[4-(pyrrolidin-1-yl)piperidin-1-yl]carbonyl}phenyl)amino]-1-methyl-1,4,5,6-tetrahydropyrazolo[4',3':6,7]cyclohepta[1,2-d]pyrimidine-3-carboxamide 37) N-(2,6-diethylphenyl)-9-[(4-{[4-(dimethylamino)piperidin-1-yl]carbonyl}-2-methoxyphenyl)amino]-1-methyl-1,4,5,6-tetrahydropyrazolo[4',3':6,7]cyclohepta[1,2-d]pyrimidine-3-carboxamide 38) N-(2,6-diethylphenyl)-9-({2-methoxy-4-[(4-methyl-1,4-diazepan-1-yl)carbonyl]phenyl}amino)-1-methyl-1,4,5,6-tetrahydropyrazolo[4',3':6,7]cyclohepta[1,2-d]pyrimidine-3-carboxamide 39) 9-{[2-methoxy-4-(4-methylpiperazin-1-yl)phenyl]amino}-N,1-dimethyl-1,4,5,6-tetrahydropyrazolo[4',3':6,7]cyclohepta[1,2-d]pyrimidine-3-carboxamide 40) N-(2,6-diethylphenyl)-1-methyl-9-({4-[(1-methylpiperidin-4-yl)carbamoyl]-2-(trifluoromethoxy)phenyl}amino)-1,4,5,6-tetrahydropyrazolo[4',3':6,7]cyclohepta[1,2-d]pyrimidine-3-carboxamide 41) N-(2,6-diethylphenyl)-1-methyl-9-{[4-{[4-(pyrrolidin-1-yl)piperidin-1-yl]carbonyl}-2-(trifluoromethoxy)phenyl]amino}-1,4,5,6-tetrahydropyrazolo[4',3':6,7]cyclohepta[1,2-d]pyrimidine-3-carboxamide 42) N-(2,6-diethylphenyl)-9-{[4-{[4-(dimethylamino)piperidin-1-yl]carbonyl}-2-(trifluoromethoxy)phenyl]amino}-1-methyl-1,4,5,6-tetrahydropyrazolo[4',3':6,7]cyclohepta[1,2-d]pyrimidine-3-carboxamide 43) N-(2,6-diethylphenyl)-1-methyl-9-({4-[(4-methyl-1,4-diazepan-1-yl)carbonyl]-2-(trifluoromethoxy)phenyl}amino)-1,4,5,6-tetrahydropyrazolo[4',3':6,7]cyclohepta[1,2-d]pyrimidine-3-carboxamide 44) 9-amino-1-methyl-1,4,5,6-tetrahydropyrazolo[4',3':6,7]cyclohepta[1,2-d]pyrimidine-3-carboxamide 45) 1-methyl-9-({4-[(4-methylpiperazin-1-yl)sulfonyl]phenyl}amino)-1,4,5,6-tetrahydropyrazolo[4',3':6,7]cyclohepta[1,2-d]pyrimidine-3-carboxamide 46) 1-methyl-9-[(4-nitrophenyl)amino]-N-propyl-1,4,5,6-tetrahydropyrazolo[4',3':6,7]cyclohepta[1,2-d]pyrimidine-3-carboxamide 47) 1-methyl-9-(methylsulfanyl)-1,4,5,6-tetrahydropyrazolo[4',3':6,7]cyclohepta[1,2-d]pyrimidine-3-carboxamide 48) N-(2,6-diethylphenyl)-1-(4-methoxybenzyl)-9-{[2-methoxy-4-(4-methylpiperazin-1-yl)phenyl]amino}-1,4,5,6-tetrahydropyrazolo[4',3':6,7]cyclohepta[1,2-d]pyrimidine-3-carboxamide 49) N-(2,6-diethylphenyl)-9-{[2-methoxy-4-(4-methylpiperazin-1-yl)phenyl]amino}-1,4,5,6-tetrahydropyrazolo[4',3':6,7]cyclohepta[1,2-d]pyrimidine-3-carboxamide 50) 1-methyl-9-({4-[(4-methylpiperazin-1-yl)sulfonyl]phenyl}amino)-N-propyl-1,4,5,6-tetrahydropyrazolo[4',3':6,7]cyclohepta[1,2-d]pyrimidine-3-carboxamide 51) 9-[(4-acetylphenyl)amino]-1-methyl-N-propyl-1,4,5,6-tetrahydropyrazolo[4',3':6,7]cyclohepta[1,2-d]pyrimidine-3-carboxamide 52) N-(2,6-diethylphenyl)-1-ethyl-9-{[2-methoxy-4-(4-methylpiperazin-1-yl)phenyl]amino}-1,4,5,6-tetrahydropyrazolo[4',3':6,7]cyclohepta[1,2-d]pyrimidine-3-carboxamide 53) N-(2,6-diethylphenyl)-9-{[2-methoxy-4-(4-methylpiperazin-1-yl)phenyl]amino}-1-(pyridin-4-ylmethyl)-1,4,5,6-tetrahydropyrazolo[4',3':6,7]cyclohepta[1,2-d]pyrimidine-3-carboxamide 54) N-(2,6-diethylphenyl)-9-{[2-methoxy-4-(4-methylpiperazin-1-yl)phenyl]amino}-1-(tetrahydro-2H-pyran-2-ylmethyl)-1,4,5,6-tetrahydropyrazolo[4',3':6,7]cyclohepta[1,2-d]pyrimidine-3-carboxamide 55) N-(2,6-diethylphenyl)-1-(3-hydroxypropyl)-9-{[2-methoxy-4-(4-methylpiperazin-1-yl)phenyl]amino}-1,4,5,6-tetrahydropyrazolo[4',3':6,7]cyclohepta[1,2-d]pyrimidine-3-carboxamide 56) N-(2,6-diethylphenyl)-9-{[2-methoxy-4-(4-methylpiperazin-1-yl)phenyl]amino}-1-(2,2,2-trifluoroethyl)-1,4,5,6-tetrahydropyrazolo[4',3':6,7]cyclohepta[1,2-d]pyrimidine-3-carboxamide 57) N-(2,6-diethylphenyl)-1-(3-hydroxybenzyl)-9-{[2-methoxy-4-(4-methylpiperazin-1-yl)phenyl]amino}-1,4,5,6-tetrahydropyrazolo[4',3':6,7]cyclohepta[1,2-d]pyrimidine-3-carboxamide 58) N-(2,6-diethylphenyl)-1-[3-(dimethylamino)propyl]-9-{[2-methoxy-4-(4-methylpiperazin-1-yl)phenyl]amino}-1,4,5,6-tetrahydropyrazolo[4',3':6,7]cyclohepta[1,2-d]pyrimidine-3-carboxamide 59) N-(2,6-diethylphenyl)-9-{[2-methoxy-4-(4-methylpiperazin-1-yl)phenyl]amino}-1-[2-(tetrahydro-2H-pyran-2-yloxy)ethyl]-1,4,5,6-tetrahydropyrazolo[4',3':6,7]cyclohepta[1,2-d]pyrimidine-3-carboxamide 60) N-(2,6-diethylphenyl)-1-(2-hydroxyethyl)-9-{[2-methoxy-4-(4-methylpiperazin-1-yl)phenyl]amino}-1,4,5,6-tetrahydropyrazolo[4',3':6,7]cyclohepta[1,2-d]pyrimidine-3-carboxamide 61) N-(2,6-diethylphenyl)-9-({4-[4-(dimethylamino)piperidin-1-yl]-2-methoxyphenyl}amino)-1-(4-methoxybenzyl)-1,4,5,6-tetrahydropyrazolo[4',3':6,7]cyclohepta[1,2-d]pyrimidine-3-carboxamide 62) N-(2,6-diethylphenyl)-9-({4-[4-(dimethylamino)piperidin-1-yl]-2-methoxyphenyl}amino)-1,4,5,6-tetrahydropyrazolo[4',3':6,7]cyclohepta[1,2-d]pyrimidine-3-carboxamide 63) N-(2,6-diethylphenyl)-9-({4-[4-(dimethylamino)piperidin-1-yl]-2-methoxyphenyl}amino)-1-ethyl-1,4,5,6-tetrahydropyrazolo[4',3':6,7]cyclohepta[1,2-d]pyrimidine-3-carboxamide 64) N-(2,6-diethylphenyl)-1-[2-(dimethylamino)ethyl]-9-({4-[4-(dimethylamino)piperidin-1-yl]-2-methoxyphenyl}amino)-1,4,5,6-tetrahydropyrazolo[4',3':6,7]cyclohepta[1,2-d]pyrimidine-3-carboxamide 65) 9-[(5-bromo-2-methylphenyl)amino]-1-methyl-1,4,5,6-tetrahydropyrazolo[4',3':6,7]cyclohepta[1,2-d]pyrimidine-3-carboxamide 66) 1-methyl-9-[(5-nitro-1H-benzimidazol-2-yl)amino]-1,4,5,6-tetrahydropyrazolo[4',3':6,7]cyclohepta[1,2-d]pyrimidine-3-carboxamide 67) 1-methyl-9-{[4-(4-methylpiperazin-1-yl)phenyl]amino}-1,4,5,6-tetrahydropyrazolo[4',3':6,7]cyclohepta[1,2-d]pyrimidine-3-carboxamide 68) 1-methyl-9-{[5-(4-methylpiperazin-1-yl)-2-(trifluoromethoxy)phenyl]amino}-1,4,5,6-tetrahydropyrazolo[4',3':6,7]cyclohepta[1,2-d]pyrimidine-3-carboxamide 69) N-(2,6-diethylphenyl)-9-({4-[4-(dimethylamino)piperidin-1-yl]-2-methoxyphenyl}amino)-1-[2-(1,3-dioxo-1,3-dihydro-2H-isoindol-2-yl)ethyl]-1,4,5,6-tetrahydropyrazolo[4',3':6,7]cyclohepta[1,2-d]pyrimidine-3-carboxamide 70) 1-(2-aminoethyl)-N-(2,6-diethylphenyl)-9-({4-[4-(dimethylamino)piperidin-1-yl]-2-methoxyphenyl}amino)-1,4,5,6-tetrahydropyrazolo[4',3':6,7]cyclohepta[1,2-d]pyrimidine-3-carboxamide 71) N-(2,6-diethylphenyl)-9-({4-[4-(dimethylamino)piperidin-1-yl]-2-methoxyphenyl}amino)-1-(2-hydroxyethyl)-1,4,5,6-tetrahydropyrazolo[4',3':6,7]cyclohepta[1,2-d]pyrimidine-3-carboxamide 72) N-methoxy-N,1-dimethyl-9-{[3-(trifluoromethyl)phenyl]amino}-1,4,5,6-tetrahydropyrazolo[4',3':6,7]cyclohepta[1,2-d]pyrimidine-3-carboxamide 73) 1-methyl-9-(phenylamino)-1,4,5,6-tetrahydropyrazolo[4',3':6,7]cyclohepta[1,2-d]pyrimidine-3-carboxamide 74) N-(2-methoxyethyl)-1-methyl-9-(phenylamino)-1,4,5,6-tetrahydropyrazolo[4',3':6,7]cyclohepta[1,2-d]pyrimidine-3-carboxamide 75) N-(2-methoxyethyl)-1-methyl-9-{[3-(trifluoromethyl)phenyl]amino}-1,4,5,6-tetrahydropyrazolo[4',3':6,7]cyclohepta[1,2-d]pyrimidine-3-carboxamide 76) 1-methyl-N-[2-(morpholin-4-yl)ethyl]-9-{[3-(trifluoromethyl)phenyl]amino}-1,4,5,6-tetrahydropyrazolo[4',3':6,7]cyclohepta[1,2-d]pyrimidine-3-carboxamide 77) 1-methyl-9-{[3-(trifluoromethyl)phenyl]amino}-1,4,5,6-tetrahydropyrazolo[4',3':6,7]cyclohepta[1,2-d]pyrimidine-3-carboxamide 78) 3-({[9-(benzylamino)-1-methyl-1,4,5,6-tetrahydropyrazolo[4',3':6,7]cyclohepta[1,2-d]pyrimidin-3-yl]carbonyl}amino)-N,N,N-trimethylpropan-1-aminium 79) 9-(benzylamino)-1-methyl-1,4,5,6-tetrahydropyrazolo[4',3':6,7]cyclohepta[1,2-d]pyrimidine-3-carboxamide 80) N-(2-methoxyethyl)-1-methyl-9-{[4-(4-methylpiperazin-1-yl)phenyl]amino}-1,4,5,6-tetrahydropyrazolo[4',3':6,7]cyclohepta[1,2-d]pyrimidine-3-carboxamide 81) 1-methyl-N-[2-(morpholin-4-yl)ethyl]-9-(phenylamino)-1,4,5,6-tetrahydropyrazolo[4',3':6,7]cyclohepta[1,2-d]pyrimidine-3-carboxamide 82) 9-(benzylamino)-N-(2-methoxyethyl)-1-methyl-1,4,5,6-tetrahydropyrazolo[4',3':6,7]cyclohepta[1,2-d]pyrimidine-3-carboxamide 83) 1-methyl-9-{[4-(4-methylpiperazin-1-yl)phenyl]amino}-N-[2-(morpholin-4-yl)ethyl]-1,4,5,6-tetrahydropyrazolo[4',3':6,7]cyclohepta[1,2-d]pyrimidine-3-carboxamide 84) 1-(2-hydroxyethyl)-9-(methylsulfanyl)-1,4,5,6-tetrahydropyrazolo[4',3':6,7]cyclohepta[1,2-d]pyrimidine-3-carboxamide 85) N-(2-methoxyethyl)-1-methyl-9-{[3-(4-methylpiperidin-1-yl)propyl]amino}-1,4,5,6-tetrahydropyrazolo[4',3':6,7]cyclohepta[1,2-d]pyrimidine-3-carboxamide 86) 1-methyl-9-{[3-(4-methylpiperidin-1-yl)propyl]amino}-1,4,5,6-tetrahydropyrazolo[4',3':6,7]cyclohepta[1,2-d]pyrimidine-3-carboxamide 87) ethyl 1-methyl-9-(methylsulfanyl)-1,4,5,6-tetrahydropyrazolo[4',3':6,7]cyclohepta[1,2-d]pyrimidine-3-carboxylate 88) ethyl 1-methyl-9-phenyl-1,4,5,6-tetrahydropyrazolo[4',3':6,7]cyclohepta[1,2-d]pyrimidine-3-carboxylate 89) ethyl 1-methyl-9-[4-(trifluoromethyl)phenyl]-1,4,5,6-tetrahydropyrazolo[4',3':6,7]cyclohepta[1,2-d]pyrimidine-3-carboxylate 90) ethyl 9-(4-methoxyphenyl)-1-methyl-1,4,5,6-tetrahydropyrazolo[4',3':6,7]cyclohepta[1,2-d]pyrimidine-3-carboxylate 91) ethyl 1-methyl-9-[4-(trifluoromethoxy)phenyl]-1,4,5,6-tetrahydropyrazolo[4',3':6,7]cyclohepta[1,2-d]pyrimidine-3-carboxylate 92) 1-methyl-9-(methylsulfanyl)-1,4,5,6-tetrahydropyrazolo[4',3':6,7]cyclohepta[1,2-d]pyrimidine-3-carboxylic acid 93) 2-methyl-9-{[4-(4-methylpiperazin-1-yl)phenyl]amino}-2,4,5,6-tetrahydropyrazolo[4',3':6,7]cyclohepta[1,2-d]pyrimidine-3-carboxamide 94) 9-[(4-bromo-2-methoxyphenyl)amino]-2-methyl-2,4,5,6-tetrahydropyrazolo[4',3':6,7]cyclohepta[1,2-d]pyrimidine-3-carboxamide 95) 9-{[2-methoxy-4-(4-methylpiperazin-1-yl)phenyl]amino}-2-methyl-2,4,5,6-tetrahydropyrazolo[4',3':6,7]cyclohepta[1,2-d]pyrimidine-3-carboxamide 96) 9-[(4-bromo-2-methoxyphenyl)amino]-N-(2,6-diethylphenyl)-2-methyl-2,4,5,6-tetrahydropyrazolo[4',3':6,7]cyclohepta[1,2-d]pyrimidine-3-carboxamide 97) N-(2,6-diethylphenyl)-9-{[2-methoxy-4-(4-methylpiperazin-1-yl)phenyl]amino}-2-methyl-2,4,5,6-tetrahydropyrazolo[4',3':6,7]cyclohepta[1,2-d]pyrimidine-3-carboxamide 98) N-(2,6-diethylphenyl)-9-({4-[4-(dimethylamino)piperidin-1-yl]-2-methoxyphenyl}amino)-5,6-dihydro-4H-isoxazolo[4',5':6,7]cyclohepta[1,2-d]pyrimidine-3-carboxamide 99) N-(2,6-diethylphenyl)-9-{[2-methoxy-4-(4-methylpiperazin-1-yl)phenyl]amino}-5,6-dihydro-4H-isoxazolo[4',5':6,7]cyclohepta[1,2-d]pyrimidine-3-carboxamide 100) N-(2,6-diethylphenyl)-9-({4-[4-(dimethylamino)piperidin-1-yl]-2-methoxyphenyl}amino)-5,6-dihydro-4H-isoxazolo[4',3':6,7]cyclohepta[1,2-d]pyrimidine-3-carboxamide and 101) N-(2,6-diethylphenyl)-9-{[2-methoxy-4-(4-methylpiperazin-1-yl)phenyl]amino}-5,6-dihydro-4H-isoxazolo[4',3':6,7]cyclohepta[1,2-d]pyrimidine-3-carboxamide.

Further preferred are the pharmaceutically acceptable salts of each of the above compounds 1-101.

For a reference to any specific compound of formula (I) of the invention, optionally in the form of a pharmaceutically acceptable salt, hydrate, solvate, complex, metabolite, prodrug, carrier, N-oxide thereof, see the experimental section and claims.

The present invention also provides a process for the preparation of a compound of formula (I) as defined above, by using the reaction routes and synthetic schemes described below, employing the techniques available in the art and starting materials readily available. The preparation of certain embodiments of the present invention is described in the examples that follow, but those of ordinary skill in the art will recognize that the preparations described may be readily adapted to prepare other embodiments of the present invention. For example, the synthesis of non-exemplified compounds according to the invention may be performed by modifications apparent to those skilled in the art, for instance by appropriately protecting interfering groups, by changing to other suitable reagents known in the art, or by making routine modifications of reaction conditions. Alternatively other reactions referred to herein or known in the art will be recognized as having adaptability for preparing other compounds of the invention.

Figure 2:
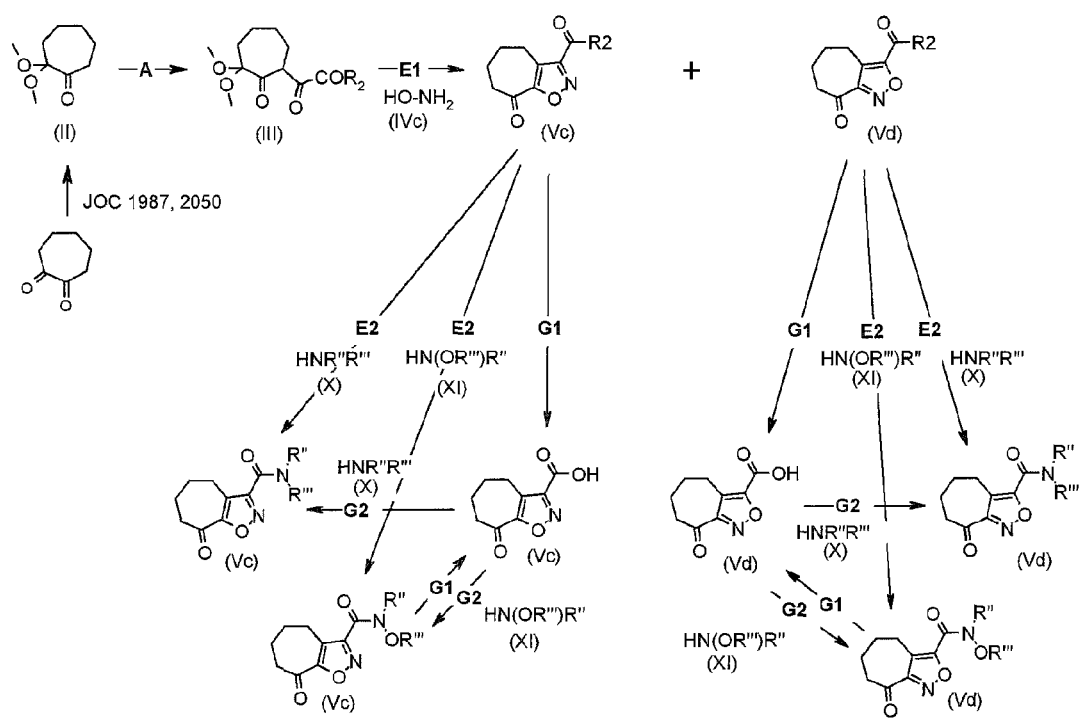
FIG. 2 illustrates the preparation of compounds of formula (Vc) and (Vd), that are intermediates for the preparation of a compound of formula (I), wherein Y is oxygen and Z is nitrogen, or Y is nitrogen and Z is oxygen.
Figure 3:
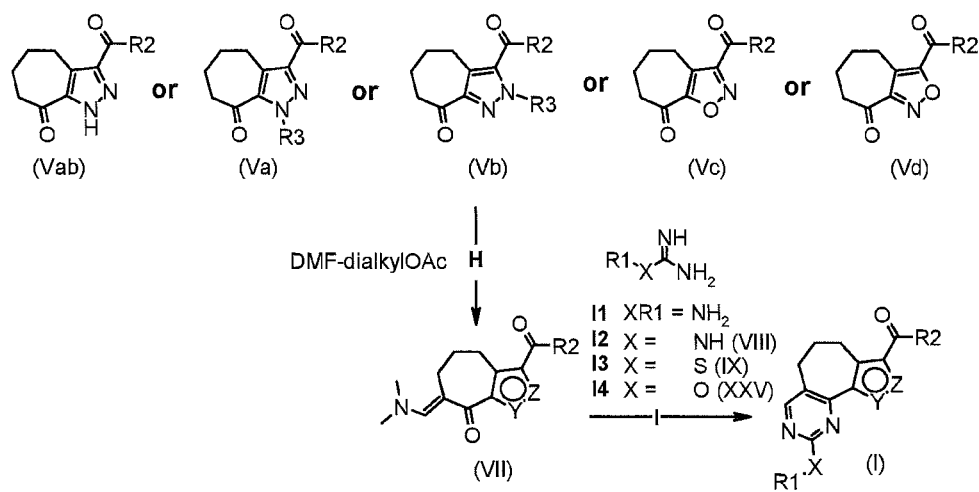
FIG. 3 illustrates the preparation of compounds of formula (I), starting from compounds of formula (Vab), (Va), (Vb), (Vc) or (Vd).

A detailed scheme implementing the above procedure is shown in FIGS. 1, 2 and 3.

FIG. 1 illustrates the preparation of compounds of formula (Vab), (Va) and (Vb) that are intermediates for the preparation of a compound of formula (I) wherein one of Y and Z is nitrogen and the other is N—R3 wherein R3 is as defined in formula (I).

FIG. 2 illustrates the preparation of compounds of formula (Vc) and (Vd), that are intermediates for the preparation of a compound of formula (I), wherein Y is oxygen and Z is nitrogen, or Y is nitrogen and Z is oxygen.

FIG. 3 illustrates the preparation of compounds of formula (I), starting from compounds of formula (Vab), (Va), (Vb), (Vc) or (Vd) as defined above.

With reference to FIG. 1, a process of the present invention comprises:

st. A) reacting a compound of formula (II), prepared as described in J. Org. Chem., 1987, 2050:

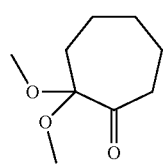

(II)

with diethyl oxalate or dimethyl oxalate, in the presence of LiN(TMS)$_2$;

st. B) reacting the resultant compound of formula (III):

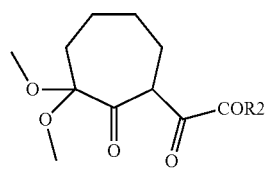

(III)

wherein R2 is ethoxy or methoxy, according to any one of the alternative steps B1 and B1b:

st. B1) with hydrazine

NH$_2$NH$_2$ (IVa)

st. B1a) alkylating the resultant compound of formula (Vab):

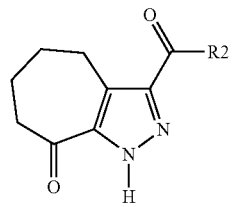

(Vab)

wherein R2 is ethoxy or methoxy, with a compound of formula (VI):

R3-L (VI)

wherein L is a suitable leaving group, such as mesyl, tosyl and halogen, and R3 is as defined above but not hydrogen;

so as to obtain a mixture of compounds of formula (Va) and (Vb):

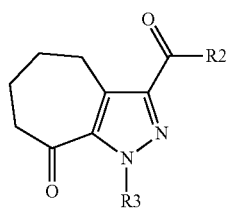

(Va)

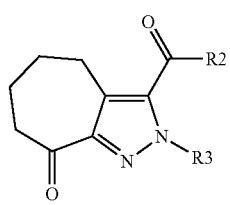

(Vb)

wherein R2 is ethoxy or methoxy, and R3 is as defined above but not hydrogen, and separating their mixture into the single compounds (Va) and (Vb);

alternatively, st. B1b) compounds (Vb) wherein R2 is ethoxy or methoxy and R3 is as defined above except hydrogen, can be obtained reacting a compound of formula (III) wherein R2 is ethoxy or methoxy with a compound of formula (IVb)

R3-NHNH$_2$ (IVb)

wherein R3 is defined above but not hydrogen;

st. B2) hydrolyzing in acidic or basic condition the resultant compound of formula (Vab), (Va) or (Vb), wherein R2 is ethoxy or methoxy and R3 is as defined above but not hydrogen, so as to obtain the corresponding compound of formula (Vab), (Va) or (Vb) respectively, wherein R2 is hydroxyl or its corresponding salt and R3 is as defined above but not hydrogen;

st. B3) reacting the resultant compound of formula (Vab), (Va) or (Vb), wherein R3 is as defined above but not hydrogen and R2 is hydroxyl, or the corresponding salt with an amine of formula (X) or (XI):

NHR"R"'(X)NH(OR"')R" (XI)

wherein R" and R"' are as defined above, in presence of the suitable condensing agents, to give a compound of formula (Vab), (Va) or (Vb) wherein R2 is a group NR"R"' or N(OR"')R" and R3 is as defined above but not hydrogen;

if needed or desired, st. B4) reacting the resultant compound of formula (Vab) wherein R2 is a group NR"R"' or N(OR"')R" with a compound of formula (VI):

R3-L (VI)

wherein L is a suitable leaving group such as mesyl, tosyl, halogen atom, and R3 is as defined above but not hydrogen atom, so as to obtain a compound of formula (Va) wherein R2 is a group NR"R"' or N(OR"')R" and R3 is as above reported but not hydrogen;

if needed or desired, st. C) hydrolyzing a compound of formula (Va) or (Vb) wherein R2 is N(OR"')R" and R3 is as defined above but not hydrogen, so as to obtain a compound of formula (Va) or (Vb) respectively wherein R2 is hydroxyl or its corresponding salt and R3 is as defined above but not hydrogen; if needed or desired, st. D) reacting a compound of formula (Vab), (Va) or (Vb) wherein R2 is ethoxy or methoxy and R3 is as defined above but not hydrogen, so as to obtain compound of formula (Vab), (Va) or (Vb) respectively wherein R2 is a group NR"R'" or N(OR'")R", R3 is as defined above but not hydrogen and R" and R'" are as defined in formula (I).

With reference to FIG. 2, another process of the present invention comprises:
st. E1) reacting a compound of formula (III) wherein R2 is ethoxy or methoxy with a compound of formula (IVc):

so as to obtain a mixture of compounds of formula (Vc) and (Vd)

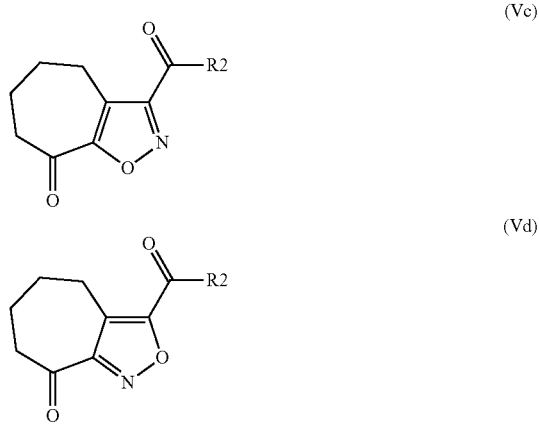

wherein R2 is ethoxy or methoxy, and separating their mixture into the single compounds (Vc) and (Vd);
st. E2) reacting a compound of formula (Vc) or (Vd) wherein R2 is ethoxy or methoxy with an amine of formula (X) or (XI) so to obtain a compound of formula (Vc) or (Vd) wherein R2 is a group NR"R'" or N(OR'")R"; if needed or desired,
st. G1) hydrolyzing a compound of formula (Vc) or (Vd), wherein R2 is ethoxy or methoxy or N(OR'")R" as defined above so as to obtain a compound of formula (Vc) or (Vd) wherein R2 is hydroxy or its corresponding salt; if needed or desired,
st. G2) reacting the resultant compound of formula (Vc) or (Vd), wherein R2 is hydroxy or the corresponding salt, with an amine of formula (X) or (XI) wherein R" and R'" are as defined above, in the presence of the suitable condensing agents, to give a compound of formula (Vc) or (Vd) wherein R2 is a group NR"R'" or N(OR'")R".

With reference to FIG. 3, the process of the present invention further comprises:
st. H) reacting the compounds of formula (Vab), (Va), (Vb), (Vc) or (Vd), prepared according to any of the steps described above, with an N,N-dimethylformamide derivative so as to obtain a compound of formula (VII):

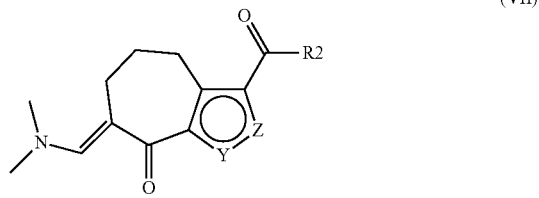

wherein R2 is ethoxy or methoxy or a group NR"R'" or N(OR'")R", wherein R" and R'" are as defined in formula (I), and Y and Z are as defined in formula (I) reported above;

st. I) the compound of formula (VII) is then reacted according to any one of the alternative steps I1, I2, I3 or I4:
st. I1) with guanidine or a salt thereof so as to obtain a compound of formula (I):

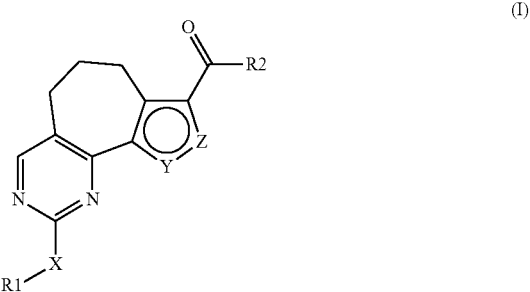

wherein R1 is hydrogen, X is amino, R2 is ethoxy or methoxy or a group NR"R'" or N(OR'")R", wherein R" and R'" are as defined in formula (I), and Z and Y and are as defined above; and optionally converting them into other derivatives of formula (I);
st. I2) with a guanidine derivative or a salt thereof of formula (VIII):

R1-NH—C(=NH)NH$_2$      (VIII)

wherein R1 is as reported in formula (I) but not hydrogen, so as to obtain a compound of formula (I), wherein R1 is as reported in formula (I) but not hydrogen, X is NH, R2 is ethoxy or methoxy or a group NR"R'" or N(OR'")R", wherein R" and R'" are as defined in formula (I), and Y and Z are as defined above; and optionally converting them into other derivatives of formula (I);
st. I3) with an isothiourea derivative or a salt thereof of formula (IX)

R1-S—C(=NH)NH$_2$      (IX)

wherein R1 is as reported in formula (I) but not hydrogen, so as to obtain a compound of formula (I) wherein R1 is as reported in formula (I) but not hydrogen, X is S, R2 is ethoxy or methoxy or a group NR"R'" or N(OR'")R", wherein R" and R'" are as defined in formula (I), and Y and Z are as defined above; and optionally converting them into other derivatives of formula (I);
st. I4) with an isourea derivative or a salt thereof of formula (XXV)

R1-O—C(=NH)NH$_2$      (XXV)

wherein R1 is as reported in formula (I) but not hydrogen, so as to obtain a compound of formula (I) wherein R1 is as reported in formula (I) but not hydrogen, X is O, R2 is ethoxy or methoxy or a group NR"R'" or N(OR'")R", wherein R" and R'" are as defined in formula (I), and Y and Z are as defined above; and optionally converting them into other derivatives of formula (I).

As said above, the compounds of formula (I), which are prepared according to the process object of the present invention, can be conveniently converted into other compounds of formula (I) by operating according to well-known synthetic conditions, the following being examples of possible conversions:
conv. 1) converting a compound of formula (Ia) or (Ib) wherein R3 is a protecting group P such as p-methoxybenzyl, trytil or t-butyl and R1, R2, and X are as defined above into the corresponding compound of formula (I) wherein R3 is hydrogen atom, under acidic conditions:
conv. 2) converting a compound of formula (Ia), wherein R3 is hydrogen, R2 is ethoxy or methoxy, R1 and X are as defined above, into the corresponding compounds of formula (Ia) and (Ib) wherein R3 is as defined above but not hydrogen, through reaction with a compound of formula R3-L (VI), wherein R3 is as defined above but not hydrogen and L is as defined above:

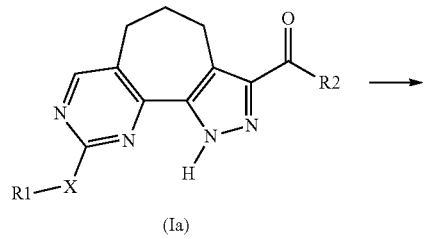
(Ia)

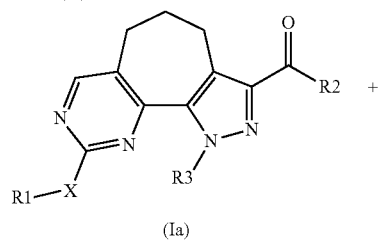
(Ia)

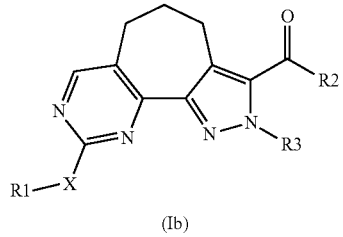
(Ib)

and separating their mixture into the single compounds (Ia) and (Ib);

conv. 3) converting a compound of formula (Ia) wherein R3 is hydrogen, R2 is —NR"R'" or —N(OR'")R", R1 and X are as defined above into the corresponding compound of formula (Ia) wherein R3 is as defined above but not hydrogen atom, through reaction with a compound of formula R3-L (VI) as defined above:

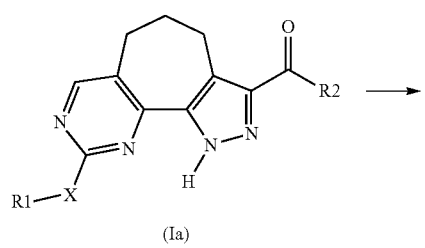
(Ia)

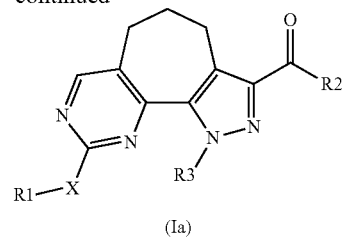
(Ia)

conv. 4) converting a compound of formula (I) wherein R2 is ethoxy or methoxy or N(OR'")R", R1, X, Y and Z are as defined above into the corresponding compound of formula (I) wherein R2 is hydroxy or a salt thereof, through acidic or basic hydrolysis:

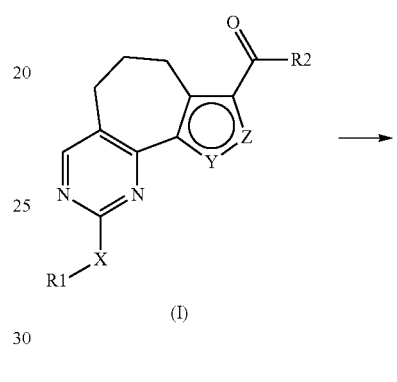
(I)

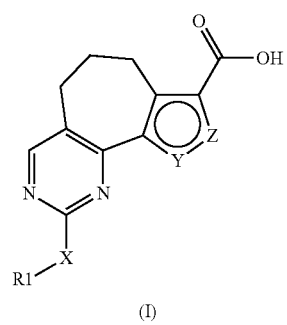
(I)

conv. 5) converting a compound of formula (I), wherein R2 is hydroxyl or a salt thereof, R1, X, Y and Z are as defined above into the corresponding compound of formula (I) wherein R2 is a group —NR"R'" or —N(OR'")R", through reaction with a derivative of formula (X) or (XI)

R"R'"NH(X)R"NHOR'"        (XI)

wherein R" and R'" are as defined above, under basic conditions and in the presence of a suitable condensing agent:

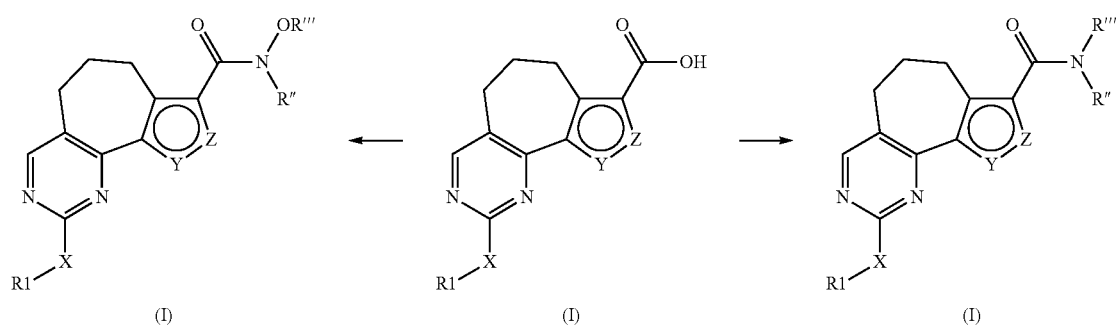
(I)      (I)      (I)

conv. 6) converting a compound of formula (I) wherein R2 is ethoxy or methoxy, Y and Z are as defined above into the corresponding compound of formula (I) wherein R2 is a group —NR"R"' or —N(OR"')R", through reaction with a derivative of formula (X) or (XI) as defined above:

conv. 7a) converting a compound of formula (Ib) wherein R3 is —(CH$_2$)$_n$—OH with n=2 or 3, R2 is ethoxy or methoxy, R1 and X are as defined in formula (I) into the corresponding compound of formula (Ib3) or (Ib4):

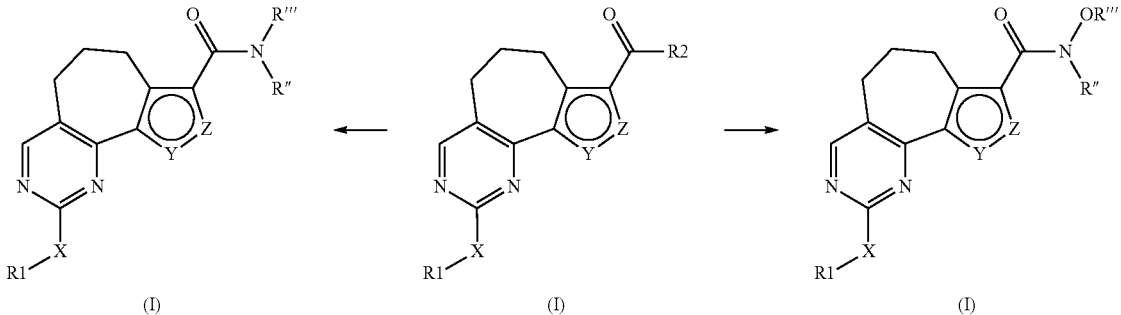

conv. 7) converting a compound of formula (Ib) wherein R3 is —(CH$_2$)$_n$—NHBoc with n=2 or 3, R2 is ethoxy or methoxy, R1 and X are as defined above into a compound of formula (Ib) or (Ib2) wherein R1 and X are as defined above, under acidic conditions, so as to convert the tert-butoxycarbonylamino group into amino (deprotection) and reacting it with Cs$_2$CO$_3$ so as to obtain any one of the two compounds of formula (Ib) or (Ib2):

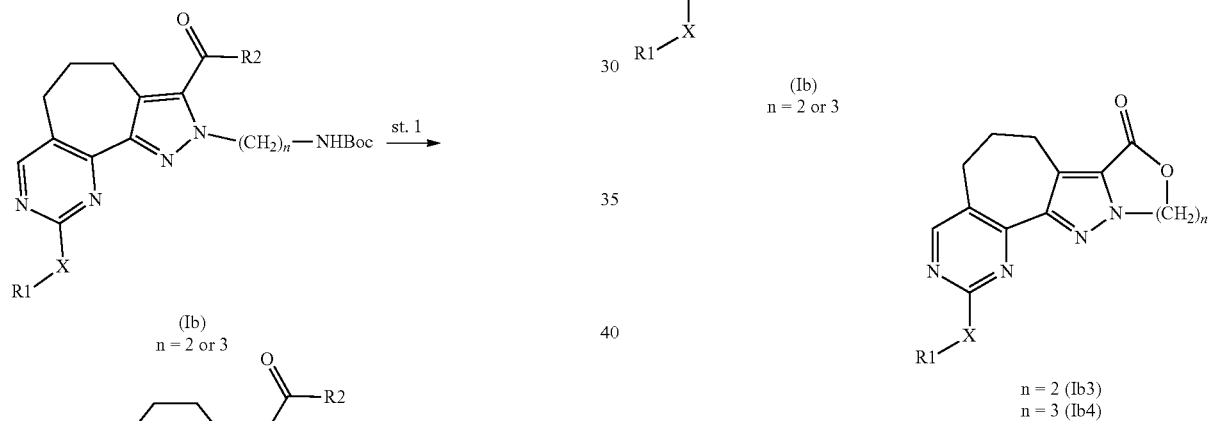

conv. 8) converting a compound of formula (I) wherein R2, Y and Z are as defined in formula (I), R1 is hydrogen and X is —NH— into the corresponding compound of formula (I) wherein R1 is iodine and X is a single bond, by reaction with iso-amylnitrite and diiodomethane or cesium iodide, in the presence of iodine and CuI, and subsequently by reacting the iododerivative with an arylamine of formula R1-NH$_2$ (XII) wherein R1 is an optionally substituted aryl, in the presence of palladium acetate and BINAP to give the corresponding compound wherein R1 is an optionally substituted aryl and X is —NH—:

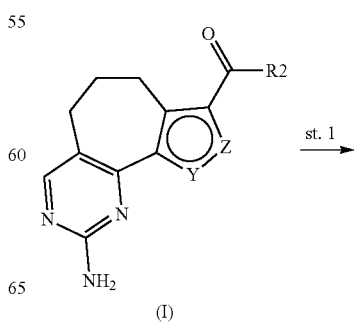

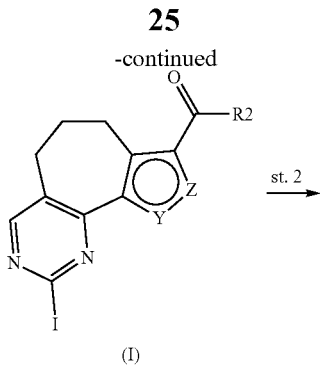

(I)

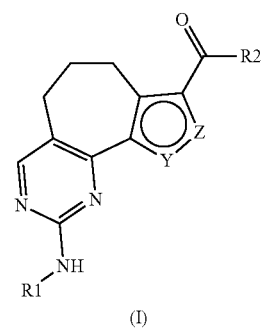

(I)

conv. 9) converting a compound of formula (I) wherein R2, Y and Z are as defined in formula (I), R1 is hydrogen and X is —NH— into the corresponding compound of formula (I) wherein R1 is iodine and X is a single bond as described in conv. 8) st.1, and subsequently by reacting the iododerivative with a compound of formula (XIII):

R1-Q     (XIII):

wherein R1 is an optionally substituted alkyl, cycloalkyl, heterocyclyl, aryl, cycloalkyl-alkyl, arylalkyl or heterocycly-lalkyl, and Q is a suitable group such as —B(OH)$_2$, —B(OAlk)$_2$, —Sn(Alk)$_4$, ZnHal, or MgHal, which can undergo palladium mediated carbon bond formation, to give a compound of formula (I), wherein R1 is an optionally substituted alkyl, cycloalkyl, heterocyclyl, aryl, cycloalkyl-alkyl, arylalkyl or heterocyclylalkyl group, and X is a single bond:

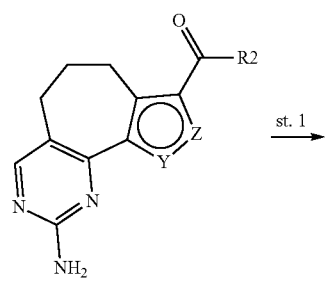

(I)

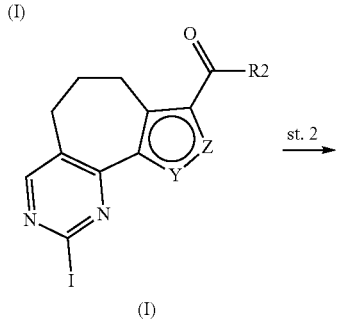

(I)

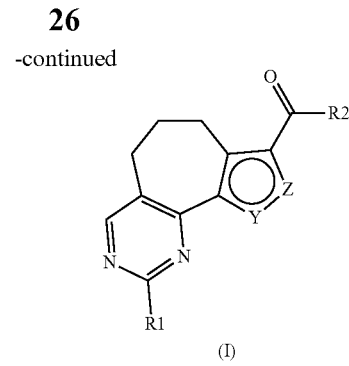

(I)

conv. 10) converting a compound of formula (I), wherein R2, Y and Z are as defined in formula (I), R1 is an optionally substituted alkyl, cycloalkyl, heterocyclyl, aryl, cycloalkyl-alkyl, arylalkyl or heterocyclylalkyl, and X is —S—, first into the corresponding compound of formula (I), wherein X is —SO$_2$—, under oxidative conditions, and then reacting the sulfonyl derivative with an amine of formula R1-NH$_2$ (XII), wherein R1 is an optionally substituted alkyl, cycloalkyl, heterocyclyl, aryl, cycloalkyl-alkyl, arylalkyl or heterocyclylalkyl group, to give the corresponding compound wherein R1 is as defined above and X is NH:

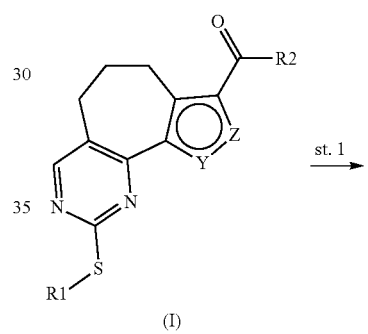

(I)

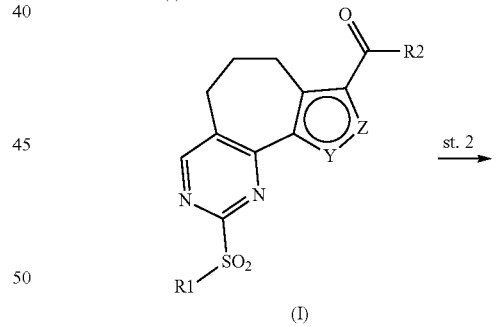

(I)

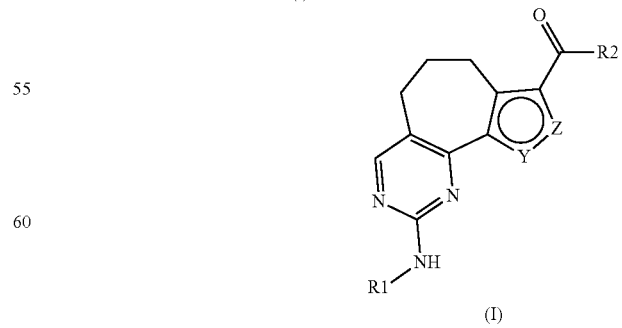

(I)

conv. 11) converting a compound of formula (I), wherein R2, Y and Z are as defined in formula (I), R1 is an optionally substituted alkyl, cycloalkyl, heterocyclyl, aryl, cycloalkyl-alkyl, arylalkyl or heterocyclylalkyl, and X is —S—, first into the corresponding compound of formula (I), wherein X is —SO₂— under oxidative conditions, and then reacting the sulfonyl derivative with a compound of formula R1-OH (XIV), wherein R1 is an optionally substituted alkyl, cycloalkyl, heterocyclyl, aryl, cycloalkyl-alkyl, arylalkyl or heterocyclylalkyl group, to give the corresponding compound wherein R1 is as defined above and X is —O—:

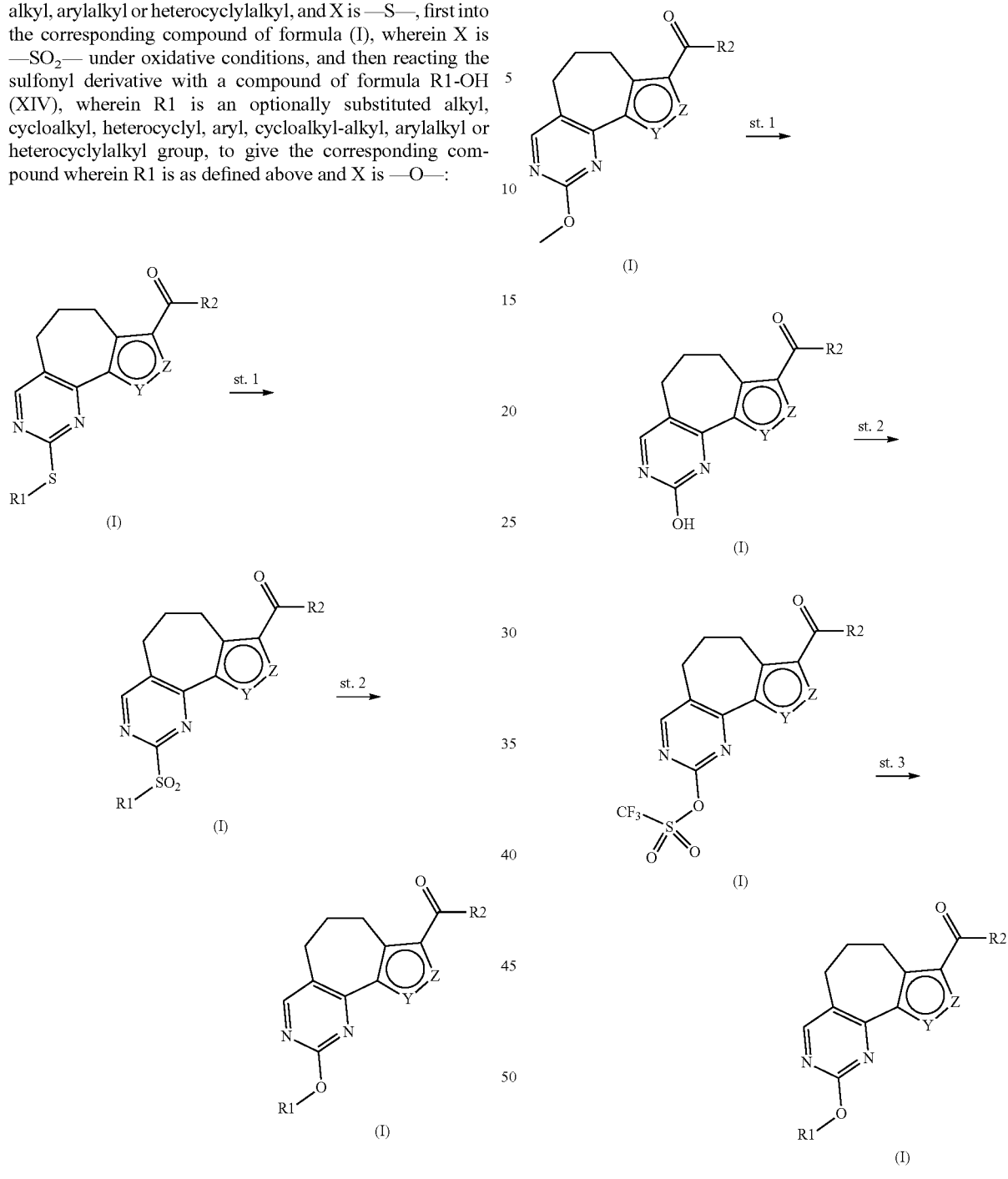

conv. 12) converting a compound of formula (I), wherein R2, Y and Z are as defined in formula (I), R1 is methyl, and X is —O—, first into the corresponding compound of formula (I) wherein R1 is hydrogen, and then reacting the resultant compound with a triflating agent so as to obtain the corresponding trifluoromethanesulfonate and finally by reacting it with a compound of formula R1-OH (XIV) wherein R1 is optionally substituted alkyl, cycloalkyl, heterocyclyl, aryl, cycloalkyl-alkyl, arylalkyl or heterocyclylalkyl group, to give the corresponding compound wherein R1 is as defined above and X is —O—:

conv. 13) converting a compound of formula (I), wherein R2, Y and Z are as defined in formula (I), R1 is methyl, and X is —O—, first into the corresponding compound of formula (I) wherein R1 is hydrogen, then by reacting the resultant compound with a triflating agent so as to obtain the corresponding trifluoromethanesulfonate and finally by reacting it with an amine of formula R1-NH₂ (XII) wherein R1 is an optionally substituted alkyl, cycloalkyl, heterocyclyl, aryl, cycloalkyl-alkyl, arylalkyl or heterocyclylalkyl group, to give the corresponding compound wherein R1 is as defined above and X is —NH—:

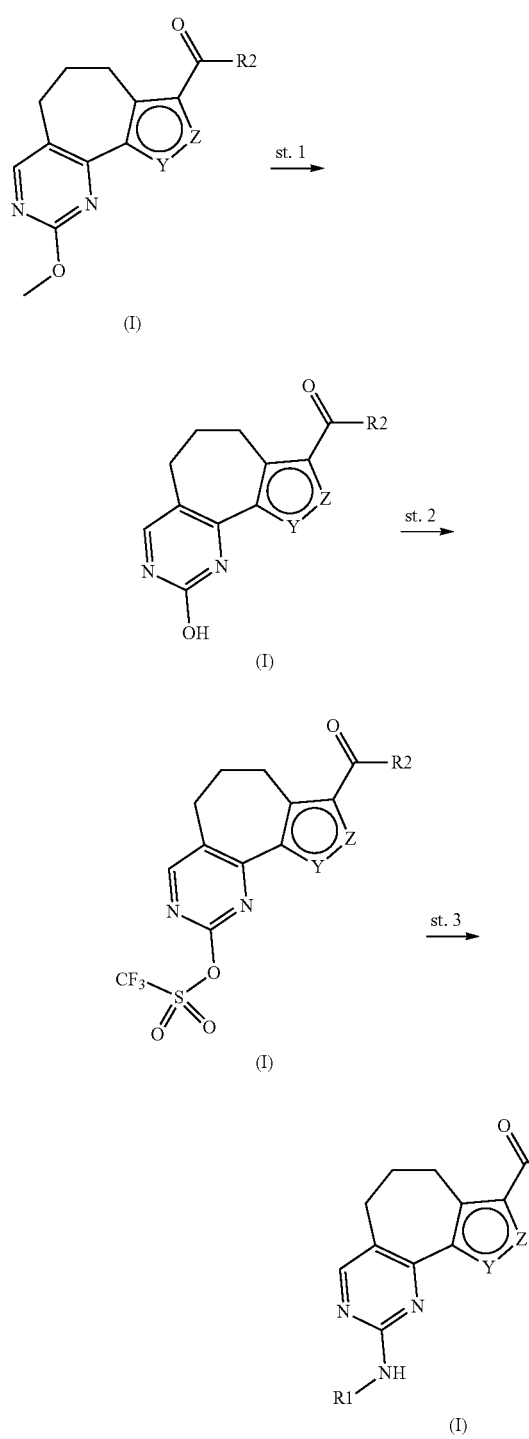

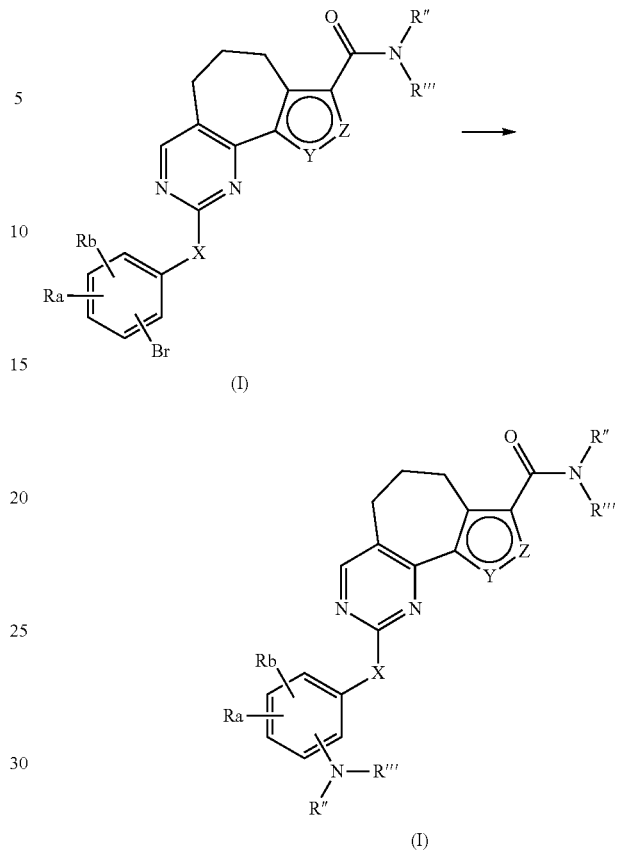

wherein Ra and Rb are independently halogen, except bromine, hydrogen, nitro, cyano, $C_1$-$C_6$ alkyl, polyfluorinated alkyl, polyfluorinated alkoxy, alkenyl, alkynyl, hydroxyalkyl, aryl, arylalkyl, heterocyclyl, $C_3$-$C_7$ cycloalkyl, hydroxy, alkoxy, aryloxy, heterocyclyloxy, methylenedioxy, alkylcarbonyloxy, arylcarbonyloxy, cycloalkenyloxy, heterocyclylcarbonyloxy, alkylideneaminooxy, carboxy, alkoxycarbonyl, aryloxycarbonyl, cycloalkyloxycarbonyl, heterocyclyloxycarbonyl, amino, ureido, alkylamino, dialkylamino, arylamino, diarylamino, heterocyclyamino, formylamino, alkylcarbonylamino, arylcarbonylamino, heterocyclylcarbonylamino, aminocarbonyl, alkylaminocarbonyl, dialkylaminocarbonyl, arylaminocarbonyl, heterocyclylaminocarbonyl, alkoxycarbonylamino, hydroxyaminocarbonyl, alkoxyimino, alkylsulfonylamino, arylsulfonylamino, heterocyclylsulfonylamino, formyl, alkylcarbonyl, arylcarbonyl, cycloalkylcarbonyl, heterocyclylcarbonyl, heterocyclylsulfonyl, alkylsulfonyl, arylsulfonyl, aminosulfonyl, alkylaminosulfonyl, dialkylaminosulfonyl, arylaminosulfonyl, heterocyclylaminosulfonyl, arylthio, alkylthio, phosphonate or alkylphosphonate;

conv. 14) converting a compound of formula (I) wherein R2 is NR"R'", X is as defined above except —SO$_2$— and —OSO$_2$—, Y and Z are as defined in formula (I), R1 is an aryl, i.e. phenyl, substituted by bromine, into the corresponding compound of formula (I) wherein R1 is an aryl, i.e. phenyl, substituted by NR"R'", by treatment with an amine of formula R"R'"-NH (X), to give the corresponding compound wherein R1 is an aryl, i.e. phenyl, substituted by NR"R'":

conv. 15) converting a compound of formula (I) wherein R2 is NR"R'", X, Y and Z are as defined in formula (I), and R1 is an aryl, i.e. phenyl, substituted by —COOPg, wherein Pg is a suitable protecting group, into the corresponding compound of formula (I) wherein R1 is an aryl, i.e. phenyl, substituted by —COOH, through conditions well known in the literature (see Teodora W. Green, Peter G. M. Wuts):

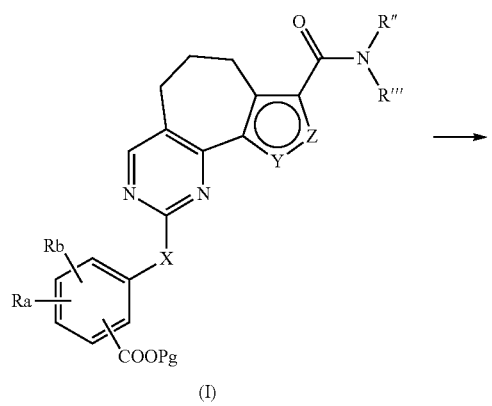

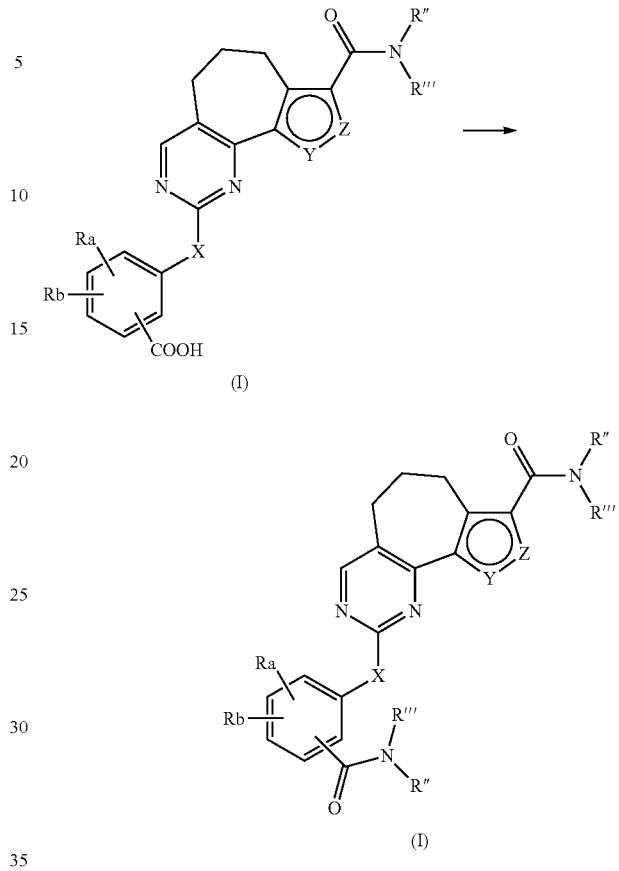

wherein Ra and Rb are independently halogen, hydrogen, nitro, cyano, $C_1$-$C_6$ alkyl, polyfluorinated alkyl, polyfluorinated alkoxy, alkenyl, alkynyl, hydroxyalkyl, aryl, arylalkyl, heterocyclyl, $C_3$-$C_7$ cycloalkyl, hydroxy, alkoxy, aryloxy, heterocyclyloxy, methylenedioxy, alkylcarbonyloxy, arylcarbonyloxy, cycloalkenyloxy, heterocyclylcarbonyloxy, alkylideneaminooxy, carboxy, alkoxycarbonyl, aryloxycarbonyl, cycloalkyloxycarbonyl, heterocyclyloxycarbonyl, amino, ureido, alkylamino, dialkylamino, arylamino, diarylamino, heterocyclyamino, formylamino, alkylcarbonylamino, arylcarbonylamino, heterocyclylcarbonylamino, aminocarbonyl, alkylaminocarbonyl, dialkylaminocarbonyl, arylaminocarbonyl, heterocyclylaminocarbonyl, alkoxycarbonylamino, hydroxyaminocarbonyl, alkoxyimino, alkylsulfonylamino, arylsulfonylamino, heterocyclylsulfonylamino, formyl, alkylcarbonyl, arylcarbonyl, cycloalkylcarbonyl, heterocyclylcarbonyl, heterocyclylsulfonyl, alkylsulfonyl, arylsulfonyl, aminosulfonyl, alkylaminosulfonyl, dialkylaminosulfonyl, arylaminosulfonyl, heterocyclylaminosulfonyl, arylthio, alkylthio, phosphonate or alkylphosphonate;

conv. 16) converting a compound of formula (I) wherein R2 is NR"R'", X, Y and Z are as defined in formula (I), and R1 is an aryl, i.e. phenyl, substituted by —COOH, into the corresponding compound of formula (I) wherein R1 is an aryl, i.e. phenyl, substituted by —CONR"R'", wherein R" and R'" are as defined above, by treatment with an amine of formula R"R'"-NH (X), in the presence of the suitable condensing agents:

wherein Ra and Rb are independently halogen atom, hydrogen, nitro, cyano, $C_1$-$C_6$ alkyl, polyfluorinated alkyl, polyfluorinated alkoxy, alkenyl, alkynyl, hydroxyalkyl, aryl, arylalkyl, heterocyclyl, $C_3$-$C_7$ cycloalkyl, hydroxy, alkoxy, aryloxy, heterocyclyloxy, methylenedioxy, alkylcarbonyloxy, arylcarbonyloxy, cycloalkenyloxy, heterocyclylcarbonyloxy, alkylideneaminooxy, carboxy, alkoxycarbonyl, aryloxycarbonyl, cycloalkyloxycarbonyl, heterocyclyloxycarbonyl, amino, ureido, alkylamino, dialkylamino, arylamino, diarylamino, heterocyclyamino, formylamino, alkylcarbonylamino, arylcarbonylamino, heterocyclylcarbonylamino, aminocarbonyl, alkylaminocarbonyl, dialkylaminocarbonyl, arylaminocarbonyl, heterocyclylaminocarbonyl, alkoxycarbonylamino, hydroxyaminocarbonyl, alkoxyimino, alkylsulfonylamino, arylsulfonylamino, heterocyclylsulfonylamino, formyl, alkylcarbonyl, arylcarbonyl, cycloalkylcarbonyl, heterocyclylcarbonyl, heterocyclylsulfonyl, alkylsulfonyl, arylsulfonyl, aminosulfonyl, alkylaminosulfonyl, dialkylaminosulfonyl, arylaminosulfonyl, heterocyclylaminosulfonyl, arylthio, alkylthio, phosphonate or alkylphosphonate;

conv. 17) converting a compound of formula (I) wherein X is —NH—, R1 is hydrogen, R2, Y and Z are as defined in formula (I), into the corresponding compound of formula (I) wherein X is —NH— and R1 is an aryl, i.e. phenyl, substituted by Ra, Rb, Rc:

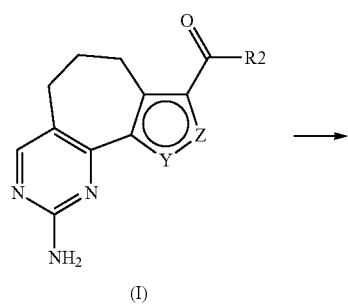

(I)

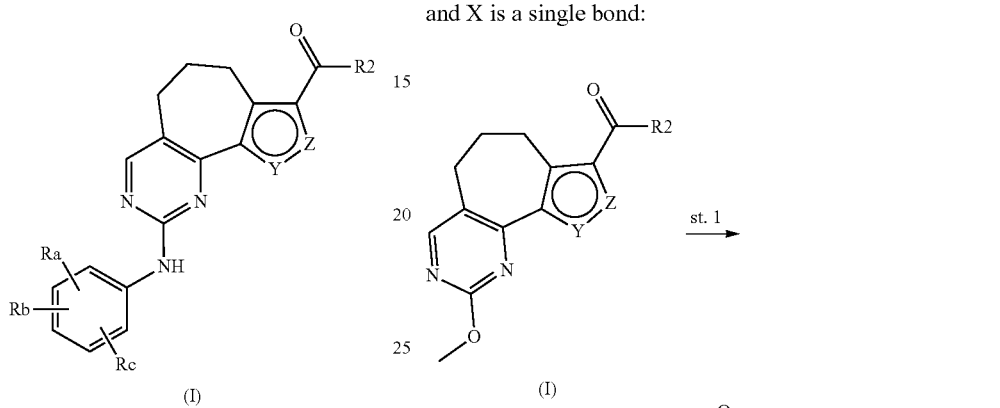

(I)

wherein Ra, Rb and Rc are independently hydrogen, nitro, cyano, $C_1$-$C_6$ alkyl, polyfluorinated alkyl, polyfluorinated alkoxy, alkenyl, alkynyl, hydroxyalkyl, aryl, arylalkyl, heterocyclyl, $C_3$-$C_7$ cycloalkyl, hydroxy, alkoxy, aryloxy, heterocyclyloxy, methylenedioxy, alkylcarbonyloxy, arylcarbonyloxy, cycloalkenyloxy, heterocyclylcarbonyloxy, alkylideneaminooxy, carboxy, alkoxycarbonyl, aryloxycarbonyl, cycloalkyloxycarbonyl, heterocyclyloxycarbonyl, amino, ureido, alkylamino, dialkylamino, arylamino, diarylamino, heterocyclyamino, formylamino, alkylcarbonylamino, arylcarbonylamino, heterocyclylcarbonylamino, aminocarbonyl, alkylaminocarbonyl, dialkylaminocarbonyl, arylaminocarbonyl, heterocyclylaminocarbonyl, alkoxycarbonylamino, hydroxyaminocarbonyl, alkoxyimino, alkylsulfonylamino, arylsulfonylamino, heterocyclylsulfonylamino, formyl, alkylcarbonyl, arylcarbonyl, cycloalkylcarbonyl, heterocyclylcarbonyl, heterocyclylsulfonyl, alkylsulfonyl, arylsulfonyl, aminosulfonyl, alkylaminosulfonyl, dialkylaminosulfonyl, arylaminosulfonyl, heterocyclylaminosulfonyl, arylthio, alkylthio, phosphonate or alkylphosphonate;

by treatment with an iodo derivative of formula (XVI):

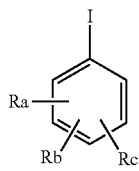

(XVI)

wherein Ra, Rb and Rc are as defined above, in presence of palladium.

conv. 18) converting a compound of formula (I) wherein R2, Y and Z are as defined in formula (I), R1 is methyl and X is O, first into the corresponding compounds of formula (I) wherein R1 is hydrogen, then by reacting the resultant compound with a triflating agent so as to obtain the corresponding trifluoromethanesulfonate and finally by reacting it with a compound of formula (XIII):

R1-Q    (XIII)

wherein R1 is an optionally substituted alkyl, cycloalkyl, heterocyclyl, aryl, cycloalkyl-alkyl, arylalkyl or heterocyclylalkyl, and Q is a suitable group such as —B(OH)$_2$, —B(OAlk)$_2$, —Sn(Alk)$_4$, ZnHal, or MgHal, which can undergo palladium mediated carbon bond formation, to give a compound of formula (I), wherein R1 is as defined above and X is a single bond:

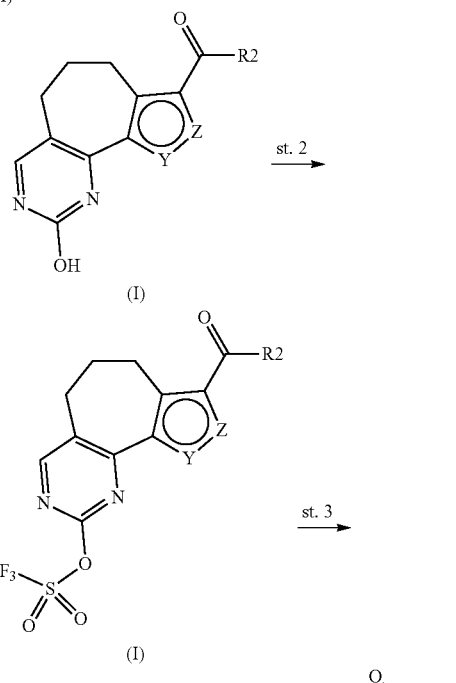

conv. 19) converting a compound of formula (I) wherein R2, Y and Z are as defined in formula (I), R1 is methyl, and X is O first into the corresponding compound of formula (I)

wherein R1 is hydrogen, then by reacting the resultant compound with a triflating agent so as to obtain the corresponding trifluoromethanesulfonate and finally by reacting it with a thiol of formula R1-SH (XXVI) wherein R1 is an optionally substituted alkyl, cycloalkyl, heterocyclyl, aryl, cycloalkylalkyl, arylalkyl or heterocyclylalkyl group, to give the corresponding compound wherein R1 is as defined above and X is S:

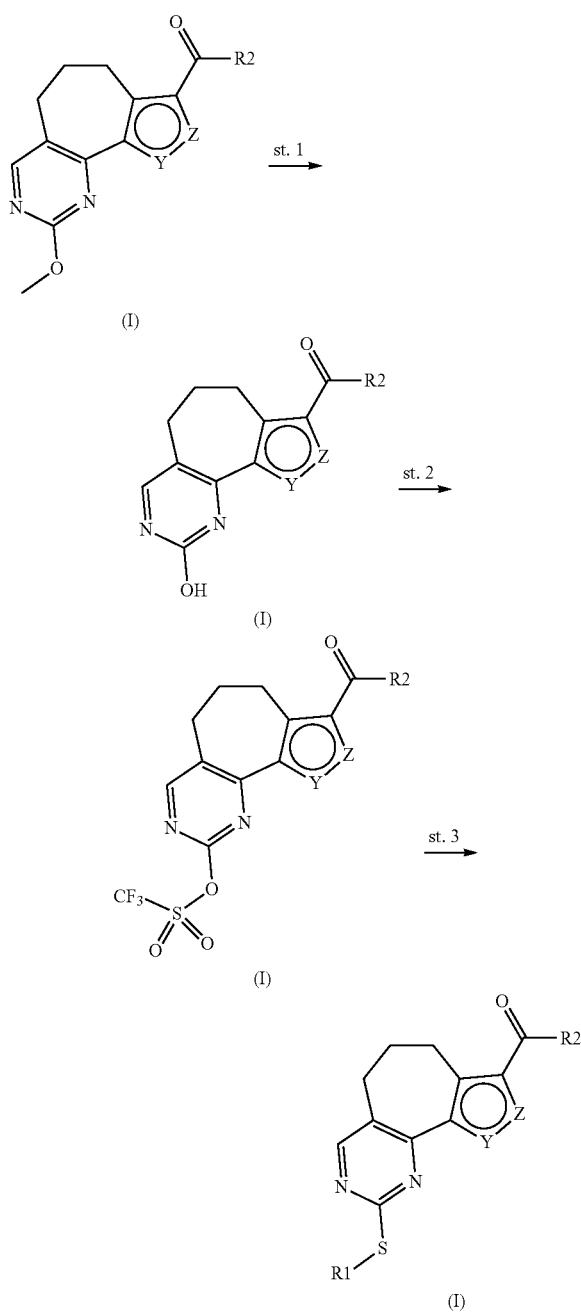

conv. 20) converting a compound of formula (I) wherein R2, Y and Z are as defined in formula (I), R1 is methyl, and X is —S— into compounds of formula (I) wherein R1 is an optionally substituted aryl and X is a single bond, by reacting it with an arylboronic acid of formula R1-B(OH)$_2$ (XIIIa), wherein R1 is an optionally substituted aryl, in the presence of a palladium derivative:

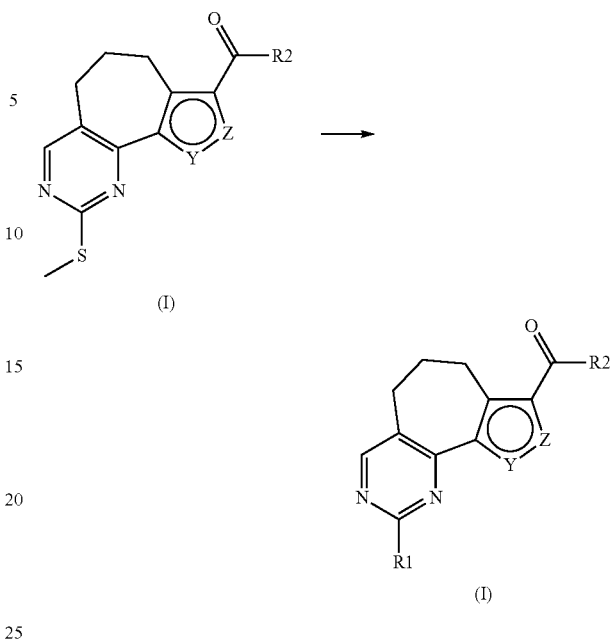

The above described process steps are now described in more detail with respect to reagents and reaction conditions:

According to step (st.A) of the process, 2,2-dimethoxycycloheptanone is reacted with diethyl oxalate or dimethyl oxalate in the presence of LiN(TMS)$_2$ and of a suitable solvent such as, for instance, dioxane, tetrahydrofurane (THF) or Et$_2$O.

According to step (st.B1), the compound of formula (III) is reacted with hydrazine (IVa), in the presence of AcOH or a lower alcohol such as MeOH, EtOH or admixtures thereof. Preferably, the above reaction is carried out in EtOH at room temperature, so as to obtain a compound of formula (Vab).

According to step (st.B1a), the compound of formula (Vab) wherein R2 is ethoxy or methoxy, is reacted with a suitable compound of formula (VI) wherein R3 is not hydrogen, in the presence of a base such as NaH, Na$_2$CO$_3$ or Cs$_2$CO$_3$ in a suitable solvent, such as for instance THF, dioxane or dimethylformamide (DMF), at a temperature ranging from room temperature to 100° C., so as to obtain a mixture of compounds (Va) and (Vb), and by separating them under conventional methods, for instance through preparative HPLC.

According to step (st.B1b), the compound of formula (III) is reacted with a suitable hydrazine derivative of formula (IVb), in the presence of AcOH or a lower alcohol such as MeOH, EtOH or admixtures thereof. Preferably, the above reaction is carried out in EtOH at room temperature, so as to obtain a compound of formula (Vb).

According to step (st.B2) of the process, the compound of formula (Vab), (Va) or (Vb) wherein R2 is ethoxy or methoxy and R3 if present is hydrogen, may be converted into a carboxylic acid derivative, by conditions widely known in the art and may comprise, for instance, the reaction with NaOH or KOH in the presence of a suitable solvent such as a lower alcohol, DMF or mixtures thereof; preferably the reaction is carried out with NaOH in a EtOH/DMF mixture, at a temperature ranging from about 25° C. to about 100° C.

According to step (st.B3) of the process, the compound of formula (Vab), (Va) or (Vb) wherein R3 is as defined above and R2 is hydroxy or the corresponding salt, may be converted into derivatives of formula (Vab), (Va) or (Vb) wherein R2 is a group NR"R'" or N(OR'")R" and R3 is as defined above. The reaction is carried out in the presence of an amine of formula either (X) or (XI) as defined above, under basic conditions, preferably with DIPEA or TEA, in a suitable solvent such as DCM, DMF, THF, or dioxane, and in the presence of a suitable condensing agent such as DCC, EDCI or TBTU; catalytic amounts of PyBOP or HOBt may be also required.

According to step (st.B4), a compound of formula (Vab), wherein R2 is NR"R"' or N(OR")R"' and R" and R"' are as defined above, is reacted with a suitable compound of formula (VI) wherein R3 is as defined above but not hydrogen, in the presence of a base such as NaH, $Na_2CO_3$ or $Cs_2CO_3$ in a suitable solvent, for instance THF, dioxane or DMF, at a temperature ranging from room temperature to 100° C., so as to obtain a compound (Va).

The reaction step (st.C) is carried out under the operative conditions set in step (st.B2) and lead to the desired compounds of formula (Va) or (Vb), respectively.

According to reaction step (st.D) of the process, a compound of formula (Vab), (Va) or (Vb) wherein R2 is ethoxy or methoxy and R3 is as defined above but not hydrogen, may be converted into another compound of formula (Vab), (Va) or (Vb) wherein R2 is an amino group of formula —NR"R"' or of formula —N(OR"')R" according to methods well-known in the art to convert carboxyester groups (—COOR') into carboxamides (—CONH$_2$), N-substituted carboxamides (—CONHR"), N,N-disubstituted carboxamides (—CONR"R"') and Weinreb amides (—CON(OR"')R"). When R" and R"' are hydrogen, preferably the reaction is carried out with ammonium hydroxide in a MeOH/DMF mixture, at a temperature ranging from about 50° C. to about 100° C.

Analogous operative conditions are applied in the preparation of N-substituted carboxamides or N,N-disubstituted carboxamides or Weinreib amides or wherein a suitable primary or secondary amine or substituted hydroxylamines are used in place of ammonia or ammonium hydroxide.

Alternatively, carboxyester groups may be converted into carboxamide or N-substituted carboxamides or N,N-disubstituted carboxamides or Weinreib amides under basic conditions such as LiN(TMS)$_2$ 1 N in THF, using ammonium chloride or a suitable primary or secondary amine; preferably the reaction is carried out in THF or Et$_2$O at a temperature ranging from 20° C. to reflux.

According to step (st.E1) of the process (FIG. 2), a compound of formula (III) is reacted with hydroxylamine or hydroxylamine hydrochloride. Preferably, the above reaction is carried out in EtOH at a temperature ranging from room temperature to reflux, so as to obtain a mixture of both compounds of formula (Vc) and (Vd). Their separation into the single compounds (Vc) and (Vd) is carried out under conventional methods, for instance through preparative HPLC.

The reactions of step (st.E2) are carried out under the operative conditions set forth in step (st.D) and lead to the desired compounds of formula (Vc) or (Vd), respectively.

The reactions of step (st.G1) are carried out under the operative conditions set forth in step (st.B2) and lead to the desired compounds of formula (Vc) or (Vd), respectively.

The reactions of step (st.G2) are carried out under the operative conditions set forth in step (st.B3) and lead to the desired compounds of formula (Vc) or (Vd), respectively.

According to step (st.H) of the process (FIG. 3), a compound of formula (Vab) or (Va) or (Vb) or (Vc) or (Vd) is reacted with N,N-dimethylformamide-di-tert-butylacetale, N,N-dimethylformamide-diisopropylacetale, N,N-dimethylformamide-dimethylacetale or N,N-dimethylformamide-diethylacetale in a suitable solvent such as, for instance, DMF or toluene, so as to get the corresponding compound of formula (VII) as defined above. Preferably, the reaction is carried out at a temperature ranging from room temperature to about 100° C.

According to step (st.I1) of the process, a compound of formula (VII) as defined above is reacted with guanidine or a salt thereof so as to obtain the corresponding compound of formula (I) as defined above wherein X is —NH— and R1 is hydrogen through pyrimidine ring formation. The reaction, is carried out in DMF or EtOH at a temperature ranging from 80° C. to reflux.

According to step (st.I2) of the process, a compound of formula (VII) as defined above is reacted with a guanidine derivative or a salt thereof of formula (VIII) so as to obtain the corresponding compound of formula (I) as defined above wherein X is —NH— and R1 is as defined above through pyrimidine ring formation. The reaction is preferably carried out in DMF or EtOH at a temperature ranging from 80° C. to reflux, possibly in the presence of a base e.g. $K_2CO_3$.

According to step (st.I3) of the process, a compound of formula (VII) as defined above is reacted with an isothiourea derivative or a salt thereof of formula (IX), wherein R1 is as above reported, so as to obtain the corresponding compound of formula (I), wherein X is —S— and R1 is as defined above, through pyrimidine ring formation. The reaction is preferably carried out in DMF or EtOH at a temperature ranging from 80° C. to reflux.

According to step (st.I4) of the process, a compound of formula (VII) as defined above is reacted with an isourea derivative or a salt thereof of formula (XXV) so as to obtain a compound of formula (I), wherein X is —O— and R1 is as defined above, through pyrimidine ring formation. Reaction is preferably carried out operating in a suitable solvent such as dioxane, DMF or CH$_3$CN in the presence of a base such as Na$_2$CO$_3$ or K$_2$CO$_3$ at a temperature ranging from 50° C. to 100° C.

According to step (st.B1) or (st.B2) or (st.B3) of the process, it is clear to the skilled person that both compounds of formula (Va) or (Vb) wherein R3 is a hydrogen atom are tautomeric forms of a given compound which can be conveniently identified as having formula (Vab)

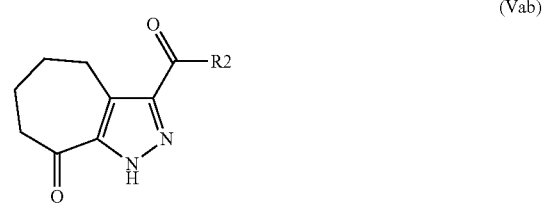

(Vab)

According to conversion (conv.1) of the process, a compound of formula (Ia) or (Ib) wherein R3 is a group selected from p-methoxybenzyl, trytil or t-butyl may be converted into the corresponding compound of formula (I) wherein R3 is hydrogen atom by reaction in acidic conditions, for instance with TFA or HCl and in the presence of a suitable solvent such as DCM or dioxane, at a temperature ranging from room temperature to 70° C. and for a time ranging from about 1 to about 12 hours.

According to conversion (conv.2) of the process, a compound of formula (Ia) wherein R3 is hydrogen atom may be converted into a mixture of compounds of formula (Ia) and (Ib) wherein R3 is as defined above except hydrogen atom, by reaction with a suitable compound of formula (VI) as defined above wherein L is a suitable leaving group such as an halogen atom, preferably chlorine, bromine or iodine, in the presence of a base such as NaH or TEA or $Cs_2CO_3$, in a suitable solvent, for instance DCM, THF, dioxane or DMF, at a temperature ranging from room temperature to 100° C., so and for a time ranging from about 1 to about 12 hours. Compounds of formula (Ia) and (Ib) may then be obtained as single compounds separating their mixture into the single compounds (Ia) and (Ib) by conventional methods for instance through chromatography or preparative HPLC;

According to conversion (conv.3) of the process, a compound of formula (Ia) wherein R3 is hydrogen atom may be converted into a compound of formula (Ia) wherein R3 is as defined above except hydrogen atom, by reaction with a suitable compound of formula (VI) as defined above where L is a suitable leaving group, such as an halogen atom, preferably chlorine, bromine or iodine, in the presence of a base such as NaH or TEA or $Cs_2CO_3$, in a suitable solvent, for instance DCM, THF, dioxane or DMF, at a temperature ranging from room temperature to reflux, for a time ranging from about 1 to about 12 hours.

According to conversion (conv.4) of the process, the compounds of formula (I) wherein R2 is ethoxy or a group —N(OR''')R'' may be converted into carboxylic acid derivatives of formula (I) as defined above or their corresponding salts through basic or acidic hydrolysis conditions, widely known in the art.

According to conversion (conv.5) of the process, the compounds of formula (I) wherein R2 is hydroxyl or a salt thereof may be converted into the corresponding derivatives of formula (I) wherein R2 is a group —NR''R''' or —N(OR''')R'' as defined above. The reaction is carried out in presence of an amine of formula (X) or (XI) as defined above, under basic conditions, preferably with DIPEA or TEA, in a suitable solvent such as DCM, DMF, THF or dioxane, and in the presence of a suitable condensing agent such as DCC, EDCI or TBTU; catalytic amounts of PyBOP or HOBt may also be required.

According to conversion (conv.6) of the process, a compound of formula (I) wherein R2 is ethoxy, may be converted into another compound of formula (I) wherein R2 is an amino group of formula —NR''R''' or —N(OR''')R'' according to methods well-known in the art to convert carboxyester groups into carboxamides (—$CONH_2$), N-substituted carboxamides (—CONHR''), N,N-disubstituted carboxamides (—CONR''R''') and Weinreib amides (—CON(OR''')R''. When R'' and R''' are hydrogens, preferably the reaction is carried out with ammonium hydroxide or hydroxylamine in a MeOH/DMF mixture, at a temperature ranging from about 50° C. to about 100° C.

Analogous operative conditions are applied in the preparation of N-substituted carboxamides, N,N-disubstituted carboxamides and Weinerib amides wherein a suitable primary, secondary amine or substituted hydroxylamines are used in place of ammonia or ammonium hydroxide.

Alternatively, carboxyester groups may be converted into carboxamide or N-substituted carboxamides, N,N-disubstituted carboxamides or Weinreib amides under basic conditions such as $LiN(TMS)_2$ 1 N in THF, using ammonium chloride or a suitable primary or secondary amine; preferably the reaction is carried out in THF or $Et_2O$ at a temperature ranging from 20° C. to reflux.

According to conversion (conv.7) of the process, a compound of formula (Ib) wherein R2 is ethoxy and R3 is —$(CH_2)_n$—NH-BOC with n=2 or 3 may be converted into a compound of formula (Ib) or (Ib2). The above compound (Ib) is first converted into the free amino derivative by working according to conventional methods, for instance under acidic conditions, preferably with HCl, in a suitable solvent such as dioxane at refluxing temperature, and subsequently cyclised to the desired tetracyclic derivative in the presence of a base such as $Cs_2CO_3$ and in a suitable solvent such as a lower alcohol, preferably MeOH, ranging from room temperature to reflux.

According to conversion (conv.7a), a compound of formula (Ib) wherein R3 is —$(CH_2)_n$—OH with n=2 or 3, is converted into to the desired tetracyclic compound of formula (Ib3) or (Ib4) under acidic conditions, preferably with HCl or p-toluensulfonic acid, in a suitable solvent such as dioxane or a lower alcohol, preferably MeOH, with a temperature ranging from room temperature to reflux.

According to conversion (conv.8) of the process, compounds of formula (I) wherein R1 is an optionally substituted aryl and X is —NH, can be obtained by the corresponding iodo derivatives which, in their turn, may be prepared by the corresponding compounds of formula (I) wherein R1 is hydrogen and X is —NH—. The preparation of the iodo derivatives may be carried out in a suitable solvent such as THF, $Et_2O$ or 1,2-dimethoxyethane (DME), at a temperature ranging from room temperature to about 70° C., and for a time of about 8 hours to about 48 hours.

The subsequent conversion of the iododerivative may be carried out in a suitable solvent such as DMF, DME or $CH_3CN$, and in the presence of catalytic amounts of Pd $(OAc)_2$, BINAP or Xantphos and a base such as $K_2CO_3$, potassium phosphate or $Cs_2CO_3$, at a temperature ranging from room temperature to 110° C. and for a time ranging from about 2 to about 24 hours.

According to conversion (conv.9) of the process, compounds of formula (I), wherein R1 is an optionally substituted alkyl, cycloalkyl, heterocyclyl, aryl, cycloalkyl-alkyl, arylalkyl or heterocyclylalkyl group and X is a single bond, can be obtained by the corresponding iodo derivatives from the iodo derivative above mentioned, by exploiting any of the cross-coupling reactions suitable for the formation of carbon-carbon bonds. Said reactions, which are well known in the art, imply coupling with a suitable organometal reagent such as for instance organoboron (Suzuki reaction), organotin (Stille reaction), organomagnesium (Kumada reaction), or organozinc (Negishi reaction) and the like. Preferred reaction is the Suzuki reaction where the appropriate aryl or heteroaryl-boronic derivative is used in the presence of a palladium based catalyst such as $PdCl_2(dppf).CH_2Cl_2$ or $Pd_2(dba)_3$ or $Pd(PPh_3)_4$, in a suitable solvent such as DMF, DCM, MeOH, $CH_3CN$, or in a mixture of solvents, such as DME and water, optionally in the presence of a base such as sodium or cesium carbonate or cesium fluoride, at a temperature ranging from room temperature to 100° C.

According to conversion (conv.10), compounds of formula (I), wherein R1 is an optionally substituted alkyl, cycloalkyl, heterocyclyl, aryl, cycloalkyl-alkyl, arylalkyl or heterocyclylalkyl group and X is —S—, may be converted into compounds of formula (I), wherein X is —NH—, by first oxidizing the thio group to sulfonyl group and by replacing it with a R—NH— group. The oxidative step may be carried out with oxone in the presence of a suitable solvent, preferably DMF or DMSO at room temperature; the subsequent replacement of the sulfonyl group with a suitable amino derivative is preferably carried out in the presence of DMF, DME, dioxane, $CH_3CN$, N-methyl-pyrrolidone or diglyme, at a temperature ranging from room temperature to about 100° C.

According to conversion (conv.11) of the process, compounds of formula (I) wherein X is —O— may be easily obtained by reacting the sulfonyl derivative above mentioned with an alcohol or phenol derivative of formula (XIV) wherein R1 is an optionally substituted alkyl, cycloalkyl, heterocyclyl, aryl, cycloalkyl-alkyl, arylalkyl or heterocyclylalkyl. The reaction may be carried out in the presence of a base such as $K_2CO_3$ or $Na_2CO_3$, butyl lithium, $LiN(TMS)_2$, NaH or the like, in a suitable solvent such as DMF or THF, and at a temperature ranging from room temperature to about 100° C.

According to conversion (conv.12) of the process, compounds of formula (I) wherein X is —$OSO_2$— and R1 is a trifluoromethyl group may be obtained by reacting the corresponding compounds of formula (I) wherein X is —O— and R1 is hydrogen with a triflating agent such as trifluoromethanesulfonic anhydride, trifluoromethanesulfonylchloride or N-phenyl-bis(trifluoromethanesulfonimide), optionally in the presence of a base such as TEA or DIPEA, in a suitable solvent such as DCM, THF or dioxane at a temperature ranging from −78° C. to room temperature.

The compounds of formula (I), wherein X is —O— and R1 an optionally substituted alkyl, cycloalkyl, heterocyclyl, aryl, cycloalkyl-alkyl, arylalkyl or heterocyclylalkyl group, may be obtained by reacting the corresponding compounds of formula (I) wherein X is —$OSO_2$— and R1 is a trifluoromethyl group with an alcohol of formula (XIV) wherein R1 is an optionally substituted alkyl, cycloalkyl, heterocyclyl, aryl, cycloalkyl-alkyl, arylalkyl or heterocyclylalkyl group, by operating in a suitable solvent such as dioxane, THF, DME, $CH_3CN$, DMF or DMSO, at a temperature ranging from room temperature to about 90° C., optionally in the presence of a base such as $K_2CO_3$, potassium tertbutoxide or NaH.

Alternatively the reaction may be carried out in a suitable solvent such as toluene, DMF, DME or $CH_3CN$, in the presence of $Pd(OAc)_2$, (±)-BINAP and a base such as potassium phosphate or $K_2CO_3$ or $Cs_2CO_3$ at a temperature ranging from 0° C. to 100° C.

According to conversion (conv.13) of the process, compounds of formula (I), wherein R1 is an optionally substituted alkyl, cycloalkyl, heterocyclyl, cycloalkyl-alkyl or a heterocyclylalkyl group and X is —NH—, can be obtained from compounds of formula (I) wherein X is —$OSO_2$— and R1 is a trifluoromethyl group by reaction with an amine of formula (XII), wherein R1 is an optionally substituted alkyl, cycloalkyl, heterocyclyl, aryl, cycloalkyl-alkyl, arylalkyl or heterocyclylalkyl group. The reaction is typically obtained by operating in a suitable solvent such as dioxane, THF, DME, $CH_3CN$, DMF or DMSO, at a temperature ranging from room temperature to 90° C., optionally in the presence of a base such as $K_2CO_3$ or TEA.

According to conversion (conv.14) of the process, replacement of bromine with —NR'R" moiety was achieved reacting the starting material with an amine of formula (X) as defined above, in a suitable solvent such as THF or dioxane, and in the presence of catalytic amounts of $Pd_2(dba)_3$, 2-dicyclohexylphosphino-2'-(N,N-dimethylamino)-biphenyl and a base such as $LiN(TMS)_2$, at a temperature ranging from room temperature to reflux and for a time ranging from 1 to about 24 hours.

According to conversion (conv.15) of the process, deprotection of the carboxylic residue into the corresponding acid can be achieved using procedures well known in the art, involving acidic conditions, for example with HCl or TFA in a suitable solvent, such as, for instance, THF or dioxane, at a temperature ranging from room temperature to 60° C. and for a time ranging from about 1 to about 12 hours.

According to conversion (conv.16) of the process, transformation of the acid residue into the corresponding amide derivatives —CONR"R'", wherein R" and R'" are as defined above, can be obtained by reaction of the acid derivatives with an amine of formula (X) as defined above, under basic conditions, preferably with DIPEA or TEA, in a suitable solvent such as DCM, DMF, THF, or dioxane, and in the presence of a suitable condensing agent such as DCC, EDCI or TBTU; catalytic amounts of PyBOP or HOBt may be also required, at a temperature ranging from room temperature to 60° C. and for a time ranging from about 1 to about 24 hours.

According to conversion (conv.17) of the process, the compound of formula (I) as defined above is reacted with compounds of formula (XVI) as defined above, according to conventional methods. As an example the reaction can be carried out in a suitable solvent such as DMF, DME, dioxane or $CH_3CN$, catalytic amounts of $Pd_2(dba)_3$, BINAP or 2-(dicyclohexylphosphino)-2',4',6'-triisopropyl-1,1'-biphenyl (X-phos) and a base such as $K_2CO_3$, potassium phosphate or $Cs_2CO_3$, at a temperature ranging from room temperature to 110° C. and for a time ranging from about 2 to about 24 hours.

According to conversion (conv.18) of the process, compounds of formula (I) wherein R1 is an optionally substituted alkyl, cycloalkyl, heterocyclyl, aryl, cycloalkyl-alkyl, arylalkyl or heterocyclylalkyl group and X is a single bond, can be obtained by the corresponding compounds of formula (I) wherein X is —$OSO_2$— and R1 is a trifluoromethyl group, by reaction with derivatives of formula (XIII), as defined above, in a suitable solvent such as DMF, DCM, MeOH, DME or $CH_3CN$, in the presence of $Pd_2(dba)_3$, $PdCl_2(dppf)$ or $Pd(PPh_3)_4$, optionally in the presence of cesium fluoride, at a temperature ranging from room temperature to 100° C.

According to conversion (conv.19) of the process, compounds of formula (I) wherein R1 is an optionally substituted alkyl, cycloalkyl, heterocyclyl, aryl, cycloalkyl-alkyl, arylalkyl or heterocyclylalkyl group and X is —S—, can be obtained by the corresponding compounds of formula (I) wherein X is —O— and R1 is the trifluoromethanesulfonyl group above mentioned. The conversion is carried out by reaction with a thiol of formula R1-SH (XXVI) wherein R1 is as defined above in a suitable solvent such as THF, DMF, DCM, MeOH, DME or $CH_3CN$, at a temperature ranging from room temperature to 100° C.

According to conversion (conv.20) of the process, compounds of formula (I) wherein R1 is an optionally substituted aryl and X is a single bond, can be obtained by the corresponding compounds of formula (I) wherein X is —S— and R1 is methyl. The conversion is carried out by reaction with boronic acids of formula (XIIIa) in a suitable solvent such as DMF, THF, DCM, MeOH, DME or $CH_3CN$, in the presence of copper(I)-thiophene-2-carboxylate (CuTC) and $Pd_2(dba)_3$ or $Pd(PPh_3)_4$, optionally in the presence of cesium fluoride, at a temperature ranging from room temperature to reflux.

According to any variant of the process for preparing the compounds of formula (I), the starting material and any other reactant are known or easily prepared according to known methods.

In addition to the above, the compounds of formula (I) may be advantageously prepared according to combinatorial chemistry techniques widely known in the art, by accomplishing the aforementioned reactions between the intermediates in a serial manner and by working under solid-phase-synthesis (SPS) conditions.

For a general reference to the preparation of the compounds of formula (I) of the invention according to combinatorial chemistry techniques, see the experimental section.

Hence, it is a further object of the present invention a library of two or more compounds of formula (Ia).

As an example, the intermediate derivatives of formula (Vab) wherein R2 is hydroxy, being obtained in step B2 of the above processes, can be easily supported onto a polymeric resin, for instance through the formation of a carboxamido group.

The intermediate thus supported may be subsequently reacted according to the remaining steps of the process. The above synthetic pathway can be summarized as follows:

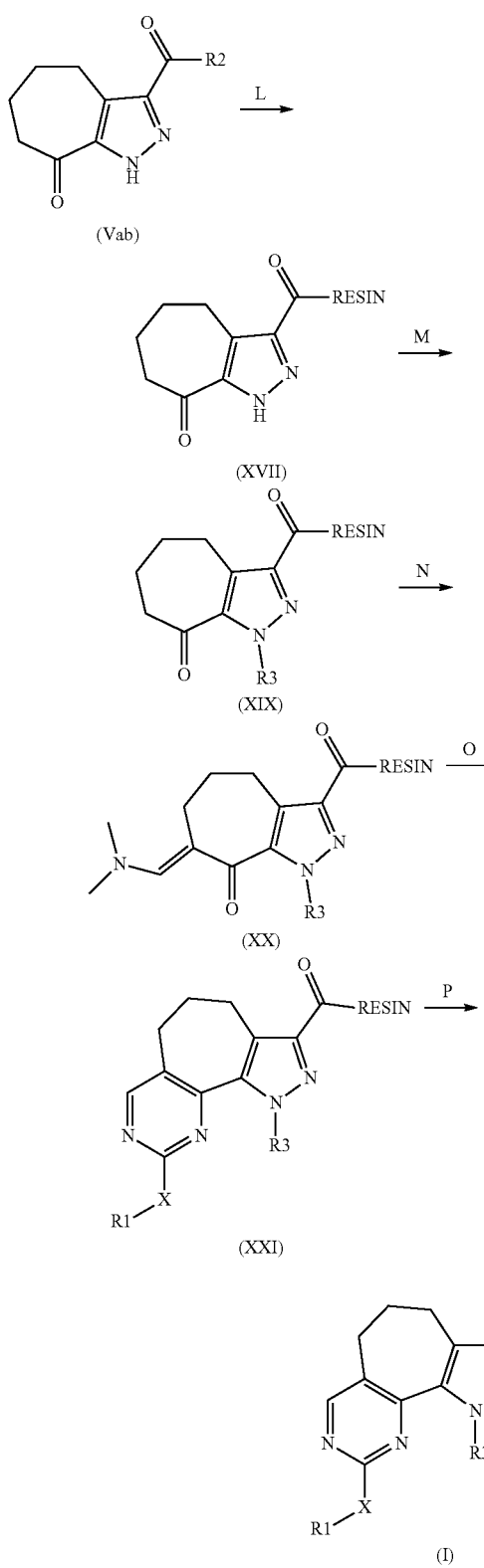

selected from straight or branched $C_1$-$C_6$ alkyl, $C_3$-$C_7$ cycloalkyl or cycloalkyl-alkyl, aryl, arylalkyl, heterocyclyl or heterocyclylalkyl.

Any of the above reactions is carried out according to known methods, by working as formerly reported, and allows obtaining compounds of formula (I) as set forth above.

According to a preferred embodiment of the invention, the polystyrenic resin is a derivatized formyl polystyrenic resin which may be obtained by reacting a commercially available formyl polystyrenic resin, e.g. 4-(4-formyl-3-methoxyphenoxy)butyryl AM resin, with a suitable amino derivative under reductive conditions, for instance in the presence of sodium triacetoxyborohydride and derivatives thereof, substantially as follows:

The reaction may be carried out in a suitable solvent such as tetrahydrofuran and in the presence of AcOH.

The polymer-supported-amino derivatives thus obtained, particularly those, which are referable to as derivatized formyl polystyrenic resin above, are widely known in the art.

In general, amines loaded onto formylpolystyrenic resins also known as Acid Sensitive Methoxyl)enzaldehyde polystyrene resins (AMEBA resin) are prepared by standard reductive amination in the presence of an excess of amine in trimethyl orthoformate (TMOF)/DCE and NaBH(OAc)$_3$ or AcOH/DMF and NaCNBH$_3$, for instance as reported in Tetrahedron Letters (1997), 38, 7151-7154; J. Am. Chem. Soc. (1998), 120, 5441; and Chem. Eur. J. (1999), 5, 2787.

Therefore, it is a further object of the present invention a process for preparing the compounds of formula (I), herein exemplified for the case where R2 is NHR" wherein R" is hydrogen or an optionally substituted group selected from straight or branched $C_1$-$C_6$ alkyl, $C_3$-$C_6$ cycloalkyl or cycloalkyl-alkyl, aryl, arylalkyl, heterocyclyl or heterocycylalkyl, and the pharmaceutically acceptable salts thereof, which process comprises:

st.L) reacting the compound of formula (Vab) wherein R2 is hydroxy with a derivatized formyl polystyrenic resin of formula (XXII):

wherein (P) is the resin and R" is as defined above;

st.M) reacting the resultant compound of formula (XVII):

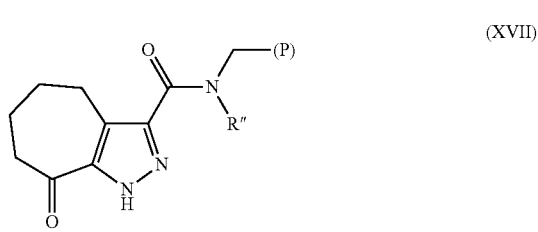

wherein, the resin is a commercially available polystyrenic resin including, for instance, Wang resin, Trityl resin, Cl-trityl resin, Rink amide resin, Tentagel OH resin and derivatives thereof; R1, X and R3 are as defined above and R2 is NHR", wherein R" is hydrogen or an optionally substituted group wherein (P) and R" are as described above, with a suitable alkylating agent R3-L (VI) as defined above in the presence of a base such as Cs$_2$CO$_3$ in an appropriate solvent such as DMF; and st.N) reacting the resultant compound of formula (XIX):

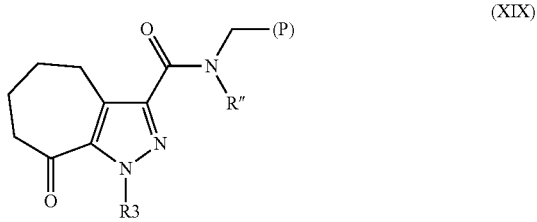

wherein R3, (P) and R" are as described above, as described under step st.H;

st.O) reacting the resultant compound of formula (XX):

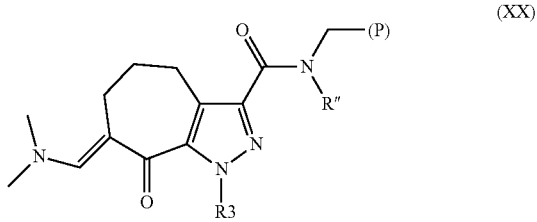

wherein (P), R" and R3 are as defined above, as described under any one of steps st.I1, st.I2, st.I3 and st.I4;

st.P) cleaving the resin under acidic conditions from the resultant compound of formula (XXI):

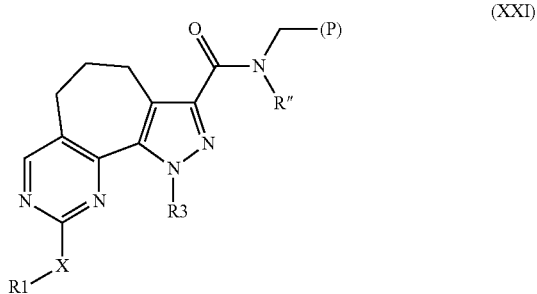

to give a compound of formula (I), wherein X, R1, R3 are as defined above and R2 is NHR" wherein R" is hydrogen or an optionally substituted group selected from straight or branched $C_1$-$C_6$ alkyl, $C_3$-$C_7$ cycloalkyl or cycloalkyl-alkyl, aryl, arylalkyl, heterocyclyl or heterocyclylalkyl; optionally separating the resultant compound of formula (I) into the single isomers; converting the resultant compound of formula (I) into a different compound of formula (I) and/or into a pharmaceutically acceptable salt if desired.

According to step (st.L) of the process, the reaction with the polystyrene resin is performed in a suitable solvent, for instance DMF, in the presence of DIPEA and of a suitable condensing agent such as, for instance, PyBOP, TBTU or 2-(1H-Benzotriazole-1-yl)-1,1,3,3-tetramethyluronium hexafluorophosphate (HBTU).

According to step (st.M) of the process, the supported compound of formula (XXIII) is alkylated to obtain the corresponding allylpyrazole derivative; the reaction is carried out in the presence of R3-L (VI), $Cs_2CO_3$ in DMF at room temperature for a time ranging from 4 to 24 hours.

According to step (st.N), the supported compound of formula (XXIV) is further reacted according to step st.H to give the corresponding enaminone, in the presence of dimethylformamide derivatives.

According to step (st.O), the supported compound of formula (XXV) is further reacted to give a variety of compounds of general formula (I), as described in any of the steps st.I1, st.I2, st.I3 and st.I4.

According to step (st.P), the cleavage of the resin is performed under acidic conditions in the presence of suitable acids such as, for instance, HCl, TFA, methanesulfonic or p-toluensulfonic acid. Preferably the reaction is carried out using TFA in DCM as solvent.

Clearly, by working according to combinatorial chemistry techniques as formerly indicated, a plurality of compounds of formula (I) may be obtained.

Hence, it is a further object of the present invention a library of two or more compounds of formula (Ia)

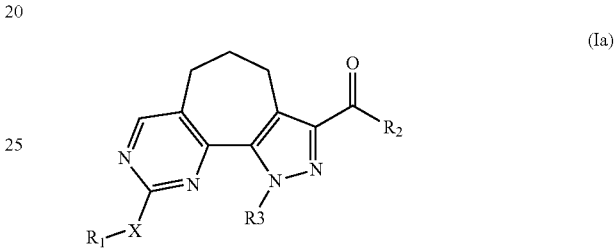

wherein:

R1 is hydrogen, or an optionally substituted group selected from amino, straight or branched $C_1$-$C_6$ alkyl, $C_3$-$C_7$ cycloalkyl, cycloalkyl-alkyl, aryl, arylalkyl, heterocyclyl and heterocyclylalkyl;

X is a single bond or a divalent radical selected from —NR'—, —CONR—, —NH—CO—NH—, —O—, —S— and —SO$_2$—, —OSO$_2$—, wherein R' is hydrogen or an optionally substituted group selected from straight or branched $C_1$-$C_6$ alkyl, $C_3$-$C_7$ cycloalkyl, cycloalkyl-alkyl, aryl, arylalkyl, heterocyclyl and heterocyclylalkyl;

R2 is —NHR", wherein R" is hydrogen or an optionally substituted group selected from straight or branched $C_1$-$C_6$ alkyl, $C_3$-$C_7$ cycloalkyl, cycloalkyl-alkyl, aryl, arylalkyl, heterocyclyl and heterocyclylalkyl;

R3 is hydrogen or an optionally substituted group selected from straight or branched $C_1$-$C_6$ alkyl, $C_3$-$C_7$ cycloalkyl, cycloalkyl-alkyl, aryl, arylalkyl, heterocyclyl and heterocyclylalkyl;

or a pharmaceutically acceptable salt thereof.

For a general reference to the above libraries of compounds of formula (I) see the experimental section.

From all of the above, it is clear to the skilled person that once a library of compounds of formula (I) is thus prepared, the said library can be very advantageously used for screening towards given kinases, as formerly reported.

See, for a general reference to libraries of compounds and uses thereof as tools for screening biological activities, J. Med. Chem. 1999, 42, 2373-2382; and Bioorg. Med. Chem. Lett. 10 (2000), 223-226.

For the purpose of pharmaceutical applications, the compounds of the present invention can be administered either as single agents or, alternatively, in combination with known anticancer treatments such as radiation therapy or chemotherapy regimen in combination with cytostatic or cytotoxic agents, antibiotic-type agents, alkylating agents, antimetabolite agents, hormonal agents, immunological agents, interferon-type agents, cyclooxygenase inhibitors (e.g. COX-2 inhibitors), matrixmetalloprotease inhibitors, telomerase inhibitors, tyrosine kinase inhibitors, anti-growth factor receptor agents, anti-HER agents, anti-EGFR agents, anti-angiogenesis agents (e.g. angiogenesis inhibitors), farnesyl transferase inhibitors, ras-raf signal transduction pathway inhibitors, cell cycle inhibitors, other cdks inhibitors, tubulin binding agents, topoisomerase I inhibitors, topoisomerase II inhibitors, and the like.

If formulated as a fixed dose, such combination products employ the compounds of this invention within the dosage range described below and the other pharmaceutically active agent within the approved dosage range.

Compounds of formula (I) may be used sequentially with known anticancer agents when a combination formulation is inappropriate.

The compounds of formula (I) of the present invention, suitable for administration to a mammal, e.g., to humans, can be administered by the usual routes and the dosage level depends upon the age, weight, conditions of the patient and administration route.

For example, a suitable dosage adopted for oral administration of a compound of formula (I) may range from about 10 to about 500 mg per dose, from 1 to 5 times daily. The compounds of the invention can be administered in a variety of dosage forms, e.g., orally, in the form tablets, capsules, sugar or film coated tablets, liquid solutions or suspensions; rectally in the form suppositories; parenterally, e.g., intramuscularly, or through intravenous and/or intrathecal and/or intraspinal injection or infusion.

The present invention also includes pharmaceutical compositions comprising a compound of formula (I) or a pharmaceutically acceptable salt thereof in association with a pharmaceutically acceptable excipient, which may be a carrier or a diluent.

The pharmaceutical compositions containing the compounds of the invention are usually prepared following conventional methods and are administered in a suitable pharmaceutical form. For example, the solid oral forms may contain, together with the active compound, diluents, e.g., lactose, dextrose saccharose, sucrose, cellulose, corn starch or potato starch; lubricants, e.g., silica, talc, stearic acid, magnesium or calcium stearate, and/or polyethylene glycols; binding agents, e.g., starches, arabic gum, gelatine methylcellulose, carboxymethylcellulose or polyvinyl pyrrolidone; disintegrating agents, e.g., starch, alginic acid, alginates or sodium starch glycolate; effervescing mixtures; dyestuffs; sweeteners; wetting agents such as lecithin, polysorbates, laurylsulphates; and, in general, non-toxic and pharmacologically inactive substances used in pharmaceutical formulations. These pharmaceutical preparations may be manufactured in known manner, for example, by means of mixing, granulating, tabletting, sugar-coating, or film-coating processes.

The liquid dispersions for oral administration may be, e.g., syrups, emulsions and suspensions. As an example, the syrups may contain, as carrier, saccharose or saccharose with glycerine and/or mannitol and sorbitol.

The suspensions and the emulsions may contain, as examples of carriers, natural gum, agar, sodium alginate, pectin, methylcellulose, carboxymethylcellulose, or polyvinyl alcohol. The suspension or solutions for intramuscular injections may contain, together with the active compound, a pharmaceutically acceptable carrier, e.g., sterile water, olive oil, ethyl oleate, glycols, e.g., propylene glycol and, if desired, a suitable amount of lidocaine hydrochloride.

The solutions for intravenous injections or infusions may contain, as a carrier, sterile water or preferably they may be in the form of sterile, aqueous, isotonic, saline solutions or they may contain propylene glycol as a carrier.

The suppositories may contain, together with the active compound, a pharmaceutically acceptable carrier, e.g., cocoa butter, polyethylene glycol, a polyoxyethylene sorbitan fatty acid ester surfactant or lecithin.

With the aim at better illustrating the present invention, without posing any limitation to it, the following examples are now given.

EXAMPLES

The synthetic preparation of some compounds of formula (I) of the invention is described in the following examples. The compounds of the present invention, as prepared according to the following examples, were also characterized by $^1$H NMR or by HPLC/MS analytical data; HPLC/MS data were collected following any one of methods 1, 2, 3 and 4.

HPLC/MS Analytic Method 1

The HPLC equipment consisted of a Waters Acquity™ UPLC system equipped with a 2996 Waters PDA detector and Micromass mod. ZQ single quadrupole mass spectrometer, equipped with an electrospray (ESI) ion source. Instrument control, data acquisition and data processing were provided by Empower and MassLynx 4.0 software.

HPLC was carried out at 45° C. at a flow rate of 0.8 mL/min using a BEH C18 1.7 microm Waters Acquity UPLC (2.1×50 mm) column. Mobile phase A was formic acid 0.1% pH=3.3 buffer with $CH_3CN$ (98:2), and mobile phase B was $H_2O/CH_3CN$ (5:95); the gradient was from 5 to 95% B in 2 minutes then hold 95% B 0.1 minutes. The injection volume was 2 microL. The mass spectrometer was operated in positive and in negative ion mode, the capillary voltage was set up at 3.5 KV ($ES^+$) and 28 V ($ES^-$); the source temperature was 120° C.; cone was 14 V ($ES^+$) and 2.8 KV ($ES^-$); full scan, mass range from 100 to 800 amu was set up.

HPLC/MS Analytic Method 2

The HPLC equipment consisted of a Waters 2795 Alliance HT system equipped with a 2996 Waters PDA detector and Micromass mod. ZQ single quadrupole mass spectrometer, equipped with an electrospray (ESI) ion source. Instrument control, data acquisition and data processing were provided by Empower and MassLynx 4.0 software.

HPLC was carried out at 30° C. at a flow rate of 1.0 mL/min using a C18, 3 microm Phenomenex (4.6×50 mm) column. Mobile phase A was ammonium acetate 5 mM pH=5.2 buffer with $CH_3CN$ (95:5), and mobile phase B was $H_2O/CH_3CN$ (5:95); the gradient was from 10 to 90% B in 8 minutes then ramp to 100% B in 1.0 minutes. The injection volume was 10 microL. The mass spectrometer was operated in positive and in negative ion mode, the capillary voltage was set up at 3.5 KV ($ES^+$) and 28 V ($ES^-$); the source temperature was 120° C.; cone was 14 V ($ES^+$) and 2.8 KV ($ES^-$); full scan, mass range from 100 to 800 amu was set up.

HPLC/MS Analytic Method 3

The HPLC equipment consisted of a Waters Acquity™ UPLC system equipped with a 2996 Waters PDA detector and Micromass mod. ZQ single quadrupole mass spectrometer, equipped with an electrospray (ESI) ion source. Instrument control, data acquisition and data processing were provided by Empower and MassLynx 4.0 software.

HPLC was carried out at 45° C. at a flow rate of 0.8 mL/min using a BEH C18 1.7 microm Waters Acquity UPLC (2.1×50 mm) column. Mobile phase A was ammonium hydroxide 0.05% pH=10 buffer with $CH_3CN$ (95:5), and mobile phase B was $H_2O/CH_3CN$ (5:95); the gradient was from 5 to 95% B in 2 minutes then hold 95% B 0.1 minutes. The injection volume was 2 microL. The mass spectrometer was operated in positive and in negative ion mode, the capillary voltage was set up at 3.5 KV (ES$^+$) and 28 V (ES$^-$); the source temperature was 120° C.; cone was 14 V (ES$^+$) and 2.8 KV (ES$^-$); full scan, mass range from 100 to 800 amu was set up.

HPLC/MS Analytical Method 4

The HPLC equipment consisted of a Waters 2790 HPLC system equipped with a 996 Waters PDA detector and Micromass mod. ZQ single quadrupole mass spectrometer, equipped with an electrospray (ESI) ion source. Instrument control, data acquisition and data processing were provided by Empower and MassLynx 4.0 software.

HPLC was carried out at 25° C. at a flow rate of 1 mL/min using a RP18 Waters X Terra (3.0×20 mm) column. Mobile phase A was ammonium hydroxide 0.05% pH=10 buffer with CH$_3$CN (95:5), and Mobile phase B was H$_2$O/CH$_3$CN (5:95); the gradient was from 10 to 90% B in 4 minutes then hold 90% B 1 minutes. The injection volume was 10 microL. The mass spectrometer was operated in positive and in negative ion mode, the capillary voltage was set up at 2.5 KV; the source temperature was 120° C.; cone was 10 V; full scan, mass range from 100 to 800 amu was set up.

Several compounds of the invention of formula (I), as prepared according to the following examples, were purified by preparative HPLC.

The operative conditions are defined below:

HPLC/MS Preparative Method 1

The HPLC equipment consisted of a Waters 2790 HPLC system equipped with a 996 Waters PDA detector and Micromass mod. ZQ single quadrupole mass spectrometer, equipped with an electrospray (ESI) ion source. Instrument control, data acquisition and data processing were provided by Empower and MassLynx 4.0 software.

HPLC was carried out at 25° C. at a flow rate of 20 mL/min using a RP18 Waters X Terra 10 microm (19×250 mm) column. Mobile phase A was ammonium hydroxide 0.05% pH=10 buffer with CH$_3$CN (95:5), and Mobile phase B was CH$_3$CN; the gradient was from 10 to 90% B in 15 minutes then hold 90% B 3 minutes. The injection volume was 10 microL.

The mass spectrometer was operated in positive and in negative ion mode, the capillary voltage was set up at 2.5 KV; the source temperature was 120° C.; cone was 10 V; full scan, mass range from 100 to 800 amu was set up.

HPLC/MS Preparative Method 2

The HPLC equipment consisted of a Waters 2790 HPLC system equipped with a 996 Waters PDA detector and Micromass mod. ZQ single quadrupole mass spectrometer, equipped with an electrospray (ESI) ion source. Instrument control, data acquisition and data processing were provided by Empower and MassLynx 4.0 software.

HPLC was carried out at 25° C. at a flow rate of 20 mL/min using a RP18 Waters X Terra 10 microm (19×250 mm) column. Mobile phase A was 0.1% TFA in water/CH$_3$CN (95:5), and mobile phase B was CH$_3$CN; the gradient was from 10 to 90% B in 15 minutes then hold 90% B 3 minutes. The injection volume was 10 microL.

The mass spectrometer was operated in positive and in negative ion mode, the capillary voltage was set up at 2.5 KV; the source temperature was 120° C.; cone was 10 V; full scan, mass range from 100 to 800 amu was set up.

NMR $^1$H-NMR spectra were recorded at a constant temperature of 28° C. on a Varian INOVA 400 spectrometer operating at 400.50 MHz and equipped with a 5 mm z-axis PFG Indirect Detection Probe ($^1$H{$^{15}$N-$^{31}$P}).

Chemical shifts were referenced with respect to the residual solvent signals (DMSO-d6: 2.50 ppm for $^1$H, where not otherwise specified). Data are reported as follows: chemical shift (δ), multiplicity (s=singlet, d=doublet, t=triplet, q=quartet, br. s=broad singlet, td=triplet of doublets, dd=doublet of doublets, ddd=doublet of doublets of doublets, m=multiplet, spt=septet), coupling constants (J, Hz), and number of protons.

MS Exact

Exact mass data ESI(+) were obtained on a Waters Q-T of Ultima mass spectrometer directly connected with a Agilent 1100 micro-HPLC system as previously described (M. Colombo, F. Riccardi-Sirtori, V. *Rizzo, Rapid Commun. Mass Spectrom.* 2004, 18, 511-517).

In the examples below, as well as troughout the application, the following abbreviations have the following meanings.

If not defined, the terms have their generally accepted meanings.

| ABBREVIATIONS | |
|---|---|
| DCM | Dichloromethane |
| DIPEA | N,N-diisopropylethylamine |
| DMF | N,N-dimethylformamide |
| DCC | N,N'-dicyclohexylcarbodiimide |
| EDCI | N-ethyl-N',N'-diisopropyl carbodiimide hydrochloride |
| AcOEt | Ethyl acetate |
| EtOH | Ethanol |
| Na$_2$CO$_3$ | Sodium carbonate |
| NaH | Sodium hydride |
| PyBOP | (Benzotriazol-1-yloxy)tripyrrolidinophosphonium hexafluorophosphate |
| HOBt | 1H-benzotriazol-1-ol |
| K$_2$CO$_3$ | Potassium carbonate |
| CH$_3$CN | Acetonitrile |
| Na$_2$SO$_4$ | Sodium sulfate |
| MeOH | Methanol |
| Na$_2$CO$_3$ | Sodium carbonate |
| Pd$_2$(dba)$_3$ | Tris(dibenzylideneacetone)dipalladium(0) |
| TEA | Triethylamine |
| THF | Tetrahydrofurane |
| LiN(TMS)$_2$ | Lithium bis(trimethylsilyl)amide |
| Et$_2$O | Diethyl ether |
| KH$_2$PO$_4$ | Potassium dihydrogen phosphate |
| AcOH | Acetic acid |
| KOH | Potassium hydroxide |
| NaOH | Sodium hydroxide |
| HCl | Hydrochloric acid |
| Cs$_2$CO$_3$ | Cesium carbonate |
| DMSO | Dimethyl sulfoxide |
| NaHCO$_3$ | Sodium hydrogen carbonate |
| MeOH | Methanol |
| TBTU | O-(benzotriazol-1-yl)-N,N,N',N'-tetramethyluronium tetrafluoroborate |
| Na$_2$S$_2$O$_5$ | Sodium metabisulphite |
| Na$_2$S$_2$O$_3$ | Sodium thiosulfate |
| TFA | Trifluoro acetic acid |
| Xantphos | 4,5-Bis(diphenylphosphino)-9,9-dimethylxanthene |
| PdCl$_2$(dppf) | [1,1'-bis(diphenylphosphino)ferrocene]palladium(II) chloride |
| DME | 1,2-Dimethoxyethane |
| Pd(OAc)$_2$ | Palladium(II) acetate |
| Pd(PPh$_3$)$_4$ | Tetrakis (triphenylphosphine) Palladium |
| BINAP | (2,2'-Bis(diphenylphosphino)-1,1'-binaphtalene |
| CuTC | Copper(I) thiophene-2-carboxylate |

Preparation A (step A)

Ethyl (3,3-dimethoxy-2-oxocycloheptyl)(oxo)acetate

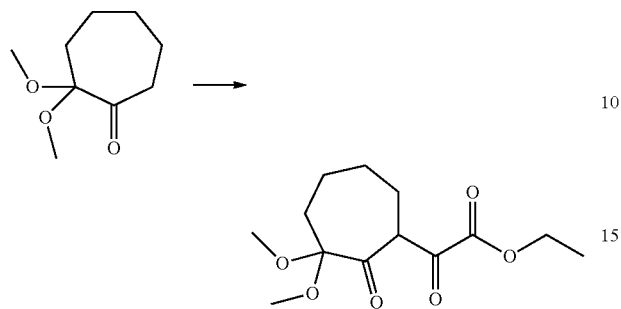

1M LiN(TMS)₂ in THF (28.5 mL, 28.5 mmol) were added dropwise at −50° C. to a solution of 2,2-dimethoxycycloheptanone (4.10 g, 23.8 mmol) in 25 mL of Et₂O under argon. After 30 minutes at the same temperature, 3.55 mL of diethyloxalate were also added under stirring. The solution was kept at room temperature overnight. 10% solution of KH₂PO₄ (20 mL) were then added and the resulting solution extracted with Et₂O (3×50 mL). The organic layer was dried over Na₂SO₄ and evaporated to dryness. The crude was purified by chromatography on a silica gel column (eluant: AcOEt/cyclohexane 1/9) to afford 3.98 g (65% yield) as a colorless oil.

¹H NMR (401 MHz, DMSO-d6) δ ppm 1.17-1.23 (m, 2H) 1.24 (t, J=7.08 Hz, 3H) 1.38-1.49 (m, 2H) 1.72-1.81 (m, 2H) 1.91-2.00 (m, 2H) 3.10 (s, 3H) 3.21 (s, 3H) 4.16-4.25 (m, 2H) 4.71 (dd, J=7.81, 4.88 Hz, 1H).

Preparation B (step B1)

Ethyl 2-methyl-8-oxo-2,4,5,6,7,8-hexahydrocyclohepta[c]pyrazole-3-carboxylate

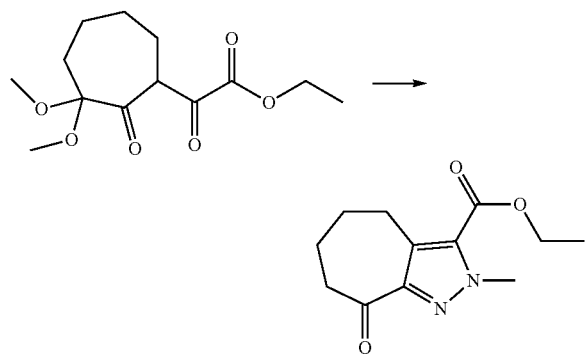

To a solution of ethyl (3,3-dimethoxy-2-oxocycloheptyl)(oxo)acetate 0.090 g (0.33 mmol) in 2 mL of EtOH and 4 mL of AcOH, 0.020 mL (0.039 mmol) of N-methylhydrazine was added. The mixture was stirred overnight at room temperature. The solvent was removed under reduced pressure and the crude solid was purified by flash chromatography on silica gel (eluant: AcOEt/hexane 8/2) to afford 0.035 g (38% yield) of the title compound as colorless oil.

¹H NMR (401 MHz, DMSO-d6) δ ppm 1.34 (t, J=7.08 Hz, 3H) 1.72-1.87 (m, 4H) 2.63-2.71 (m, 2H) 3.00-3.07 (m, 2H) 4.09 (s, 3H) 4.34 (q, J=7.08 Hz, 2H)
MS calc: 237.1234; MS found: 237.1239

According to this same methodology, but employing suitable substituted derivatives, the following compound was prepared:

ethyl 8-oxo-1,4,5,6,7,8-hexahydrocyclohepta[c]pyrazole-3-carboxylate

¹H NMR (401 MHz, DMSO-d6) δ ppm 1.29 (t, J=7.14 Hz, 3H) 1.73-1.93 (m, 4H) 2.70-2.76 (m, 2H) 3.07 (t, J=6.47 Hz, 2H) 4.27 (q, J=7.08 Hz, 2H) 14.08 (br. s., 1H)
MS calc: 223.1077; MS found: 223.1078

Preparation C (step B1a)

Ethyl 2-methyl-8-oxo-2,4,5,6,7,8-hexahydrocyclohepta[c]pyrazole-3-carboxylate and ethyl 1-methyl-8-oxo-1,4,5,6,7,8-hexahydrocyclohepta[c]pyrazole-3-carboxylate

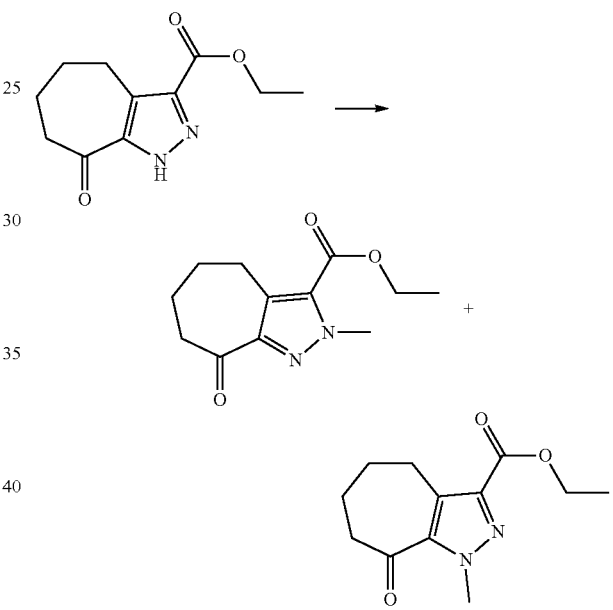

To a solution of ethyl 8-oxo-1,4,5,6,7,8-hexahydrocyclohepta[c]pyrazole-3-carboxylate (2.0 g, 9.00 mmol) in DMF (20 mL) Cs₂CO₃ (3.52 g, 10.00 mmol) and methyl iodide (0.60 mL, 10.00 mmol) were added. The reaction was stirred at room temperature for 1 h, solvent was removed under vacuo, then DCM (50 mL) was added and the organic phase washed with water (3×50 mL). The aqueous fraction was extracted with DCM (50 mL). The organic fractions were combined, dried over Na₂SO₄, filtered, and concentrated in vacuo. Purification by flash chromatography on silica gel (eluant: AcOEt/hexane 2/8) provided 0.70 g (33% yield) as colorless oil of ethyl 2-methyl-8-oxo-2,4,5,6,7,8-hexahydrocyclohepta[c]pyrazole-3-carboxylate ¹H NMR (401 MHz, DMSO-d6) δ ppm 1.34 (t, J=7.08 Hz, 3H) 1.72-1.87 (m, 4H) 2.63-2.71 (m, 2H) 3.00-3.07 (m, 2H) 4.09 (s, 3H) 4.34 (q, J=7.08 Hz, 2H)
MS calc: 237.1234; MS found: 237.1239
and 1.40 g (66% yield) as a white solid of ethyl 1-methyl-8-oxo-1,4,5,6,7,8-hexahydrocyclohepta[c]pyrazole-3-carboxylate $^1$H NMR (401 MHz, DMSO-d6) δ ppm 1.29 (t, J=7.16 Hz, 3H) 1.74-1.83 (m, 4H) 2.68-2.77 (m, 2H) 3.11 (t, J=6.16 Hz, 2H) 4.04 (s, 3H) 4.28 (q, J=7.16 Hz, 2H)

MS calc: 237.1234; MS found: 237.1233

According to this same methodology, but employing suitable substituted derivatives, the following compounds were prepared:

ethyl 1-[3-(dimethylamino)propyl]-8-oxo-1,4,5,6,7,8-hexahydrocyclohepta[c]pyrazole-3-carboxylate $^1$H NMR (401 MHz, DMSO-d6) δ ppm 1.30 (t, J=7.08 Hz, 3H) 1.70-1.88 (m, 6H) 2.10 (s, 6H) 2.20 (t, J=6.84 Hz, 2H) 2.67-2.76 (m, 2H) 3.05-3.16 (m, 2H) 4.29 (q, J=7.08 Hz, 2H) 4.43 (t, J=7.45 Hz, 2H)

MS calc: 308.1969; MS found: 308.1972 ethyl 5-acetyl-4-butyl-1-(2-hydroxyethyl)-1H-pyrazole-3-carboxylate ethyl 2-(2-hydroxyethyl)-8-oxo-2,4,5,6,7,8-hexahydrocyclohepta[c]pyrazole-3-carboxylate

Preparation D (step B2)

8-oxo-1,4,5,6,7,8-hexahydrocyclohepta[c]pyrazole-3-carboxylic acid

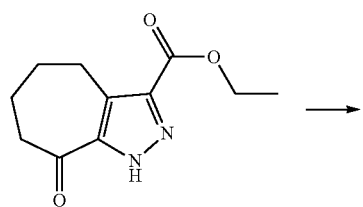

Ethyl 8-oxo-1,4,5,6,7,8-hexahydrocyclohepta[c]pyrazole-3-carboxylate (2.67 g, 12.01 mmol) was suspended in EtOH (80 mL) and treated with a 2 M solution of NaOH (24 mL, 48.0 mmol) at reflux temperature for 1 h. After cooling the mixture is neutralized with 2 N HCl (24 mL) and the resulting precipitate was collected by filtration to give 2.0 g of the title compound (90% yield) as a white solid.

$^1$H NMR (401 MHz, DMSO-d6) δ ppm 1.69-1.93 (m, 4H) 2.71 (t, J=6.35 Hz, 2H) 3.07 (t, J=5.61 Hz, 2H) 12.73 (br. s., 1H) 13.98 (br. s., 1H)

Preparation E (step B3)

N-(2,6-diethylphenyl)-8-oxo-1,4,5,6,7,8-hexahydrocyclohepta[c]pyrazole-3-carboxamide

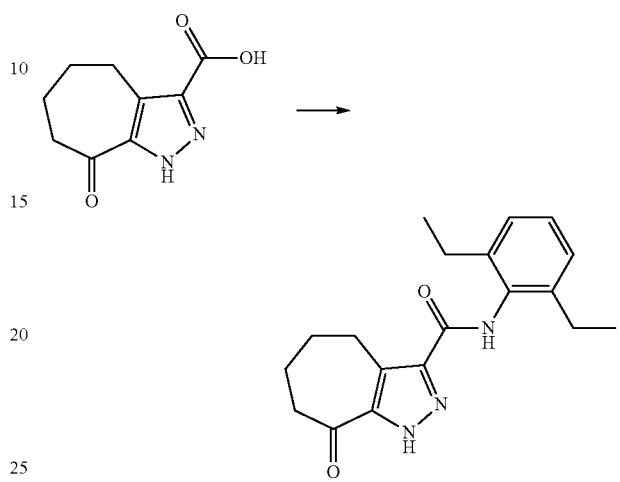

A suspension of 8-oxo-1,4,5,6,7,8-hexahydrocyclohepta[c]pyrazole-3-carboxylic acid (0.045 g, 0.232 mmol) in anhydrous DMF (2 mL) was treated with HOBt (0.047 g, 0.347 mmol), EDCI (0.065 g, 0.347 mmol), 2,6-diethylaniline (0.253 mL, 0.925 mmol) and DIPEA (0.188 mL, 1.390 mmol). The reaction was stirred at room temperature overnight. The reaction was diluted with water, extracted with AcOEt (2×20 mL). The organic fractions were combined, dried over Na$_2$SO$_4$, filtered, and concentrated in vacuo. Purification by flash chromatography on silica gel (eluant: AcOEt/hexane 2/8) provided 0.027 g (35% yield) of the title compound.

$^1$H NMR (401 MHz, DMSO-d6) δ ppm 1.10 (t, J=7.57 Hz, 6H) 1.77-1.92 (m, 4H) 2.53 (q, J=7.57 Hz, 4H) 2.70-2.79 (m, 2H) 3.12 (t, J=5.92 Hz, 2H) 7.04-7.16 (m, 2H) 7.16-7.25 (m, 1H) 9.55 (s, 1H) 13.96 (s, 1H)

MS calc: 326.1863; MS found: 326.1869

According to this same methodology, but employing suitable substituted derivatives, the following compounds were prepared:

1-methyl-8-oxo-N-propyl-1,4,5,6,7,8-hexahydrocyclohepta[c]pyrazole-3-carboxamide $^1$H NMR (401 MHz, DMSO-d6) δ ppm 0.85 (t, J=7.45 Hz, 3H) 1.42-1.58 (m, 2H) 1.70-1.90 (m, 4H) 2.68-2.75 (m, 2H) 3.07-3.21 (m, 4H) 8.13 (t, J=5.86 Hz, 1H) 13.42-14.11 (m, 1H)

MS calc: 236.1394; MS found: 236.1397

8-oxo-N-(pyridin-4-ylmethyl)-1,4,5,6,7,8-hexahydrocyclohepta[c]pyrazole-3-carboxamide $^1$H NMR (401 MHz, DMSO-d6) δ ppm 1.71-1.93 (m, 4H) 2.69-2.76 (m, 2H) 3.12 (d, J=5.92 Hz, 2H) 4.42 (d, J=6.23 Hz, 2H) 7.24-7.31 (m, 2H) 8.46-8.50 (m, 2H) 8.89 (t, J=6.41 Hz, 1H) 13.94 (s, 1H)

MS calc: 285.1346; MS found: 285.1344

8-oxo-1,4,5,6,7,8-hexahydrocyclohepta[c]pyrazole-3-carboxamide $^1$H NMR (401 MHz, DMSO-d6) δ ppm 1.75-1.90 (m, 4H) 2.68-2.74 (m, 2H) 3.121 (t, J=6.04 Hz, 2H) 7.20 (br.s., 1H), 7.50 (br.s., 1H)

Preparation F (step B4)

N-(2,6-diethylphenyl)-1-methyl-8-oxo-1,4,5,6,7,8-hexahydrocyclohepta[c]pyrazole-3-carboxamide

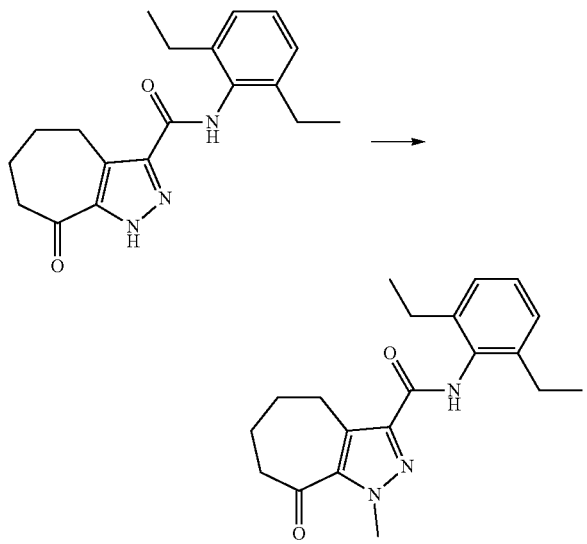

To a solution of N-(2,6-diethylphenyl)-8-oxo-1,4,5,6,7,8-hexahydrocyclohepta[c]pyrazole-3-carboxamide (1.04 g, 3.211 mmol) in DMF (12 mL) Cs$_2$CO$_3$ (1.255 g, 3.85 mmol) and methyl iodide (0.22 mL, 3.532 mmol) were added. The reaction was stirred at room temperature for 1 h, then AcOEt (60 mL) was added and the organic phase washed with water (3×50 mL). The organic fraction was dried over Na$_2$SO$_4$, filtered, and concentrated in vacuo. Purification by flash chromatography on silica gel (eluant: AcOEt/hexane 1/9) provided 0.99 g (91% yield) of the title compound as a white solid.

$^1$H NMR (401 MHz, DMSO-d6) δ ppm 1.10 (t, J=7.57 Hz, 6H) 1.69-1.86 (m, 4H) 2.53 (q, J=7.57 Hz, 4H) 2.71-2.77 (m, 2H) 3.13-3.20 (m, 2H) 4.09 (s, 3H) 7.03-7.15 (m, 2H) 7.15-7.25 (m, 1H) 9.58 (s, 1H)

MS calc: 340.2020; MS found: 340.2015

According to this same methodology, but employing suitable substituted derivatives, the following compounds were prepared:

N-methoxy-N,1-dimethyl-8-oxo-1,4,5,6,7,8-hexahydrocyclohepta[c]pyrazole-3-carboxamide $^1$H NMR (401 MHz, DMSO-d6) δ ppm 1.70-1.83 (m, 4H) 2.68-2.73 (m, 2H) 2.82 (t, J=6.04 Hz, 2H) 3.27 (br.s., 3H) 3.67 (s, 3H) 4.01 (s, 3H)

N-(2,6-diethylphenyl)-1-(4-methoxybenzyl)-8-oxo-1,4,5,6,7,8-hexahydrocyclohepta[c]pyrazole-3-carboxamide $^1$H NMR (401 MHz, DMSO-d6) δ ppm 1.11 (t, J=7.57 Hz, 6H) 1.70-1.83 (m, 4H) 2.55 (q, J=7.57 Hz, 4H) 2.64-2.73 (m, 2H) 3.16 (t, J=5.98 Hz, 2H) 3.72 (s, 3H) 5.62 (s, 2H) 6.84-6.92 (m, 2H) 7.10-7.16 (m, 2H) 7.17-7.24 (m, 3H) 9.63 (s, 1H)

MS calc: 446.2438; MS found: 446.2437

1-methyl-8-oxo-N-propyl-1,4,5,6,7,8-hexahydrocyclohepta[c]pyrazole-3-carboxamide $^1$H NMR (401 MHz, DMSO-d6) δ ppm 0.85 (t, J=7.45 Hz, 3H) 1.50 (sxt, J=7.32 Hz, 2H) 1.68-1.84 (m, 4H) 2.65-2.76 (m, 2H) 3.11-3.20 (m, 4H) 4.02 (s, 3H) 8.12 (t, J=5.25 Hz, 1H)

MS calc: 250.1550; MS found: 250.1547

Preparation G (step C1)

1-methyl-8-oxo-1,4,5,6,7,8-hexahydrocyclohepta[c]pyrazole-3-carboxylic acid

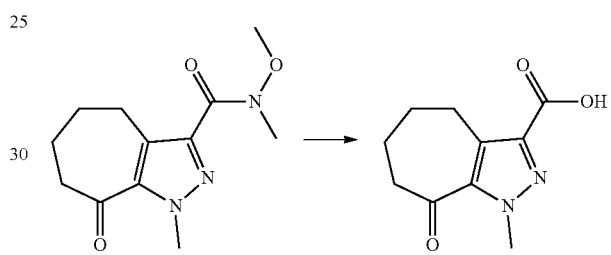

To a solution of N-methoxy-N,1-dimethyl-8-oxo-1,4,5,6,7,8-hexahydrocyclohepta[c]pyrazole-3-carboxamide (14 mg, 0.055 mmol) in EtOH (1 mL), a solution of NaOH (2M, 55 μL) was added. The reaction was stirred under reflux for 1 h, the solvent was removed under vacuum, then DCM (5 mL) was added and the organic phase was washed with HCl 25% (3×5 mL). The aqueous phase was back-extracted with DCM (5 mL). The organic fractions were combined, dried over Na$_2$SO$_4$, filtered, and concentrated under vacuum to give 11 mg of a white solid (quantitative yield).

$^1$H NMR (401 MHz, DMSO-d6) δ ppm 1.70-1.83 (m, 4H) 2.68-2.76 (m, 2H) 3.08-3.15 (m, 2H) 4.02 (s, 3H) 12.83 (br. s., 1H)

Preparation H (step D)

N-methoxy-N,1-dimethyl-8-oxo-1,4,5,6,7,8-hexahydrocyclohepta[c]pyrazole-3-carboxamide

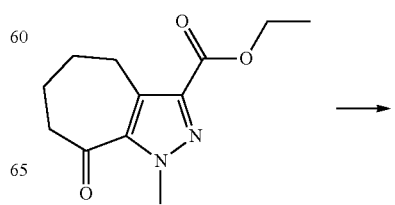

-continued

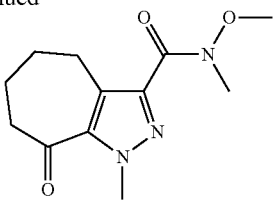

To a solution of N,O-dimethylhydroxylamine hydrochloride (650 mg, 0.67 mmol) in 2 mL of anhydrous THF under argon, 1M solution of LiN(TMS)$_2$ in THF (1.32 mL, 1.32 mmol) at 0° C. were added dropwise. The mixture was stirred at 0° C. for 0.5 h then ethyl 1-methyl-8-oxo-1,4,5,6,7,8-hexahydrocyclohepta[c]pyrazole-3-carboxylate (50 mg, 0.22 mmol) in 5 mL of anhydrous THF at 0° C. were added dropwise. Ice bath was removed and the mixture was stirred at room temperature overnight. Water (20 mL) was added and the mixture was extracted with AcOEt (2×30 mL). The organic layer was dried over anhydrous Na$_2$SO$_4$ and the solvent evaporated to dryness. The crude solid was used without further purification. 52 mg (quantitative yield).

$^1$H NMR (401 MHz, DMSO-d6) δ ppm 1.70-1.83 (m, 4H) 2.68-2.73 (m, 2H) 2.82 (t, J=6.04 Hz, 2H) 3.27 (br.s., 3H) 3.67 (s, 3H) 4.01 (s, 3H)

According to this same methodology, but employing suitable substituted derivatives, the following compounds were prepared:

N-methoxy-N,2-dimethyl-8-oxo-2,4,5,6,7,8-hexahydrocyclohepta[c]pyrazole-3-carboxamide N-methoxy-N-methyl-8-oxo-1,4,5,6,7,8-hexahydrocyclohepta[c]pyrazole-3-carboxamide Preparation I (step D)

N-(2,6-diethylphenyl)-8-oxo-1,4,5,6,7,8-hexahydrocyclohepta[c]pyrazole-3-carboxamide

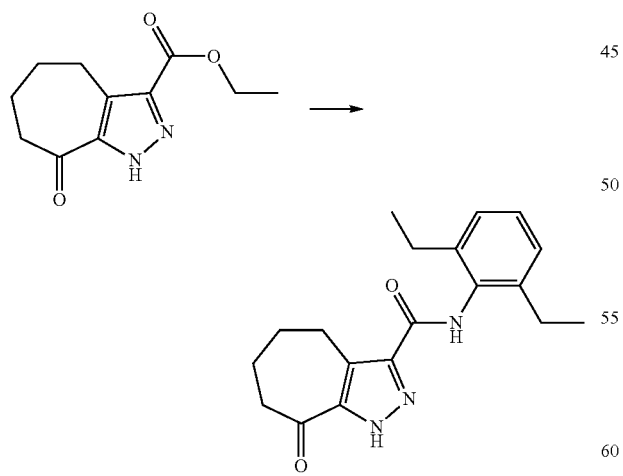

To a solution of 2,6-diethylaniline (0.106 mL, 0.66 mmol) in 5 mL of anhydrous THF under argon, 1M solution of LiN(TMS)$_2$ in THF (0.660 mL, 0.66 mmol) at 0° C. was added dropwise. The mixture was stirred at 0° C. for 0.5 h then ethyl 8-oxo-1,4,5,6,7,8-hexahydrocyclohepta[c]pyrazole-3-carboxylate (0.050 g, 0.22 mmol) in 5 mL of anhydrous THF at 0° C. were added dropwise. Ice bath was removed and the mixture was stirred at room temperature for 1 h. Water (20 mL) was added and the mixture was extracted with AcOEt (2×30 mL). The organic layer was dried over anhydrous Na$_2$SO$_4$ and the solvent evaporated to dryness. The crude solid was purified by flash chromatography on silica gel (eluant: AcOEt/hexane 2/8) to afford 0.055 g (80% yield) of the title compound.

$^1$H NMR (401 MHz, DMSO-d6) δ ppm 1.10 (t, J=7.57 Hz, 6H) 1.77-1.92 (m, 4H) 2.53 (q, J=7.57 Hz, 4H) 2.70-2.79 (m, 2H) 3.12 (t, J=5.92 Hz, 2H) 7.04-7.16 (m, 2H) 7.16-7.25 (m, 1H) 9.55 (s, 1H) 13.96 (s, 1H)

MS calc: 326.1863; MS found: 326.1869

According to this same methodology, but employing suitable substituted derivatives, the following compound was prepared:

N-(2,6-diethylphenyl)-N,1-dimethyl-8-oxo-1,4,5,6,7, 8-hexahydrocyclohepta[c]pyrazole-3-carboxamide $^1$H NMR (401 MHz, DMSO-d6) δ ppm 1.14 (t, J=7.51 Hz, 6H) 1.65-1.77 (m, 4H) 1.75-1.87 (m, 2H) 2.51-2.58 (m, 4H) 2.58-2.64 (m, 4H) 2.83-2.94 (m, 2H) 3.16 (s, 3H) 3.59 (s, 3H) 7.00-7.09 (m, 2H) 7.14-7.20 (m, 1H)

MS calc: 354.2176; MS found: 354.2164

Preparation L (step E1)

Ethyl 8-oxo-5,6,7,8-tetrahydro-4H-cyclohepta[d]isoxazole-3-carboxylate and ethyl 8-oxo-5,6,7,8-tetrahydro-4H-cyclohepta[c]isoxazole-3-carboxylate

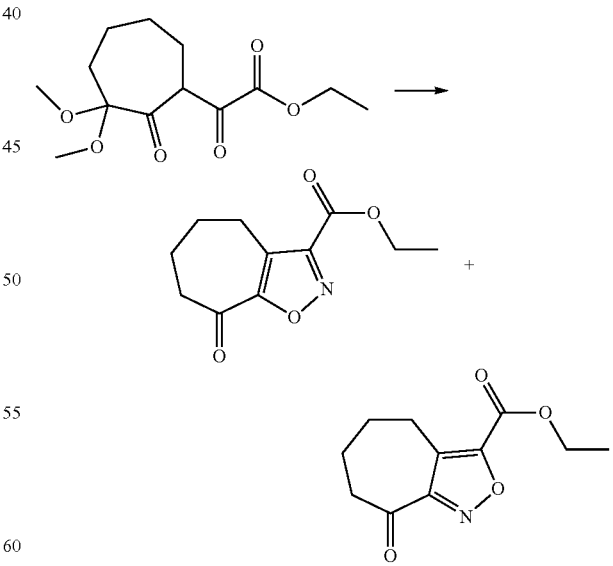

To a solution of ethyl (3,3-dimethoxy-2-oxocycloheptyl)(oxo)acetate (0.850 g, 3.12 mmol) in 15 mL of EtOH, hydroxylamine hydrochloride (0.225 g, 3.24 mmol) was added. The mixture was stirred at room temperature overnight. The solvent was removed under reduced pressure and the crude solid was purified by flash chromatography on silica gel (eluant: AcOEt/hexane:1/9) to afford 0.245 g (35% yield) of:

ethyl 8-oxo-5,6,7,8-tetrahydro-4H-cyclohepta[d]isoxazole-3-carboxylate

¹H NMR (401 MHz, DMSO-d6) δ ppm 1.33 (t, J=7.08 Hz, 3H) 1.80-1.89 (m, 2H) 1.89-1.99 (m, 2H) 2.74-2.84 (m, 2H) 2.96 (t, J=6.10 Hz, 2H) 4.38 (q, J=7.08 Hz, 2H) and 0.120 g (17% yield) of:

ethyl 8-oxo-5,6,7,8-tetrahydro-4H-cyclohepta[c]isoxazole-3-carboxylate

Preparation M (step H)

Ethyl (7E)-7-[(dimethylamino)methylidene]-1-methyl-8-oxo-1,4,5,6,7,8-hexahydrocyclohepta[c]pyrazole-3-carboxylate

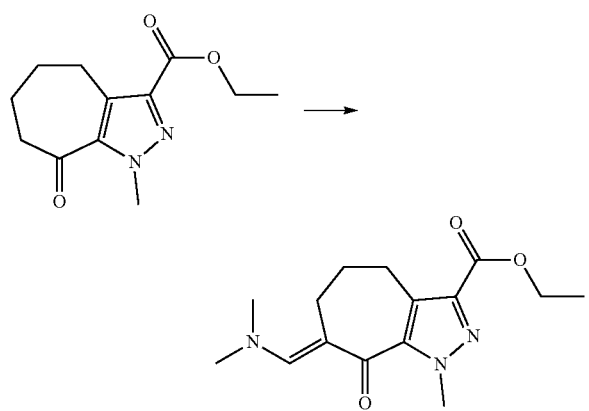

To a solution of ethyl 1-methyl-8-oxo-1,4,5,6,7,8-hexahydrocyclohepta[c]pyrazole-3-carboxylate (210 mg, 0.94 mmol) in DMF (2 mL), N,N-dimethylformamide di-tertbutyl acetal (0.68 mL, 2.82 mmol) was added. The mixture was stirred at 80° C. for 3 h. Solvent was removed under reduced pressure and the residue used without further purification.

¹H NMR (401 MHz, DMSO-d6) δ ppm 1.29 (t, J=7.08 Hz, 3H) 1.72-1.87 (m, 2H) 2.32 (t, J=6.47 Hz, 2H) 2.87 (t, J=7.08 Hz, 2H) 3.12 (s, 6H) 3.98 (s, 3H) 4.26 (q, J=7.08 Hz, 2H) 7.55 (s, 1H)

According to this same methodology, but employing suitable substituted derivatives, the following compounds were prepared:

(7E)-N-(2,6-diethylphenyl)-7-[(dimethylamino)methylidene]-1-methyl-8-oxo-1,4,5,6,7,8-hexahydrocyclohepta[c]pyrazole-3-carboxamide ¹H NMR (401 MHz, DMSO-d6) δ ppm 1.10 (t, J=7.57 Hz, 6H) 1.74-1.82 (m, 2H) 2.36 (t, J=6.40 Hz, 2H) 2.53 (q, J=7.57 Hz, 4H) 2.88-2.96 (m, 2H) 3.13 (s, 6H) 4.03 (s, 3H) (m, 2H) 7.09-7.13 (m, 2H) 7.17-7.22 (m, 1H) 7.55 (s, 1H) 9.45 (br.s., 1H)

MS calc: 395.2442; MS found: 395.2437

(7E)-7-[(dimethylamino)methylidene]-N-methoxy-N,1-dimethyl-8-oxo-1,4,5,6,7,8-hexahydrocyclohepta[c]pyrazole-3-carboxamide ¹H NMR (401 MHz, DMSO-d6) δ ppm 1.72-1.73 (m, 2H) 2.33 (t, J=6.47 Hz, 2H) 2.61 (t, J=7.20 Hz, 2H) 3.11 (s, 6H) 3.28 (s, 3H) 3.67 (s, 3H) 3.95 (s, 3H) 7.52 (s, 1H)

MS calc: 307.1765; MS found: 307.1761

(7E)-N-(2,6-diethylphenyl)-7-[(dimethylamino)methylidene]-1-(4-methoxybenzyl)-8-oxo-1,4,5,6,7,8-hexahydrocyclohepta[c]pyrazole-3-carboxamide ¹H NMR (401 MHz, DMSO-d6) δ ppm 1.10 (t, J=7.51 Hz, 6H) 1.77 (quin, J=6.60 Hz, 2H) 2.25 (t, J=6.60 Hz, 2H) 2.54 (q, J=7.51 Hz, 4H) 2.85-2.96 (m, 4H) 3.12 (s, 6H) 3.72 (s, 3H) 5.59 (s, 2H) 6.83-6.91 (m, 2H) 7.07-7.13 (m, 2H) 7.14-7.24 (m, 3H) 7.57 (s, 1H) 9.47 (s, 1H)

MS calc: 501.2860; MS found: 501.2856 ethyl (7E)-7-[(dimethylamino)methylidene]-8-oxo-5,6,7,8-tetrahydro-4H-cyclohepta[d]isoxazole-3-carboxylate ¹H NMR (401 MHz, DMSO-d6) δ ppm 1.33 (t, J=7.14 Hz, 3H) 1.83-1.93 (m, 2H) 2.53-2.59 (m, 2H) 2.84 (t, J=6.65 Hz, 2H) 3.12-3.17 (m, 6H) 4.37 (q, J=7.14 Hz, 2H) 7.61 (s, 1H)

MS calc: 279.1340; MS found: 279.1342 ethyl (7E)-7-[(dimethylamino)methylidene]-8-oxo-5,6,7,8-tetrahydro-4H-cyclohepta[c]isoxazole-3-carboxylate ethyl (7E)-7-[(dimethylamino)methylidene]-8-oxo-1,4,5,6,7,8-hexahydrocyclohepta[c]pyrazole-3-carboxylate ethyl (7E)-7-[(dimethylamino)methylidene]-2-methyl-8-oxo-2,4,5,6,7,8-hexahydrocyclohepta[c]pyrazole-3-carboxylate (7E)-7-[(dimethylamino)methylidene]-1-methyl-8-oxo-N-propyl-1,4,5,6,7,8-hexahydrocyclohepta[c]pyrazole-3-carboxamide (7E)-7-[(dimethylamino)methylidene]-1-methyl-8-oxo-1,4,5,6,7,8-hexahydrocyclohepta[c]pyrazole-3-carboxamide ethyl 5-acetyl-4-[(4Z)-5-(dimethylamino)pent-4-en-1-yl]-1-(2-hydroxyethyl)-1H-pyrazole-3-carboxylate ethyl 3-acetyl-4-[(4Z)-5-(dimethylamino)pent-4-en-1-yl]-1-(2-hydroxyethyl)-1H-pyrazole-5-carboxylate Example 1

Step I1 ethyl 9-amino-1-methyl-1,4,5,6-tetrahydropyrazolo[4',3':6,7]cyclohepta[1,2-d]pyrimidine-3-carboxylate

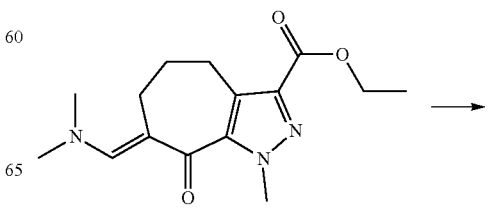

-continued

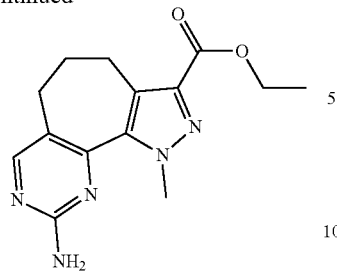

To a solution of ethyl (7E)-7-[(dimethylamino)methylidene]-1-methyl-8-oxo-1,4,5,6,7,8-hexahydrocyclohepta[c]pyrazole-3-carboxylate (240 mg, 0.86 mmol) in EtOH (7.5 mL), guanidine carbonate (86 mg, 0.47 mmol) was added. The reaction mixture was stirred under reflux for 24 h. The solvent was removed under reduced pressure, the crude was triturated with hexane and EtOH and collected by filtration to give 84 mg of a white solid (79% yield).

$^1$H NMR (401 MHz, DMSO-d6) δ ppm 1.30 (t, J=7.14 Hz, 3H) 1.86-1.97 (m, 2H) 2.45-2.50 (m, 2H) 2.96 (t, J=7.02 Hz, 2H) 4.20 (s, 3H) 4.28 (q, J=7.14 Hz, 2H) 6.58 (s, 2H) 8.17 (s, 1H)

MS calc: 288.1455; MS found: 288.1456

According to this same methodology, but employing suitable substituted derivatives, the following compounds were prepared:

9-amino-N-(2,6-diethylphenyl)-1-methyl-1,4,5,6-tetrahydropyrazolo[4',3':6,7]cyclohepta[1,2-d]pyrimidine-3-carboxamide (30)

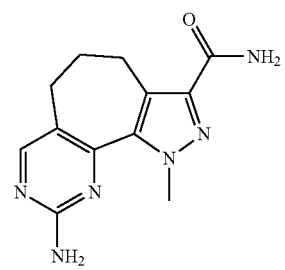

$^1$H NMR (401 MHz, DMSO-d6) δ ppm 1.11 (t, J=7.57 Hz, 6H) 1.84-1.97 (m, 2H) 2.49-2.58 (m, 6H) 2.99 (t, J=6.96 Hz, 2H) 4.25 (s, 3H) 6.57 (s, 2H) 7.07-7.15 (m, 2H) 7.16-7.24 (m, 1H) 8.18 (s, 1H) 9.47 (s, 1H)

MS calc: 391.2241; MS found: 391.2234

9-amino-1-methyl-N-propyl-1,4,5,6-tetrahydropyrazolo[4',3':6,7]cyclohepta[1,2-d]pyrimidine-3-carboxamide

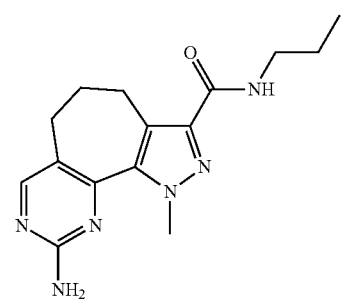 [SMILES: CCCNC(=O)c1nn(C)c2c1CCCc1cnc(N)nc1-2]

$^1$H NMR (401 MHz, DMSO-d6) δ ppm 0.86 (t, J=7.57 Hz, 3H) 1.44-1.59 (m, 2H) 1.84-1.96 (m, 2H) 2.42-2.48 (m, 2H) 2.98 (t, J=7.08 Hz, 2H) 3.12-3.21 (m, 2H) 4.17 (s, 3H) 6.55 (s, 2H) 8.01 (t, J=5.92 Hz, 1H) 8.16 (s, 1H)

MS calc: 301.1772; MS found: 301.1771

9-amino-1-methyl-1,4,5,6-tetrahydropyrazolo[4',3':6,7]cyclohepta[1,2-d]pyrimidine-3-carboxamide (44)

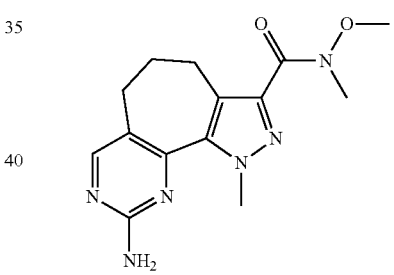

$^1$H NMR (401 MHz, DMSO-d6) δ ppm 1.84-1.96 (m, 2H) 2.42-2.48 (m, 2H) 2.99 (t, J=7.08 Hz, 3H) 4.17 (s, 3H) 6.54 (s, 2H) 7.15 (br. s., 1H) 7.38 (br. s., 1H) 8.16 (s, 1H)

MS calc: 259.1302; MS found: 259.1309

9-amino-N-methoxy-N,1-dimethyl-1,4,5,6-tetrahydropyrazolo[4',3':6,7]cyclohepta[1,2-d]pyrimidine-3-carboxamide

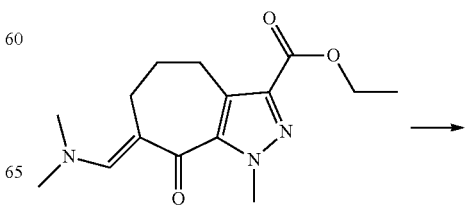

Example 2

Step I2

Ethyl 9-[(4-bromo-2-methoxyphenyl)amino]-1-methyl-1,4,5,6-tetrahydropyrazolo[4',3':6,7]cyclohepta[1,2-d]pyrimidine-3-carboxylate ethyl 9-{[2-methoxy-4-(4-methylpiperazin-1-yl)phenyl]amino}-1,4,5,6-tetrahydropyrazolo[4',3':6,7]cyclohepta[1,2-d]pyrimidine-3-carboxylate (6)

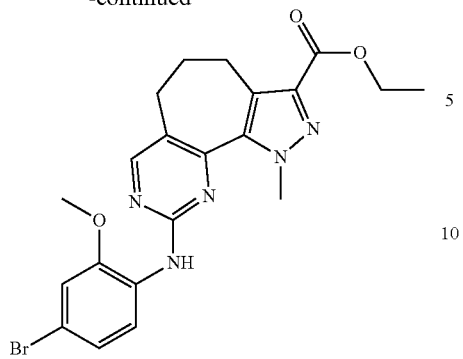

To a suspension of ethyl (7E)-7-[(dimethylamino)methylidene]-1-methyl-8-oxo-1,4,5,6,7,8-hexahydrocyclohepta[c]pyrazole-3-carboxylate 1.72 g (5.92 mmol) in 20 mL of DMF N-(4-Bromo-2-methoxy-phenyl)-guanidine 1.60 g (6.511 mmol) was added. The mixture was stirred at 120° C. for 4 h. The resulting mixture was cooled at room temperature and dried to dryness. The crude solid was purified by flash chromatography on silica gel (eluant: AcOEt/hexane 4/6) to afford 2.30 g (82% yield) of the title compound as a yellow solid.

$^1$H NMR (401 MHz, DMSO-d6) δ ppm 1.30 (t, J=7.14 Hz, 3H) 1.89-2.08 (m, 2H) 2.55-2.62 (m, 2H) 2.98 (t, J=7.07 Hz, 2H) 3.86 (s, 3H) 4.12 (s, 3H) 4.28 (q, J=7.14 Hz, 2H) 7.15 (dd, J=8.50, 2.10 Hz, 1H) 7.23 (d, J=2.10 Hz, 1H) 7.95 (d, J=8.50 Hz, 1H) 8.29 (s, 1H) 8.40 (s, 1H)

MS calc: 472.0979; MS found: 472.0972

According to this same methodology, but employing suitable substituted derivatives, the following compounds were prepared:

ethyl 9-[(4-bromo-2-methoxyphenyl)amino]-1,4,5,6-tetrahydropyrazolo[4',3':6,7]cyclohepta[1,2-d]pyrimidine-3-carboxylate

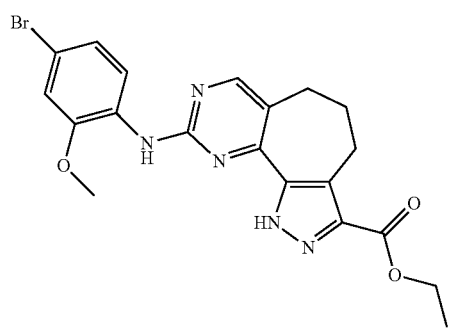 [SMILES: CCOC(=O)c1n[nH]c2c1CCCc1cnc(Nc3ccc(Br)cc3OC)nc1-2]

$^1$H NMR (401 MHz, DMSO-d6) δ ppm 1.32 (t, J=7.14 Hz, 3H) 1.87-1.99 (m, 2H) 2.76-2.85 (m, 2H) 3.10 (t, J=6.04 Hz, 2H) 3.93 (s, 3H) 4.30 (q, J=7.14 Hz, 2H) 7.15 (dd, J=8.54, 1.95 Hz, 1H) 7.23 (d, J=1.95 Hz, 1H) 7.87 (s, 1H) 8.40 (d, J=8.54 Hz, 1H) 8.41 (s, 1H) 13.88 (s, 1H)

MS calc: 458.0823; MS found: 458.0812

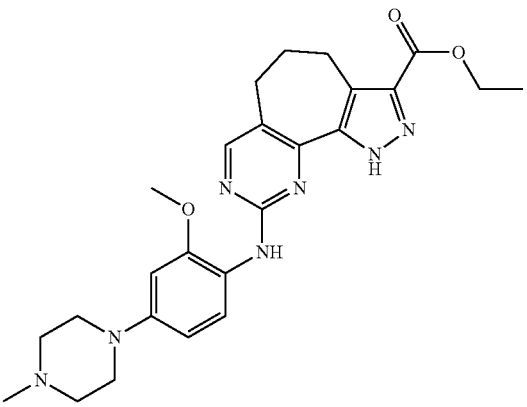 [SMILES: CCOC(=O)c1n[nH]c2c1CCCc1cnc(Nc3ccc(N4CCN(C)CC4)cc3OC)nc1-2]

$^1$H NMR (401 MHz, DMSO-d6) δ ppm 1.31 (t, J=7.14 Hz, 3H) 1.84-1.96 (m, 2H) 2.26 (br.s., 3H) 2.51-2.56 (m, 4H) 2.72-2.80 (m, 2H) 3.04-3.19 (m, 6H) 3.87 (s, 3H) 4.29 (q, J=7.14 Hz, 1H) 6.51 (dd, J=8.79 and 2.44 Hz, 1H) 6.67 (d, J=2.44 Hz, 1H) 7.63 (s, 1H) 8.10 (d, J=8.79 Hz, 1H) 8.31 (s, 1H) 13.81 (br. s., 1H)

MS calc: 478.2561; MS found: 478.2539 methyl 1-methyl-9-({4-[(4-methylpiperazin-1-yl)sulfonyl]phenyl}amino)-1,4,5,6-tetrahydropyrazolo[4',3':6,7]cyclohepta[1,2-d]pyrimidine-3-carboxylate $^1$H NMR (401 MHz, DMSO-d6) δ ppm 1.96-2.07 (m, 2H) 2.14 (s, 3H) 2.31-2.40 (m, 4H) 2.59-2.65 (m, 2H) 2.82-2.92 (m, 4H) 3.00 (t, J=7.08 Hz, 2H) 3.82 (s, 3H) 4.24 (s, 3H) 7.64-7.70 (m, 2H) 7.91-8.08 (m, 2H) 8.53 (s, 1H) 10.13 (s, 1H)

MS calc: 512.2075; MS found: 512.2067

65

N-(2,6-diethylphenyl)-9-[(2-methoxyphenyl)amino]-1-methyl-1,4,5,6-tetrahydropyrazolo[4',3':6,7]cyclohepta[1,2-d]pyrimidine-3-carboxamide (24)

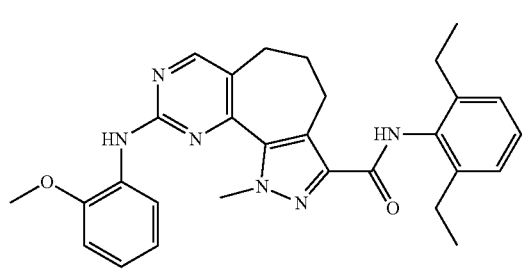 [SMILES: CCc1cccc(CC)c1NC(=O)c1nn(C)c2c1CCCc1cnc(Nc3ccccc3OC)nc1-2]

¹H NMR (401 MHz, DMSO-d6) δ ppm 1.11 (t, J=7.57 Hz, 6H) 1.91-2.01 (m, 2H) 2.51-2.63 (m, 6H) 3.02 (t, J=7.08 Hz, 2H) 3.85 (s, 3H) 4.15 (s, 3H) 6.93-7.01 (m, 1H) 7.04-7.08 (m, 2H) 7.10-7.14 (m, 2H) 7.18-7.23 (m, 1H) 8.00 (d, J=7.69 Hz, 1H) 8.21 (s, 1H) 8.39 (s, 1H) 9.50 (s, 1H)

MS calc: 497.2660; MS found: 497.2648

N-(2,6-diethylphenyl)-1-methyl-9-{[4-(4-methylpiperazin-1-yl)phenyl]amino}-1,4,5,6-tetrahydropyrazolo[4',3':6,7]cyclohepta[1,2-d]pyrimidine-3-carboxamide (29)

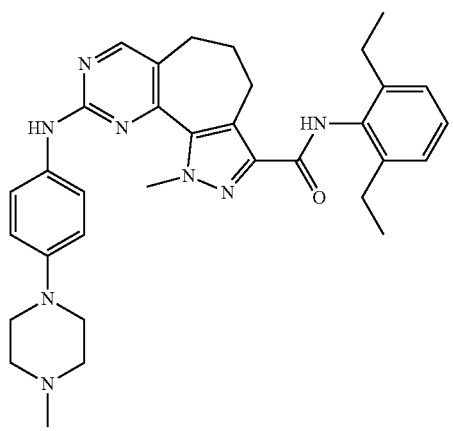 [SMILES: CCc1cccc(CC)c1NC(=O)c1nn(C)c2c1CCCc1cnc(Nc3ccc(N4CCN(C)CC4)cc3)nc1-2]

¹H NMR (401 MHz, DMSO-d6) δ ppm 1.12 (t, J=7.57 Hz, 6H) 1.1-2.01 (m, 2H) 2.22 (s, 3H) 2.43-2.48 (m, 4H) 2.52-2.62 (m, 6H) 3.01 (t, J=7.02 Hz, 2H) 3.04-3.11 (m, 4H) 4.21 (s, 3H) 6.87-6.95 (m, 2H) 7.10-7.15 (m, 2H) 7.17-7.23 (m, 1H) 7.50-7.57 (m, 2H) 8.36 (s, 1H) 9.28 (s, 1H) 9.48 (s, 1H)

MS calc: 565.3398; MS found: 565.3387

66

1-methyl-9-({4-[(4-methylpiperazin-1-yl)sulfonyl]phenyl}amino)-1,4,5,6-tetrahydropyrazolo[4',3':6,7]cyclohepta[1,2-d]pyrimidine-3-carboxamide (45)

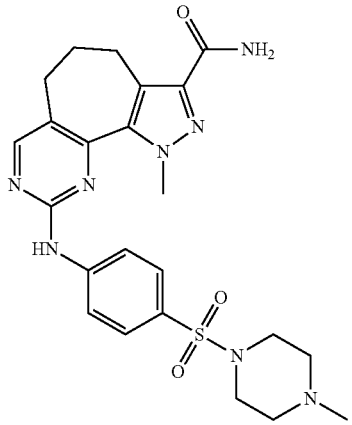 [SMILES: CN1CCN(S(=O)(=O)c2ccc(Nc3ncc4c(n3)-c3c(c(C(N)=O)nn3C)CCC4)cc2)CC1]

¹H NMR (401 MHz, DMSO-d6) δ ppm 1.62 (br. s., 3H) 1.88-2.02 (m, 2H) 2.07-2.23 (m, 2H) 2.25-2.43 (m, 4H) 2.78-2.95 (m, 4H) 3.05 (t, J=7.14 Hz, 2H) 4.27 (s, 3H) 7.06 (br. s., 1H) 7.14 (br. s., 1H) 7.64-7.74 (m, 2H) 8.06-8.14 (m, 2H) 8.10 (s, 1H) 10.50 (s, 1H)

MS calc: 497.2078; MS found: 497.2080

1-methyl-9-[(4-nitrophenyl)amino]-N-propyl-1,4,5,6-tetrahydropyrazolo[4',3':6,7]cyclohepta[1,2-d]pyrimidine-3-carboxamide (46)

¹H NMR (401 MHz, DMSO-d6) δ ppm 0.87 (t, J=7.38 Hz, 3H) 1.39-1.59 (m, 2H) 1.96-2.05 (m, 2H) 2.56-2.64 (m, 2H) 3.03 (t, J=7.08 Hz, 2H) 3.15-3.25 (m, 2H) 4.22 (s, 3H) 7.97-8.05 (m, 2H) 8.09 (t, J=6.04 Hz, 1H) 8.20-8.26 (m, 2H) 8.56 (s, 1H) 10.39 (s, 1H)

MS calc: 422.1935; MS found: 422.1933

9-[(4-bromo-2-methoxyphenyl)amino]-N-(2,6-diethylphenyl)-1-(4-methoxybenzyl)-1,4,5,6-tetrahydropyrazolo[4',3':6,7]cyclohepta[1,2-d]pyrimidine-3-carboxamide

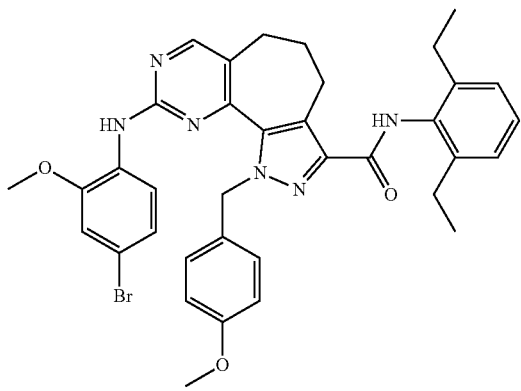 [SMILES: CCc1cccc(CC)c1NC(=O)c1nn(Cc2ccc(OC)cc2)c2c1CCCc1cnc(Nc3ccc(Br)cc3OC)nc1-2]

1-methyl-9-({4-[(4-methylpiperazin-1-yl)sulfonyl]phenyl}amino)-N-propyl-1,4,5,6-tetrahydropyrazolo[4',3':6,7]cyclohepta[1,2-d]pyrimidine-3-carboxamide (50)

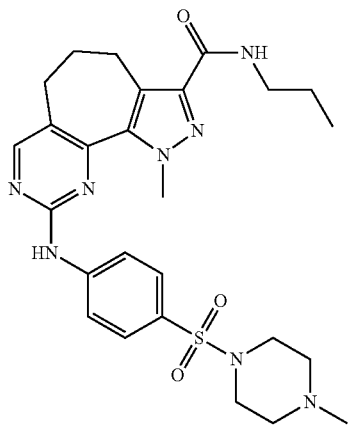 [SMILES: CCCNC(=O)c1nn(C)c2c1CCCc1cnc(Nc3ccc(S(=O)(=O)N4CCN(C)CC4)cc3)nc1-2]

$^1$H NMR (401 MHz, DMSO-d6) δ ppm 0.87 (t, J=7.38 Hz, 3H) 1.45-1.58 (m, 2H) 1.92-2.04 (m, 2H) 2.14 (s, 3H) 2.31-2.41 (m, 4H) 2.55-2.64 (m, 2H) 2.82-2.92 (m, 4H) 3.02 (t, J=7.08 Hz, 2H) 3.15-3.23 (m, 2H) 4.21 (s, 3H) 7.62-7.72 (m, 2H) 7.97-8.03 (m, 2H) 8.07 (t, J=6.04 Hz, 1H) 8.52 (s, 1H) 10.12 (s, 1H)

MS calc: 539.2548; MS found: 539.2548

9-[(4-acetylphenyl)amino]-1-methyl-N-propyl-1,4,5,6-tetrahydropyrazolo[4',3':6,7]cyclohepta[1,2-d]pyrimidine-3-carboxamide (51)

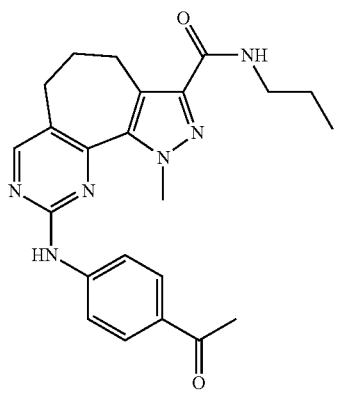 [SMILES: CCCNC(=O)c1nn(C)c2c1CCCc1cnc(Nc3ccc(C(C)=O)cc3)nc1-2]

$^1$H NMR (401 MHz, DMSO-d6) δ ppm 0.87 (t, J=7.38 Hz, 3H) 1.48-1.56 (m, 2H) 1.96-2.03 (m, 2H) 2.55-2.62 (m, 2H) 3.03 (t, J=7.02 Hz, 2H) 3.15-3.23 (m, 2H) 4.21 (s, 3H) 7.87-7.96 (m, 4H) 8.07 (t, J=6.10 Hz, 1H) 8.51 (s, 1H) 10.03 (s, 1H)

MS calc: 419.2190; MS found: 419.2192

9-[(5-bromo-2-methylphenyl)amino]-1-methyl-1,4,5,6-tetrahydropyrazolo[4',3':6,7]cyclohepta[1,2-d]pyrimidine-3-carboxamide (65)

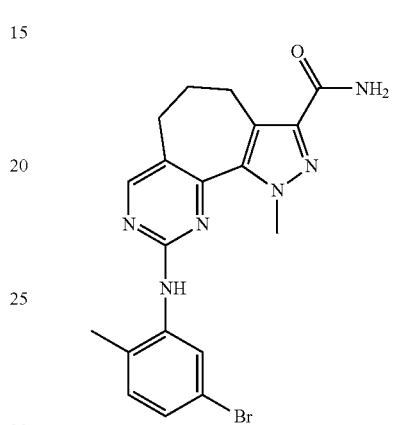

$^1$H NMR (401 MHz, DMSO-d6) δ ppm 1.89-1.97 (m, 2H) 2.24 (s, 3H) 2.52-2.57 (m, 2H) 3.01 (t, J=7.02 Hz, 2H) 3.98 (s, 3H) 7.16 (br. s., 1H) 7.33-7.37 (m, 1H) 7.38 (br. s., 1H) 7.44 (d, J=1.71 Hz, 1H) 7.47-7.49 (m, 1H) 8.32 (s, 1H) 8.78 (s, 1H)

MS calc: 427.0877; MS found: 427.0875

1-methyl-9-[(5-nitro-1H-benzimidazol-2-yl)amino]-1,4,5,6-tetrahydropyrazolo[4',3':6,7]cyclohepta[1,2-d]pyrimidine-3-carboxamide (66)

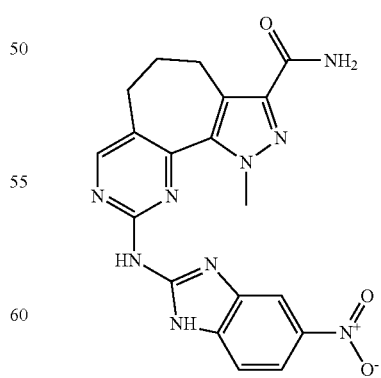

MS calc: 420.1527; MS found: 420.1537

69 ethyl 1-methyl-9-{[4-(4-methylpiperazin-1-yl)phenyl]amino}-1,4,5,6-tetrahydropyrazolo[4',3':6,7]cyclohepta[1,2-d]pyrimidine-3-carboxylate hydrochloride

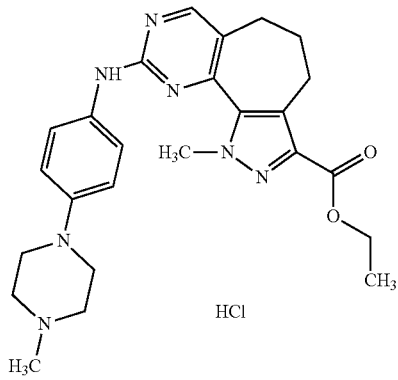 [SMILES: CCOC(=O)c1nn(C)c2c1CCCc1cnc(Nc3ccc(N4CCN(C)CC4)cc3)nc1-2 ; Cl]

MS calc: 462.2612; MS found: 462.2629

1-methyl-9-{[5-(4-methylpiperazin-1-yl)-2-(trifluoromethoxy)phenyl]amino}-1,4,5,6-tetrahydropyrazolo[4',3':6,7]cyclohepta[1,2-d]pyrimidine-3-carboxamide (68)

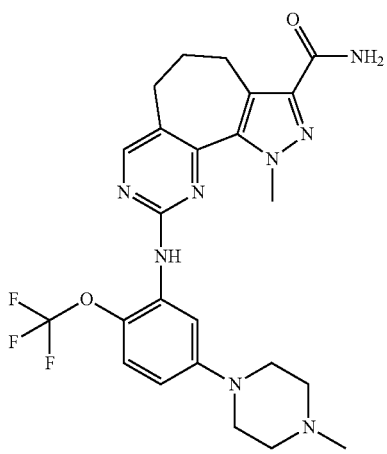 [SMILES: CN1CCN(c2ccc(OC(F)(F)F)c(Nc3ncc4c(n3)-c3c(c(C(N)=O)nn3C)CCC4)c2)CC1]

MS calc: 517.2282; MS found: 517.2277

N-methoxy-N,1-dimethyl-9-{[3-(trifluoromethyl)phenyl]amino}-1,4,5,6-tetrahydropyrazolo[4',3':6,7]cyclohepta[1,2-d]pyrimidine-3-carboxamide (72)

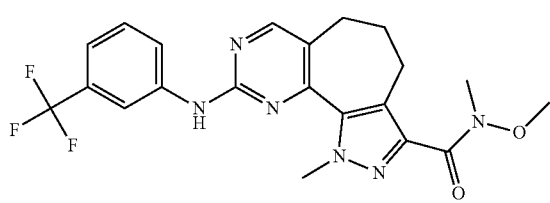 [SMILES: CON(C)C(=O)c1nn(C)c2c1CCCc1cnc(Nc3cccc(C(F)(F)F)c3)nc1-2]

MS calc: 447.1751; MS found: 447.1738

70

1-methyl-9-(phenylamino)-1,4,5,6-tetrahydropyrazolo[4',3':6,7]cyclohepta[1,2-d]pyrimidine-3-carboxamide trifluoroacetate (73)

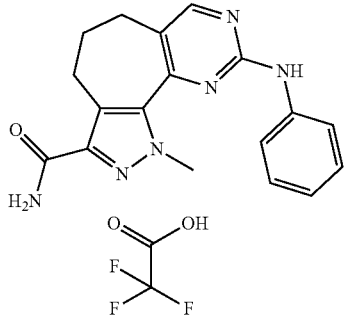

$^1$H NMR (401 MHz, DMSO-d6) δ ppm 1.89-2.04 (m, 2H) 2.53-2.60 (m, 2H) 3.02 (t, J=7.02 Hz, 2H) 4.23 (s, 3H) 6.96 (t, J=7.32 Hz, 1H) 7.19 (br. s., 1H) 7.26-7.34 (m, 2H) 7.42 (br. s., 1H) 7.72 (d, J=7.69 Hz, 2H) 8.41 (s, 1H) 9.53 (s, 1H)

MS calc: 335.1615; MS found: 335.1622 ethyl 9-({2-methoxy-4-[(1-methylpiperidin-4-yl)carbamoyl]phenyl}amino)-1-methyl-1,4,5,6-tetrahydropyrazolo[4',3':6,7]cyclohepta[1,2-d]pyrimidine-3-carboxylate

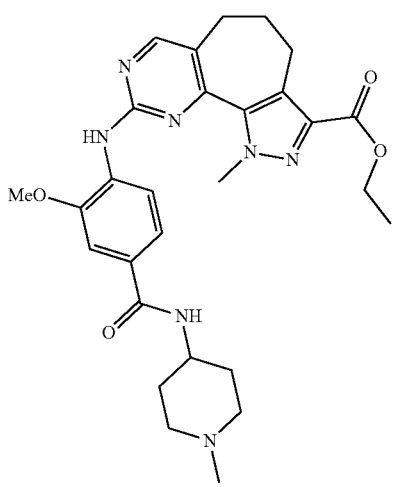 [SMILES: CCOC(=O)c1nn(C)c2c1CCCc1cnc(Nc3ccc(C(=O)NC4CCN(C)CC4)cc3OC)nc1-2]

1-methyl-9-{[3-(trifluoromethyl)phenyl]amino}-1,4,5,6-tetrahydropyrazolo[4',3':6,7]cyclohepta[1,2-d]pyrimidine-3-carboxamide (77),

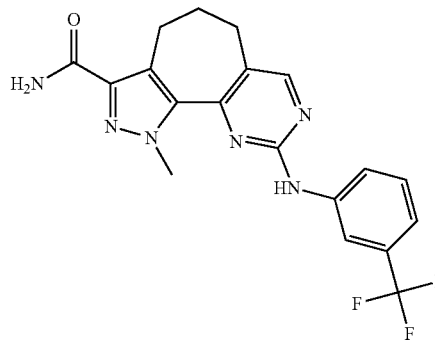

¹H NMR (401 MHz, DMSO-d6) δ ppm 1.93-2.03 (m, 2H) 2.55-2.61 (m, 2H) 3.02 (t, J=7.08 Hz, 2H) 4.18 (s, 3H) 7.20 (br. s., 1H) 7.28 (d, J=8.06 Hz, 1H) 7.45 (br. s., 1H) 7.53 (t, J=8.06 Hz, 1H) 7.96 (d, J=8.06 Hz, 1H) 8.24 (s, 1H) 8.49 (s, 1H) 9.92 (s, 1H)

MS calc: 403.1489; MS found: 403.1480

9-(benzylamino)-1-methyl-1,4,5,6-tetrahydropyrazolo[4',3':6,7]cyclohepta[1,2-d]pyrimidine-3-carboxamide (79)

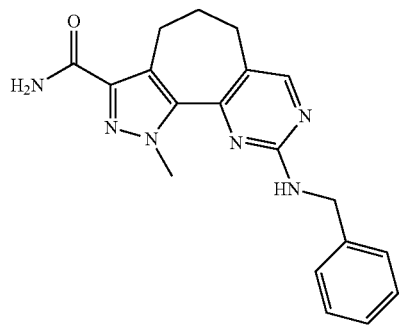 [SMILES: Cn1nc(C(N)=O)c2c1-c1nc(NCc3ccccc3)ncc1CCC2]

¹H NMR (401 MHz, DMSO-d6) δ ppm 1.83-1.95 (m, 2H) 2.44-2.49 (m, 2H) 2.98 (t, J=7.02 Hz, 2H) 3.96 (br. s., 3H) 4.52-4.57 (m, 2H) 7.15 (br. s., 1H) 7.18-7.24 (m, 1H) 7.28-7.34 (m, 4H) 7.37 (br. s., 1H) 7.76 (br. s., 1H) 8.22 (s, 1H)
MS calc: 349.1772; MS found: 349.1761

1-methyl-9-{[4-(4-methylpiperazin-1-yl)phenyl]amino}-1,4,5,6-tetrahydropyrazolo[4',3':6,7]cyclohepta[1,2-d]pyrimidine-3-carboxamide trifluoroacetate (67)

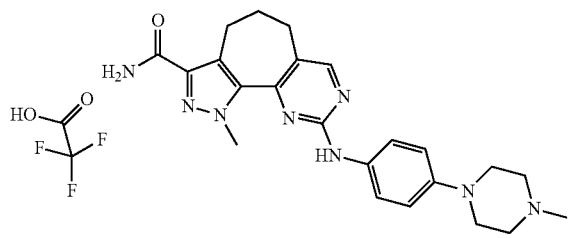 [SMILES: O=C(O)C(F)(F)F ; CN1CCN(c2ccc(Nc3ncc4c(n3)-c3c(c(C(N)=O)nn3C)CCC4)cc2)CC1]

¹H NMR (401 MHz, DMSO-d6) δ ppm 1.82-2.05 (m, 2H) 2.52-2.57 (m, 2H) 2.79-2.96 (m, 5H) 3.01 (t, J=7.02 Hz, 3H) 3.12-3.23 (m, 2H) 3.48-3.61 (m, 2H) 3.68-3.80 (m, 2H) 4.15 (s, 3H) 6.82-7.07 (m, 2H) 7.20 (br. s., 1H) 7.38 (br. s., 1H) 7.53-7.64 (m, 2H) 8.36 (s, 1H) 9.35 (s, 1H) 9.57 (br. s., 1H)

MS calc: 433.2459; MS found: 433.2470 ethyl 2-methyl-9-{[4-(4-methylpiperazin-1-yl)phenyl]amino}-2,4,5,6-tetrahydropyrazolo[4',3':6,7]cyclohepta[1,2-d]pyrimidine-3-carboxylate

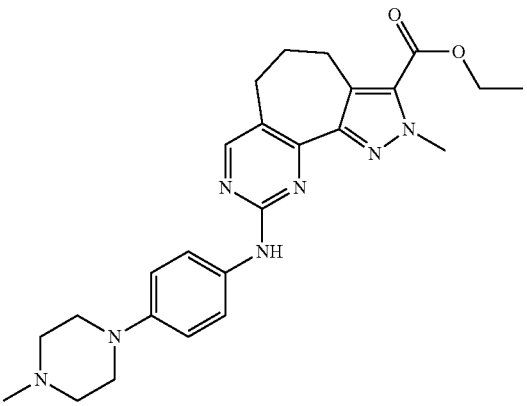 [SMILES: CCOC(=O)c1c2c(nn1C)-c1nc(Nc3ccc(N4CCN(C)CC4)cc3)ncc1CCC2]

¹H NMR (401 MHz, DMSO-d6) δ ppm 1.32 (t, J=7.08 Hz, 3H) 1.85-1.98 (m, 2H) 2.19 (s, 3H) 2.58-2.68 (m, 2H) 2.91-3.10 (m, 6H) 4.14 (s, 3H) 4.32 (q, J=7.08 Hz, 2H) 6.83 (d, J=9.03 Hz, 2H) 7.68 (d, J=9.03 Hz, 2H) 8.23 (s, 1H) 9.27 (s, 1H)

MS calc: 462.2612; MS found: 462.2619 ethyl 9-[(4-bromo-2-methoxyphenyl)amino]-2-methyl-2,4,5,6-tetrahydropyrazolo[4',3':6,7]cyclohepta[1,2-d]pyrimidine-3-carboxylate

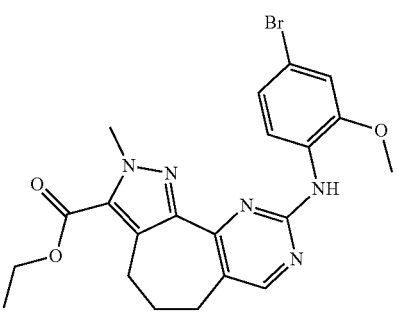 [SMILES: CCOC(=O)c1c2c(nn1C)-c1nc(Nc3ccc(Br)cc3OC)ncc1CCC2]

¹H NMR (401 MHz, DMSO-d6) δ ppm 1.35 (t, J=7.08 Hz, 3H) 1.89-1.98 (m, 2H) 2.68-2.76 (m, 2H) 3.05 (t, J=6.47 Hz, 2H) 3.92 (s, 3H) 4.19 (s, 3H) 4.35 (q, J=7.08 Hz, 2H) 7.15 (dd, J=8.67, 2.20 Hz, 1H) 7.20 (d, J=2.20 Hz, 1H) 7.90 (s, 1H) 8.35 (s, 1H) 8.52 (d, J=8.67 Hz, 1H)

MS calc: 472.0979; MS found: 472.0979

73 ethyl 9-[(4-bromo-2-methoxyphenyl)amino]-5,6-dihydro-4H-isoxazolo[4',3':6,7]cyclohepta[1,2-d]pyrimidine-3-carboxylate

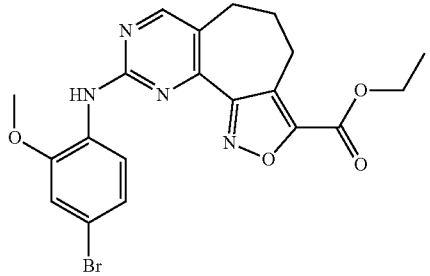 [SMILES: CCOC(=O)c1onc2c1CCCc1cnc(Nc3ccc(Br)cc3OC)nc1-2]

¹H NMR (401 MHz, DMSO-d6) δ ppm 1.35 (t, J=7.08 Hz, 3H) 1.89-2.05 (m, 2H) 2.43-2.47 (m, 2H) 3.01 (t, J=6.20 Hz, 2H) 3.89 (s, 3H) 4.36-4.43 (m, 2H) 7.14-7.20 (m, 1H) 7.22-7.25 (m, 1H) 8.22 (s, 1H) 8.31 (s, 1H) 8.48 (s, 1H)

MS calc: 459.0663; MS found: 459.0684 ethyl 9-[(4-bromo-2-methoxyphenyl)amino]-5,6-dihydro-4H-isoxazolo[4',5':6,7]cyclohepta[1,2-d]pyrimidine-3-carboxylate

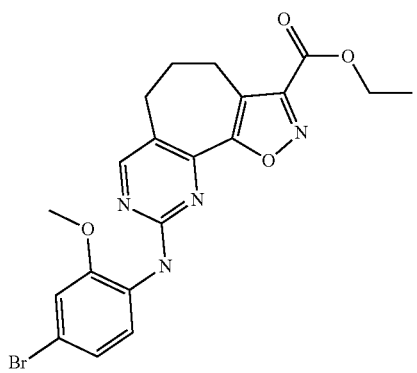 [SMILES: CCOC(=O)c1noc2c1CCCc1cnc(Nc3ccc(Br)cc3OC)nc1-2]

ethyl 1-methyl-9-[(3-nitrophenyl)amino]-1,4,5,6-tetrahydropyrazolo[4',3':6,7]cyclohepta[1,2-d]pyrimidine-3-carboxylate

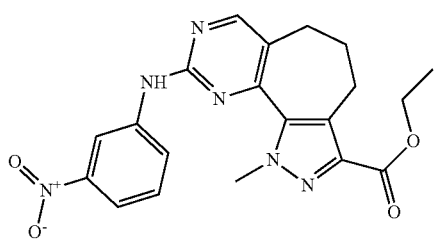 [SMILES: CCOC(=O)c1nn(C)c2c1CCCc1cnc(Nc3cccc([N+](=O)[O-])c3)nc1-2]

MS calc: 409.1619; MS found: 409.1614

74

Example 3

Conv 1

N-(2,6-diethylphenyl)-9-{[2-methoxy-4-(4-methylpiperazin-1-yl)phenyl]amino}-1,4,5,6-tetrahydropyrazolo[4',3':6,7]cyclohepta[1,2-d]pyrimidine-3-carboxamide (49)

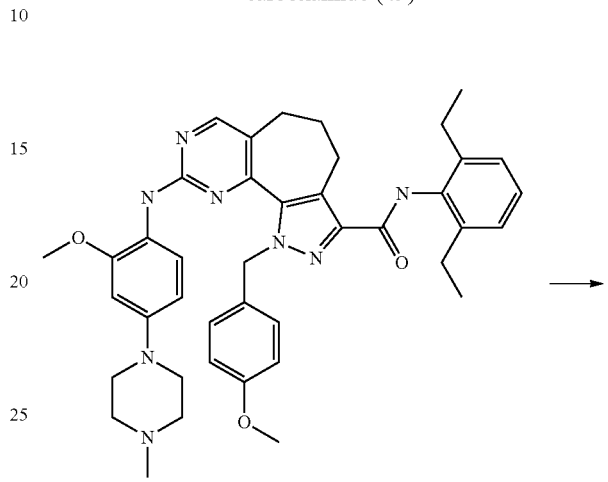

N-(2,6-diethylphenyl)-1-(4-methoxybenzyl)-9-{[2-methoxy-4-(4-methylpiperazin-1-yl)phenyl]amino}-1,4,5,6-tetrahydropyrazolo[4',3':6,7]cyclohepta[1,2-d]pyrimidine-3-carboxamide (0.905, 1.29 mmol) was dissolved in TFA. The mixture was stirred for 2 hours at 70° C. The organic solvent was evaporated to dryness and the residue was dissolved in DCM (50 mL) and washed with NaHCO₃. The organic layer was dried over anhydrous NaSO₄ and the solvent evaporated to dryness. The crude solid was purified by flash chromatography on silica gel eluant: DCM/MeOH:95/5) to afford 0.628 mg (84% yield) of the title compound.

¹H NMR (401 MHz, DMSO-d6) δ ppm 1.12 (t, J=7.57 Hz, 6H) 1.85-1.95 (m, 2H) 2.24 (s, 3H) 2.44-2.49 (m, 4H) 2.57 (q, J=7.57 Hz, 4H) 2.73-2.82 (m, 2H) 3.06-3.17 (m, 6H) 3.88 (s, 3H) 6.52 (dd, J=8.79, 2.56 Hz, 1H) 6.67 (d, J=2.56 Hz, 1H) 7.10-7.15 (m, 2H) 7.18-7.25 (m, 1H) 7.63 (s, 1H) 8.13 (d, J=8.79 Hz, 1H) 8.32 (s, 1H) 9.50 (s, 1H) 13.69 (s, 1H)

MS calc: 581.3347; MS found: 581.3331

According to this same methodology, but employing suitable substituted derivatives, the following compound was prepared:

N-(2,6-diethylphenyl)-9-({4-[4-(dimethylamino)piperidin-1-yl]-2-methoxyphenyl}amino)-1,4,5,6-tetrahydropyrazolo[4',3':6,7]cyclohepta[1,2-d]pyrimidine-3-carboxamide (62)

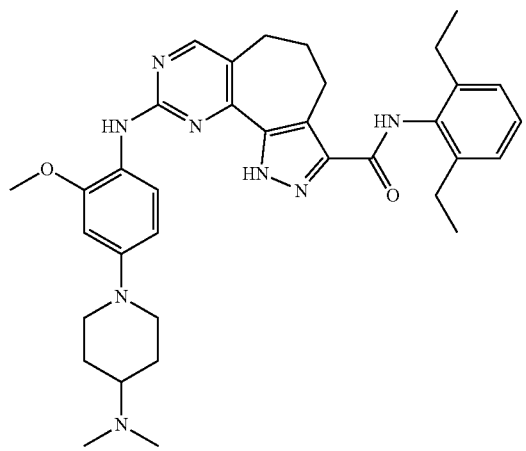 [SMILES: CCc1cccc(CC)c1NC(=O)c1n[nH]c2c1CCCc1cnc(Nc3ccc(N4CCC(N(C)C)CC4)cc3OC)nc1-2]

$^1$H NMR (401 MHz, DMSO-d6) δ ppm 1.12 (t, J=7.57 Hz, 6H) 1.42-1.57 (m, 2H) 1.80-1.95 (m, 4H) 2.20 (s, 6H) 2.57 (q, J=7.57 Hz, 4H) 2.60-2.70 (m, 2H) 2.71-2.81 (m, 2H) 3.12 (t, J=6.16 Hz, 2H) 3.61-3.70 (m, 2H) 3.87 (s, 3H) 6.52 (dd, J=8.79, 2.50 Hz, 1H) 6.66 (d, J=2.50 Hz, 1H) 7.10-7.15 (m, 2H) 7.19 (s, 1H) 7.64 (s, 1H) 8.11 (d, J=8.79 Hz, 1H) 8.29 (s, 1H) 9.48 (br. s., 1H)

MS calc: 609.3660; MS found: 609.3660

Example 4

Conv 2

Ethyl 9-[(4-bromo-2-methoxyphenyl)amino]-1-methyl-1,4,5,6-tetrahydropyrazolo[4',3':6,7]cyclohepta[1,2-d]pyrimidine-3-carboxylate and ethyl 9-[(4-bromo-2-methoxyphenyl)amino]-2-methyl-2,4,5,6-tetrahydropyrazolo[4',3':6,7]cyclohepta[1,2-d]pyrimidine-3-carboxylate

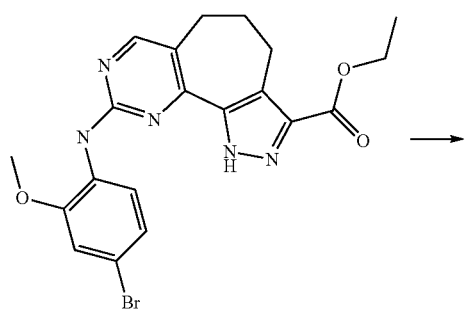 →

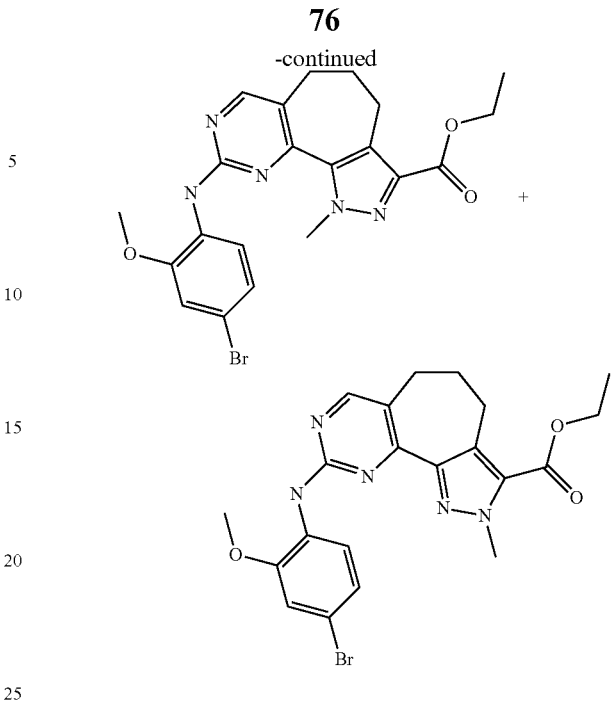

To a solution of ethyl 9-[(4-bromo-2-methoxyphenyl)amino]-1,4,5,6-tetrahydropyrazolo[4',3':6,7]cyclohepta[1,2-d]pyrimidine-3-carboxylate (0.155 g, 0.338 mmol) in DMF (4 mL), Cs$_2$CO$_3$ (0.165 g, 0.506 mmol) and methyl iodide (0.019 mL, 0.304 mmol) were added. The reaction was stirred at room temperature for 1 h, solvent was removed under vacuo, then AcOEt (20 mL) was added and the organic phase washed with water (20 mL). The aqueous fraction was extracted with AcOEt (20 mL). The organic fractions were combined, dried over Na$_2$SO$_4$, filtered, and concentrated in vacuo. Purification by flash chromatography on silica gel (eluant: AcOEt/hexane 3/7) provided 0.040 g (25% yield) of ethyl 9-[(4-bromo-2-methoxyphenyl)amino]-1-methyl-1,4,5,6-tetrahydropyrazolo[4',3':6,7]cyclohepta[1,2-d]pyrimidine-3-carboxylate $^1$H NMR (401 MHz, DMSO-d6) δ ppm 1.30 (t, J=7.14 Hz, 3H) 1.89-2.08 (m, 2H) 2.55-2.62 (m, 2H) 2.98 (t, J=7.07 Hz, 2H) 3.86 (s, 3H) 4.12 (s, 3H) 4.28 (q, J=7.14 Hz, 2H) 7.15 (dd, J=8.50, 2.10 Hz, 1H) 7.23 (d, J=2.10 Hz, 1H) 7.95 (d, J=8.50 Hz, 1H) 8.29 (s, 1H) 8.40 (s, 1H)

MS calc: 472.0979; MS found: 472.0972 and 0.045 g (28% yield) of ethyl 9-[(4-bromo-2-methoxyphenyl)amino]-2-methyl-2,4,5,6-tetrahydropyrazolo[4',3':6,7]cyclohepta[1,2-d]pyrimidine-3-carboxylate $^1$H NMR (401 MHz, DMSO-d6) δ ppm 1.35 (t, J=7.08 Hz, 3H) 1.89-1.98 (m, 2H) 2.68-2.76 (m, 2H) 3.05 (t, J=6.47 Hz, 2H) 3.92 (s, 3H) 4.19 (s, 3H) 4.35 (q, J=7.08 Hz, 2H) 7.15 (dd, J=8.67, 2.20 Hz, 1H) 7.20 (d, J=2.20 Hz, 1H) 7.90 (s, 1H) 8.35 (s, 1H) 8.52 (d, J=8.67 Hz, 1H)

MS calc: 472.0979; MS found: 472.0979

According to this same methodology, but employing suitable substituted derivatives, the following compound was prepared:

ethyl 1-[3-(dimethylamino)propyl]-9-(methylsulfanyl)-1,4,5,6-tetrahydropyrazolo[4',3':6,7]cyclohepta[1,2-d]pyrimidine-3-carboxylate $^1$H NMR (401 MHz, DMSO-d6) δ ppm 1.31 (t, J=7.08 Hz, 3H) 1.80-1.92 (m, 2H) 1.97-2.08 (m, 8H) 2.19 (t, J=7.08 Hz, 2H) 2.57 (s, 3H) 2.58-2.63 (m, 2H) 2.97 (t, J=7.08 Hz, 2H) 4.29 (q, J=7.08 Hz, 2H) 4.66 (t, J=7.32 Hz, 2H) 8.60 (s, 1H)
MS calc: 390.1958; MS found: 390.1951

Example 5

Conv. 3

N-(2,6-diethylphenyl)-1-ethyl-9-{[2-methoxy-4-(4-methyl piperazin-1-yl)phenyl]amino}-1,4,5,6-tetrahydropyrazolo[4',3':6,7]cyclohepta[1,2-d]pyrimidine-3-carboxamide (52)

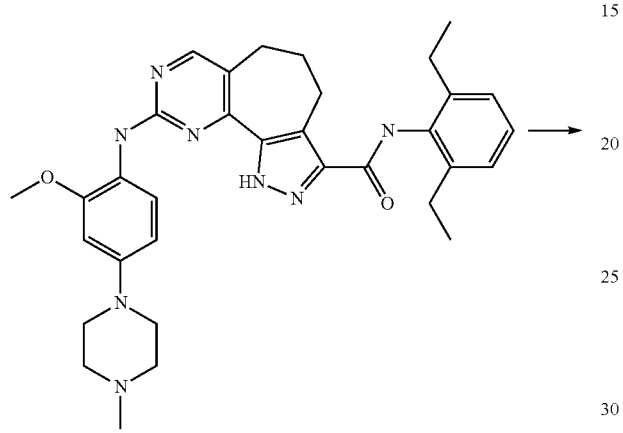

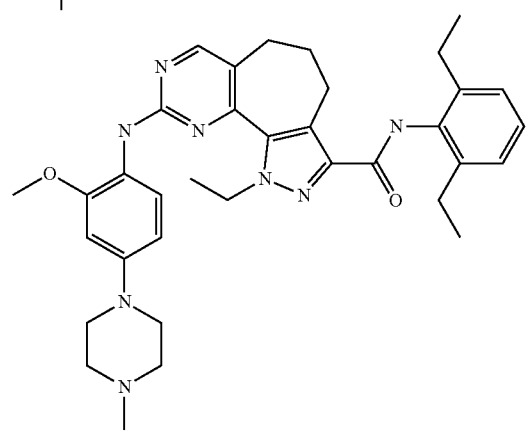

To a solution of N-(2,6-diethylphenyl)-9-{[2-methoxy-4-(4-methylpiperazin-1-yl)phenyl]amino}-1,4,5,6-tetrahydropyrazolo[4',3':6,7]cyclohepta[1,2-d]pyrimidine-3-carboxamide (0.065 g, 0.11 mmol) in DMF (1.1 mL), Cs$_2$CO$_3$ (0.073 g, 0.22 mmol) and bromoethane (0.008 mL, 0.11 mmol) were added. The mixture was stirred at room temperature for 12 h, solvent was removed under vacuo, then DCM (10 mL) was added and the organic phase washed with water (2×15 mL). The organic fraction was, dried over Na$_2$SO$_4$, filtered, and concentrated in vacuo. Purification by flash chromatography on silica gel (eluant: DCM/MeOH95/5) provided 30 mg (30%) of the title compound as a pale yellow solid.

$^1$H NMR (401 MHz, DMSO-d6) δ ppm 1.11 (t, J=7.51 Hz, 6H) 1.20 (t, J=7.08 Hz, 3H) 1.87-2.01 (m, 2H) 2.26-2.43 (m, 4H) 2.52-2.58 (m, 7H) 2.58-2.71 (m, 2H) 2.96 (t, J=7.02 Hz, 2H) 3.10-3.24 (m, 4H) 3.78 (s, 3H) 4.51 (q, J=7.08 Hz, 2H) 6.51 (dd, J=8.67, 2.44 Hz, 1H) 6.65 (d, J=2.44 Hz, 1H) 7.06-7.16 (m, 2H) 7.16-7.25 (m, 1H) 7.47 (d, J=8.67 Hz, 1H) 8.11 (s, 1H) 8.32 (s, 1H) 9.40 (s, 1H)
MS calc: 609.3660; MS found: 609.3666

According to this same methodology, but employing suitable substituted derivatives, the following compounds were prepared:

N-(2,6-diethylphenyl)-9-{[2-methoxy-4-(4-methylpiperazin-1-yl)phenyl]amino}-1-(pyridin-4-ylmethyl)-1,4,5,6-tetrahydropyrazolo[4',3':6,7]cyclohepta[1,2-d]pyrimidine-3-carboxamide (53)

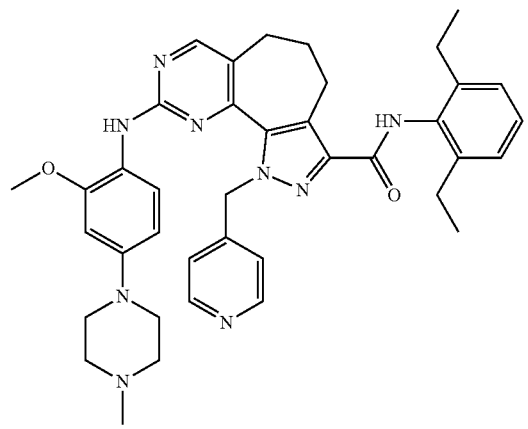 [SMILES: CCc1cccc(CC)c1NC(=O)c1nn(Cc2ccncc2)c2c1CCCc1cnc(Nc3ccc(N4CCN(C)CC4)cc3OC)nc1-2]

$^1$H NMR (401 MHz, DMSO-d6) δ ppm 1.11 (t, J=7.57 Hz, 6H) 1.85-2.00 (m, 2H) 2.25 (s, 3H) 2.44-2.50 (m, 4H) 2.52-2.60 (m, 6H) 3.07 (t, J=6.96 Hz, 2H) 3.09-3.17 (m, 4H) 3.77 (s, 3H) 5.93 (s, 2H) 6.40 (dd, J=8.79, 2.56 Hz, 1H) 6.59 (d, J=2.56 Hz, 1H) 6.90-6.97 (m, 2H) 7.06-7.15 (m, 2H) 7.17-7.25 (m, 1H) 7.47 (d, J=8.79 Hz, 1H) 7.92 (s, 1H) 8.26 (s, 1H) 8.39-8.45 (m, 2H) 9.53 (s, 1H)
MS calc: 672.3769; MS found: 672.3759

N-(2,6-diethylphenyl)-9-{[2-methoxy-4-(4-methylpiperazin-1-yl)phenyl]amino}-1-(tetrahydro-2H-pyran-2-ylmethyl)-1,4,5,6-tetrahydropyrazolo[4',3':6,7]cyclohepta[1,2-d]pyrimidine-3-carboxamide (54)

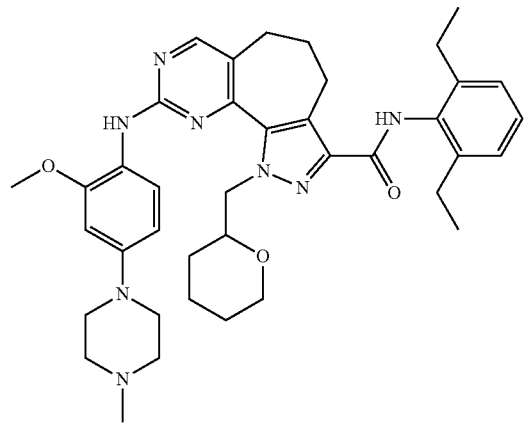 [SMILES: CCc1cccc(CC)c1NC(=O)c1nn(CC2CCCCO2)c2c1CCCc1cnc(Nc3ccc(N4CCN(C)CC4)cc3OC)nc1-2]

$^1$H NMR (401 MHz, DMSO-d6) δ ppm 1.11 (t, J=7.57 Hz, 6H) 1.29-1.43 (m, 5H) 1.64-1.74 (m, 1H) 1.85-2.04 (m, 2H) 2.26 (br. s., 3H) 2.45-2.52 (m, 4H) 2.55 (q, J=7.57 Hz, 4H) 2.79-3.04 (m, 4H) 3.09-3.19 (m, 4H) 3.17-3.23 (m, 1H) 3.61-3.68 (m, 1H) 3.69-3.75 (m, 1H) 3.81 (s, 3H) 4.51-4.61 (m, 1H) 4.61-4.72 (m, 1H) 6.51 (dd, J=8.54, 2.45 Hz, 1H) 6.65 (d, J=2.454 Hz, 1H) 7.02-7.16 (m, 2H) 7.16-7.26 (m, 1H) 7.62 (d, J=8.54 Hz, 1H) 8.01 (s, 1H) 8.34 (s, 1H) 9.43 (s, 1H)
MS calc: 679.4079; MS found: 679.4076

N-(2,6-diethylphenyl)-1-(3-hydroxypropyl)-9-{[2-methoxy-4-(4-methylpiperazin-1-yl)phenyl]amino}-1,4,5,6-tetrahydropyrazolo[4',3':6,7]cyclohepta[1,2-d]pyrimidine-3-carboxamide (55)

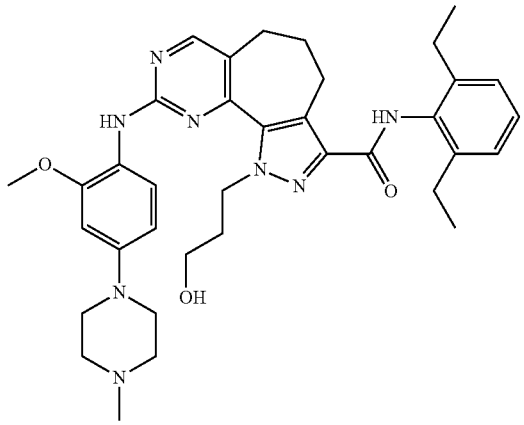 [SMILES: CCc1cccc(CC)c1NC(=O)c1nn(CCCO)c2c1CCCc1cnc(Nc3ccc(N4CCN(C)CC4)cc3OC)nc1-2]

¹H NMR (401 MHz, DMSO-d6) δ ppm 1.11 (t, J=7.57 Hz, 6H) 1.86 (quin, J=6.74 Hz, 2H) 1.91-2.04 (m, 2H) 2.25 (s, 3H) 2.47-2.52 (m, 4H) 2.56 (q, J=7.57 Hz, 8H) 2.97 (t, J=6.74 Hz, 2H) 3.08-3.17 (m, 4H) 3.32-3.39 (m, 2H) 3.80 (s, 3H) 4.43-4.50 (m, 1H) 4.57-4.66 (m, 2H) 6.50 (dd, J=8.67, 2.44 Hz, 1H) 6.64 (d, J=2.44 Hz, 1H) 7.07-7.15 (m, 2H) 7.17-7.25 (m, 1H) 7.60 (d, J=8.67 Hz, 1H) 8.08 (s, 1H) 8.32 (s, 1H) 9.43 (s, 1H)
MS calc: 639.3766; MS found: 639.3769

N-(2,6-diethylphenyl)-9-{[2-methoxy-4-(4-methylpiperazin-1-yl)phenyl]amino}-1-(2,2,2-trifluoroethyl)-1,4,5,6-tetrahydropyrazolo[4',3':6,7]cyclohepta[1,2-d]pyrimidine-3-carboxamide (56)

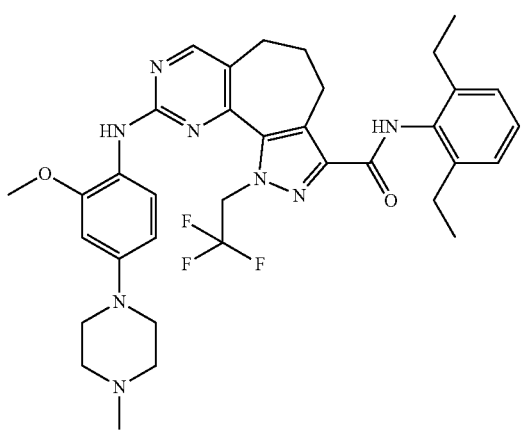 [SMILES: CCc1cccc(CC)c1NC(=O)c1nn(CC(F)(F)F)c2c1CCCc1cnc(Nc3ccc(N4CCN(C)CC4)cc3OC)nc1-2]

¹H NMR (401 MHz, DMSO-d6) δ ppm 1.110 (t, J=7.57 Hz, 6H) 1.88-2.00 (m, 2H) 2.26 (br. s., 3H) 2.52-2.61 (m, 10H) 3.03 (t, J=7.02 Hz, 2H) 3.10-3.20 (m., 4H) 3.77 (s, 3H) 5.67 (q, J=8.99 Hz, 2H) 6.51 (dd, J=8.45, 2.44 Hz, 1H) 6.65 (d, J=2.44 Hz, 1H) 7.10-7.15 (m, 2H) 7.18-7.25 (m, 1H) 7.40 (d, J=8.45 Hz, 1H) 8.35 (s, 1H) 8.35 (s, 1H) 9.52 (s, 1H)
MS calc: 663.3378; MS found: 663.3370

N-(2,6-diethylphenyl)-1-(3-hydroxybenzyl)-9-{[2-methoxy-4-(4-methylpiperazin-1-yl)phenyl]amino}-1,4,5,6-tetrahydropyrazolo[4',3':6,7]cyclohepta[1,2-d]pyrimidine-3-carboxamide (57)

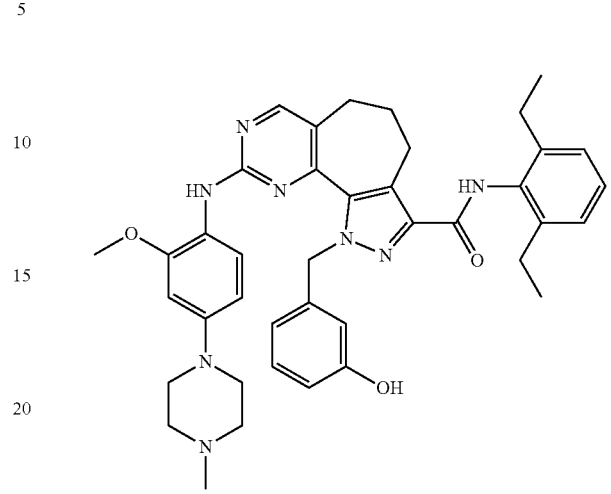

¹H NMR (401 MHz, DMSO-d6) δ ppm 1.11 (t, J=7.57 Hz, 6H) 1.92-2.02 (m, 2H) 2.41 (br.s., 3H) 2.52-2.60 (m, 6H) 2.64-2.83 (m, 4H) 3.01 (t, J=7.02 Hz, 2H) 3.10-3.27 (m, 4H) 3.78 (s, 3H) 5.84 (s, 2H) 6.30-6.33 (m, 1H) 6.38-6.44 (m, 1H) 6.46 (dd, J=8.54, 2.44 Hz, 1H) 6.58 (dd, J=8.06, 2.07 Hz, 1H) 6.64 (d, J=2.44 Hz, 1H) 7.03 (t, J=8.06 Hz, 1H) 7.09-7.15 (m, 2H) 7.17-7.23 (m, 1H) 7.59 (d, J=8.54 Hz, 1H) 8.00 (s, 1H) 8.28 (s, 1H) 9.32 (s, 1H) 9.50 (s, 1H)

MS calc: 687.3766; MS found: 687.3771

N-(2,6-diethylphenyl)-1-[3-(dimethylamino)propyl]-9-{[2-methoxy-4-(4-methylpiperazin-1-yl)phenyl]amino}-1,4,5,6-tetrahydropyrazolo[4',3':6,7]cyclohepta[1,2-d]pyrimidine-3-carboxamide (58)

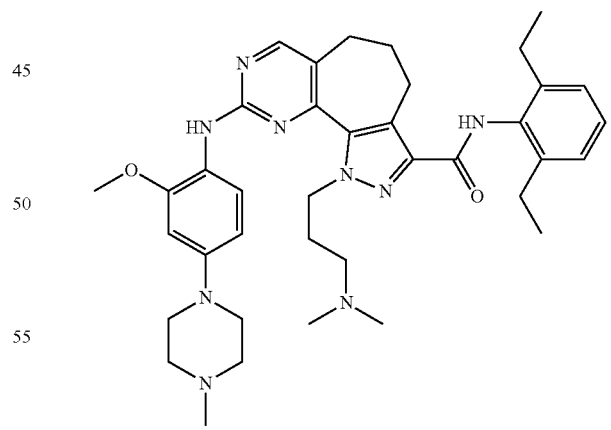

¹H NMR (401 MHz, DMSO-d6) δ ppm 1.09 (t, J=7.57 Hz, 6H) 1.80-1.99 (m, 4H) 2.30 (s, 3H) 2.35-2.48 (m, 4H) 2.49-2.63 (m, 8H) 2.96 (t, J=7.08 Hz, 2H) 3.08-3.19 (m, 4H) 3.77 (s, 3H) 4.53 (t, J=6.45 Hz, 2H) 6.50 (dd, J=8.73, 2.44 Hz, 1H) 6.63 (d, J=2.44 Hz, 1H) 7.08-7.13 (m, 2H) 7.16-7.22 (m, 1H) 7.48 (d, J=8.73 Hz, 1H) 8.10 (s, 1H) 8.30 (s, 1H) 9.35 (s, 1H)
MS calc: 666.4239; MS found: 666.4233

81

N-(2,6-diethylphenyl)-9-{[2-methoxy-4-(4-methylpiperazin-1-yl)phenyl]amino}-1-[2-(tetrahydro-2H-pyran-2-yloxy)ethyl]-1,4,5,6-tetrahydropyrazolo[4',3':6,7]cyclohepta[1,2-d]pyrimidine-3-carboxamide (59)

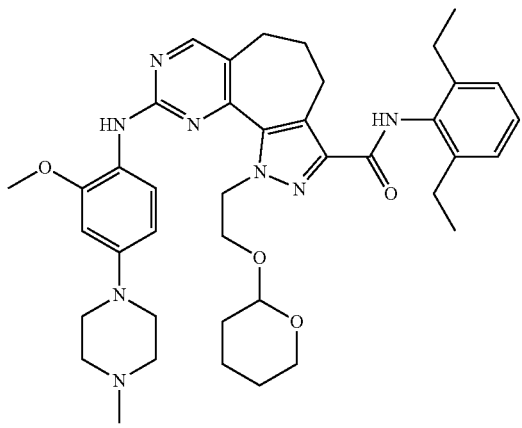 [SMILES: CCc1cccc(CC)c1NC(=O)c1nn(CCOC2CCCCO2)c2c1CCCc1cnc(Nc3ccc(N4CCN(C)CC4)cc3OC)nc1-2]

$^1$H NMR (401 MHz, DMSO-d6) δ ppm 1.11 (t, J=7.57 Hz, 6H) 1.16-0.147 (m, 6H) 1.91-2.01 (m, 2H) 2.28 (br. s., 3H) 2.48-2.59 (m, 10H) 2.97 (t, J=7.20 Hz, 2H) 3.10-3.21 (m, 4H) 3.35-3.47 (m, 1H) 3.57-3.66 (m, 1H) 3.74-3.78 (m, 1H) 3.80 (s, 3H) 4.37-4.42 (m, 1H) 4.82 (t, J=5.07 Hz, 2H) 6.52 (dd, J=8.67, 2.44 Hz, 1H) 6.65 (d, J=2.44 Hz, 1H) 7.07-7.16 (m, 2H) 7.17-7.23 (m, 1H) 7.55 (d, J=8.67 Hz, 1H) 8.08 (s, 1H) 8.32 (s, 1H) 9.44 (s, 1H)

MS calc: 709.4185; MS found: 709.4171

N-(2,6-diethylphenyl)-9-({4-[4-(dimethylamino)piperidin-1-yl]-2-methoxyphenyl}amino)-1-ethyl-1,4,5,6-tetrahydropyrazolo[4',3':6,7]cyclohepta[1,2-d]pyrimidine-3-carboxamide trifluoroacetate (63)

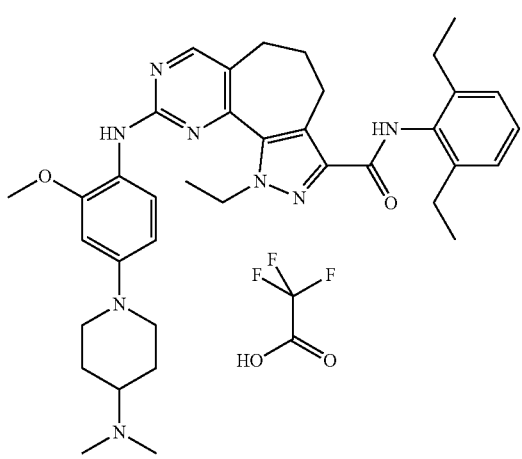 [SMILES: CCc1cccc(CC)c1NC(=O)c1nn(CC)c2c1CCCc1cnc(Nc3ccc(N4CCC(N(C)C)CC4)cc3OC)nc1-2 ; O=C(O)C(F)(F)F]

$^1$H NMR (401 MHz, DMSO-d6) δ ppm 1.11 (t, J=7.57 Hz, 6H) 1.21 (t, J=7.08 Hz, 3H) 1.63-1.79 (m, 2H) 1.87-1.99 (m, 2H) 2.00-2.19 (m, 2H) 2.55 (q, J=7.57 Hz, 4H) 2.66-2.75 (m, 2H) 2.79 (d, J=5.00 Hz, 6H) 2.96 (t, J=7.08 Hz, 2H) 3.79 (s, 3H) 3.81-3.87 (m, 2H) 4.52 (q, J=7.08 Hz, 2H) 6.55 (dd, J=8.73, 2.50 Hz, 2H) 6.68 (d, J=2.50 Hz, 1H) 7.10-7.14 (m, 2H) 7.17-7.21 (m, 1H) 7.48 (d, J=8.73 Hz, 1H) 8.15 (s, 1H) 8.32 (s, 1H) 9.39 (s, 1H) 9.54 (br. s., 1H)

MS calc: 637.3973; MS found: 637.3961

82

N-(2,6-diethylphenyl)-1-[2-(dimethylamino)ethyl]-9-({4-[4-(dimethylamino)piperidin-1-yl]-2-methoxyphenyl}amino)-1,4,5,6-tetrahydropyrazolo[4',3':6,7]cyclohepta[1,2-d]pyrimidine-3-carboxamide bis(trifluoroacetate) (64)

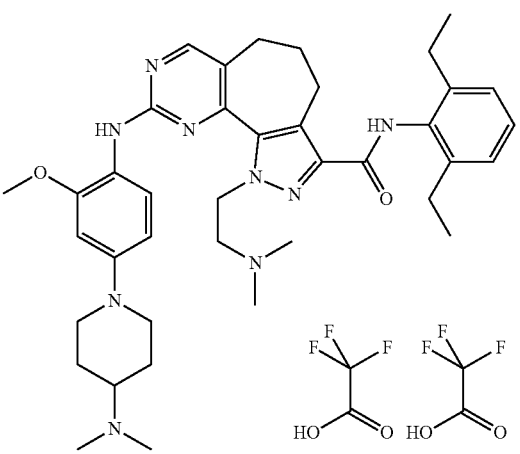

$^1$H NMR (401 MHz, DMSO-d6) δ ppm 1.13 (t, J=7.57 Hz, 6H) 1.62-1.78 (m, 2H) 1.89-2.00 (m, 2H) 2.03-2.16 (m, 2H) 2.54-2.58 (m, 2H) 2.59 (q, J=7.53 Hz, 4H) 2.67-2.74 (m, 2H) 2.80 (d, J=4.76 Hz, 6H) 2.86 (d, J=3.91 Hz, 6H) 3.04 (t, J=6.96 Hz, 2H) 3.80 (s, 3H) 3.82-3.91 (m, 2H) 4.94 (t, J=5.61 Hz, 1H) 6.56 (dd, J=8.73, 2.44 Hz, 1H) 6.69 (d, J=2.44 Hz, 1H) 7.15-7.19 (m, 2H) 7.23-7.28 (m, 1H) 7.49 (d, J=8.73 Hz, 1H) 8.27 (s, 1H) 8.33 (s, 1H) 9.10 (br. s., 1H) 9.50 (s, 1H) 9.63 (br. s., 1H)

MS calc: 680.4395; MS found: 680.4382

N-(2,6-diethylphenyl)-9-({4-[4-(dimethylamino)piperidin-1-yl]-2-methoxyphenyl}amino)-1-[2-(1,3-dioxo-1,3-dihydro-2H-isoindol-2-yl)ethyl]-1,4,5,6-tetrahydropyrazolo[4',3':6,7]cyclohepta[1,2-d]pyrimidine-3-carboxamide (69)

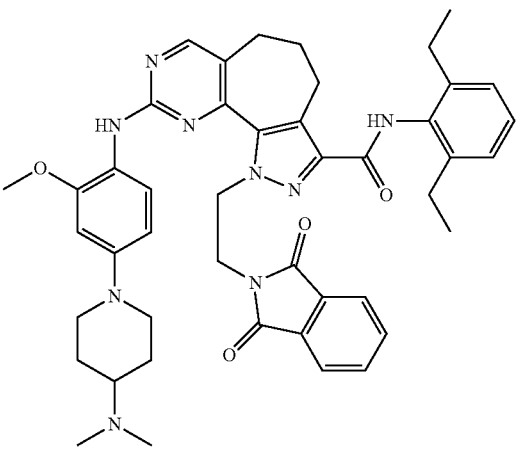 [SMILES: CCc1cccc(CC)c1NC(=O)c1nn(CCN2C(=O)c3ccccc3C2=O)c2c1CCCc1cnc(Nc3ccc(N4CCC(N(C)C)CC4)cc3OC)nc1-2]

MS calc: 782.4137; MS found: 782.4117

N-(2,6-diethylphenyl)-9-({4-[4-(dimethylamino)piperidin-1-yl]-2-methoxyphenyl}amino)-1-[2-(tetrahydro-2H-pyran-2-yloxy)ethyl]-1,4,5,6-tetrahydropyrazolo[4',3':6,7]cyclohepta[1,2-d]pyrimidine-3-carboxamide

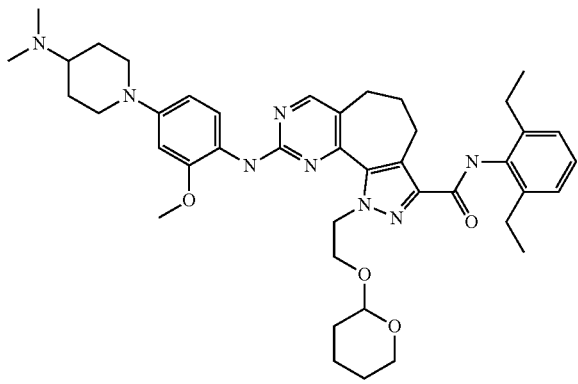 [SMILES: CCc1cccc(CC)c1NC(=O)c1nn(CCOC2CCCCO2)c2c1CCCc1cnc(Nc3ccc(N4CCC(N(C)C)CC4)cc3OC)nc1-2]

Example 6

Conv. 4

9-[(4-bromo-2-methoxyphenyl)amino]-2-methyl-2,4,5,6-tetrahydropyrazolo[4',3':6,7]cyclohepta[1,2-d]pyrimidine-3-carboxylic acid

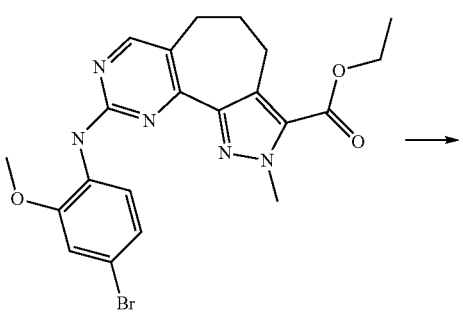

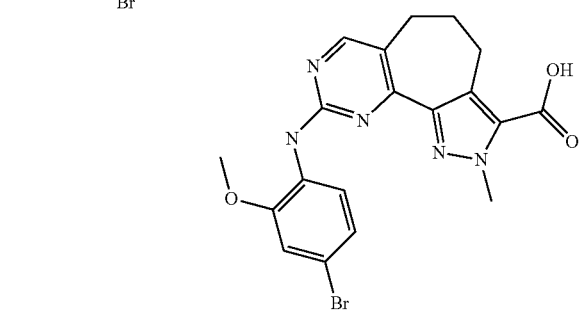

Ethyl 9-[(4-bromo-2-methoxyphenyl)amino]-2-methyl-2,4,5,6-tetrahydropyrazolo[4',3':6,7]cyclohepta[1,2-d]pyrimidine-3-carboxylate (0.250 g, 0.530 mmol) was suspended in anhydrous EtOH (5 mL) and treated with a 2 M solution of NaOH (0.260 mL, 0.5 eq.) at reflux temperature for 1 hour. Solvent was evaporated to dryness and the residue dissolved in water. After treatment with AcOH, the resulting precipitate was collected by filtration to give the title compound (190 mg, 80% yield) as a white solid.

$^1$H NMR (401 MHz, DMSO-d6) δ ppm 1.86-2.02 (m, 2H) 2.65-2.75 (m, 2H) 3.05 (t, J=6.47 Hz, 2H) 3.92 (s, 3H) 4.18 (s, 3H) 7.15 (dd, J=8.67, 2.20 Hz, 1H) 7.20 (d, J=2.20 Hz, 1H) 7.89 (s, 1H) 8.34 (s, 1H) 8.53 (d, J=8.67 Hz, 1H) 13.50 (s, 1H)

MS calc: 444.0666; MS found: 444.0667

According to this same methodology, but employing suitable substituted derivatives, the following compounds were prepared:

sodium 9-[(4-bromo-2-methoxyphenyl)amino]-1-methyl-1,4,5,6-tetrahydropyrazolo[4',3':6,7]cyclohepta[1,2-d]pyrimidine-3-carboxylate $^1$H NMR (401 MHz, DMSO-d6) δ ppm 1.85-1.97 (m, 2H) 2.51-2.54 (m, 2H) 3.00 (t, J=7.14 Hz, 2H) 3.87 (s, 3H) 3.98 (s, 3H) 7.15 (dd, J=8.54, 2.20 Hz, 1H) 7.21 (d, J=2.20 Hz, 1H) 8.03 (d, J=8.54 Hz, 1H) 8.11 (s, 1H) 8.34 (s, 1H)

MS calc: 444.0666; MS found: 444.0646

9-[(4-bromo-2-methoxyphenyl)amino]-5,6-dihydro-4H-isoxazolo[4',5':6,7]cyclohepta[1,2-d]pyrimidine-3-carboxylic acid MS calc: 430.0509; MS found: 430.0510

9-[(4-bromo-2-methoxyphenyl)amino]-5,6-dihydro-4H-isoxazolo[4',3':6,7]cyclohepta[1,2-d]pyrimidine-3-carboxylic acid MS calc: 430.0509; MS found: 430.0514

2-methyl-9-{[4-(4-methylpiperazin-1-yl)phenyl]amino}-2,4,5,6-tetrahydropyrazolo[4',3':6,7]cyclohepta[1,2-d]pyrimidine-3-carboxylic acid 9-({2-methoxy-4-[(1-methylpiperidin-4-yl)carbamoyl]phenyl}amino)-1-methyl-1,4,5,6-tetrahydropyrazolo[4',3':6,7]cyclohepta[1,2-d]pyrimidine-3-carboxylic acid 1-methyl-9-(methylsulfanyl)-1,4,5,6-tetrahydropyrazolo[4',3':6,7]cyclohepta[1,2-d]pyrimidine-3-carboxylic acid (92)

MS calc: 291.0910; MS found: 291.0922

1-methyl-9-{[4-(4-methylpiperazin-1-yl)phenyl]amino}-1,4,5,6-tetrahydropyrazolo[4',3':6,7]cyclohepta[1,2-d]pyrimidine-3-carboxylic acid MS calc: 434.2299; MS found: 434.2306

1-methyl-9-[(3-nitrophenyl)amino]-1,4,5,6-tetrahydropyrazolo[4',3':6,7]cyclohepta[1,2-d]pyrimidine-3-carboxylic acid $^1$H NMR (401 MHz, DMSO-d6) δ ppm 1.94-2.05 (m, 2H) 2.57-2.63 (m, 2H) 2.99 (t, J=7.08 Hz, 2H) 4.23 (s, 3H) 7.49 (s, 1H) 7.59 (t, J=8.15 Hz, 1H) 7.80 (dd, J=8.15, 2.30 Hz, 1H) 8.04-8.08 (m, 1H) 8.53 (s, 1H) 8.86 (t, J=2.30 Hz, 1H) 10.13 (s, 1H) 12.70 (br.s, 1H)

MS calc: 381.1306; MS found: 381.1313

Example 7

Conv. 5

N-benzyl-9-[(4-bromo-2-methoxyphenyl)amino]-1-methyl-1,4,5,6-tetrahydropyrazolo[4',3':6,7]cyclohepta[1,2-d]pyrimidine-3-carboxamide

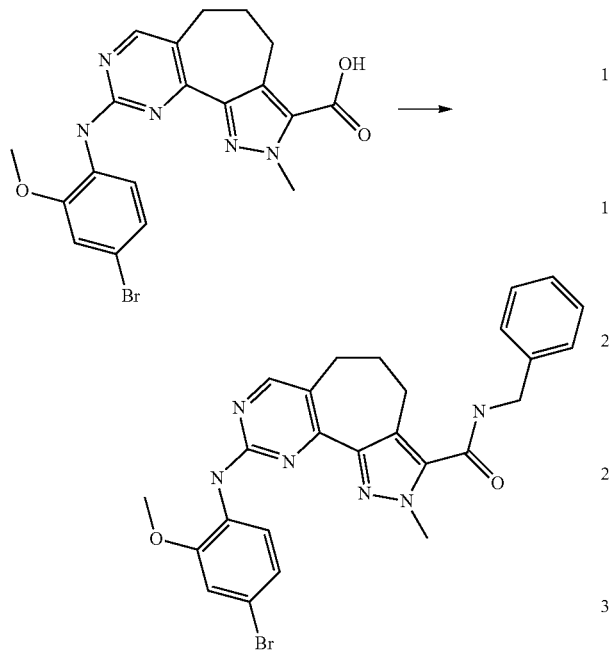

A suspension of potassium 9-[(4-bromo-2-methoxyphenyl)amino]-2-methyl-2,4,5,6-tetrahydropyrazolo[4',3':6,7]cyclohepta[1,2-d]pyrimidine-3-carboxylic acid (0.050 g, 0.110 mmol) in anhydrous DMF (5.0 mL) was treated with DIPEA (0.056 mL, 0.033 mmol) and TBTU (0.065 g, 0.200 mmol). The mixture was then treated with benzylamine (0.015 mL, 0.011 mmol). The reaction was stirred at room temperature for 1 h. The reaction was diluted with water and the resulting precipitate was collected by filtration to afford the title compound (0.045 mg, 77% yield) as a pale yellow solid.

$^1$H NMR (401 MHz, DMSO-d6) δ ppm 1.91-2.02 (m, 2H) 2.54-2.60 (m, 2H) 3.01 (t, J=7.14 Hz, 2H) 3.87 (s, 3H) 4.11 (s, 3H) 4.42 (d, J=6.35 Hz, 2H) 7.15 (dd, J=8.54, 2.20 Hz, 1H) 7.19-7.25 (m, 3H) 7.27-7.36 (m, 3H) 7.98 (d, J=8.54 Hz, 1H) 8.25 (s, 1H) 8.41 (s, 1H) 8.64 (t, J=6.35 Hz, 1H)

MS calc: 533.1295; MS found: 533.1292

According to this same methodology, but employing suitable substituted derivatives, the following compounds were prepared:

9-[(4-bromo-2-methoxyphenyl)amino]-1-methyl-1,4,5,6-tetrahydropyrazolo[4',3':6,7]cyclohepta[1,2-d]pyrimidine-3-carboxamide (1)

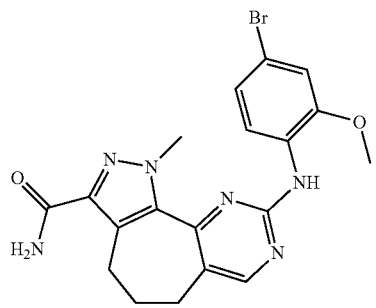 [SMILES: COc1cc(Br)ccc1Nc1ncc2c(n1)-c1c(c(C(N)=O)nn1C)CCC2]

$^1$H NMR (401 MHz, DMSO-d6) δ ppm 1.99-2.02 (m, 2H) 2.53-2.60 (m, 2H) 3.01 (t, J=7.02 Hz, 2H) 3.87 (s, 3H) 4.09 (s, 3H) 7.15 (dd, J=8.54, 1.83 Hz, 1H) 7.18 (br. s., 1H) 7.23 (d, J=1.83 Hz, 1H) 7.42 (br. s., 1H) 7.98 (d, J=8.54 Hz, 1H) 8.25 (s, 1H) 8.40 (s, 1H)

MS calc: 443.0826; MS found: 443.0829

9-[(4-bromo-2-methoxyphenyl)amino]-1-methyl-N-phenyl-1,4,5,6-tetrahydropyrazolo[4',3':6,7]cyclohepta[1,2-d]pyrimidine-3-carboxamide

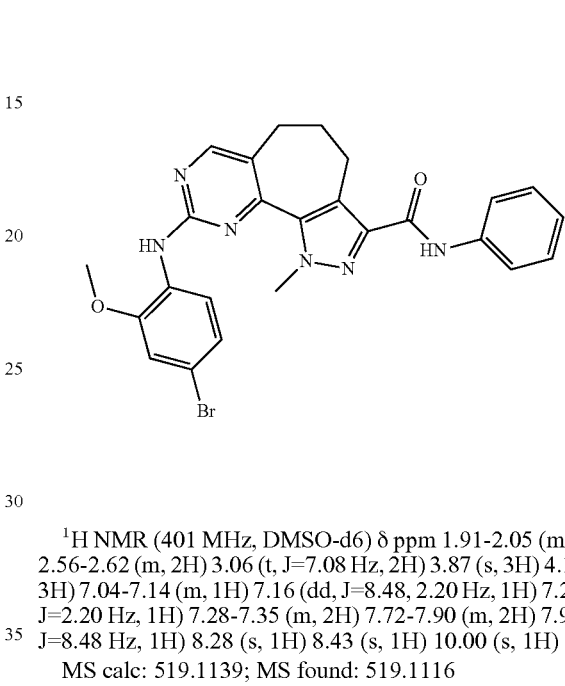

$^1$H NMR (401 MHz, DMSO-d6) δ ppm 1.91-2.05 (m, 2H) 2.56-2.62 (m, 2H) 3.06 (t, J=7.08 Hz, 2H) 3.87 (s, 3H) 4.17 (s, 3H) 7.04-7.14 (m, 1H) 7.16 (dd, J=8.48, 2.20 Hz, 1H) 7.24 (d, J=2.20 Hz, 1H) 7.28-7.35 (m, 2H) 7.72-7.90 (m, 2H) 7.99 (d, J=8.48 Hz, 1H) 8.28 (s, 1H) 8.43 (s, 1H) 10.00 (s, 1H)

MS calc: 519.1139; MS found: 519.1116

9-[(4-bromo-2-methoxyphenyl)amino]-N-(2-ethylphenyl)-1-methyl-1,4,5,6-tetrahydropyrazolo[4',3':6,7]cyclohepta[1,2-d]pyrimidine-3-carboxamide

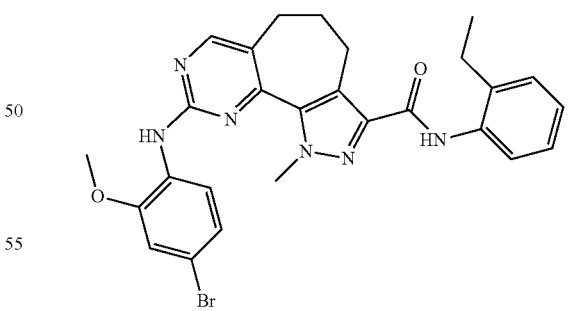

$^1$H NMR (401 MHz, DMSO-d6) δ ppm 1.17 (t, J=7.57 Hz, 3H) 1.91-2.05 (m, 2H) 2.55-2.69 (m, 4H) 3.06 (t, J=7.02 Hz, 2H) 3.87 (s, 3H) 4.16 (s, 3H) 7.13-7.22 (m, 3H) 7.24 (d, J=2.20 Hz, 1H) 7.21-7.35 (m, 1H) 7.55-7.61 (m, 1H) 7.98 (d, J=8.54 Hz, 1H) 8.29 (s, 1H) 8.42 (s, 1H) 9.46 (s, 1H)

MS calc: 547.1452; MS found: 547.1439

87

9-[(4-bromo-2-methoxyphenyl)amino]-1-methyl-N-[(1S)-2-(morpholin-4-yl)-1-phenylethyl]-1,4,5,6-tetrahydropyrazolo[4',3':6,7]cyclohepta[1,2-d]pyrimidine-3-carboxamide (16)

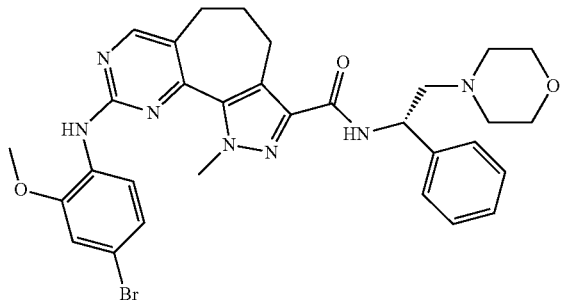 [SMILES: COc1cc(Br)ccc1Nc1ncc2c(n1)-c1c(c(C(=O)N[C@H](CN3CCOCC3)c3ccccc3)nn1C)CCC2]

$^1$H NMR (401 MHz, DMSO-d6) δ ppm 1.88-2.00 (m, 2H) 2.36-2.45 (m, 1H) 2.50-2.59 (m, 4H) 2.87 (dd, J=12.45, 9.40 Hz, 1H) 2.96 (t, J=7.14 Hz, 2H) 3.49-3.62 (m, 4H) 3.87 (s, 3H) 4.13 (s, 3H) 5.09-5.19 (m, 1H) 7.16 (dd, J=8.54, 2.14 Hz, 1H) 7.20-7.27 (m, 2H) 7.28-7.36 (m, 2H) 7.37-7.44 (m, 2H) 7.99 (d, J=8.54 Hz, 1H) 8.25 (s, 1H) 8.36 (d, J=7.81 Hz, 1H) 8.40 (s, 1H)

MS calc: 632.1979; MS found: 632.1982

88

9-[(4-bromo-2-methoxyphenyl)amino]-N-cyclohexyl-1-methyl-1,4,5,6-tetrahydropyrazolo[4',3':6,7]cyclohepta[1,2-d]pyrimidine-3-carboxamide

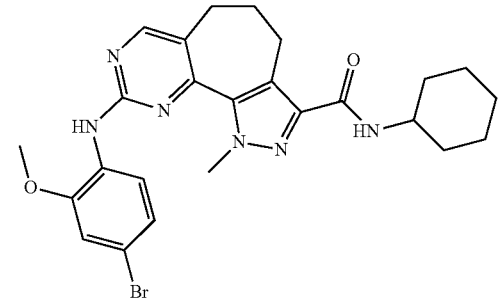

$^1$H NMR (401 MHz, DMSO-d6) δ ppm 1.06-1.20 (m, 1H) 1.21-1.43 (m, 4H) 1.54-1.64 (m, 1H) 1.66-1.84 (m, 4H) 1.90-2.02 (m, 2H) 2.52-2.59 (m, 2H) 3.00 (t, J=7.14 Hz, 2H) 3.67-3.81 (m, 1H) 3.87 (s, 3H) 4.10 (s, 3H) 7.15 (dd, J=8.54, 2.20 Hz, 1H) 7.22 (d, J=2.20 Hz, 1H) 7.71 (d, J=8.42 Hz, 1H) 7.98 (d, J=8.54 Hz, 1H) 8.25 (s, 1H) 8.40 (s, 1H)

MS calc: 525.1608; MS found: 525.1599

9-[(4-bromo-2-methoxyphenyl)amino]-N-(2,6-dimethylphenyl)-1-methyl-1,4,5,6-tetrahydropyrazolo[4',3':6,7]cyclohepta[1,2-d]pyrimidine-3-carboxamide (17)

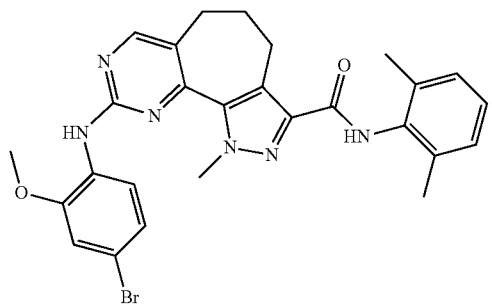 [SMILES: COc1cc(Br)ccc1Nc1ncc2c(n1)-c1c(c(C(=O)Nc3c(C)cccc3C)nn1C)CCC2]

$^1$H NMR (401 MHz, DMSO-d6) δ ppm 1.90-2.03 (m, 2H) 2.18 (s, 6H) 2.55-2.64 (m, 2H) 3.03 (t, J=7.08 Hz, 1H) 3.88 (s, 2H) 4.16 (s, 3H) 7.07-7.14 (m, 3H) 7.17 (dd, J=8.54, 2.20 Hz, 1H) 7.24 (d, J=2.20 Hz, 1H) 8.00 (d, J=8.54 Hz, 1H) 8.26 (s, 1H) 8.42 (s, 1H) 9.51 (s, 1H)

MS calc: 547.1452; MS found: 547.1447

9-[(4-bromo-2-methoxyphenyl)amino]-N-(2-ethyl-6-methylphenyl)-1-methyl-1,4,5,6-tetrahydropyrazolo[4',3':6,7]cyclohepta[1,2-d]pyrimidine-3-carboxamide (19)

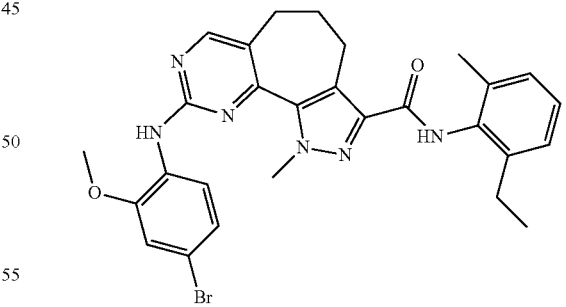

$^1$H NMR (401 MHz, DMSO-d6) δ ppm 1.11 (t, J=7.57 Hz, 3H) 1.91-2.03 (m, 2H) 2.18 (s, 3H) 2.56 (q, J=7.57 Hz, 2H) 2.57-2.63 (m, 2H) 3.02 (t, J=7.08 Hz, 2H) 3.88 (s, 3H) 4.16 (s, 3H) 7.08-7.19 (m, 3H) 7.24 (d, J=2.20 Hz, 1H) 8.00 (d, J=8.54 Hz, 1H) 8.26 (s, 1H) 8.42 (s, 1H) 9.50 (s, 1H)

MS calc: 561.1608; MS found: 561.1600

89

9-[(4-bromo-2-methoxyphenyl)amino]-N,1-dimethyl-1,4,5,6-tetrahydropyrazolo[4',3':6,7]cyclohepta[1,2-d]pyrimidine-3-carboxamide (32)

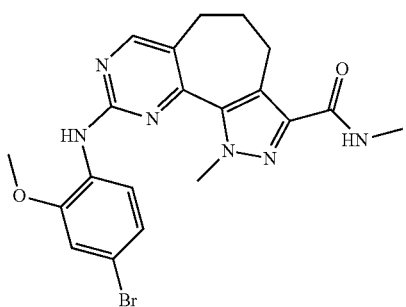

$^1$H NMR (401 MHz, DMSO-d6) δ ppm 1.84-2.03 (m, 2H) 2.53-2.59 (m, 2H) 2.73 (d, J=4.64 Hz, 3H) 3.01 (t, J=7.08 Hz, 2H) 3.87 (s, 3H) 4.09 (s, 3H) 7.15 (dd, J=8.54, 2.20 Hz, 1H) 7.22 (d, J=2.20 Hz, 1H) 7.98 (d, J=8.54 Hz, 1H) 8.04 (q, J=4.64 Hz, 1H) 8.24 (s, 1H) 8.40 (s, 1H)

MS calc: 457.0982; MS found: 457.0961

9-methoxy-1-methyl-N-propyl-1,4,5,6-tetrahydropyrazolo[4',3':6,7]cyclohepta[1,2-d]pyrimidine-3-carboxamide

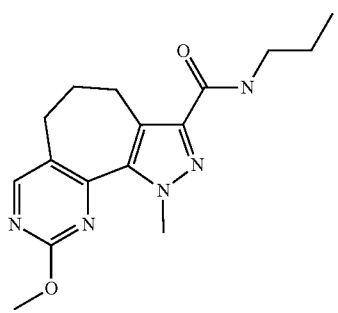 [SMILES: CCCNC(=O)c1nn(C)c2c1CCCc1cnc(OC)nc1-2]

2-methyl-9-{[4-(4-methylpiperazin-1-yl)phenyl]amino}-2,4,5,6-tetrahydropyrazolo[4',3':6,7]cyclohepta[1,2-d]pyrimidine-3-carboxamide (93)

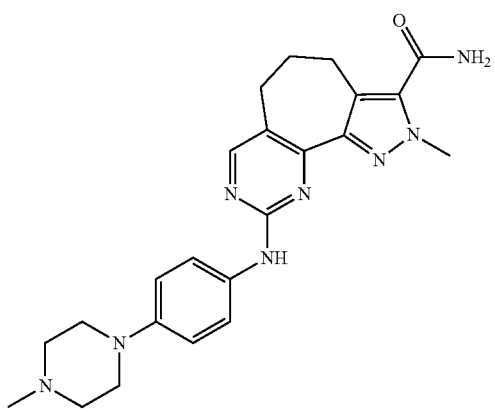 [SMILES: CN1CCN(c2ccc(Nc3ncc4c(n3)-c3nn(C)c(C(N)=O)c3CCC4)cc2)CC1]

$^1$H NMR (401 MHz, DMSO-d6) δ ppm 1.86-2.01 (m, 2H) 2.22 (s, 3H) 2.40-2.48 (m, 4H) 2.60-2.70 (m, 2H) 2.90 (t, J=6.53 Hz, 2H) 2.97-3.13 (m, 4H) 3.99 (s, 3H) 6.82-6.90 (m, 2H) 7.67-7.73 (m, 2H) 7.76 (br. s., 1H) 7.83 (br. s., 1H) 8.24 (s, 1H) 9.28 (s, 1H)

MS calc: 433.2459; MS found: 433.2471

90

9-[(4-bromo-2-methoxyphenyl)amino]-2-methyl-2,4,5,6-tetrahydropyrazolo[4',3':6,7]cyclohepta[1,2-d]pyrimidine-3-carboxamide (94)

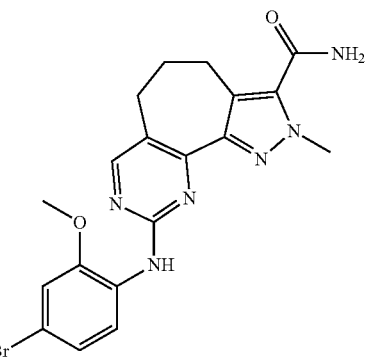

$^1$H NMR (401 MHz, DMSO-d6) δ ppm 1.88-2.00 (m, 2H) 2.68-2.75 (m, 2H) 2.92 (t, J=6.47 Hz, 2H) 3.92 (s, 3H) 4.01 (s, 3H) 7.14 (dd, J=8.67, 2.20 Hz, 1H) 7.20 (d, J=2.20 Hz, 1H) 7.78 (br. s., 1H) 7.85 (br. s., 1H) 7.87 (s, 1H) 8.33 (s, 1H) 8.52 (d, J=8.67 Hz, 1H)

MS calc: 443.0826; MS found: 443.0838

9-[(4-bromo-2-methoxyphenyl)amino]-N-(2,6-diethylphenyl)-2-methyl-2,4,5,6-tetrahydropyrazolo[4',3':6,7]cyclohepta[1,2-d]pyrimidine-3-carboxamide (96)

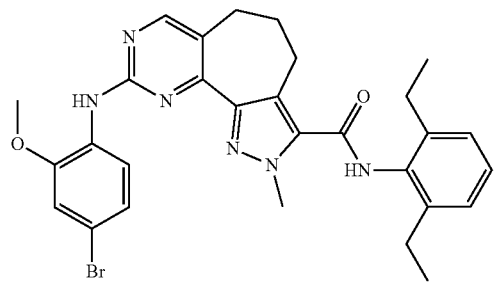 [SMILES: CCc1cccc(CC)c1NC(=O)c1c2c(nn1C)-c1nc(Nc3ccc(Br)cc3OC)ncc1CCC2]

$^1$H NMR (401 MHz, DMSO-d6) δ ppm 1.17 (t, J=7.57 Hz, 6H) 1.97-2.05 (m, 2H) 2.62 (q, J=7.57 Hz, 4H) 2.73-2.80 (m, 2H) 3.08 (t, J=6.47 Hz, 2H) 3.93 (s, 3H) 4.06 (s, 3H) 7.15 (dd, J=8.67, 2.20 Hz, 1H) 7.17-7.20 (m, 2H) 7.21 (d, J=2.20 Hz, 1H) 7.24-7.31 (m, 1H) 7.91 (s, 1H) 8.37 (s, 1H) 8.53 (d, J=8.67 Hz, 1H) 9.85 (s, 1H)

MS calc: 575.1765; MS found: 575.1746

9-[(4-bromo-2-methoxyphenyl)amino]-N-(2,6-diethylphenyl)-5,6-dihydro-4H-isoxazolo[4',3':6,7]cyclohepta[1,2-d]pyrimidine-3-carboxamide

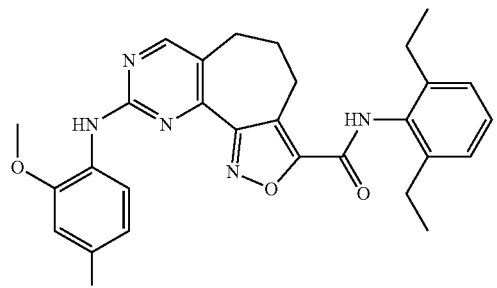

$^1$H NMR (401 MHz, DMSO-d6) δ ppm 1.14 (t, J=7.53 Hz, 6H) 1.92-2.02 (m, 2H) 2.58 (q, J=7.53 Hz, 4H) 2.82-2.88 (m, 2H) 3.00 (t, J=6.10 Hz, 2H) 3.91 (s, 3H) 7.12-7.21 (m, 3H) 7.22-7.30 (m, 2H) 8.25 (s, 1H) 8.31 (d, J=8.54 Hz, 1H) 8.50 (s, 1H) 10.30 (s, 1H)

MS calc: 562.1449; MS found: 562.1456

9-[(4-bromo-2-methoxyphenyl)amino]-N-(2,6-diethylphenyl)-5,6-dihydro-4H-isoxazolo[4',5':6,7]cyclohepta[1,2-d]pyrimidine-3-carboxamide

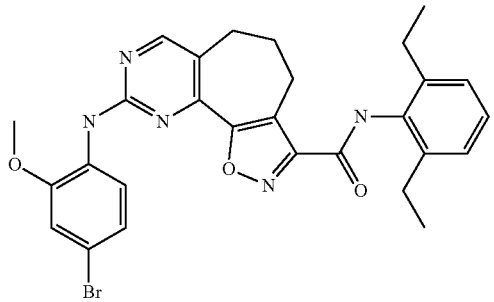 [SMILES: CCc1cccc(CC)c1NC(=O)c1noc2c1CCCc1cnc(Nc3ccc(Br)cc3OC)nc1-2]

tert-butyl[(2S)-2-({[9-({2-methoxy-4-[(1-methylpiperidin-4-yl)carbamoyl]phenyl}amino)-1-methyl-1,4,5,6-tetrahydropyrazolo[4',3':6,7]cyclohepta[1,2-d]pyrimidin-3-yl]carbonyl}amino)-2-phenylethyl]carbamate

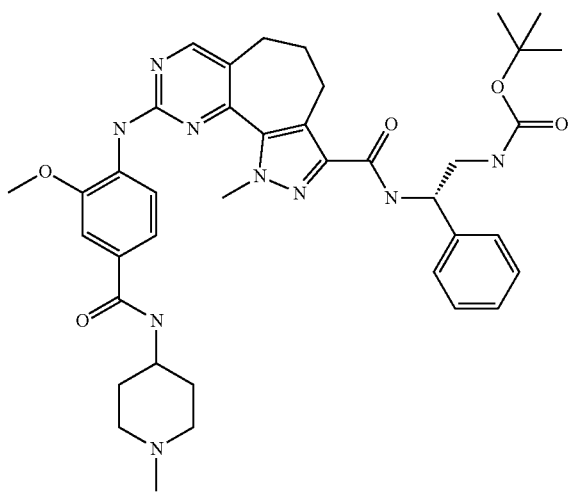 [SMILES: COc1cc(C(=O)NC2CCN(C)CC2)ccc1Nc1ncc2c(n1)-c1c(c(C(=O)N[C@H](CNC(=O)OC(C)(C)C)c3ccccc3)nn1C)CCC2]

N-(3-methoxypropyl)-1-methyl-9-(methylsulfanyl)-1,4,5,6-tetrahydropyrazolo[4',3':6,7]cyclohepta[1,2-d]pyrimidine-3-carboxamide

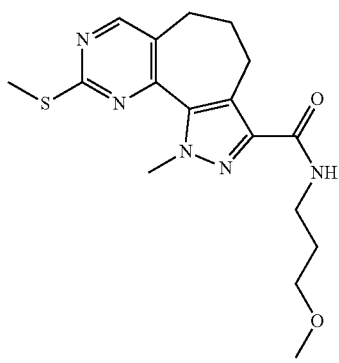 [SMILES: COCCCNC(=O)c1nn(C)c2c1CCCc1cnc(SC)nc1-2]

¹H NMR (401 MHz, DMSO-d6) δ ppm 1.68-1.81 (m, 2H) 1.91-2.01 (m, 2H) 2.56 (s, 3H) 2.60-2.68 (m, 2H) 3.05 (t, J=7.02 Hz, 2H) 3.17-3.32 (m, 7H) 4.18 (s, 3H) 7.20 (br. s., 1H) 8.12 (t, J=5.75 Hz, 1H) 8.56 (s, 1H)

MS calc: 362.1645; MS found: 362.1651

1-methyl-9-[(3-nitrophenyl)amino]-1,4,5,6-tetrahydropyrazolo[4',3':6,7]cyclohepta[1,2-d]pyrimidine-3-carboxamide

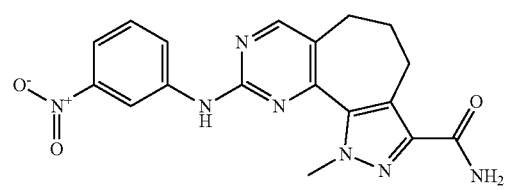 [SMILES: Cn1nc(C(N)=O)c2c1-c1nc(Nc3cccc([N+](=O)[O-])c3)ncc1CCC2]

MS calc: 380.1466; MS found: 380.1462

Example 8

Conv. 6

9-[(4-bromo-2-methoxyphenyl)amino]-N-(2,6-diethylphenyl)-1-methyl-1,4,5,6-tetrahydropyrazolo[4',3':6,7]cyclohepta[1,2-d]pyrimidine-3-carboxamide (2)

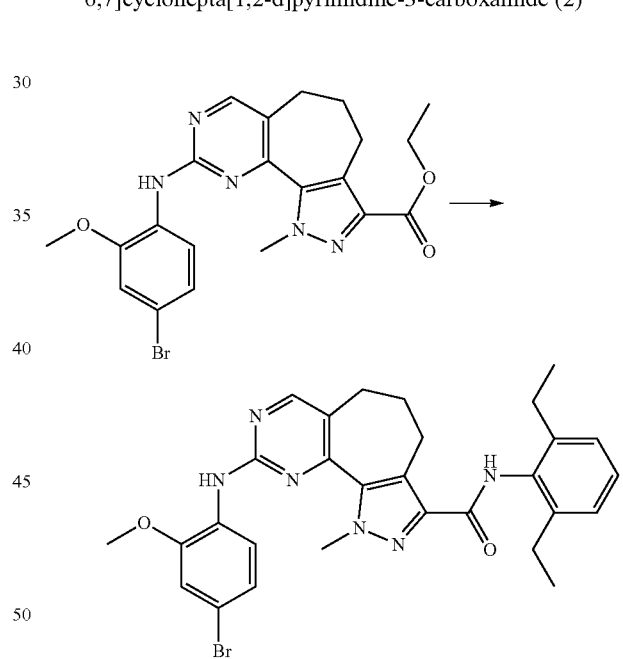

To a solution of 2,6-diethylaniline (0.300 g, 2.01 mmol) in 10 mL of anhydrous THF under argon, 1M in THF solution of LiN(TMS)₂ (4.02 mL, 4.02 mmol) at 0° C. were added dropwise. The mixture was stirred at 0° C. for 10 minutes then ethyl 9-[(4-bromo-2-methoxyphenyl)amino]-1-methyl-1,4,5,6-tetrahydropyrazolo[4',3':6,7]cyclohepta[1,2-d]pyrimidine-3-carboxylate (0.300 g, 0.67 mmol) in 10 mL of anhydrous THF at 0° C. were added dropwise. Ice bath was removed and the mixture was stirred at room temperature for 1 hour. Water (20 mL) was added and the mixture was extracted with AcOEt (2×30 mL). The organic layer was dried over anhydrous Na₂SO₄ and the solvent evaporated to dryness. The crude solid was purified by flash chromatography on silica gel (eluant: AcOEt/cyclohexane 1/1) to afford 0.350 g (95% yield) of the title compound as a white solid.

¹H NMR (401 MHz, DMSO-d6) δ ppm 1.11 (t, J=7.49 Hz, 6H) 1.91-2.02 (m, 2H) 2.55 (q, J=7.49 Hz, 4H) 2.57-2.73 (m, 2H) 3.02 (t, J=7.02 Hz, 2H) 3.88 (s, 3H) 4.16 (s, 3H) 7.09-7.14 (m, 2H) 7.15-7.23 (m, 2H) 7.24 (d, J=2.20 Hz, 1H) 8.00 (d, J=8.67 Hz, 1H) 8.26 (s, 1H) 8.42 (s, 1H) 9.51 (s, 1H)

MS calc: 575.1765; MS found: 575.1761

According to this same methodology, but employing suitable substituted derivatives, the following compound was prepared:

1-(2-hydroxyethyl)-9-(methylsulfanyl)-1,4,5,6-tetrahydropyrazolo[4',3':6,7]cyclohepta[1,2-d]pyrimidine-3-carboxamide (84)

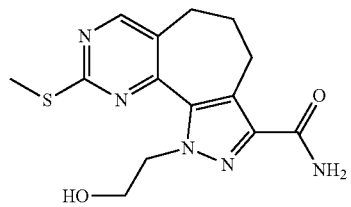 [SMILES: CSc1ncc2c(n1)-c1c(c(C(N)=O)nn1CCO)CCC2]

¹H NMR (401 MHz, DMSO-d6) δ ppm 1.95-2.05 (m, 2H) 2.56 (s, 3H) 2.56-2.61 (m, 2H) 2.97 (t, J=7.20 Hz, 2H) 3.71 (q, J=5.94 Hz, 2H) 4.67 (t, J=5.94 Hz, 2H) 4.74 (t, J=5.94 Hz, 1H) 7.22 (br. s., 1H) 7.48 (br. s., 1H) 8.58 (s, 1H)

MS calc: 320.1176; MS found: 320.1174

1-[3-(dimethylamino)propyl]-9-(methylsulfanyl)-1,4,5,6-tetrahydropyrazolo[4',3':6,7]cyclohepta[1,2-d]pyrimidine-3-carboxamide trifluoroacetate (31)

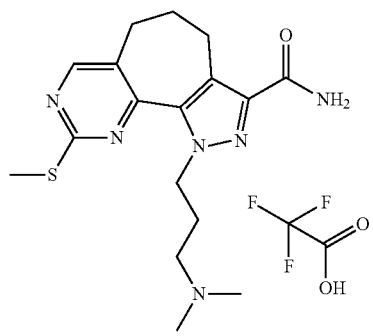

¹H NMR (401 MHz, DMSO-d6) δ ppm 2.00 (m, J=5.86 Hz, 2H) 2.17-2.28 (m, 2H) 2.57 (s, 3H) 2.60-2.65 (m, 2H) 2.78 (d, J=4.88 Hz, 6H) 3.02 (t, J=7.14 Hz, 2H) 3.07-3.15 (m, 2H) 4.61 (t, J=6.65 Hz, 2H) 7.34 (br. s., 1H) 7.45 (br. s., 1H) 8.61 (s, 1H) 9.30 (br. s., 1H)

MS calc: 361.1805; MS found: 361.1809

9-amino-1-methyl-N-{4-[(4-methylpiperazin-1-yl)sulfonyl]phenyl}-1,4,5,6-tetrahydropyrazolo[4',3':6,7]cyclohepta[1,2-d]pyrimidine-3-carboxamide

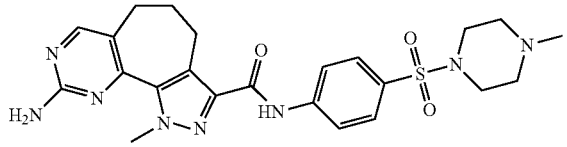 [SMILES: CN1CCN(S(=O)(=O)c2ccc(NC(=O)c3nn(C)c4c3CCCc3cnc(N)nc3-4)cc2)CC1]

¹H NMR (401 MHz, DMSO-d6) δ ppm 1.58-1.67 (m, 3H) 1.94-2.04 (m, 2H) 2.10-2.20 (m, 2H) 2.32-2.45 (m, 4H) 2.78-2.95 (m, 4H) 3.03 (t, J=7.02 Hz, 2H) 4.21 (s, 3H) 7.63-7.71 (m, 2H) 7.94-8.05 (m, 2H) 8.51 (s, 1H) 10.12 (s, 1H)

MS calc: 497.2078; MS found: 497.2060

1-methyl-9-(methylsulfanyl)-1,4,5,6-tetrahydropyrazolo[4',3':6,7]cyclohepta[1,2-d]pyrimidine-3-carboxamide (47)

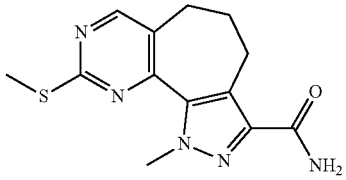 [SMILES: CSc1ncc2c(n1)-c1c(c(C(N)=O)nn1C)CCC2]

¹H NMR (401 MHz, DMSO-d6) δ ppm 1.89-2.01 (m, 2H) 2.56 (s, 3H) 2.60-2.67 (m, 2H) 3.05 (t, J=7.02 Hz, 2H) 4.18 (s, 3H) 7.20 (br. s., 1H) 7.46 (br. s., 1H) 8.55 (s, 1H)

MS calc: 290.1070; MS found: 290.1071

N-benzyl-9-(4-methoxyphenyl)-1-methyl-1,4,5,6-tetrahydropyrazolo[4',3':6,7]cyclohepta[1,2-d]pyrimidine-3-carboxamide

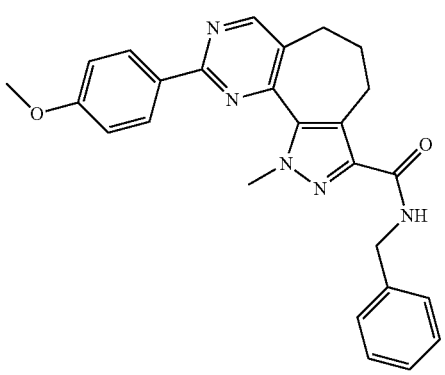 [SMILES: COc1ccc(-c2ncc3c(n2)-c2c(c(C(=O)NCc4ccccc4)nn2C)CCC3)cc1]

¹H NMR (401 MHz, DMSO-d6) δ ppm 1.96-2.05 (m, 2H) 2.68-2.79 (m, 2H) 3.11 (t, J=7.02 Hz, 2H) 3.84 (s, 3H) 4.33 (s, 3H) 4.43 (d, J=6.35 Hz, 2H) 7.07-7.12 (m, 2H) 7.19-7.28 (m, 1H) 7.30-7.35 (m, 4H) 8.36-8.39 (m, 2H) 8.70 (t, J=6.35 Hz, 1H) 8.76 (s, 1H)

MS calc: 440.2081; MS found: 440.2066

95

N-benzyl-1-methyl-9-[4-(trifluoromethyl)phenyl]-1,4,5,6-tetrahydropyrazolo[4',3':6,7]cyclohepta[1,2-d]pyrimidine-3-carboxamide

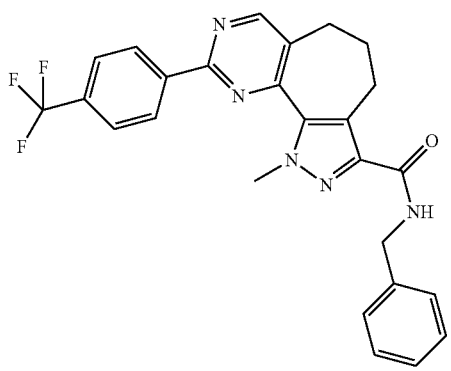 [SMILES: Cn1nc(C(=O)NCc2ccccc2)c2c1-c1nc(-c3ccc(C(F)(F)F)cc3)ncc1CCC2]

¹H NMR (401 MHz, DMSO-d6) δ ppm 1.97-2.08 (m, 2H) 2.75-2.85 (m, 2H) 3.13 (t, J=6.96 Hz, 2H) 4.34 (s, 3H) 4.44 (d, J=6.35 Hz, 2H) 7.20-7.26 (m, 1H) 7.29-7.36 (m, 4H) 7.88-7.96 (m, 2H) 8.59-8.66 (m, 2H) 8.72 (t, J=6.23 Hz, 1H) 8.89 (s, 1H)

MS calc: 478.1849; MS found: 478.1838

N-(3-methoxypropyl)-1-methyl-9-[4-(trifluoromethyl)phenyl]-1,4,5,6-tetrahydropyrazolo[4',3':6,7]cyclohepta[1,2-d]pyrimidine-3-carboxamide

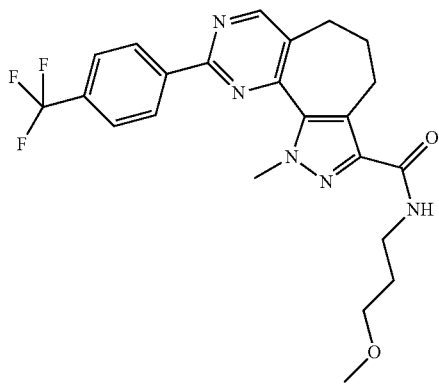 [SMILES: COCCCNC(=O)c1nn(C)c2c1CCCc1cnc(-c3ccc(C(F)(F)F)cc3)nc1-2]

¹H NMR (401 MHz, DMSO-d6) δ ppm 1.75 (m, 2H) 1.97-2.10 (m, 2H) 2.73-2.83 (m, 2H) 3.12 (t, J=6.96 Hz, 2H) 3.25 (s, 3H) 3.28-3.32 (m, 2H) 3.38 (t, J=6.29 Hz, 2H) 4.33 (s, 3H) 7.88-7.95 (m, 2H) 8.15 (t, J=5.86 Hz, 1H) 8.59-8.66 (m, 2H) 8.89 (s, 1H)

MS calc: 460.1955; MS found: 460.1943

96

9-(4-methoxyphenyl)-N-(3-methoxypropyl)-1-methyl-1,4,5,6-tetrahydropyrazolo[4',3':6,7]cyclohepta[1,2-d]pyrimidine-3-carboxamide

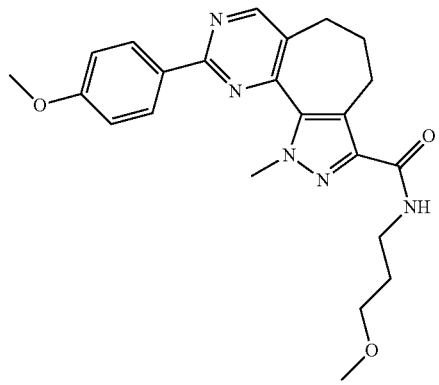 [SMILES: COCCCNC(=O)c1nn(C)c2c1CCCc1cnc(-c3ccc(OC)cc3)nc1-2]

¹H NMR (401 MHz, DMSO-d6) δ ppm 1.75 (m, 2H) 1.95-2.05 (m, 2H) 2.68-6.78 (m, 2H) 3.09 (t, J=6.96 Hz, 2H) 3.25 (s, 3H) 3.27-3.34 (m, 2H) 3.38 (t, J=3.23 Hz, 2H) 3.85 (s, 3H) 4.32 (s, 3H) 7.06-7.12 (m, 2H) 8.14 (t, J=5.86 Hz, 1H) 8.34-8.40 (m, 2H) 8.76 (s, 1H)

MS calc: 422.2187; MS found: 422.2179

Example 9

Conv. 8 Step 1

9-iodo-N-methoxy-N,1-dimethyl-1,4,5,6-tetrahydropyrazolo[4',3':6,7]cyclohepta[1,2-d]pyrimidine-3-carboxamide

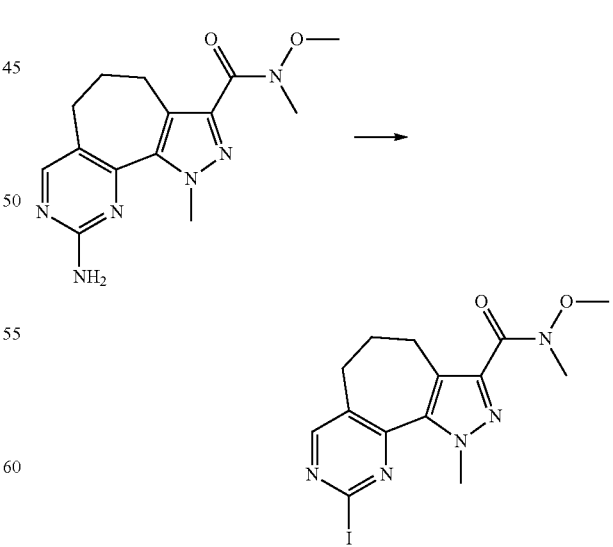

A mixture of N-methoxy-N,1-dimethyl-8-oxo-1,4,5,6-tetrahydropyrazolo[4',3':6,7]cyclohepta[1,2-d]pyrimidine-3-carboxamide (100 mg; 0.33 mmol), cesium iodide (103 mg;

0.39 mmol), iodine (50 mg; 0.2 mmol), copper(I) iodide (23 mg; 0.12 mmol), isoamyl nitrite (75 µL; 0.56 mmol) in DME (2 mL) was stirred at 70° C. for 24 h. An aqueous solution of Na$_2$S$_2$O$_5$ (5 mL) and DCM were then added and the layers separated. The organic phase was finally dried over Na$_2$SO$_4$ and evaporated. The crude was purified by flash chromatography on silica gel (hexane/AcOEt:4/6) to afford 24 mg (18% yield) of the title compound.

$^1$H NMR (401 MHz, DMSO-d6) δ ppm 1.91-2.00 (m, 2H) 2.64-2.71 (m, 2H) 2.84 (t, J=6.90 Hz, 2H) 3.27 (s, 3H) 3.71 (s, 3H) 4.13 (s, 3H) 8.47 (s, 1H)

MS calc: 414.0422; MS found: 414.0419

According to this same methodology, but employing suitable substituted derivatives, the following compound was prepared:

ethyl 9-iodo-1-methyl-1,4,5,6-tetrahydropyrazolo[4', 3':6,7]cyclohepta[1,2-d]pyrimidine-3-carboxylate

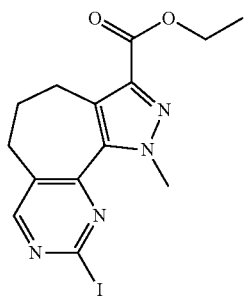 [SMILES: CCOC(=O)c1nn(C)c2c1CCCc1cnc(I)nc1-2]

$^1$H NMR (401 MHz, DMSO-d6) δ ppm 1.30 (t, J=7.08 Hz, 3H) 1.90-2.02 (m, 2H) 2.63-2.73 (m, 2H) 3.04 (t, J=6.90 Hz, 2H) 4.16 (s, 3H) 4.29 (q, J=7.08 Hz, 2H) 8.48 (s, 1H)

MS calc: 399.0313; MS found: 399.0323

Example 10

Conv. 12 Step 1

9-hydroxy-N-methoxy-N,1-dimethyl-1,4,5,6-tetrahydropyrazolo[4',3':6,7]cyclohepta[1,2-d]pyrimidine-3-carboxamide

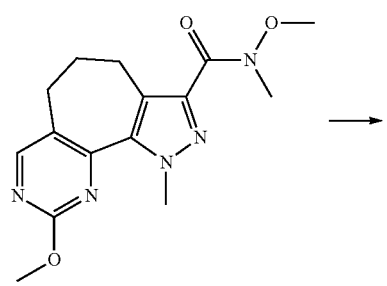

-continued

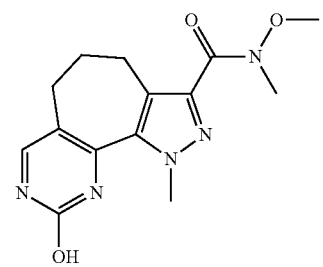

To a solution of N,9-dimethoxy-N,1-dimethyl-1,4,5,6-tetrahydropyrazolo[4',3':6,7]cyclohepta[1,2-d]pyrimidine-3-carboxamide (583 mg, 1.8 mmol) in CH$_3$CN (35 mL), sodium iodide (550 mg, 3.67 mmol) and trimethylsilylchloride (0.525 mL, 4.14 mmol) were added in sequence. Mixture was stirred for 24 h under argon atmosphere at room temperature then a second portion of sodium iodide (275 mg, 1.8 mmol) and trimethylsilylchloride (0.276 mL, 2.1 mmol) were added in sequence. After 24 h the solvent was evaporated, the residue dissolved with a mixture of DCM/MeOH (4/1) and washed with a saturated aqueous solution of Na$_2$S$_2$O$_3$. The organic layer was dried over Na$_2$SO$_4$. The residue was crystallized from MeOH to give 452 mg (83% yield) of a white solid.

$^1$H NMR (401 MHz, DMSO-d6) δ ppm 1.85-2.01 (m, 2H) 2.63-2.70 (m, 2H) 2.82 (t, J=7.02 Hz, 2H) 3.71 (s, 3H) 3.81 (s, 3H) 3.97 (s, 3H) 4.22 (s, 3H) 7.36 (s, 1H) 8.52 (s, 1H)

MS calc: 318.1561; MS found: 318.1553

According to this same methodology, but employing suitable substituted derivatives, the following compounds were prepared:

9-hydroxy-1-methyl-N-propyl-1,4,5,6-tetrahydropyrazolo[4',3':6,7]cyclohepta[1,2-d]pyrimidine-3-carboxamide

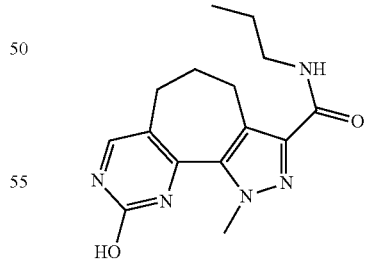

$^1$H NMR (401 MHz, DMSO-d6) δ ppm 0.86 (t, J=7.45 Hz, 3H) 1.43-1.56 (m, 2H) 1.83-1.96 (m, 2H) 2.38-2.46 (m, 2H) 3.00 (t, J=7.08 Hz, 2H) 3.12-3.21 (m, 2H) 4.12 (s, 3H) 7.90 (br. s., 1H) 8.08 (br. s, 1H) 11.81 (s, 1H)

MS calc: 302.1612; MS found: 302.1611

9-hydroxy-1-methyl-N-[3-(trifluoromethyl)phenyl]-1,4,5,6-tetrahydropyrazolo[4',3':6,7]cyclohepta[1,2-d]pyrimidine-3-carboxamide

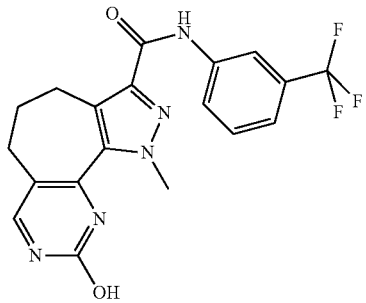 [SMILES: Cn1nc(C(=O)Nc2cccc(C(F)(F)F)c2)c2c1-c1nc(O)ncc1CCC2]

¹H NMR (401 MHz, DMSO-d6) δ ppm 1.89-2.04 (m, 2H) 2.54-2.62 (m, 2H) 2.99 (t, J=7.08 Hz, 2H) 4.19 (s, 3H) 7.25-7.31 (m, 1H) 7.54 (t, J=8.06 Hz, 1H) 7.96 (d, J=8.06 Hz, 1H) 8.23 (s, 1H) 8.49 (s, 1H) 9.92 (s, 1H)

MS calc: 404.1329; MS found: 404.1313

Example 11

Conv. 12 Step 2

3-[methoxy(methyl)carbamoyl]-1-methyl-1,4,5,6-tetrahydropyrazolo[4',3':6,7]cyclohepta[1,2-d]pyrimidin-9-yl trifluoromethanesulfonate

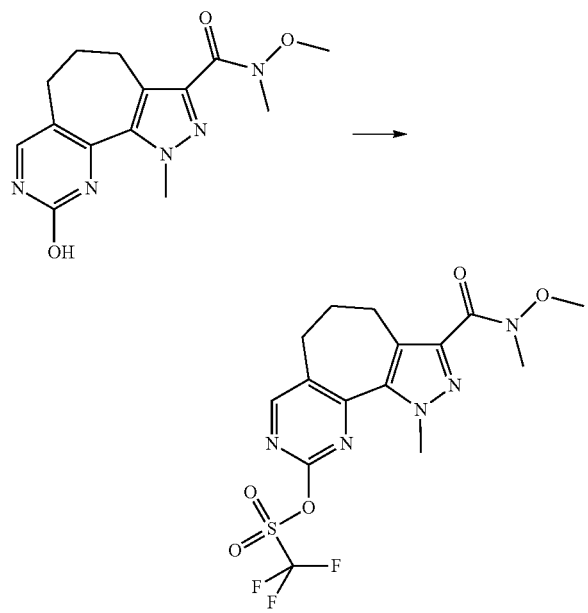

A solution of 9-hydroxy-N-methoxy-N,1-dimethyl-1,4,5,6-tetrahydropyrazolo[4',3':6,7]cyclohepta[1,2-d]pyrimidine-3-carboxamide (452 mg, 1.49 mmol) and TEA (0.415 mL, 2.98 mmol) in dry DCM (36 mL) was stirred at −78° C. for 5 h. Trifluoromethanesulfonic anhydride (0.190 mL, 1.78 mmol) was then added. The reaction was stirred overnight and the temperature was allowed to rise to room temperature; then it was washed with aqueous $NaHCO_3$, dried over $Na_2SO_4$ and evaporated. The crude was triturated with $Et_2O$ and collected by filtration to give 440 mg of a white solid (68% yield).

¹H NMR (401 MHz, DMSO-d6) δ ppm 1.94-2.04 (m, 2H) 2.79-2.86 (m, 2H) 2.89 (t, J=6.90 Hz, 2H) 3.31 (s, 3H) 3.71 (s, 3H) 4.16 (s, 3H) 8.87 (s, 1H)

MS calc: 436.0897; MS found: 436.0894

Example 12

Conv. 14

N-(2-ethylphenyl)-9-{[2-methoxy-4-(4-methylpiperazin-1-yl)phenyl]amino}-1-methyl-1,4,5,6-tetrahydropyrazolo[4',3':6,7]cyclohepta[1,2-d]pyrimidine-3-carboxamide (15)

$Pd_2(dba)_3$, (0.002 g, 0.002 mmol), 2-dicyclohexylphosphino-2'-(N,N-dimethylamino)-biphenyl (0.002 g, 0.005 mmol), 9-[(4-bromo-2-methoxyphenyl)amino]-N-(2-ethylphenyl)-1-methyl-1,4,5,6-tetrahydropyrazolo[4',3':6,7]cyclohepta[1,2-d]pyrimidine-3-carboxamide (0.040 g, 0.07 mmol) in THF (1 mL) were charged in a round-bottomed flask flushed with argon. The flask was evacuated and backfilled with argon. $LiN(TMS)_2$ solution (1M in THF, 0.9 mL) and N-methylpiperazine (0.030 mL, 0.30 mmol) were added and the reaction mixture was heated at 85° C. for 0.5 h. The reaction mixture was then allowed to cool to room temperature and concentrated. The crude solid was purified by flash chromatography on silica gel (eluant: DCM/MeOH 95/5) to afford 0.040 g (95% yield) of the title compound as yellow solid.

¹H NMR (401 MHz, DMSO-d6) δ ppm 1.17 (t, J=7.51 Hz, 3H) 1.88-2.03 (m, 2H) 2.25 (s, 3H) 2.53-2.59 (m, 2H) 2.64 (q, J=7.51 Hz, 2H) 3.05 (t, J=7.08 Hz, 2H) 3.10-3.19 (m, 4H) 3.79 (s, 3H) 4.07 (s, 3H) 6.51 (dd, J=8.67, 2.56 Hz, 1H) 6.63 (d, J=2.56 Hz, 1H) 7.10-7.25 (m, 2H) 7.27 (dd, J=7.38, 1.77 Hz, 1H) 7.53 (d, J=8.67 Hz, 1H) 7.59 (dd, J=7.75, 1.40 Hz, 1H) 8.12 (s, 1H) 8.30 (s, 1H) 9.41 (s, 1H)

MS calc: 567.3191; MS found: 567.3173

101

According to this same methodology, but employing suitable substituted derivatives, the following compounds were prepared:

9-{[2-methoxy-4-(4-methylpiperazin-1-yl)phenyl]amino}-1-methyl-1,4,5,6-tetrahydropyrazolo[4',3':6,7]cyclohepta[1,2-d]pyrimidine-3-carboxamide (3)

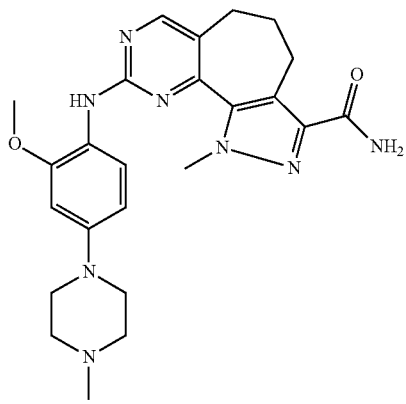 [SMILES: COc1cc(N2CCN(C)CC2)ccc1Nc1ncc2c(n1)-c1c(c(C(N)=O)nn1C)CCC2]

$^1$H NMR (401 MHz, DMSO-d6) δ ppm 1.86-1.99 (m, 2H) 2.25 (s, 3H) 2.51-2.56 (m, 6H) 3.00 (t, J=7.08 Hz, 2H) 3.09-3.17 (m, 4H) 3.78 (s, 3H) 4.00 (s, 3H) 6.49 (dd, J=8.79, 2.56 Hz, 1H) 6.62 (d, J=2.56 Hz, 1H) 7.16 (br. s., 1H) 7.37 (br. s., 1H) 7.53 (d, J=8.79 Hz, 1H) 8.07 (s, 1H) 8.28 (s, 1H)

MS calc: 463.2565; MS found: 463.2553

N-(2,6-diethylphenyl)-9-{[2-methoxy-4-(4-methylpiperazin-1-yl)phenyl]amino}-1-methyl-1,4,5,6-tetrahydropyrazolo[4',3':6,7]cyclohepta[1,2-d]pyrimidine-3-carboxamide (4)

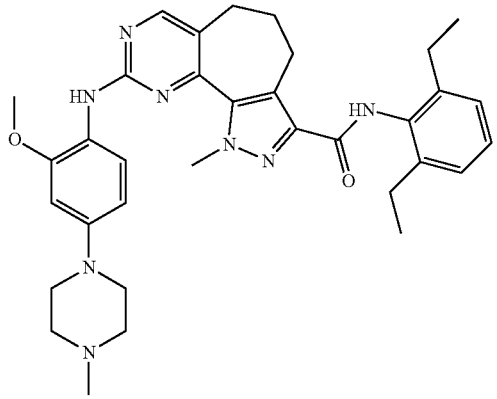 [SMILES: CCc1cccc(CC)c1NC(=O)c1nn(C)c2c1CCCc1cnc(Nc3ccc(N4CCN(C)CC4)cc3OC)nc1-2]

$^1$H NMR (401 MHz, DMSO-d6) δ ppm 1.10 (t, J=7.51 Hz, 6H) 1.86-1.99 (m, 2H) 2.30 (br. s., 3H) 2.52-2.60 (m, 6H) 3.00 (t, J=7.02 Hz, 2H) 3.10-3.21 (m, 4H) 3.79 (s, 3H) 4.07 (s, 3H) 6.52 (dd, J=8.67, 2.44 Hz, 1H) 6.64 (d, J=2.44 Hz, 1H) 7.03-7.16 (m, 2H) 7.16-7.27 (m, 1H) 7.56 (d, J=8.67 Hz, 1H) 8.10 (s, 1H) 8.30 (s, 1H) 9.45 (s, 1H)

MS calc: 595.3504; MS found: 595.3499

102

N-benzyl-9-{[2-methoxy-4-(4-methylpiperazin-1-yl)phenyl]amino}-1-methyl-1,4,5,6-tetrahydropyrazolo[4',3':6,7]cyclohepta[1,2-d]pyrimidine-3-carboxamide (7)

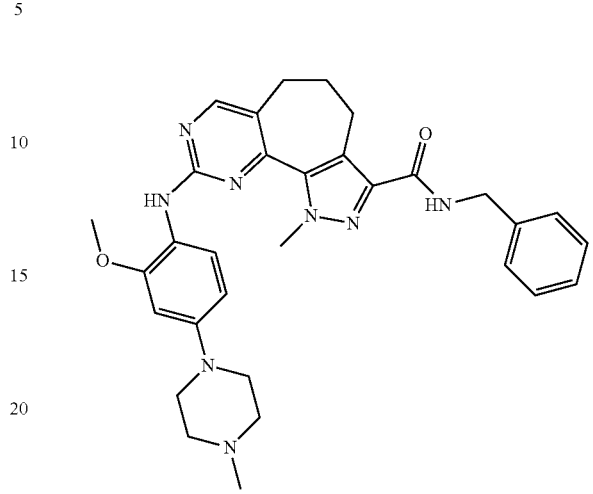

$^1$H NMR (401 MHz, DMSO-d6) δ ppm 1.85-1.99 (m, 2H) 2.23 (s, 3H) 2.43-2.48 (m, 4H) 2.51-2.56 (m, 2H) 3.00 (t, J=7.08 Hz, 2H) 3.08-3.17 (m, 4H) 3.78 (s, 3H) 4.02 (s, 3H) 4.41 (d, J=6.23 Hz, 2H) 6.49 (dd, J=8.67, 2.56 Hz, 1H) 6.62 (d, J=2.56 Hz, 1H) 7.18-7.26 (m, 1H) 7.27-7.34 (m, 4H) 7.53 (d, J=8.67 Hz, 1H) 8.08 (s, 1H) 8.28 (s, 1H) 8.59 (t, J=6.23 Hz, 1H)

MS calc: 553.3034; MS found 553.3019

9-{[2-methoxy-4-(4-methylpiperazin-1-yl)phenyl]amino}-1-methyl-N-phenyl-1,4,5,6-tetrahydropyrazolo[4',3':6,7]cyclohepta[1,2-d]pyrimidine-3-carboxamide (8)

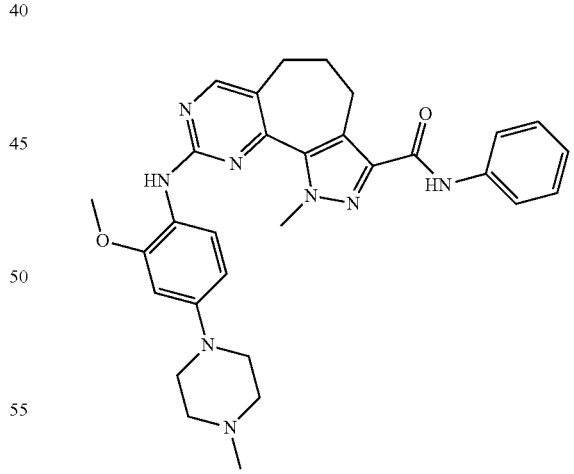

$^1$H NMR (401 MHz, DMSO-d6) δ ppm 1.82-2.04 (m, 2H) 2.25 (s, 3H) 2.50-2.53 (m, 4H) 2.53-2.61 (m, 2H) 3.05 (t, J=7.02 Hz, 2H) 3.10-3.18 (m, 4H) 3.78 (s, 3H) 4.08 (s, 3H) 6.50 (dd, J=8.67, 2.56 Hz, 1H) 6.63 (d, J=2.56 Hz, 1H) 6.87-7.16 (m, 1H) 7.23-7.38 (m, 2H) 7.53 (d, J=8.67 Hz, 1H) 7.70-7.89 (m, 2H) 8.12 (s, 1H) 8.30 (s, 1H) 9.95 (s, 1H)

MS calc: 539.2878; MS found 539.2855

103

N-(2,6-diethylphenyl)-9-({4-[(4-hydroxycyclohexyl)amino]-2-methoxyphenyl}amino)-1-methyl-1,4,5,6-tetrahydropyrazolo[4',3':6,7]cyclohepta[1,2-d]pyrimidine-3-carboxamide (9)

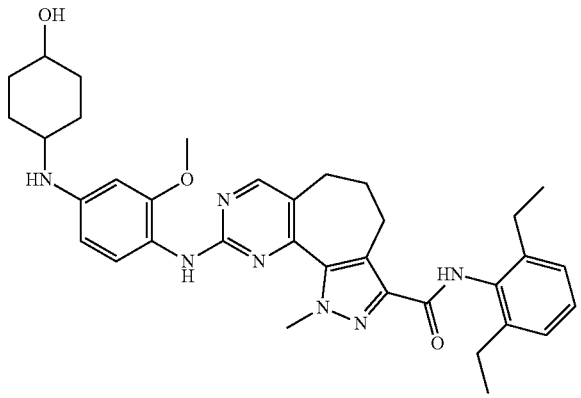 [SMILES: CCc1cccc(CC)c1NC(=O)c1nn(C)c2c1CCCc1cnc(Nc3ccc(NC4CCC(O)CC4)cc3OC)nc1-2]

$^1$H NMR (401 MHz, DMSO-d6) δ ppm 1.10 (t, J=7.57 Hz, 6H) 1.13-1.21 (m, 2H) 1.22-1.35 (m, 2H) 1.79-1.88 (m, 2H) 1-88-2-01 (m, 4H) 2.52-2.58 (m, 6H) 3.00 (t, J=7.02 Hz, 2H) 3.09-3.21 (m, 1H) 3.39-3.48 (m, 1H) 3.69 (s, 3H) 4.02 (s, 3H) 4.51 (d, J=4.39 Hz, 1H) 5.22 (d, J=8.18 Hz, 1H) 6.14 (dd, J=8.61, 2.32 Hz, 1H) 6.29 (d, J=2.32 Hz, 1H) 7.06-7.13 (m, 2H) 7.16-7.25 (m, 2H) 8.00 (s, 1H) 8.24 (s, 1H) 9.43 (s, 1H)

MS calc: 610.3500; MS found 610.3483

N-(2,6-diethylphenyl)-9-[(4-{[3-(dimethylamino)propyl](methyl)amino}-2-methoxyphenyl)amino]-1-methyl-1,4,5,6-tetrahydropyrazolo[4',3':6,7]cyclohepta[1,2-d]pyrimidine-3-carboxamide (10)

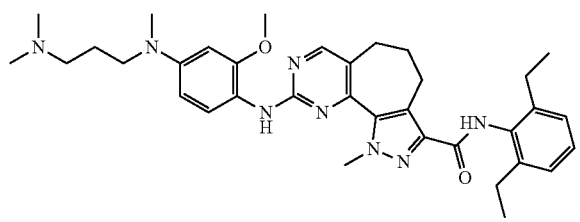 [SMILES: CCc1cccc(CC)c1NC(=O)c1nn(C)c2c1CCCc1cnc(Nc3ccc(N(C)CCCN(C)C)cc3OC)nc1-2]

$^1$H NMR (401 MHz, DMSO-d6) δ ppm 1.10 (t, J=7.57 Hz, 6H) 1.64 (quin, J=7.02 Hz, 2H) 1.86-1.98 (m, 2H) 2.13 (s, 6H) 2.23 (t, J=6.90 Hz, 1H) 2.51-2.60 (m, 6H) 2.89 (s, 3H) 3.00 (t, J=6.90 Hz, 2H) 3.28-3.36 (m, 4H) 3.76 (s, 3H) 4.04 (s, 3H) 6.29 (dd, J=8.67, 2.56 Hz, 1H) 6.39 (d, J=2.56 Hz, 1H) 7.05-7.15 (m, 2H) 7.15-7.23 (m, 1H) 7.37 (d, J=8.67 Hz, 1H) 8.05 (s, 1H) 8.26 (s, 1H) 9.42 (s, 1H)

MS calc: 611.3817; MS found 611.3798

104

N-(2,6-diethylphenyl)-9-({2-methoxy-4-[4-(pyrrolidin-1-yl)piperidin-1-yl]phenyl}amino)-1-methyl-1,4,5,6-tetrahydropyrazolo[4',3':6,7]cyclohepta[1,2-d]pyrimidine-3-carboxamide (11)

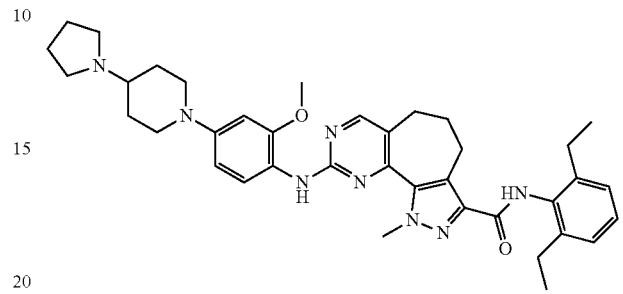

$^1$H NMR (401 MHz, DMSO-d6) δ ppm 1.10 (t, J=7.57 Hz, 6H) 1.42-1.60 (m, 2H) 1.64-1.75 (m, 4H) 1.83-2.00 (m, 4H) 2.05-2.19 (m, 1H) 2.52-2.59 (m, 8H) 267-2.77 (m, 2H) 3.00 (t, J=7.02 Hz, 2H) 3.56-3.65 (m 2H) 3.78 (s, 3H) 4.07 (s, 3H) 6.51 (dd, J=8.67, 2.56 Hz, 1H) 6.63 (d, J=2.56 Hz, 1H) 7.04-7.14 (m, 2H) 7.16-7.24 (m, 1H) 7.53 (d, J=8.67 Hz, 1H) 8.09 (s, 1H) 8.29 (s, 1H) 9.45 (s, 1H)

MS calc: 649.3973; MS found: 649.3962

N-(2,6-diethylphenyl)-9-({4-[(3R)-3-(dimethylamino)pyrrolidin-1-yl]-2-methoxyphenyl}amino)-1-methyl-1,4,5,6-tetrahydropyrazolo[4',3':6,7]cyclohepta[1,2-d]pyrimidine-3-carboxamide (12)

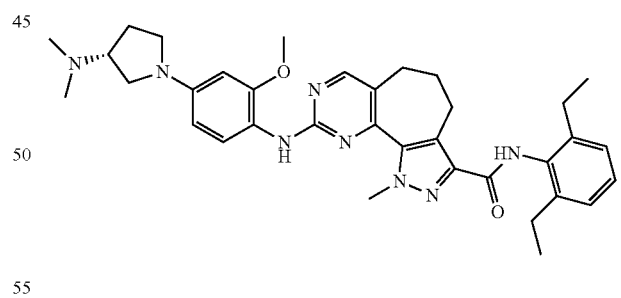

$^1$H NMR (401 MHz, DMSO-d6) δ ppm 1.10 (t, J=7.51 Hz, 6H) 1.76-1.86 (m, 1H) 2.10-2.18 (m, 1H) 2.21 (s, 6H) 2.52-2.60 (m, 6H) 2.75-2.86 (m, 1H) 3.00 (t, J=7.02 Hz, 2H) 3.05 (t, J=9.03 Hz, 1H) 3.34-3.41 (m, 2H) 3.45 (dd, J=9.03, 7.20 Hz, 1H) 3.77 (s, 3H) 4.05 (s, 3H) 6.12 (dd, J=8.54, 2.45 Hz, 1H) 6.21 (d, J=2.45 Hz, 1H) 7.09-7.14 (m, 2H) 7.15-7.24 (m, 1H) 7.37 (d, J=8.54 Hz, 1H) 8.04 (s, 1H) 8.25 (s, 1H) 9.43 (s, 1H)

MS calc: 609.3660; MS found: 609.3638

105

N-(2,6-diethylphenyl)-9-[(4-{[2-(dimethylamino)ethyl](methyl)amino}-2-methoxyphenyl)amino]-1-methyl-1,4,5,6-tetrahydropyrazolo[4',3':6,7]cyclohepta[1,2-d]pyrimidine-3-carboxamide (13)

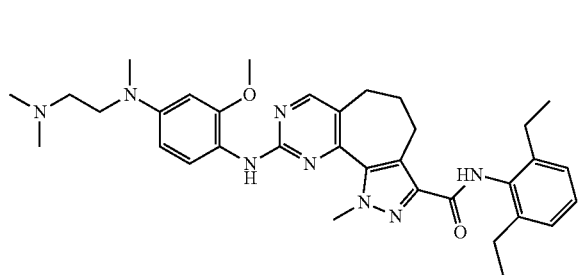 [SMILES: CCc1cccc(CC)c1NC(=O)c1nn(C)c2c1CCCc1cnc(Nc3ccc(N(C)CCN(C)C)cc3OC)nc1-2]

¹H NMR (401 MHz, DMSO-d6) δ ppm 1.10 (t, J=7.57 Hz, 6H) 1.84-1.98 (m, 2H) 2.19 (s, 6H) 2.39 (t, J=6.96 Hz, 2H) 2.51-2.60 (m, 8H) 2.92 (s, 3H) 3.00 (t, J=6.96 Hz, 2H) 3.42 (t, J=7.32 Hz, 2H) 3.76 (s, 3H) 4.04 (s, 3H) 6.28 (dd, J=8.67, 2.44 Hz, 1H) 6.36 (d, J=2.44 Hz, 1H) 7.08-7.14 (m, 2H) 7.16-7.23 (m, 1H) 7.37 (d, J=8.67 Hz, 1H) 8.06 (s, 1H) 8.26 (s, 1H) 9.43 (s, 1H)

MS calc: 597.3660; MS found: 597.3634

N-(2,6-diethylphenyl)-9-({4-[4-(2-hydroxyethyl)piperazin-1-yl]-2-methoxyphenyl}amino)-1-methyl-1,4,5,6-tetrahydropyrazolo[4',3':6,7]cyclohepta[1,2-d]pyrimidine-3-carboxamide (14)

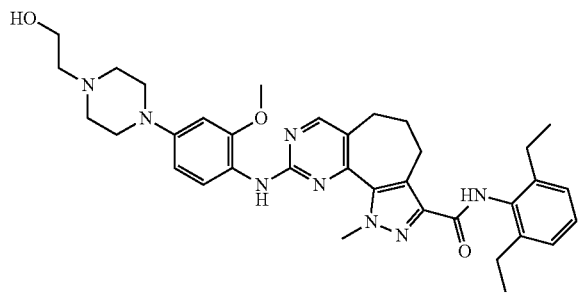 [SMILES: CCc1cccc(CC)c1NC(=O)c1nn(C)c2c1CCCc1cnc(Nc3ccc(N4CCN(CCO)CC4)cc3OC)nc1-2]

¹H NMR (401 MHz, DMSO-d6) δ ppm 1.10 (t, J=7.57 Hz, 6H) 1.88-2.00 (m, 2H) 2.44 (t, J=6.29 Hz, 2H) 2.52-2.61 (m, 10H) 3.00 (t, J=7.02 Hz, 2H) 3.09-3.16 (m, 4H) 3.54 (q, J=6.29 Hz, 2H) 3.79 (s, 3H) 4.07 (s, 2H) 4.41 (t, J=5.25 Hz, 1H) 6.50 (dd, J=8.79, 2.50 Hz, 1H) 6.63 (d, J=2.50 Hz, 1H) 7.07-7.14 (m, 2H) 7.17-7.23 (m, 1H) 7.54 (d, J=8.79 Hz, 1H) 8.10 (s, 1H) 8.30 (s, 1H) 9.45 (s, 1H)

MS calc: 625.3609; MS found: 625.3602

106

9-{[2-methoxy-4-(4-methylpiperazin-1-yl)phenyl]amino}-1-methyl-N-[(1S)-2-(morpholin-4-yl)-1-phenylethyl]-1,4,5,6-tetrahydropyrazolo[4',3':6,7]cyclohepta[1,2-d]pyrimidine-3-carboxamide (18)

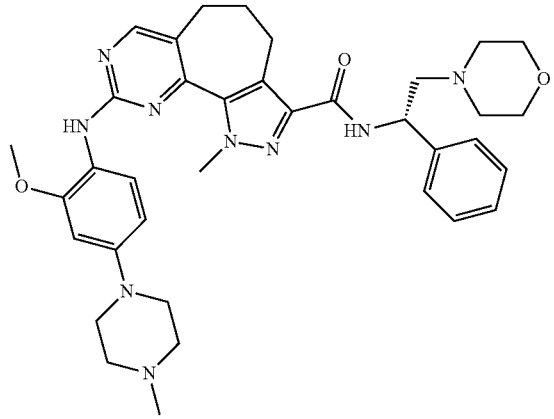 [SMILES: COc1cc(N2CCN(C)CC2)ccc1Nc1ncc2c(n1)-c1c(c(C(=O)N[C@H](CN3CCOCC3)c3ccccc3)nn1C)CCC2]

¹H NMR (401 MHz, DMSO-d6) δ ppm 1.85-1.96 (m, 2H) 2.24 (s, 3H) 2.36-2.44 (m, 2H) 2.49-2.56 (m, 8H) 2.80-2.91 (m, 2H) 2.95 (t, J=7.14 Hz, 2H) 3.09-3.18 (m, 4H) 3.47-3.66 (m, 4H) 3.78 (s, 3H) 4.05 (s, 3H) 5.08-5.18 (m, 1H) 6.50 (dd, J=8.79, 2.56 Hz, 1H) 6.63 (d, J=2.56 Hz, 1H) 7.18-7.26 (m, 2H) 7.37-7.43 (m, 2H) 7.54 (d, J=8.79 Hz, 1H) 8.08 (s, 1H) 8.28 (s, 1H) 8.31 (d, J=7.81 Hz, 1H)

MS calc: 652.3718; MS found: 652.3702

N-(2,6-dimethylphenyl)-9-{[2-methoxy-4-(4-methylpiperazin-1-yl)phenyl]amino}-1-methyl-1,4,5,6-tetrahydropyrazolo[4',3':6,7]cyclohepta[1,2-d]pyrimidine-3-carboxamide (20)

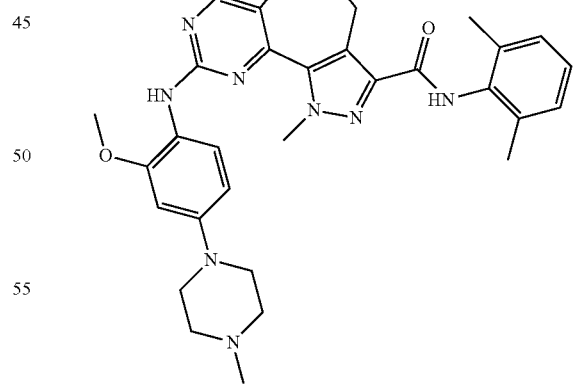

¹H NMR (401 MHz, DMSO-d6) δ ppm 1.89-1.97 (m, 2H) 2.18 (s, 6H) 2.24 (s, 3H) 2.43-2.48 (m, 4H) 2.54-2.60 (m, 2H) 3.02 (t, J=7.02 Hz, 2H) 3.09-3.16 (m, 4H) 3.79 (s, 3H) 4.07 (s, 3H) 6.51 (dd, J=8.54, 2.56 Hz, 1H) 6.63 (d, J=2.56 Hz, 1H) 7.07-7.10 (m, 3H) 7.55 (d, J=8.54 Hz, 1H) 8.10 (s, 1H) 8.30 (s, 1H) 9.46 (s, 1H)

MS calc: 567.3191; MS found: 567.3163

107

9-{[4-(dimethylamino)-2-methoxyphenyl]amino}-N-(2,6-dimethylphenyl)-1-methyl-1,4,5,6-tetrahydropyrazolo[4',3':6,7]cyclohepta[1,2-d]pyrimidine-3-carboxamide (21)

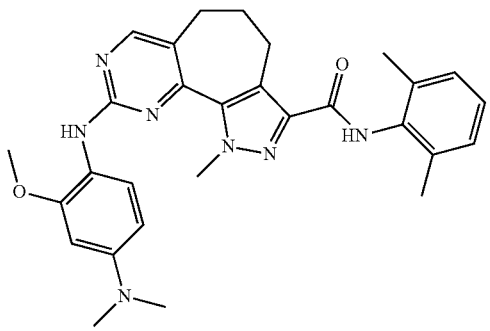 [SMILES: COc1cc(N(C)C)ccc1Nc1ncc2c(n1)-c1c(c(C(=O)Nc3c(C)cccc3C)nn1C)CCC2]

¹H NMR (401 MHz, DMSO-d6) δ ppm 1.88-1.99 (m, 2H) 2.17 (s, 6H) 2.53-2.60 (m, 2H) 2.90 (s, 6H) 3.02 (t, J=7.02 Hz, 2H) 3.78 (s, 3H) 4.06 (s, 3H) 6.32 (dd, J=8.54, 2.56 Hz, 1H) 6.41 (d, J=2.56 Hz, 1H) 7.07-7.11 (m, 3H) 7.43 (d, J=8.54 Hz, 1H) 8.06 (s, 1H) 8.27 (s, 1H) 9.44 (s, 1H)

MS calc: 512.2769; MS found: 512.2755

N-(2,6-diethylphenyl)-9-({4-[4-(dimethylamino)piperidin-1-yl]-2-methoxyphenyl}amino)-1-methyl-1,4,5,6-tetrahydropyrazolo[4',3':6,7]cyclohepta[1,2-d]pyrimidine-3-carboxamide (22)

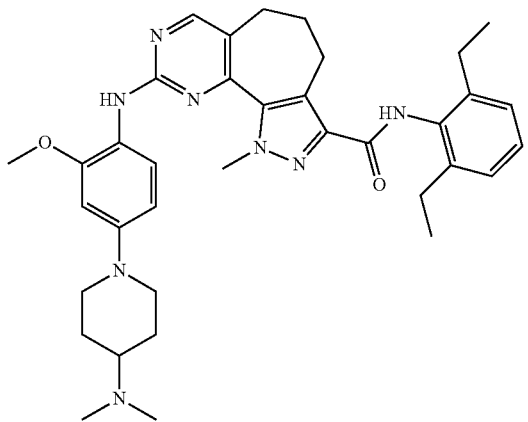 [SMILES: CCc1cccc(CC)c1NC(=O)c1nn(C)c2c1CCCc1cnc(Nc3ccc(N4CCC(N(C)C)CC4)cc3OC)nc1-2]

¹H NMR (401 MHz, DMSO-d6) δ ppm 1.11 (t, J=7.57 Hz, 6H) 1.50 (qd, J=11.84, 3.78 Hz, 2H) 1.79-1.88 (m, 2H) 1.89-2.00 (m, 2H) 2.12-2.26 (m, 7H) 2.51-2.59 (m, 6H) 2.61-2.71 (m, 2H) 3.01 (t, J=7.02 Hz, 2H) 3.64-3.73 (m, 2H) 3.78 (s, 3H) 4.07 (s, 3H) 6.51 (dd, J=8.67, 2.44 Hz, 1H) 6.63 (d, J=2.44 Hz, 1H) 7.07-7.14 (m, 2H) 7.16-7.24 (m, 1H) 7.53 (d, J=8.67 Hz, 1H) 8.09 (s, 1H) 8.30 (s, 1H) 9.45 (s, 1H)

MS calc: 623.3817; MS found: 623.3820

108

N-(2,6-diethylphenyl)-9-{[2-methoxy-4-(4-methyl-1,4-diazepan-1-yl)phenyl]amino}-1-methyl-1,4,5,6-tetrahydropyrazolo[4',3':6,7]cyclohepta[1,2-d]pyrimidine-3-carboxamide (23)

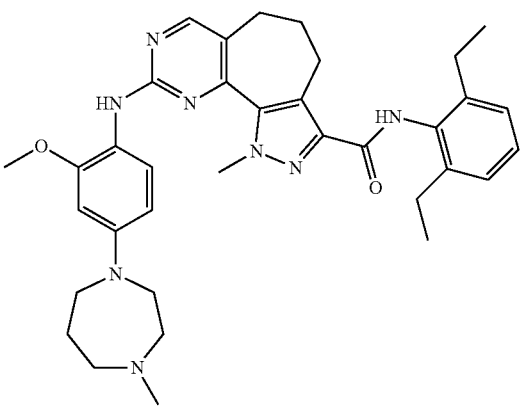 [SMILES: CCc1cccc(CC)c1NC(=O)c1nn(C)c2c1CCCc1cnc(Nc3ccc(N4CCCN(C)CC4)cc3OC)nc1-2]

¹H NMR (401 MHz, DMSO-d6) δ ppm 1.10 (t, J=7.57 Hz, 6H) 1.84-1.97 (m, 4H) 2.27 (s, 3H) 2.43-2.48 (m, 2H) 2.51-2.60 (m, 6H) 2.61-2.66 (m, 2H) 3.01 (t, J=6.96 Hz, 2H) 3.46 (t, J=6.23 Hz, 2H) 3.50-3.55 (m, 2H) 3.75 (s, 3H) 4.04 (s, 3H) 6.27 (dd, J=8.67, 2.569 Hz, 1H) 6.33 (d, J=2.56 Hz, 1H) 7.09-7.13 (m, 2H) 7.18-7.24 (m, 1H) 7.33 (d, J=8.67 Hz, 1H) 8.05 (s, 1H) 8.25 (s, 1H) 9.43 (s, 1H)

MS calc: 609.3660; MS found: 609.3633

N-(2,6-diethylphenyl)-9-({2-methoxy-4-[(1-methylpiperidin-4-yl)amino]phenyl}amino)-1-methyl-1,4,5,6-tetrahydropyrazolo[4',3':6,7]cyclohepta[1,2-d]pyrimidine-3-carboxamide (25)

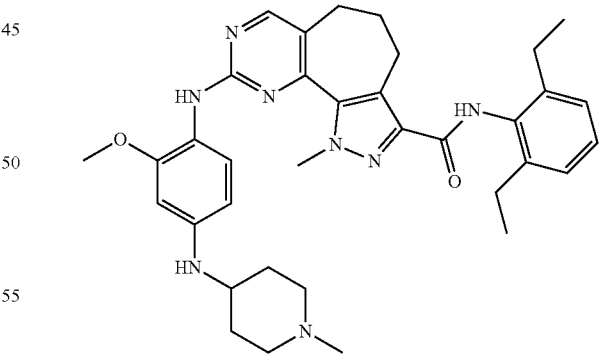

¹H NMR (401 MHz, DMSO-d6) δ ppm 1.10 (t, J=7.57 Hz, 6H) 1.33-1.48 (m, 2H) 1.86-1.98 (m, 4H) 2.00-2.14 (m, 2H) 2.20 (s, 3H) 2.51-2.59 (m, 6H) 2.86-2.93 (m, 2H) 3.00 (t, J=6.96 Hz, 2H) 3.13-3.25 (m, 1H) 3.70 (s, 3H) 4.03 (s, 3H) 5.32 (d, J=8.18 Hz, 1H) 6.16 (dd, J=8.67, 2.32 Hz, 1H) 6.31 (d, J=2.32 Hz, 1H) 7.08-7.15 (m, 2H) 7.16-7.28 (m, 2H) 8.00 (s, 1H) 8.24 (s, 1H) 9.43 (s, 1H)

MS calc: 609.3660; MS found: 609.3636

9-{[4-(1-azabicyclo[2.2.2]oct-3-ylamino)-2-methoxyphenyl]amino}-N-(2,6-diethylphenyl)-1-methyl-1,4,5,6-tetrahydropyrazolo[4',3':6,7]cyclohepta[1,2-d]pyrimidine-3-carboxamide (26)

N-cyclohexyl-9-{[2-methoxy-4-(4-methylpiperazin-1-yl)phenyl]amino}-1-methyl-1,4,5,6-tetrahydropyrazolo[4',3':6,7]cyclohepta[1,2-d]pyrimidine-3-carboxamide (28)

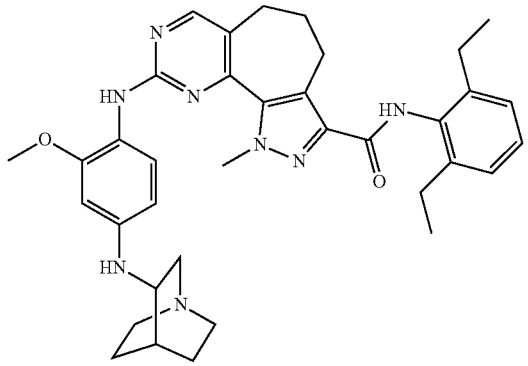 [SMILES: CCc1cccc(CC)c1NC(=O)c1nn(C)c2c1CCCc1cnc(Nc3ccc(NC4CN5CCC4CC5)cc3OC)nc1-2]

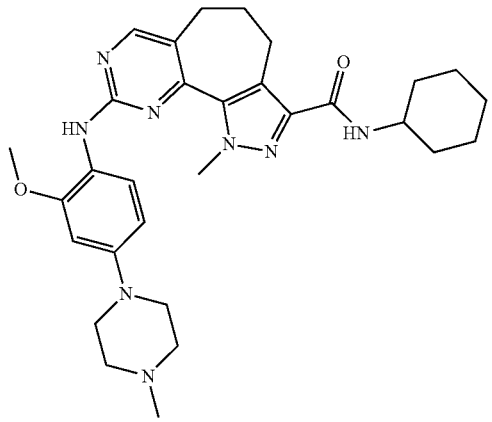

¹H NMR (401 MHz, DMSO-d6) δ ppm 1.10 (t, J=7.51 Hz, 6H) 1.22-1.38 (m, 1H) 1.53-1.69 (m, 2H) 1.75-1.87 (m, 1H) 1.88-1.98 (m, 3H) 2.48-2.52 (m, 2H) 2.52-2.60 (m, 6H) 2.63-2.67 (m, 3H) 2.77-2.88 (m, 1H) 3.00 (t, J=7.02 Hz, 2H) 3.15-3.26 (m, 2H) 3.37-3.48 (m, 1H) 3.71 (s, 3H) 4.03 (s, 3H) 5.62 (d, J=6.84 Hz, 1H) 6.14 (dd, J=8.54, 2.20, 2 Hz, 1H) 6.32 (d, J=2.20 Hz, 1H) 7.08-7.14 (m, 2H) 7.16-7.22 (m, 1H) 7.24 (d, J=8.54 Hz, 1H) 8.01 (s, 1H) 8.24 (s, 1H) 9.44 (s, 1H)

MS calc: 621.3660; MS found: 621.3649

¹H NMR (401 MHz, DMSO-d6) δ ppm 1.03-1.20 (m, 1H) 1.21-1.41 (m, 4H) 1.53 (m, 1H) 1.65-1.82 (m, 4H) 1.87-1.98 (m, 2H) 2.25 (s, 3H) 2.46-2.54 (m, 6H) 2.99 (t, J=7.02 Hz, 2H) 3.09-3.17 (m, 4H) 3.70 (s, 1H) 3.77 (s, 3H) 4.01 (s, 3H).49 (dd, J=8.67, 2.44 Hz, 1H) 6.62 (d, J=2.44 Hz, 1H) 7.53 (d, J=8.67 Hz, 1H) 7.65 (d, J=8.42 Hz, 1H) 8.08 (s, 1H) 8.28 (s, 1H)

MS calc: 545.3347; MS found: 545.3325

N-(2-ethyl-6-methylphenyl)-9-{[2-methoxy-4-(4-methylpiperazin-1-yl)phenyl]amino}-1-methyl-1,4,5,6-tetrahydropyrazolo[4',3':6,7]cyclohepta[1,2-d]pyrimidine-3-carboxamide (27)

9-{[2-methoxy-4-(4-methylpiperazin-1-yl)phenyl]amino}-N,1-dimethyl-1,4,5,6-tetrahydropyrazolo[4',3':6,7]cyclohepta[1,2-d]pyrimidine-3-carboxamide (39)

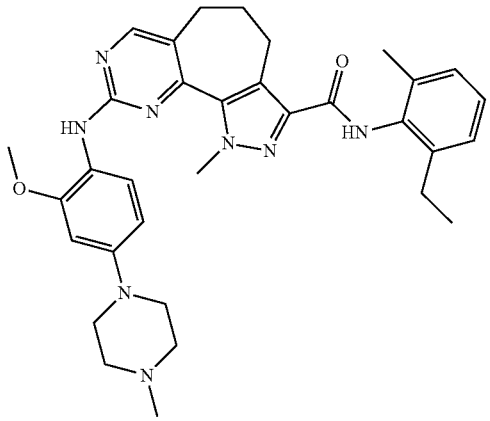 [SMILES: CCc1cccc(C)c1NC(=O)c1nn(C)c2c1CCCc1cnc(Nc3ccc(N4CCN(C)CC4)cc3OC)nc1-2]

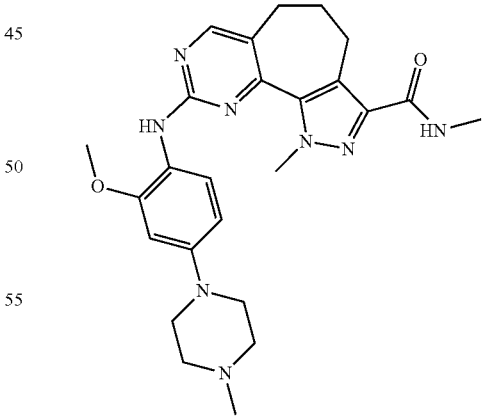

¹H NMR (401 MHz, DMSO-d6) δ ppm 1.10 (t, J=7.51 Hz, 3H) 1.90-1.99 (m, 2H) 2.17 (s, 3H) 2.25 (s, 2H) 2.52-2.60 (m, 4H) 3.01 (t, J=7.02 Hz, 2H) 3.10-3.18 (m, 4H) 3.79 (s, 3H) 4.07 (s, 3H) 6.51 (dd, J=8.67, 2.56 Hz, 1H) 6.64 (d, J=2.56 Hz, 1H) 7.07-7.18 (m, 3H) 7.55 (d, J=8.67 Hz, 1H) 8.10 (s, 1H) 8.30 (s, 1H) 9.45 (s, 1H)

MS calc: 581.3347; MS found: 581.3325

¹H NMR (401 MHz, DMSO-d6) δ ppm 1.87-1.99 (m, 2H) 2.29 (br. s., 3H) 2.73 (d, J=4.76 Hz, 3H) 2.99 (t, J=7.08 Hz, 2H) 3.10-3.19 (m., 4H) 3.78 (s, 3H) 4.01 (s, 3H) 6.50 (dd, J=8.54, 2.56 Hz, 1H) 6.63 (d, J=2.56 Hz, 1H) 7.54 (d, J=8.54 Hz, 1H) 7.99 (q, J=4.76 Hz, 1H) 8.08 (s, 1H) 8.28 (s, 1H)

MS calc: 477.2721; MS found: 477.2714

111

N-(2,6-diethylphenyl)-1-(4-methoxybenzyl)-9-{[2-methoxy-4-(4-methylpiperazin-1-yl)phenyl]amino}-1,4,5,6-tetrahydropyrazolo[4',3':6,7]cyclohepta[1,2-d]pyrimidine-3-carboxamide (48)

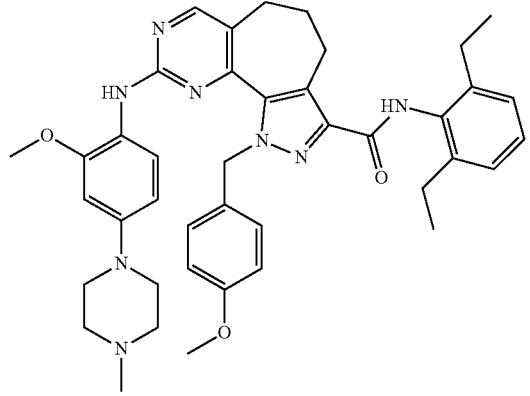 [SMILES: CCc1cccc(CC)c1NC(=O)c1nn(Cc2ccc(OC)cc2)c2c1CCCc1cnc(Nc3ccc(N4CCN(C)CC4)cc3OC)nc1-2]

$^1$H NMR (401 MHz, DMSO-d6) δ ppm 1.11 (t, J=7.57 Hz, 6H) 1.88-2.00 (m, 2H) 2.24 (s, 2H) 2.41-2.52 (m, 6H) 2.56 (q, J=7.57 Hz, 4H) 2.99 (t, J=7.02 Hz, 2H) 3.07-3.18 (m, 4H) 3.68 (s, 3H) 3.78 (s, 3H) 5.81 (s, 2H) 6.44 (dd, J=8.79, 2.32 Hz, 1H) 6.62 (d, J=2.32 Hz, 1H) 6.75-6.82 (m, 2H) 6.92-6.99 (m, 2H) 7.09-7.15 (m, 2H) 7.16-7.26 (m, 1H) 7.53 (d, J=8.79 Hz, 1H) 8.09 (s, 1H) 8.27 (s, 1H) 9.49 (s, 1H)

MS calc: 701.3922; MS found: 701.3929

N-(2,6-diethylphenyl)-9-({4-[4-(dimethylamino)piperidin-1-yl]-2-methoxyphenyl}amino)-1-(4-methoxybenzyl)-1,4,5,6-tetrahydropyrazolo[4',3':6,7]cyclohepta[1,2-d]pyrimidine-3-carboxamide (61)

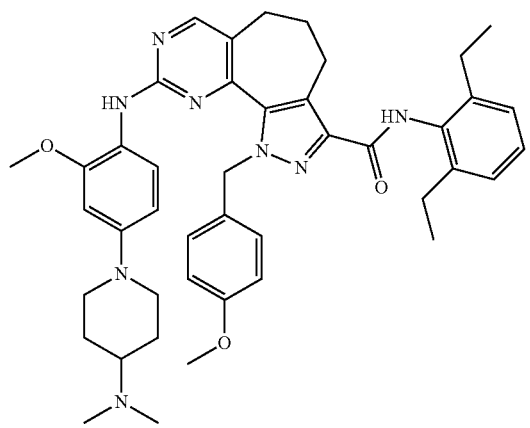 [SMILES: CCc1cccc(CC)c1NC(=O)c1nn(Cc2ccc(OC)cc2)c2c1CCCc1cnc(Nc3ccc(N4CCC(N(C)C)CC4)cc3OC)nc1-2]

$^1$H NMR (401 MHz, DMSO-d6) δ ppm 1.12 (t, J=7.57 Hz, 6H) 1.58-1.74 (m, 2H) 1.88-2.04 (m, 4H) 2.43-2.48 (m, 2H) 2.56 (q, J=7.57 Hz, 4H) 2.60-2.72 (m, 6H) 3.00 (t, J=7.08 Hz, 2H) 3.68 (s, 3H) 3.73-3.78 (m, 2H) 3.79 (s, 3H) 5.82 (s, 2H) 6.48 (dd, J=8.73, 2.38 Hz, 1H) 6.65 (d, J=2.38 Hz, 1H) 6.75-6.85 (m, 2H) 6.92-6.99 (m, 2H) 7.05-7.16 (m, 2H) 7.16-7.29 (m, 1H) 7.55 (d, J=8.73 Hz, 1H) 8.10 (s, 1H) 8.27 (s, 1H) 9.49 (s, 1H)

MS calc: 729.4235; MS found: 729.4211

112

9-{[2-methoxy-4-(4-methylpiperazin-1-yl)phenyl]amino}-2-methyl-2,4,5,6-tetrahydropyrazolo[4',3':6,7]cyclohepta[1,2-d]pyrimidine-3-carboxamide (95)

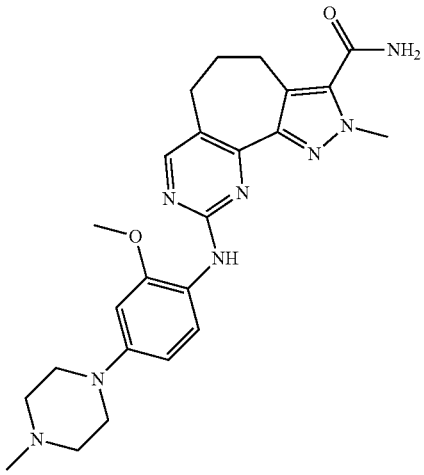 [SMILES: COc1cc(N2CCN(C)CC2)ccc1Nc1ncc2c(n1)-c1nn(C)c(C(N)=O)c1CCC2]

$^1$H NMR (401 MHz, DMSO-d6) δ ppm 1.87-2.02 (m, 2H) 2.25 (s, 3H) 2.62-2.69 (m, 2H) 2.89 (t, J=6.53 Hz, 2H) 3.06-3.17 (m, 4H) 3.85 (s, 3H) 3.99 (s, 3H) 6.49 (dd, J=8.67, 2.56 Hz, 1H) 6.64 (d, J=2.56 Hz, 1H) 7.68 (s, 1H) 7.77 (br. s., 1H) 7.83 (br. s., 1H) 8.10 (d, J=8.67 Hz, 1H) 8.22 (s, 1H)

MS calc: 463.2565; MS found: 463.2565

N-(2,6-diethylphenyl)-9-{[2-methoxy-4-(4-methylpiperazin-1-yl)phenyl]amino}-2-methyl-2,4,5,6-tetrahydropyrazolo[4',3':6,7]cyclohepta[1,2-d]pyrimidine-3-carboxamide (97)

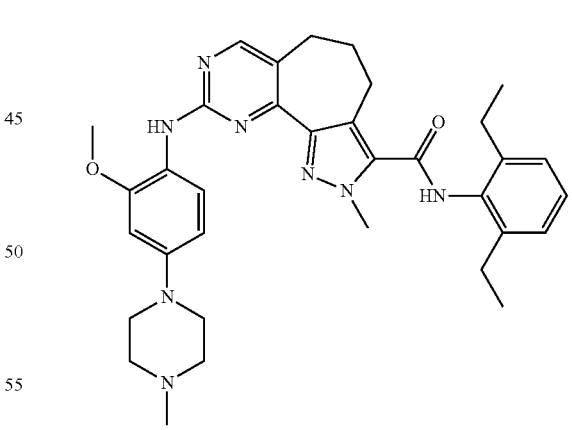

$^1$H NMR (401 MHz, DMSO-d6) δ ppm 1.17 (t, J=7.57 Hz, 6H) 1.95-2.06 (m, 2H) 2.33 (br.s., 3H) 2.54-2.66 (m, 8H) 2.69-2.75 (m, 2H) 3.06 (t, J=6.53 Hz, 2H) 3.10-3.20 (m, 4H) 3.86 (s, 3H) 4.05 (s, 3H) 6.51 (dd, J=8.79, 2.56 Hz, 1H) 6.66 (d, J=2.56 Hz, 1H) 7.14-7.22 (m, 2H) 7.24-7.30 (m, 1H) 7.73 (s, 1H) 8.11 (d, J=8.79 Hz, 1H) 8.26 (s, 1H) 9.84 (s, 1H)

MS calc: 595.3504; MS found: 595.3499

113

N-(2,6-diethylphenyl)-9-({4-[4-(dimethylamino)piperidin-1-yl]-2-methoxyphenyl}amino)-5,6-dihydro-4H-isoxazolo[4',5':6,7]cyclohepta[1,2-d]pyrimidine-3-carboxamide (98)

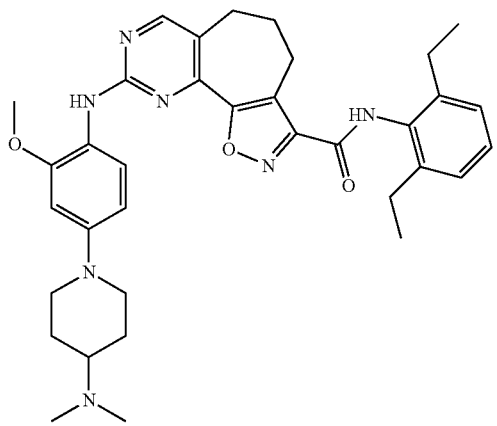 [SMILES: CCc1cccc(CC)c1NC(=O)c1noc2c1CCCc1cnc(Nc3ccc(N4CCC(N(C)C)CC4)cc3OC)nc1-2]

¹H NMR (401 MHz, DMSO-d6) δ ppm 1.14 (t, J=7.57 Hz, 6H) 1.49-1.73 (m, 2H) 1.88-2.01 (m, 2H) 2.52-2.62 (m, 5H) 2.63-2.73 (m, 2H) 2.76-2.86 (m, 2H) 2.99 (t, J=6.16 Hz, 2H) 3.72-3.82 (m, 2H) 3.84 (s, 3H) 6.55 (dd, J=8.42 and 2.44 Hz, 1H) 6.67 (d, J=2.44 Hz, 1H) 7.07-7.20 (m, 2H) 7.20-7.34 (m, 1H) 7.93 (d, J=8.42 Hz, 1H) 8.08 (s, 1H) 8.38 (s, 1H) 10.25 (s, 1H)

MS calc: 610.3500; MS found: 610.3498

114

N-(2,6-diethylphenyl)-9-({4-[4-(dimethylamino)piperidin-1-yl]-2-methoxyphenyl}amino)-5,6-dihydro-4H-isoxazolo[4',3':6,7]cyclohepta[1,2-d]pyrimidine-3-carboxamide (100)

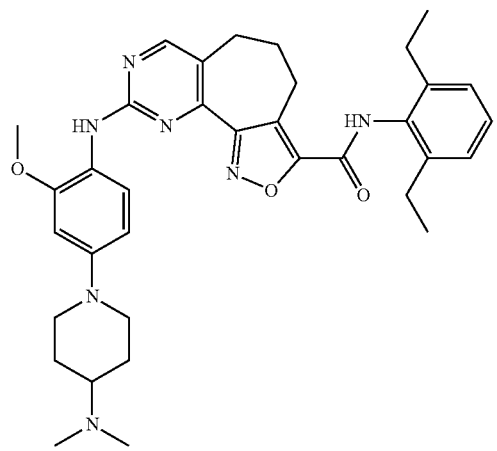

¹H NMR (401 MHz, DMSO-d6) δ ppm 1.13 (t, J=7.57 Hz, 6H) 1.60-1.80 (m, 2H) 1.90-2.03 (m, 2H) 2.03-2.13 (m, 2H) 2.58 (q, J=7.57 Hz, 4H) 2.65-2.76 (m, 2H) 2.79 (s, 6H) 3.06 (t, J=6.71 Hz, 2H) 3.76-3.92 (m, 7H) 6.48-6.61 (m, 1H) 6.66-6.72 (m, 1H) 7.12-7.21 (m, 2H) 7.23-7.31 (m, 1H) 7.94-7.02 (m, 1H) 8.09 (s, 1H) 8.43 (s, 1H) 10.31 (s, 1H)

MS calc: 610.3500; MS found: 610.3472

N-(2,6-diethylphenyl)-9-{[2-methoxy-4-(4-methylpiperazin-1-yl)phenyl]amino}-5,6-dihydro-4H-isoxazolo[4',5':6,7]cyclohepta[1,2-d]pyrimidine-3-carboxamide (99)

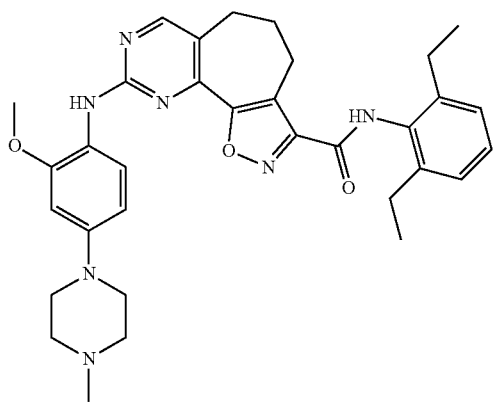 [SMILES: CCc1cccc(CC)c1NC(=O)c1noc2c1CCCc1cnc(Nc3ccc(N4CCN(C)CC4)cc3OC)nc1-2]

¹H NMR (401 MHz, DMSO-d6) δ ppm 1.14 (t, J=7.57 Hz, 6H) 1.90-2.02 (m, 2H) 2.39 (br.s., 3H) 2.58 (q, J=7.57 Hz, 4H) 2.63-2.75 (m, 2H) 2.78-2.84 (m, 2H) 2.99 (t, J=6.16 Hz, 2H) 3.13-3-26 (m, 4H) 3.84 (s, 3H) 6.54 (dd, J=8.67, 2.50 Hz, 1H) 6.68 (d, J=2.50 Hz, 1H) 7.09-7.21 (m, 2H) 7.21-7.32 (m, 1H) 7.94 (d, J=8.67 Hz, 1H) 8.08 (s, 1H) 8.38 (s, 1H) 10.26 (s, 1H)

MS calc: 582.3187; MS found: 582.3163

N-(2,6-diethylphenyl)-9-{[2-methoxy-4-(4-methylpiperazin-1-yl)phenyl]amino}-5,6-dihydro-4H-isoxazolo[4',3':6,7]cyclohepta[1,2-d]pyrimidine-3-carboxamide (101)

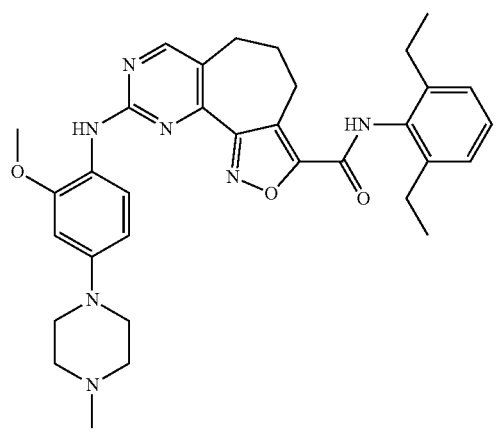 [SMILES: CCc1cccc(CC)c1NC(=O)c1onc2c1CCCc1cnc(Nc3ccc(N4CCN(C)CC4)cc3OC)nc1-2]

¹H NMR (401 MHz, DMSO-d6) δ ppm 1.13 (t, J=7.57 Hz, 6H) 1.93-2.04 (m, 2H) 2.50-2.54 (m, 5H) 2.56 (q, J=7.57 Hz, 4H) 2.60-2.71 (m, 4H) 2.71-2.80 (m, 2 h) 3.06 (t, J=6.65 Hz, 3H) 3.19-3.24 (m, 2H) 3.85 (s, 3H) 6.55 (dd, J=8.54, 2.32 Hz, 1H) 6.71 (d, J=2.32 Hz, 1H) 7.15-7.20 (m, 2H) 7.22-7.32 (m, 1H) 8.03 (d, J=8.54 Hz, 1H) 8.07 (s, 1H) 8.44 (s, 1H) 10.31 (s, 1H)

MS calc: 582.3187; MS found: 582.3163

Example 13

Conv. 15

4-({3-[(2,6-diethylphenyl)carbamoyl]-1-methyl-1,4,5,6-tetrahydropyrazolo[4',3':6,7]cyclohepta[1,2-d]pyrimidin-9-yl}amino)-3-methoxybenzoic acid trifluoroacetate (33)

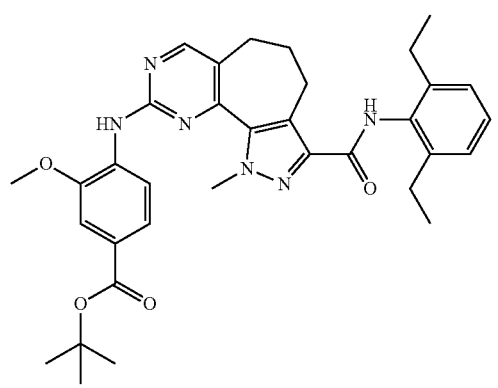

→

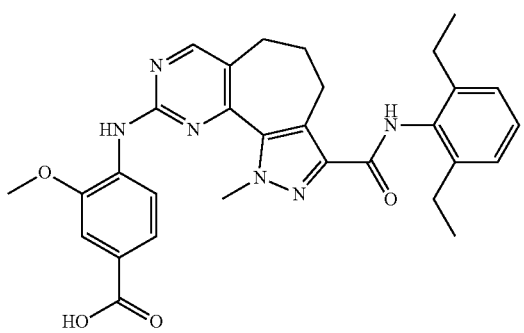

To a solution of tert-butyl 4-({3-[(2,6-diethylphenyl)carbamoyl]-1-methyl-1,4,5,6-tetrahydropyrazolo[4',3':6,7]cyclohepta[1,2-d]pyrimidin-9-yl}amino)-3-methoxybenzoate (0.450 g, 0.75 mmol) in DCM (6 mL), TFA (1 mL) was added. The mixture was stirred at room temperature for 2 hours. The organic solvent was evaporated to dryness to give the title compound in quantitative yield.

$^1$H NMR (401 MHz, DMSO-d6) δ ppm 1.12 (t, J=7.57 Hz, 6H) 1.94-2.06 (m, 2H) 2.56 (q, J=7.57 Hz, 4H) 2.60-2.67 (m, 2H) 3.03 (t, J=7.14 Hz, 2H) 3.95 (s, 3H) 4.23 (s, 3H) 7.03-7.17 (m, 2H) 7.17-7.28 (m, 1H) 7.54 (d, J=1.83 Hz, 1H) 7.65 (dd, J=8.42, 1.83 Hz, 1H) 8.37 (s, 1H) 8.38 (d, J=8.42 Hz, 1H) 8.51 (s, 1H) 9.54 (s, 1H) 12.54 (s, 1H)

MS calc: 541.2558; MS found: 541.2545

According to this same methodology, but employing suitable substituted derivatives, the following compound was prepared:

4-({3-[(2,6-diethylphenyl)carbamoyl]-1-methyl-1,4,5,6-tetrahydropyrazolo[4',3':6,7]cyclohepta[1,2-d]pyrimidin-9-yl}amino)-3-(trifluoromethoxy)benzoic acid trifluoroacetate (34)

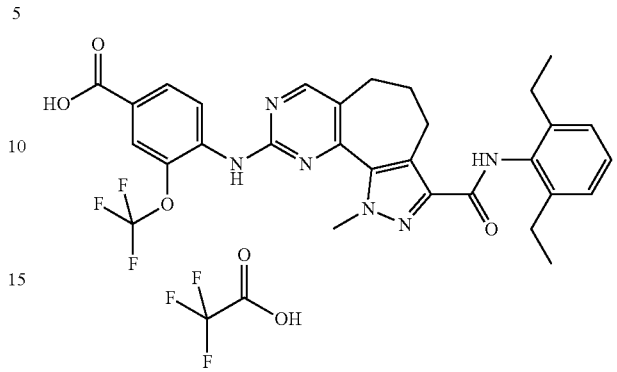

$^1$H NMR (401 MHz, DMSO-d6) δ ppm 1.11 (t, J=7.57 Hz, 6H) 1.93-2.03 (m, 2H) 2.55 (q, J=7.57 Hz, 4H) 2.62-2.68 (m, 2H) 3.04 (t, J=7.02 Hz, 2H) 4.16 (s, 3H) 7.08-7.16 (m, 2H) 7.18-7.24 (m, 1H) 7.85 (d, J=1.89 Hz, 1H) 7.97 (dd, J=8.54, 1.89 Hz, 1H) 8.26 (d, J=8.54 Hz, 1H) 8.50 (s, 1H) 9.41 (s, 1H) 9.52 (s, 1H)

MS calc: 595.2275; MS found: 595.2263

Example 14

Conv. 16

N-(2,6-diethylphenyl)-9-({2-methoxy-4-[(1-methylpiperidin-4-yl)carbamoyl]phenyl}amino)-1-methyl-1,4,5,6-tetrahydropyrazolo[4',3':6,7]cyclohepta[1,2-d]pyrimidine-3-carboxamide (35)

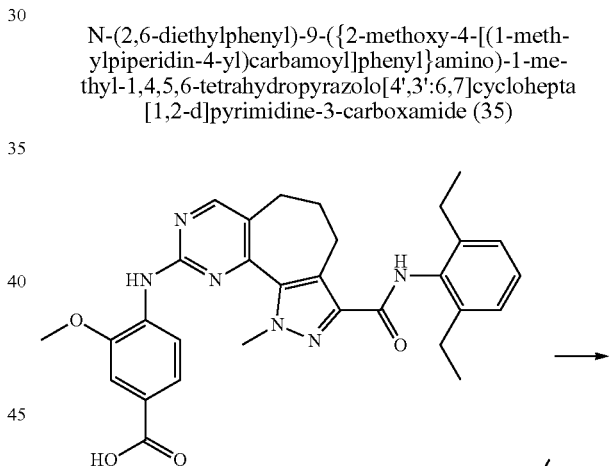

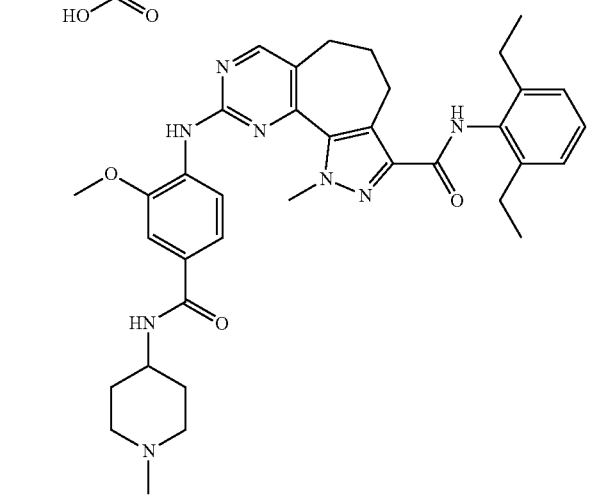

A solution of 4-({3-[(2,6-diethylphenyl)carbamoyl]-1-methyl-1,4,5,6-tetrahydropyrazolo[4',3':6,7]cyclohepta[1,2- d]pyrimidin-9-yl}amino)-3-methoxybenzoic acid (50 mg, 0.092 mmol) in anhydrous DMF (0.5 mL) was treated with DIPEA (0.150 mL) and TBTU (50 mg, 0.150 mmol). The mixture was then treated with 1-methylpiperidin-4-amine (18 mg, 1.38 mmol) and was stirred at room temperature for 2 hours. The reaction was diluted with water and extracted twice with DCM. The organic layer was dried over $Na_2SO_4$ and the solvent was evaporated to dryness. The crude solid was purified by flash chromatography on silica gel (DCM/MeOH) to afford 43 mg (72% yield) of the title compound.

$^1$H NMR (401 MHz, DMSO-d6) δ ppm 1.12 (t, J=7.57, 6H) 1.62-1.81 (m, 2H) 1.82-1.93 (m, 2H) 1.93-2.04 (m, 2H) 2.43 (br.s., 3H) 2.45-2.50 (m, 4H) 2.56 (q, J=7.57 Hz, 4H) 2.60-2.65 (m, 2H) 3.03 (t, J=7.08 Hz, 3H) 3.83-3.92 (m, 1H) 3.95 (s, 3H) 4.22 (s, 3H) 7.07-7.16 (m, 2H) 7.17-7.23 (m, 1H) 7.51-7.61 (m, 1H) 8.22 (br. s., 1H) 8.24 (d, J=8.30 Hz, 1H) 8.31 (s, 1H) 8.48 (s, 1H) 9.51 (s, 1H)

MS calc: 637.3609; MS found: 637.3586

According to this same methodology, but employing suitable substituted derivatives, the following compounds were prepared:

N-(2,6-diethylphenyl)-9-[(2-methoxy-4-{[4-(pyrrolidin-1-yl)piperidin-1-yl]carbonyl}phenyl)amino]-1-methyl-1,4,5,6-tetrahydropyrazolo[4',3':6,7]cyclohepta[1,2-d]pyrimidine-3-carboxamide (36)

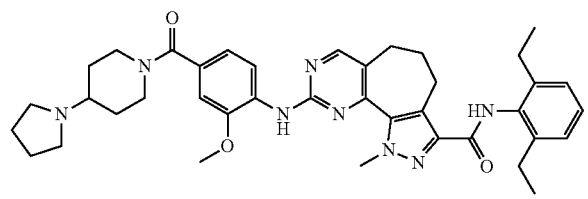 [SMILES: CCc1cccc(CC)c1NC(=O)c1nn(C)c2c1CCCc1cnc(Nc3ccc(C(=O)N4CCC(N5CCCC5)CC4)cc3OC)nc1-2]

$^1$H NMR (401 MHz, DMSO-d6) δ ppm 1.12 (t, J=7.57 Hz, 6H) 1.47-1.66 (m, 2H) 1.77-1.92 (m, 2H) 1.93-2.06 (m, 4H) 2.06-2.14 (m, 2H) 2.55 (q, J=7.57 Hz, 4H) 2.59-2.66 (m, 2H) 3.03 (t, J=7.08 Hz, 2H) 3.06-3.17 (m, 2H) 3.26-3.31 (m, 4H) 3.38-3.47 (m, 1H) 3.48-3.57 (m, 2H) 3.91 (s, 3H) 4.21 (s, 3H) 7.00-7.09 (m, 2H) 7.10-7.16 (m, 2H) 7.17-7.26 (m, 1H) 8.22 (d, J=8.06 Hz, 1H) 8.33 (s, 1H) 8.46 (s, 1H) 9.50 (s, 1H) 9.65 (br. s., 1H)

MS calc: 677.3922; MS found: 677.3918

N-(2,6-diethylphenyl)-9-[(4-{[4-(dimethylamino)piperidin-1-yl]carbonyl}-2-methoxyphenyl)amino]-1-methyl-1,4,5,6-tetrahydropyrazolo[4',3':6,7]cyclohepta[1,2-d]pyrimidine-3-carboxamide (37)

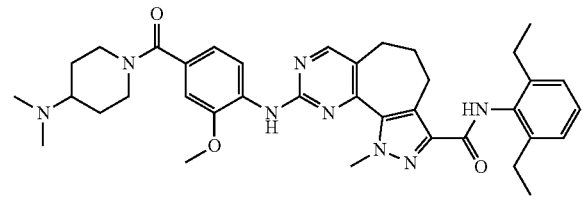 [SMILES: CCc1cccc(CC)c1NC(=O)c1nn(C)c2c1CCCc1cnc(Nc3ccc(C(=O)N4CCC(N(C)C)CC4)cc3OC)nc1-2]

$^1$H NMR (401 MHz, DMSO-d6) δ ppm 1.11 (t, J=7.57 hz, 6H) 1.29-1.42 (m, 2H) 1.71-1.85 (m, 2H) 1.92-2.02 (m, 2H) 2.19 (s, 6H) 2.31-2.41 (m, 1H) 2.55 (q, J=7.57 Hz, 4H) 2.59-2.65 (m, 2H) 2.94-2.96 (m, 2H) 3.02 (t, J=7.08 Hz, 2H) 3.14-3.19 (m, 2H) 3.90 (s, 3H) 4.19 (s, 3H) 7.03 (dd, J=8.18, 1.71 Hz, 1H) 7.07 (d, J=1.71 Hz, 1H) 7.10-7.16 (m, 2H) 7.18-7.24 (m, 1H) 8.15 (d, J=8.18 Hz, 1H) 8.30 (s, 1H) 8.45 (s, 1H) 9.52 (s, 1H)

MS calc: 651.3766; MS found: 651.3734

N-(2,6-diethylphenyl)-9-({2-methoxy-4-[(4-methyl-1,4-diazepan-1-yl)carbonyl]phenyl}amino)-1-methyl-1,4,5,6-tetrahydropyrazolo[4',3':6,7]cyclohepta[1,2-d]pyrimidine-3-carboxamide (38)

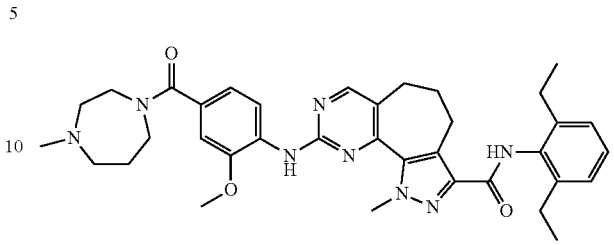

$^1$H NMR (401 MHz, DMSO-d6) δ ppm 1.11 (t, J=7.57 Hz, 6H) 1.71-1.90 (m, 2H) 1.92-2.03 (m, 2H) 2.21-2.34 (m, 2H) 2.49-2.54 (m, 5H) 2.55 (q, J=7.57 Hz, 4H) 2.59-2.66 (m, 2H) 3.02 (t, J=7.08 Hz, 2H) 3.40-3.54 (m, 2H) 3.56-3.68 (m, 2H) 3.89 (s, 3H) 4.18 (s, 3H) 7.02 (dd, J=8.18, 1.53 Hz, 1H) 7.06 (d, J=1.53 Hz, 1H) 7.10-7.15 (m, 2H) 7.18-7.24 (m, 1H) 8.14 (d, J=8.18 Hz, 1H) 8.29 (s, 1H) 8.45 (s, 1H) 9.52 (s, 1H)

MS calc: 637.3609; MS found: 637.3597

N-(2,6-diethylphenyl)-1-methyl-9-({4-[(1-methylpiperidin-4-yl)carbamoyl]-2-(trifluoromethoxy)phenyl}amino)-1,4,5,6-tetrahydropyrazolo[4',3':6,7]cyclohepta[1,2-d]pyrimidine-3-carboxamide (40)

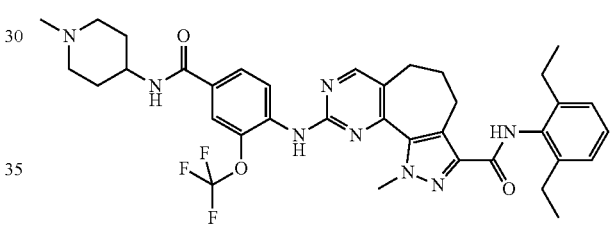

$^1$H NMR (401 MHz, DMSO-d6) δ ppm 1.11 (t, J=7.57 Hz, 6H) 1.55-1.71 (m, 2H) 1.76-1.88 (m, 2H) 1.92-2.02 (m, 2H) 2.05-2.20 (m, 2H) 2.28 (br. s., 3H) 2.55 (q, J=7.57 Hz, 4H) 2.61-2.66 (m, 2H) 2.83-2.97 (m, 2H) 3.04 (t, J=7.02 Hz, 2H) 3.73-3.84 (m, 1H) 4.13 (s, 3H) 7.07-7.16 (m, 2H) 7.16-7.25 (m, 1H) 7.87 (d, J=1.95 Hz, 1H) 7.90 (dd, J=8.54, 1.95 Hz, 1H) 8.10 (d, J=8.54 Hz, 1H) 8.33 (d, J=7.69 Hz, 1H) 8.46 (s, 1H) 9.31 (s, 1H) 9.49 (s, 1H)

MS calc: 691.3327; MS found: 691.3333

N-(2,6-diethylphenyl)-1-methyl-9-{[4-{[4-(pyrrolidin-1-yl)piperidin-1-yl]carbonyl}-2-(trifluoromethoxy)phenyl]amino}-1,4,5,6-tetrahydropyrazolo[4',3':6,7]cyclohepta[1,2-d]pyrimidine-3-carboxamide (41)

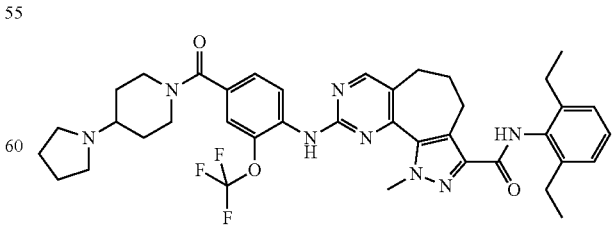

$^1$H NMR (401 MHz, DMSO-d6) δ ppm 1.11 (t, J=7.57 Hz, 6H) 1.35-1.50 (m, 4H) 1.62-1.78 (m, 4H) 1.82-1.92 (m, 1H) 1.92-2.03 (m, 2H) 2.41-2.48 (4H) 2.55 (q, J=7.57 Hz, 4H)

2.59-2.66 (m, 2H) 3.03 (t, J=6.96 Hz, 2H) 4.11 (s, 3H) 7.06-7.14 (m, 2H) 7.17-7.22 (m, 1H) 7.37-7.47 (m, 2H) 8.03 (d, J=8.30 Hz, 1H) 8.44 (s, 1H) 9.26 (s, 1H) 9.49 (s, 1H)

MS calc: 731.3640; MS found: 731.3639

N-(2,6-diethylphenyl)-9-{[4-{[4-(dimethylamino)piperidin-1-yl]carbonyl}-2-(trifluoromethoxy)phenyl]amino}-1-methyl-1,4,5,6-tetrahydropyrazolo[4',3':6,7]cyclohepta[1,2-d]pyrimidine-3-carboxamide (42)

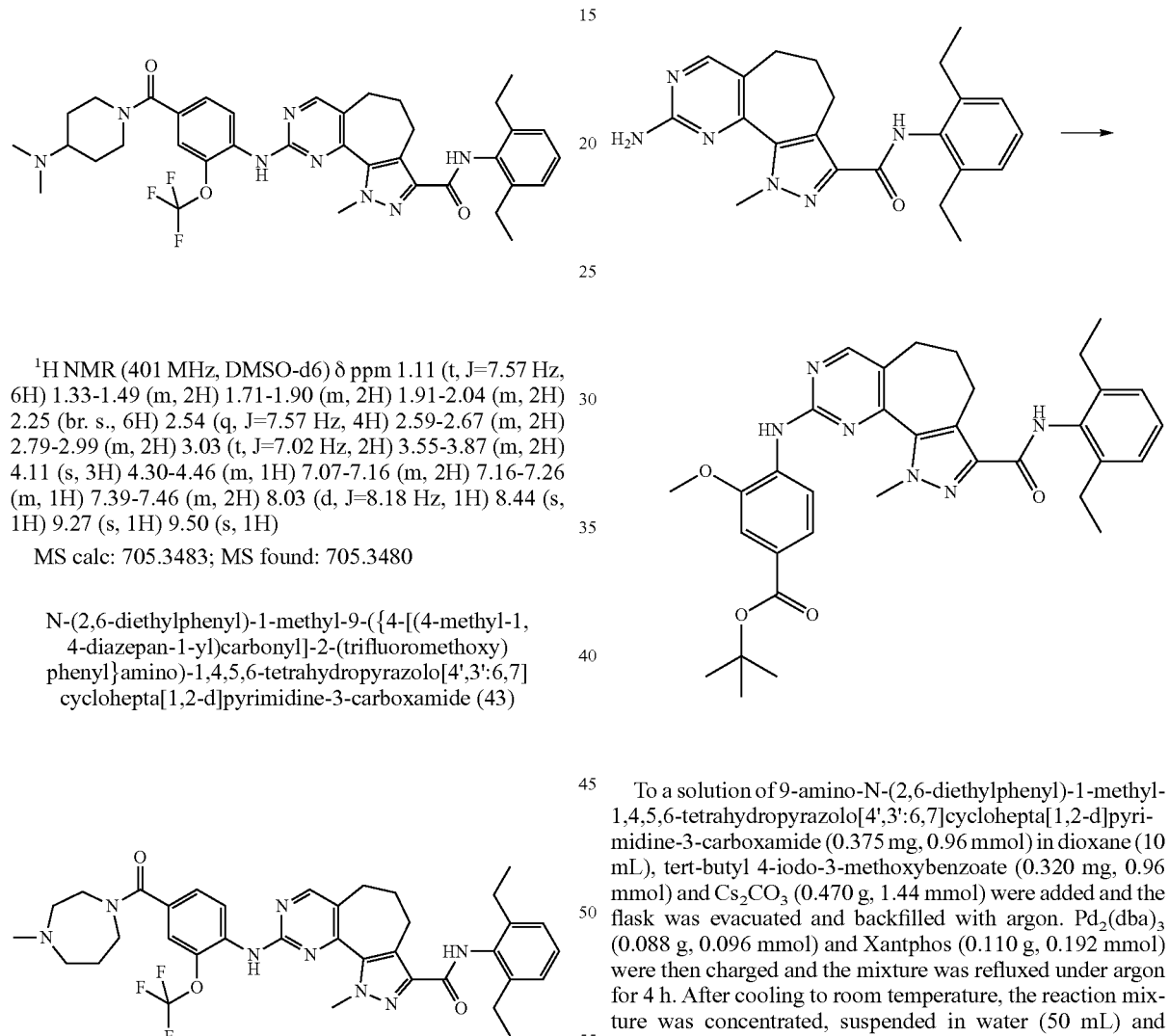

¹H NMR (401 MHz, DMSO-d6) δ ppm 1.11 (t, J=7.57 Hz, 6H) 1.33-1.49 (m, 2H) 1.71-1.90 (m, 2H) 1.91-2.04 (m, 2H) 2.25 (br. s., 6H) 2.54 (q, J=7.57 Hz, 4H) 2.59-2.67 (m, 2H) 2.79-2.99 (m, 2H) 3.03 (t, J=7.02 Hz, 2H) 3.55-3.87 (m, 2H) 4.11 (s, 3H) 4.30-4.46 (m, 1H) 7.07-7.16 (m, 2H) 7.16-7.26 (m, 1H) 7.39-7.46 (m, 2H) 8.03 (d, J=8.18 Hz, 1H) 8.44 (s, 1H) 9.27 (s, 1H) 9.50 (s, 1H)

MS calc: 705.3483; MS found: 705.3480

N-(2,6-diethylphenyl)-1-methyl-9-({4-[(4-methyl-1,4-diazepan-1-yl)carbonyl]-2-(trifluoromethoxy)phenyl}amino)-1,4,5,6-tetrahydropyrazolo[4',3':6,7]cyclohepta[1,2-d]pyrimidine-3-carboxamide (43)

¹H NMR (401 MHz, DMSO-d6) δ ppm 1.11 (t, J=7.57 Hz, 6H) 1.72-1.92 (m, 2H) 1.92-2.03 (m, 2H) 2.23-2.39 (m, 4H) 2.54 (q, J=7.57 Hz, 4H) 2.60-2.65 (m, 2H) 2.69 (s, 3H) 3.03 (t, J=7.08 Hz, 2H) 3.39-3.53 (m, 2H) 3.55-3.50 (m, 2H) 4.10 (s, 3H) 7.04-7.16 (m, 2H) 7.16-7.24 (m, 1H) 7.38-7.48 (m, 2H) 8.02 (d, J=8.30 Hz, 1H) 8.44 (s, 1H) 9.25 (s, 1H) 9.50 (s, 1H)

MS calc: 691.3327; MS found: 691.3337

Example 15

Conv. 17 tert-butyl 4-({3-[(2,6-diethylphenyl)carbamoyl]-1-methyl-1,4,5,6-tetrahydropyrazolo[4',3':6,7]cyclohepta[1,2-d]pyrimidin-9-yl}amino)-3-methoxybenzoate To a solution of 9-amino-N-(2,6-diethylphenyl)-1-methyl-1,4,5,6-tetrahydropyrazolo[4',3':6,7]cyclohepta[1,2-d]pyrimidine-3-carboxamide (0.375 mg, 0.96 mmol) in dioxane (10 mL), tert-butyl 4-iodo-3-methoxybenzoate (0.320 mg, 0.96 mmol) and Cs₂CO₃ (0.470 g, 1.44 mmol) were added and the flask was evacuated and backfilled with argon. Pd₂(dba)₃ (0.088 g, 0.096 mmol) and Xantphos (0.110 g, 0.192 mmol) were then charged and the mixture was refluxed under argon for 4 h. After cooling to room temperature, the reaction mixture was concentrated, suspended in water (50 mL) and extracted with AcOEt. The organic phase was anidrified on Na₂SO₄, filtered and evaporated to dryness, the crude solid was purified by flash chromatography on silica gel (eluant: hexane/AcOEt 8/2) to afford 0.480 g (84% yield) of the title compound.

¹H NMR (401 MHz, DMSO-d6) δ ppm 1.12 (t, J=7.57 Hz, 6H) 1.56 (s, 9H) 1.93-2.04 (m, 2H) 2.56 (q, J=7.57 Hz, 4H) 2.60-2.66 (m, 2H) 3.03 (t, J=7.08 Hz, 2H) 3.95 (s, 3H) 4.23 (s, 3H) 7.05-7.18 (m, 2H) 7.17-7.29 (m, 1H) 7.50 (d, J=1.77 Hz, 1H) 7.60 (dd, J=8.48, 1.77 Hz, 1H) 8.37 (s, 1H) 8.38 (d, J=8.48 Hz, 1H) 8.51 (s, 1H) 9.53 (s, 1H)

MS calc: 597.3184; MS found: 597.3180

According to this same methodology, but employing suitable substituted derivatives, the following compound was prepared:

tert-butyl 4-({3-[(2,6-diethylphenyl)carbamoyl]-1-methyl-1,4,5,6-tetrahydropyrazolo[4',3':6,7]cyclohepta[1,2-d]pyrimidin-9-yl}amino)-3-(trifluoromethoxy)benzoate

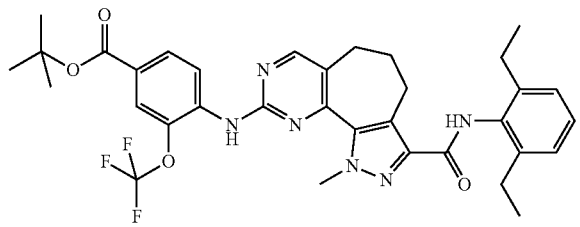 [SMILES: CCc1cccc(CC)c1NC(=O)c1nn(C)c2c1CCCc1cnc(Nc3ccc(C(=O)OC(C)(C)C)cc3OC(F)(F)F)nc1-2]

¹H NMR (500 MHz, DMSO-d6) δ ppm 1.11 (t, J=7.57 Hz, 6H) 1.55 (s, 9H) 1.93-2.05 (m, 2H) 2.55 (q, J=7.57 Hz, 4H) 2.61-2.68 (m, 3H) 3.04 (t, J=7.00 Hz, 2H) 4.16 (s, 3H) 7.10-7.14 (m, 2H) 7.17-7.29 (m, 1H) 7.81 (d, J=1.92 Hz, 1H) 7.93 (dd, J=8.51, 1.92 Hz, 1H) 8.27 (d, J=8.51 Hz, 1H) 8.50 (s, 1H) 9.48 (s, 1H) 9.55 (s, 1H)

MS calc: 651.2901; MS found: 651.2905

Example 16

N-(2,6-diethylphenyl)-1-(2-hydroxyethyl)-9-{[2-methoxy-4-(4-methyl piperazin-1-yl)phenyl]amino}-1,4,5,6-tetrahydropyrazolo[4',3':6,7]cyclohepta[1,2-d]pyrimidine-3-carboxamide hydrochloride (60)

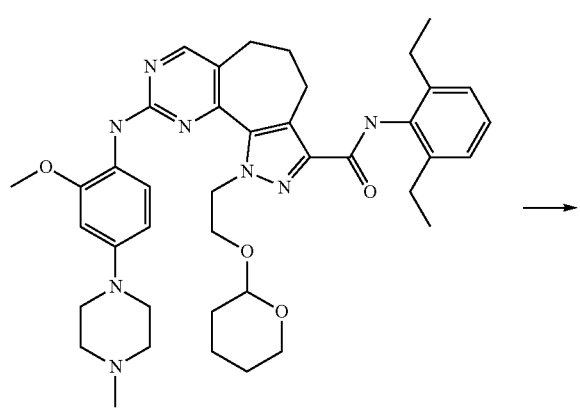

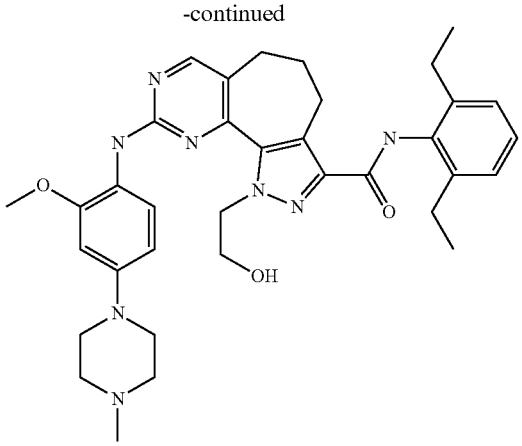

To a solution of N-(2,6-diethylphenyl)-9-{[2-methoxy-4-(4-methylpiperazin-1-yl)phenyl]amino}-1-[2-(tetrahydro-2H-pyran-2-yloxy)ethyl]-1,4,5,6-tetrahydropyrazolo[4',3':6,7]cyclohepta[1,2-d]pyrimidine-3-carboxamide (0.040 g, 0.056 mmol) in MeOH (0.6 mL), 4M HCl in dioxane (0.010 mL) was added. The mixture was stirred at room temperature for 1 h. The organic solvent was evaporated to dryness to give the title compound in quantitative yield.

¹H NMR (401 MHz, DMSO-d6) δ ppm 1.12 (t, J=7.57 Hz, 6H) 1.98 (quin, J=7.08 Hz, 2H) 2.51-2.61 (m, 6H) 2.84 (d, J=4.64 Hz, 3H) 2.95 (t, J=7.08 Hz, 2H) 3.00-3.10 (m, 2H) 3.10-3.23 (m, 1H) 3.47-3.55 (m, 4H) 3.64-3.74 (m, 2H) 3.77-3.89 (m, 4H) 4.64 (t, J=5.55 Hz, 2H) 6.59 (dd, J=8.67, 2.50 Hz, 1H) 6.73 (d, J=2.50 Hz, 1H) 7.08-7.16 (m, 2H) 7.17-7.25 (m, 1H) 7.64 (d, J=8.67 Hz, 1H) 8.23-8.43 (m, 2H) 9.48 (s, 1H) 10.44 (br. s., 1H)

MS calc: 625.3609; MS found: 625.3621

According to this same methodology, but employing suitable substituted derivatives, the following compound was prepared:

N-(2,6-diethylphenyl)-9-({4-[4-(dimethylamino)piperidin-1-yl]-2-methoxyphenyl}amino)-1-(2-hydroxyethyl)-1,4,5,6-tetrahydropyrazolo[4',3':6,7]cyclohepta[1,2-d]pyrimidine-3-carboxamide trifluoroacetate (71)

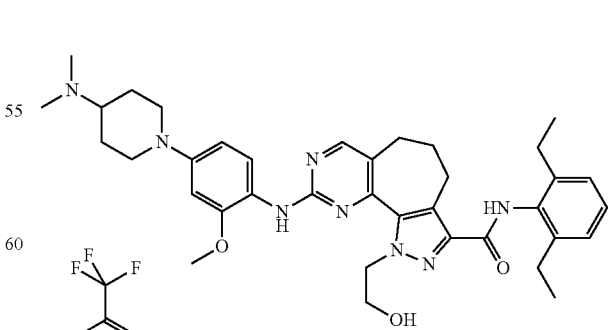

¹H NMR (401 MHz, DMSO-d6) δ ppm 1.12 (t, J=7.57 Hz, 6H) 1.64-1.78 (m, 1H) 1.78-1.91 (m, 1H) 1.90-2.03 (m, 2H) 2.03-2.11 (m, 1H) 2.14-2.24 (m, 1H) 2.50-2.54 (m, 2H) 2.56

(q, J=7.57 Hz, 4H) 2.66-2.77 (m, 2H) 2.80 (d, J=4.88 Hz, 6H) 2.94 (t, J=7.14 Hz, 2H) 3.66-3.71 (m, 2H) 3.82 (d, J=1.59 Hz, 3H) 3.84-3.93 (m, 4H) 4.61-4.67 (m, 2H) 6.57 (dd, J=8.79, 2.50 Hz, 1H) 6.69 (d, J=2.50 Hz, 1H) 7.11-7.15 (m, 2H) 7.18-7.25 (m, 1H) 7.61 (d, J=8.79 Hz, 1H) 8.14 (s, 1H) 8.33 (s, 1H) 9.41-9.58 (m, 2H)

MS calc: 653.3922; MS found: 653.3915

Example 17

1-(2-aminoethyl)-N-(2,6-diethylphenyl)-9-({4-[4-(dimethylamino)piperidin-1-yl]-2-methoxyphenyl}amino)-1,4,5,6-tetrahydropyrazolo[4',3':6,7]cyclohepta[1,2-d]pyrimidine-3-carboxamide bis(trifluoroacetate) (70)

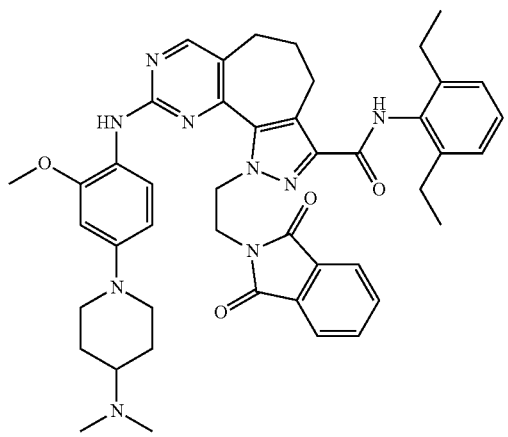

To a solution of N-(2,6-diethylphenyl)-9-({4-[4-(dimethylamino)piperidin-1-yl]-2-methoxyphenyl}amino)-1-[2-(1,3-dioxo-1,3-dihydro-2H-isoindol-2-yl)ethyl]-1,4,5,6-tetrahydropyrazolo[4',3':6,7]cyclohepta[1,2-d]pyrimidine-3-carboxamide (50 mg, 0.06 mmol) in MeOH (1 mL) was added hydrazine hydrate (0.6 mol) and the reaction mixture was refluxed overnight. The solvent was evaporated under vacuum and the crude material purified by prep-HPLC to obtain 52 mg of the title compound in quantitative yield.

$^1$H NMR (401 MHz, DMSO-d6) δ ppm 1.10 (t, J=7.57 Hz, 6H) 1.61-1.76 (m, 2H) 1.87-1.97 (m, 2H) 2.00-2.11 (m, 2H) 2.49-2 53 (m, 2H) 2.55 (q, J=7.57 Hz, 4H) 2.63-2.73 (m, 2H) 2.77 (d, J=4.88 Hz, 6H) 3.00 (t, J=6.96 Hz, 2H) 3.22-3.31 (m, 2H) 3.78 (s, 3H) 3.79-3.84 (m, 2H) 4.75-4.83 (m, 2H) 6.53 (dd, J=8.54, 2.50 Hz, 1H) 6.66 (d, J=2.50 Hz, 1H) 7.11-7.18 (m, 2H) 7.18-7.29 (m, 1H) 7.50 (d, J=8.54 Hz, 1H) 7.82-7.93 (m, 3H) 8.21 (s, 1H) 8.29 (s, 1H) 9.54 (s, 1H) 9.59 (br. s., 1H)

MS calc: 652.4082; MS found: 652.4075

Example 18

N-[(1S)-2-amino-1-phenylethyl]-9-({2-methoxy-4-[(1-methylpiperidin-4-yl)carbamoyl]phenyl}amino)-1-methyl-1,4,5,6-tetrahydropyrazolo[4',3':6,7]cyclohepta[1,2-d]pyrimidine-3-carboxamide dihydrochloride (5)

To a solution of tert-butyl[(2S)-2-({[9-({2-methoxy-4-[(1-methylpiperidin-4-yl)carbamoyl]phenyl}amino)-1-methyl-1,4,5,6-tetrahydropyrazolo[4',3':6,7]cyclohepta[1,2-d]pyrimidin-3-yl]carbonyl}amino)-2-phenylethyl]carbamate (0.010 g, 0.014 mmol) in MeOH (0.2 mL) and THF (0.5 mL), 4M HCl in dioxane (0.2 mL) was added. The mixture was stirred at room temperature for 4 h. The organic solvent was evaporated to dryness to give the title compound in quantitative yield.

$^1$H NMR (500 MHz, DMSO-d6) δ ppm 1.80-2.05 (m, 6H) 2.53-2.59 (m, 2H) 2.75 (s, 3H) 2.98-3.12 (m, 6H) 3.93 (s, 3H) 3.98-4.06 (m, 1H) 4.20 (s, 3H) 5.30-5.38 (m, 1H) 7.29-7.34 (m, 1H) 7.37-7.41 (m, 2H) 7.42-7.45 (m, 2H) 7.58-7.55 (m, 2H) 7.97 (br. s., 4H) 8.18 (br. s., 1H) 8.24 (d, J=9.06 Hz, 1H) 8.35 (s, 1H) 8.40 (d, J=7.69 Hz, 1H) 8.48 (s, 1H) 8.84 (d, J=8.79 Hz, 1H) 9.71 (br. s., 1H)

Example 19

Step. 14

N,9-dimethoxy-N,1-dimethyl-1,4,5,6-tetrahydropyrazolo[4',3':6,7]cyclohepta[1,2-d]pyrimidine-3-carboxamide

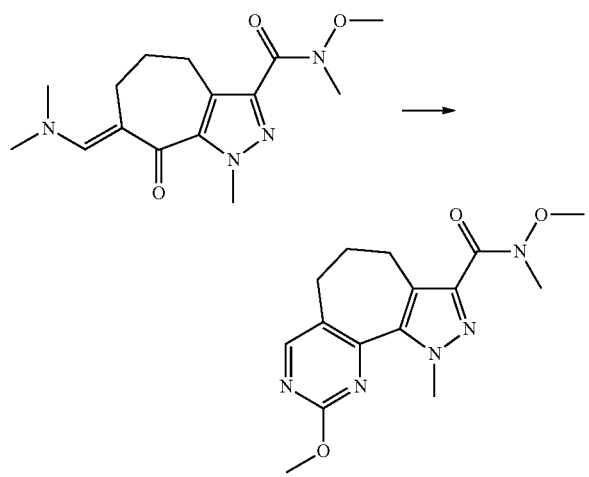

To a solution of ethyl (7E)-7-[(dimethylamino)methylidene]-N-methoxy-N,1-dimethyl-8-oxo-1,4,5,6,7,8-hexahydrocyclohepta[c]pyrazole-3-carboxamide (1.62 g, 5.3 mmol) in CH$_3$CN (130 ml), O-methylisourea sulphate (5.22 g, 21.2 mmol) and K$_2$CO$_3$ (3 g, 22.2 mmol) were added. The reaction mixture was stirred at reflux for 16 h, then it was filtered to remove salts and the solvent was evaporated. The residue was suspended in DCM and washed with water; the organic phase was dried on Na$_2$SO$_4$, filtered and concentrated. The crude was purified by flash-chromatography in silica gel (hexane/AcOEt:1/1) to afford 1 g (62% yield) of the title compound as a white solid.

$^1$H NMR (401 MHz, DMSO-d6) δ ppm 1.85-2.01 (m, 2H) 2.63-2.70 (m, 2H) 2.82 (t, J=7.02 Hz, 2H) 3.71 (s, 3H) 3.81 (s, 3H) 3.97 (s, 3H) 4.22 (s, 3H) 7.36 (s, 1H) 8.52 (s, 1H)

MS calc: 318.1561; MS found: 318.1553

Example 20

Conv. 4

9-methoxy-1-methyl-1,4,5,6-tetrahydropyrazolo[4',3':67]cyclohepta[1,2-d]pyrimidine-3-carboxylic acid

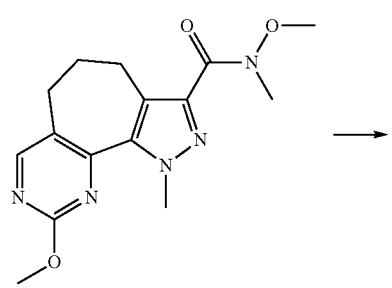

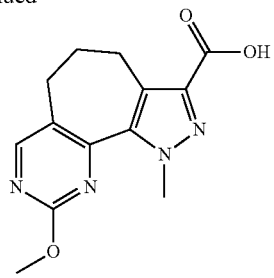

To a solution of N,9-dimethoxy-N,1-dimethyl-1,4,5,6-tetrahydropyrazolo[4',3':6,7]cyclohepta[1,2-d]pyrimidine-3-carboxamide (50 mg, 0.16 mmol) in MeOH (4 mL) sodium methoxide (1M in MeOH, 0.820 mL) was added and the solution was refluxed overnight. The solvent was evaporated and the residue dissolved in water, acidified with 1N HCl, extracted with DCM and dried on Na$_2$SO$_4$ to give 43 mg of the title compound in quantitative yield.

$^1$H NMR (401 MHz, DMSO-d6) δ ppm 1.90-2.00 (m, 2H) 2.63-2.69 (m, 2H) 3.03 (t, J=6.96 Hz, 2H) 3.96 (s, 3H) 4.24 (s, 3H) 8.52 (s, 1H) 12.72 (br.s., 1H)

MS calc: 275.1139; MS found: 275.1136

Example 21

Conv. 18

N-methoxy-N,1-dimethyl-9-phenyl-1,4,5,6-tetrahydropyrazolo[4',3':6,7]cyclohepta[1,2-d]pyrimidine-3-carboxamide A mixture of PdCl$_2$(dppf), complex with DCM (1:1) (24 mg, 0.002 mmol), Cs$_2$CO$_3$ (40 mg; 0.29 mmol), 3-[methoxy(methyl)carbamoyl]-1-methyl-1,4,5,6-tetrahydropyrazolo[4',3':6,7]cyclohepta[1,2-d]pyrimidin-9-yl trifluoromethanesulfonate (94 mg, 0.21 mmol), phenylboronic acid (34 mg;

0.28 mmol) in DME (7 mL) were charged in a round-bottom flask flushed with argon. The flask was evacuated and backfilled with argon and the reaction mixture was heated at 85° C. for 2 h.

The crude was filtered and purified by flash chromatography on silica gel (hexane/AcOEt:1/1) to afford 20 mg (31% yield) of the title compound as a white solid.

¹H NMR (401 MHz, DMSO-d6) δ ppm 1.99-2.08 (m, 2H) 2.74-2.80 (m, 2H) 2.87 (t, J=6.96 Hz, 2H) 3.30 (s, 3H) 3.73 (s, 3H) 4.30-4.34 (m, 3H) 7.52-7.59 (m, 3H) 8.41-8.47 (m, 2H) 8.83 (s, 1H)

MS calc: 364.1768; MS found: 364.1757

Example 22

Conv. 19

9-[(4-bromophenyl)sulfanyl]-N-methoxy-N,1-dimethyl-1,4,5,6-tetrahydropyrazolo[4',3':6,7]cyclohepta[1,2-d]pyrimidine-3-carboxamide

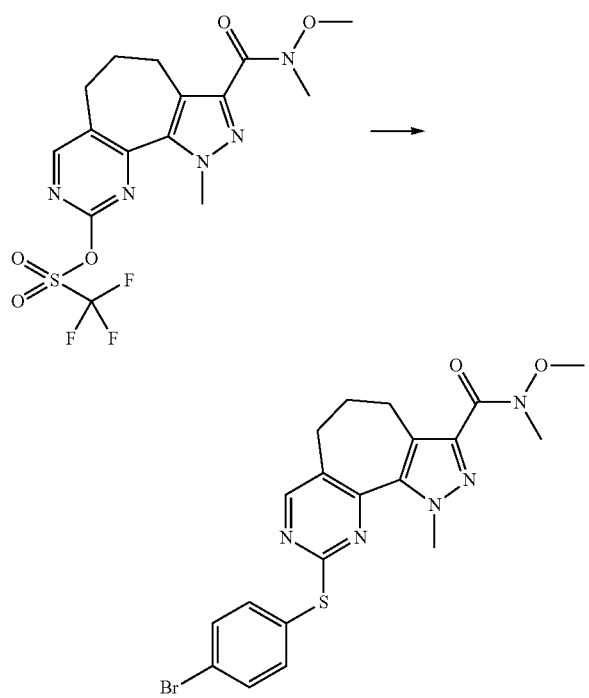

To a solution of 3-[methoxy(methyl)carbamoyl]-1-methyl-1,4,5,6-tetrahydropyrazolo[4',3':6,7]cyclohepta[1,2-d]pyrimidin-9-yl trifluoromethanesulfonate (70 mg, 0.16 mmol) in THF (3 mL), 4-bromothiophenol was added in microwave vial flushed under argon. The reaction mixture was stirred at 60° C. for 48 h. The solvent was removed under reduced pressure, the crude was purified by preparative HPLC to give 2 mg (2% yield) of the title compound.

¹H NMR (401 MHz, DMSO-d6) δ ppm 1.87-2.00 (m, 2H) 2.61-2.68 (m, 2H) 2.80 (t, J=7.02 Hz, 2H) 3.27 (s, 3H) 3.61 (s, 3H) 3.68 (s, 3H) 7.58-7.64 (m, 2H) 7.69-7.73 (m, 2H) 8.56 (s, 1H)

MS calc: 474.0594; MS found: 474.0590

Example 23

Conv. 12 Step 3

9-(2,4-dichlorophenoxy)-N-methoxy-N,1-dimethyl-1,4,5,6-tetrahydropyrazolo[4',3':6,7]cyclohepta[1,2-d]pyrimidine-3-carboxamide

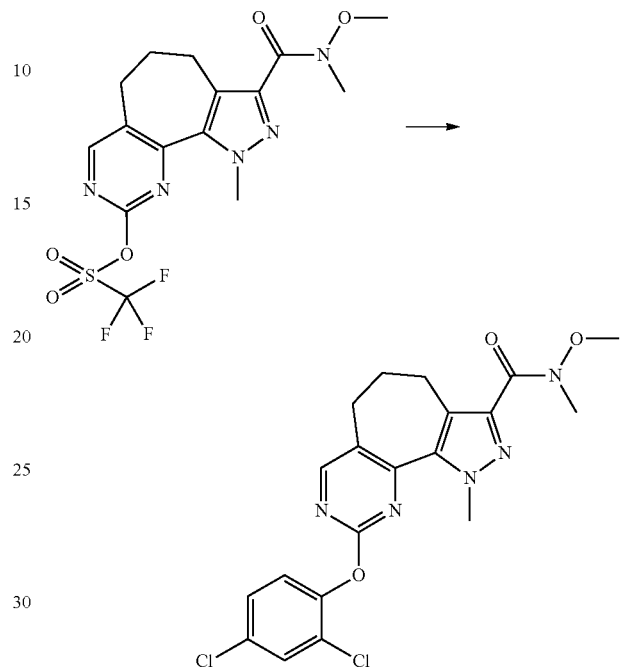

To a solution of 3-[methoxy(methyl)carbamoyl]-1-methyl-1,4,5,6-tetrahydropyrazolo[4',3':6,7]cyclohepta[1,2-d]pyrimidin-9-yl trifluoromethanesulfonate (73 mg, 0.17 mmol) in THF (3 mL), 2,4-dichlorophenol was added in a microwave vial flushed with argon. The reaction mixture was stirred at 60° C. for 48 h. The solvent was removed under reduced pressure, the crude was purified by preparative HPLC to give 2 mg (2% yield) of the title compound.

¹H NMR (401 MHz, DMSO-d6) δ ppm 1.87-1.99 (m, 2H) 2.70-2.75 (m, 2H) 2.84 (t, J=6.84 Hz, 2H) 3.27 (s, 3H) 3.68 (s, 3H) 3.74 (s, 3H) 7.50-7.53 (m, 1H) 7.53-7.57 (m, 1H) 7.82 (d, J=2.20 Hz, 1H) 8.62 (s, 1H)

MS calc: 448.0938; MS found: 448.0917

Example 24

Conv. 13 Step 3

N-methoxy-N,1-dimethyl-9-{[4-(morpholin-4-yl)phenyl]amino}-1,4,5,6-tetrahydropyrazolo[4',3':6,7]cyclohepta[1,2-d]pyrimidine-3-carboxamide

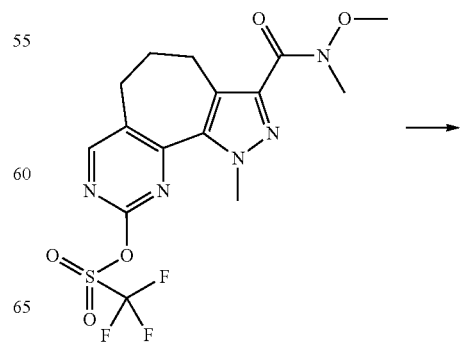

129
-continued

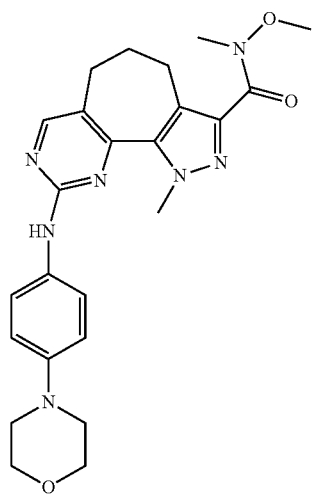

A mixture of Pd(OAc)₂ (2 mg, 0.009 mmol), Xantphos (11 mg, 0.019 mmol), 3-[methoxy(methyl)carbamoyl]-1-methyl-1,4,5,6-tetrahydropyrazolo[4',3':6,7]cyclohepta[1,2-d]pyrimidin-9-yl trifluoromethanesulfonate (40 mg, 0.09 mmol), K₂CO₃ (248 mg, 1.8 mmol), 4-Morpholin-4-yl-phenylamine (21 mg, 0.12 mmol) in dioxane (3 mL) were charged in a round-bottom flask flushed with argon. The flask was evacuated and backfilled with argon and the reaction mixture was heated at 80° C. for 48 h. The reaction mixture was then allowed to cool to room temperature and concentrated. The crude solid was purified by RP flash chromatography to afford 13 mg (30% yield) of the title compound.

¹H NMR (401 MHz, DMSO-d6) δ ppm 1.88-2.02 (m, 2H) 2.52-2.59 (m, 2H) 2.75 (t, J=7.08 Hz, 2H) 3.04-3.14 (m, 4H) 3.30 (s, 3H) 3.71 (s, 3H) 3.73-3.80 (m, 4H) 4.14 (s, 3H) 6.93-7.03 (m, 2H) 7.53-7.52 (m, 2H) 8.36 (s, 1H) 9.34 (s, 1H)

MS calc: 464.2405; MS found: 464.2388

According to this same methodology, but employing suitable substituted derivatives, the following compounds were prepared:

9-(dimethylamino)-N-methoxy-N,1-dimethyl-1,4,5,6-tetrahydropyrazolo[4',3':6,7]cyclohepta[1,2-d]pyrimidine-3-carboxamide

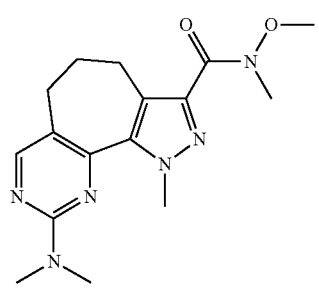 [SMILES: CON(C)C(=O)c1nn(C)c2c1CCCc1cnc(N(C)C)nc1-2]

¹H NMR (401 MHz, DMSO-d6) δ ppm 1.87-1.96 (m, 2H) 2.50-2.53 (m, 2H) 2.75 (t, J=7.02 Hz, 2H) 3.15 (s, 6H) 3.28 (m, 3H) 3.07 (s, 3H) 4.19 (s, 3H) 8.27 (s, 1H)

MS calc: 331.1877; MS found: 331.1887

130

Example 25

Conv. 8 Step 2

N-methoxy-N,1-dimethyl-9-{[4-(piperidin-1-ylmethyl)phenyl]amino}-1,4,5,6-tetrahydropyrazolo[4',3':6,7]cyclohepta[1,2-d]pyrimidine-3-carboxamide trifluoroacetate

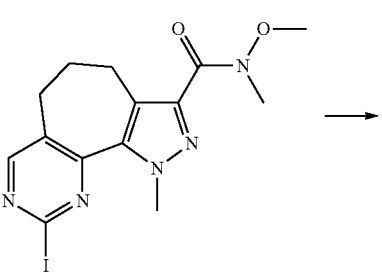

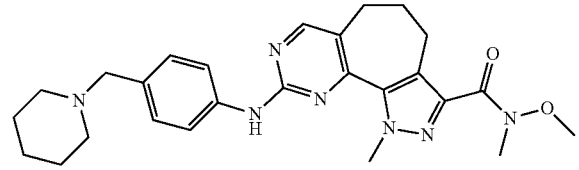

A mixture of Pd(OAc)₂ (1.5 mg, 0.007 mmol), Xantphos (8 mg, 0.014 mmol), Cs₂CO₃ (93 mg, 2.9 mmol), 9-iodo-N-methoxy-N,1-dimethyl-1,4,5,6-tetrahydropyrazolo[4',3':6,7]cyclohepta[1,2-d]pyrimidine-3-carboxamide (24 mg, 0.06 mmol), 4-piperidin-1-yl-methylaniline (14 mg, 0.075 mmol) in DME (3 mL) were charged in a round-bottomed flask flushed with argon. The flask was evacuated and backfilled with argon and the reaction mixture was heated at 85° C. for 3 h.

The crude was filtered and purified by RP flash chromatography to afford 8 mg (31% yield) of the title compound.

¹H NMR (401 MHz, DMSO-d6) δ ppm 1.28-1.44 (m, 1H) 1.53-1.72 (m, 3H) 1.77-1.89 (m, 2H) 1.92-2.04 (m, 2H) 2.55-2.61 (m, 2H) 2.76 (t, J=6.96 Hz, 2H) 2.79-2.94 (m, 2H) 3.34-3.39 (m, 2H) 3.71 (s, 3H) 4.12-4.24 (m, 5H) 7.36-7.46 (m, 2H) 7.78-7.86 (m, 2H) 8.46 (s, 1H) 9.16 (br. s., 1H) 9.77 (s, 1H)

MS calc: 476.2769; MS found: 476.2779

Example 26

St. I3

Ethyl 2-methyl-9-(methylsulfanyl)-2,4,5,6-tetrahydropyrazolo[4',3':6,7]cyclohepta[1,2-d]pyrimidine-3-carboxylate

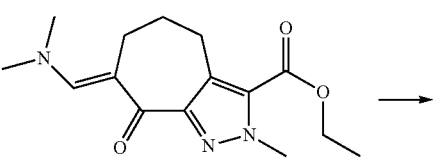

131

-continued

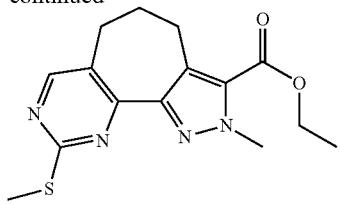

To a solution of ethyl (7E)-7-[(dimethylamino)methylidene]-2-methyl-8-oxo-2,4,5,6,7,8-hexahydrocyclohepta[c]pyrazole-3-carboxylate (621 mg, 2.13 mmol) in EtOH (18 mL) S-methylisothiourea sulfate (593 mg, 2.13 mmol) was added. The mixture was stirred at 80° C. for 72 h, then filtered to remove salts; the crude was purified by flash chromatography on silica gel (hexane/AcOEt:7/3) to afford 584 mg (87% yield) of the title compound.

$^1$H NMR (401 MHz, DMSO-d6) δ ppm 1.35 (t, J=7.08 Hz, 3H) 1.80-2.02 (m, 2H) 2.54 (s, 3H) 2.65-2.87 (m, 2H) 3.04 (t, J=6.53 Hz, 2H) 4.17 (s, 3H) 4.35 (q, J=7.08 Hz, 2H) 8.48 (s, 1H)

MS calc: 319.1223; MS found: 319.1224

According to this same methodology, but employing suitable substituted derivatives, the following compounds were prepared:

ethyl 1-methyl-9-(methylsulfanyl)-1,4,5,6-tetrahydropyrazolo[4',3':6,7]cyclohepta[1,2-d]pyrimidine-3-carboxylate (87)

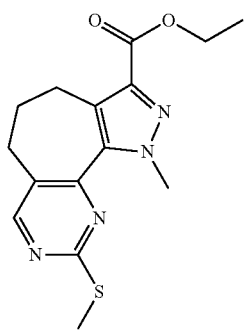 [SMILES: CCOC(=O)c1nn(C)c2c1CCCc1cnc(SC)nc1-2]

$^1$H NMR (401 MHz, DMSO-d6) δ ppm 1.31 (t, J=7.08 Hz, 3H) 1.90-2.04 (m, 2H) 2.57 (s, 3H) 2.62-2.69 (m, 2H) 3.02 (t, J=7.02 Hz, 2H) 4.21 (s, 3H) 4.29 (q, J=7.08 Hz, 2H) 8.57 (s, 1H)

MS calc: 319.1223; MS found: 319.1229 ethyl 9-(methylsulfanyl)-1,4,5,6-tetrahydropyrazolo[4',3':6,7]cyclohepta[1,2-d]pyrimidine-3-carboxylate

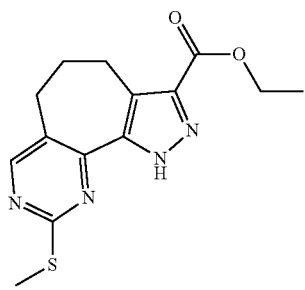 [SMILES: CCOC(=O)c1n[nH]c2c1CCCc1cnc(SC)nc1-2]

132 ethyl 1-(2-hydroxyethyl)-9-(methylsulfanyl)-1,4,5,6-tetrahydropyrazolo[4',3':6,7]cyclohepta[1,2-d]pyrimidine-3-carboxylate

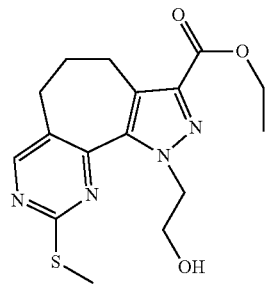 [SMILES: CCOC(=O)c1nn(CCO)c2c1CCCc1cnc(SC)nc1-2]

ethyl 2-(2-hydroxyethyl)-9-(methysufanyl)-2,4,5,6-tetrahydropyrazolo[4',3':6,7]cyclohepta[1,2-d]pyrimidine-3-carboxylate

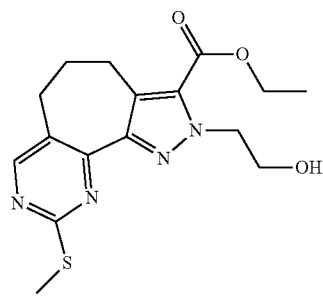 [SMILES: CCOC(=O)c1c2c(nn1CCO)-c1nc(SC)ncc1CCC2]

Example 27

Conv.10 Step 1

Ethyl 2-methyl-9-(methylsulfonyl)-2,4,5,6-tetrahydropyrazolo[4',3':6,7]cyclohepta[1,2-d]pyrimidine-3-carboxylate

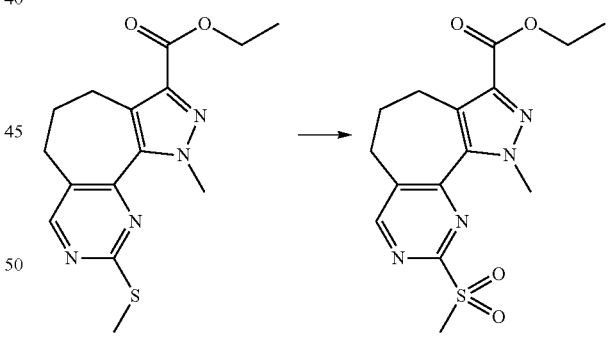

To a solution of ethyl 2-methyl-9-(methylsulfanyl)-2,4,5,6-tetrahydropyrazolo[4',3':6,7]cyclohepta[1,2-d]pyrimidine-3-carboxylate (100 mg, 0.31 mmol) in DMF (15 mL), oxone (580 mg, 0.94 mmol) was added. The mixture was stirred at room temperature overnight then water and AcOEt was added and the layers separated. The organic phase was finally dried over Na$_2$SO$_4$ and evaporated. The residue was triturated with Et$_2$O and collected by filtration to give 105 mg (97% yield) of the title compound.

$^1$H NMR (401 MHz, DMSO-d6) δ ppm 1.36 (t, J=7.08 Hz, 3H) 1.85-2.06 (m, 2H) 2.90-2.96 (m, 2H) 3.11 (t, J=6.41 Hz, 2H) 3.41 (s, 3H) 4.22 (s, 3H) 4.36 (q, J=7.08 Hz, 2H) 8.88 (s, 1H)

MS calc: 351.1122; MS found: 351.1129

Example 28

Conv. 20

Ethyl 2-methyl-9-(phenylamino)-2,4,5,6-tetrahydro-pyrazolo[4',3':6,7]cyclohepta[1,2-d]pyrimidine-3-carboxylate

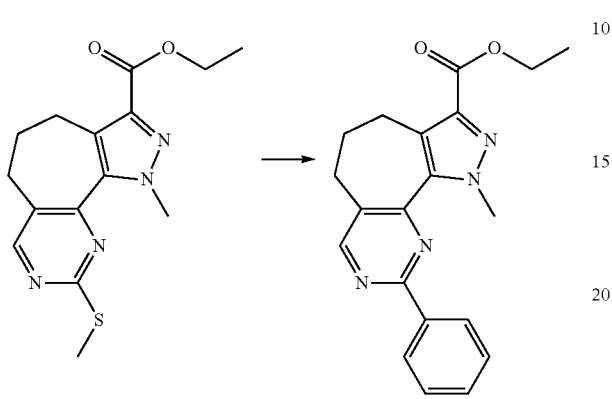

A mixture of Pd(PPh₃)₄ (11 mg, 0.01 mmol), CuTC (51 mg, 0.28 mmol), ethyl 2-methyl-9-(methylsulfanyl)-2,4,5,6-tetrahydropyrazolo[4',3':6,7]cyclohepta[1,2-d]pyrimidine-3-carboxylate (30 mg, 0.09 mmol), phenylboronic acid (23 mg, 0.19 mmol) in THF (1 mL) were charged in a microwave vial flushed with argon. The vial was evacuated and backfilled with argon and the reaction mixture was heated under microwaves at 130° C. for 1 h.

The crude was filtered and purified by RP flash chromatography to afford 20 mg (65% yield) of the title compound.

¹H NMR (401 MHz, DMSO-d6) δ ppm 1.35 (t, J=7.14 Hz, 3H) 1.88-2.02 (m, 2H) 2.64-2.73 (m, 2H) 3.05 (t, J=6.59 Hz, 2H) 4.18 (s, 3H) 4.36 (q, J=7.14 Hz, 2H) 6.85-6.96 (m, 1H) 7.19-7.32 (m, 2H) 7.85-7.96 (m, 2H) 8.33 (s, 1H) 9.57 (s, 1H)

MS calc: 364.1768; MS found: 364.1781

According to this same methodology, but employing suitable substituted derivatives, the following compounds were prepared:

ethyl 1-methyl-9-phenyl-1,4,5,6-tetrahydropyrazolo[4',3':6,7]cyclohepta[1,2-d]pyrimidine-3-carboxylate (88)

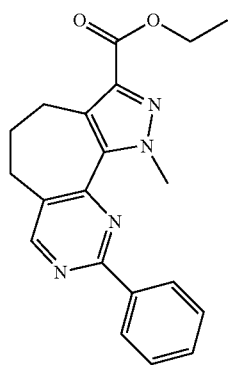 [SMILES: CCOC(=O)c1nn(C)c2c1CCCc1cnc(-c3ccccc3)nc1-2]

¹H NMR (401 MHz, DMSO-d6) δ ppm 1.32 (t, J=7.08 Hz, 3H) 1.92-2.10 (m, 2H) 2.71-2.81 (m, 2H) 3.08 (t, J=6.96 Hz, 2H) 4.31 (q, J=7.08 Hz, 2H) 4.36 (s, 3H) 7.51-7.66 (m, 3H) 8.32-8.46 (m, 2H) 8.84 (s, 1H)

MS calc: 349.1659; MS found: 349.1662 ethyl 1-methyl-9-[4-(trifluoromethyl)phenyl]-1,4,5,6-tetrahydropyrazolo[4',3':6,7]cyclohepta[1,2-d]pyrimidine-3-carboxylate (89)

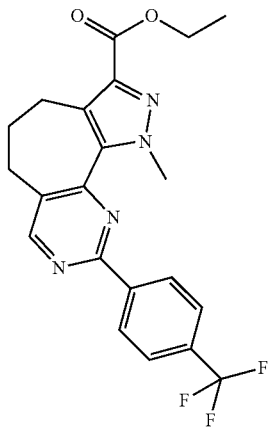 [SMILES: CCOC(=O)c1nn(C)c2c1CCCc1cnc(-c3ccc(C(F)(F)F)cc3)nc1-2]

¹H NMR (401 MHz, DMSO-d6) δ ppm 1.32 (t, J=7.14 Hz, 3H) 1.99-2.09 (m, 2H) 2.76-2.83 (m, 2H) 3.09 (t, J=6.96 Hz, 2H) 4.31 (q, J=7.14 Hz, 2H) 4.36 (s, 3H) 7.89-7.96 (m, 2H) 8.59-8.65 (m, 2H) 8.90 (s, 1H)

MS calc: 417.1533; MS found: 417.1525 ethyl 9-(4-methoxyphenyl)-1-methyl-1,4,5,6-tetrahydropyrazolo[4',3':6,7]cyclohepta[1,2-d]pyrimidine-3-carboxylate (90)

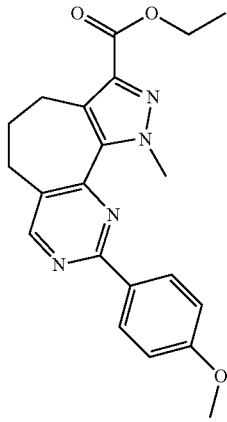 [SMILES: CCOC(=O)c1nn(C)c2c1CCCc1cnc(-c3ccc(OC)cc3)nc1-2]

¹H NMR (401 MHz, DMSO-d6) δ ppm 1.32 (t, J=7.08 Hz, 3H) 1.96-2.07 (m, 2H) 2.71-2.77 (m, 2H) 3.07 (t, J=6.90 Hz, 2H) 3.84 (s, 3H) 4.30 (q, J=7.16 Hz, 2H) 4.34 (s, 3H) 7.06-7.13 (m, 2H) 8.33-8.41 (m, 2H) 8.77 (s, 1H)

MS calc: 379.1765; MS found: 379.1759

135 ethyl 1-methyl-9-[4-(trifluoromethoxy)phenyl]-1,4,5,6-tetrahydropyrazolo[4',3':6,7]cyclohepta[1,2-d]pyrimidine-3-carboxylate (91)

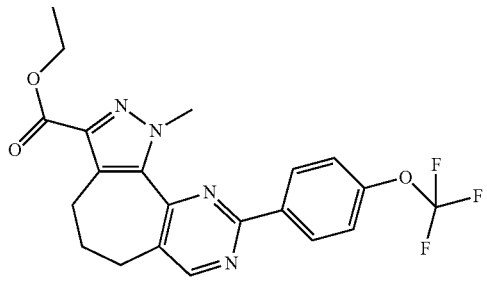 [SMILES: CCOC(=O)c1nn(C)c2c1CCCc1cnc(-c3ccc(OC(F)(F)F)cc3)nc1-2]

MS calc: 433.1482; MS found 433.1476

Example 29

Conv. 7a 2-(methylsulfanyl)-6,7,10,11-tetrahydropyrimido[5'',4'':6',7']cyclohepta[1',2':3,4]pyrazolo[5,1-c][1,4]oxazin-8(5H)-one

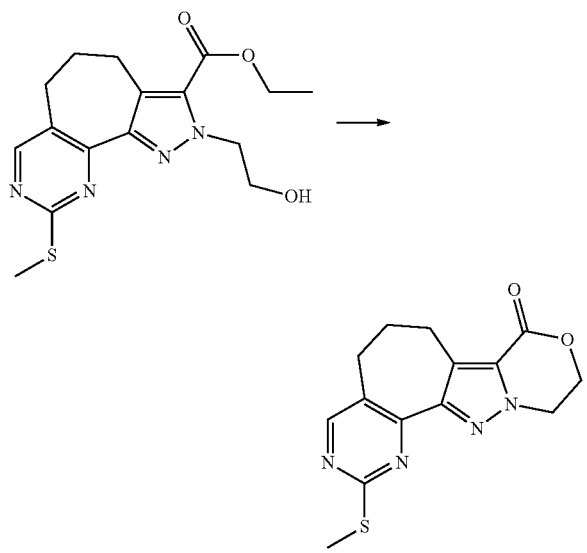

To a solution of ethyl 2-(2-hydroxyethyl)-9-(methylsulfanyl)-2,4,5,6-tetrahydropyrazolo[4',3':6,7]cyclohepta[1,2-d]pyrimidine-3-carboxylate 34.8 mg (0.1 mmol) in THF (3 ml) was added p-toluensulfonic acid 1.9 mg (0.01 mmol). The mixture was stirred at 60° C. for 4 hours. Upon completion, the volatiles were removed in vacuo, the residue was purified by flash chromatography eluting with EtOAc/hexane 5/5 to afford 15 mg of the title compound (50% yield).

$^1$H NMR (401 MHz, DMSO-d6) δ ppm 1.90-2.03 (m, 2H) 2.55 (s, 3H) 2.76-2.83 (m, 2H) 3.09 (t, J=6.47 Hz, 2H) 4.6 (t, J=5.86 Hz, 2H) 4.77 (t, J=8.86 Hz, 2H) 8.51 (s, 1H)

MS calc: 320.1176; MS found 320.1171

136

Preparation P1 (step L)

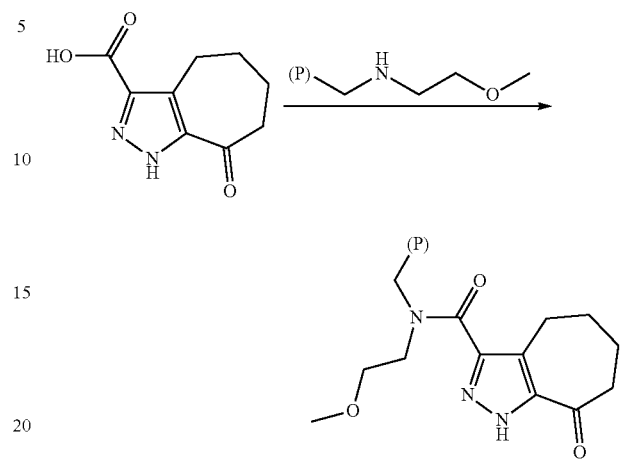

A suspension of 8-oxo-1,4,5,6,7,8-hexahydrocyclohepta[c]pyrazole-3-carboxylic acid (307 mg, 1.59 mmol) in dry DMF (5 mL) was treated with DIPEA (0.813 mL, 3.19 mmol) and TBTU (510 mg, 1.59 mmol). The mixture was added to resin (1.325 g, 1 eq, 0.80 mmol/g) swelling in DMF (5 mL) and the suspension was stirred at room temperature for 36 h. The resin was washed with 3×[DMF(×1), MeOH(×1)], 3×[MeOH(×1), DCM(×1)] and with DCM(×3).

Preparation P2 (step M)

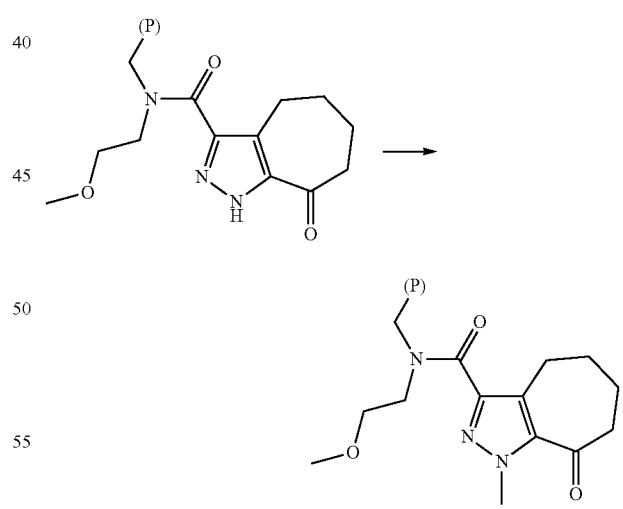

Methyl iodide (0.72 mL, 1.15 mmol) and Cs$_2$CO$_3$ (373 mg, 1.15 mmol) were added to resin (0.388 g, 0.29 mmol, 1 eq, 0.74 mmol/g) swelling in DMF (3.5 ml) and the suspension was stirred at room temperature for 48 h. The resin was washed with 3×[DMF(×1), MeOH(×1)], 3×[MeOH(×1), DCM(×1)] and with DCM(×3).

Preparation P3 (step N)

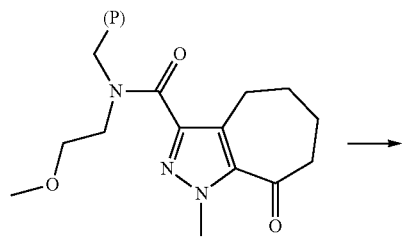

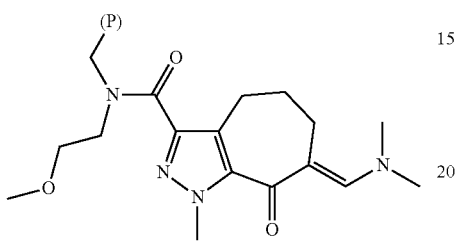

The resin was swelled in a mixture toluene/N,N-dimethylformamide diisopropyl acetal (20 mL 1:1) and the suspension was stirred at 70° C. temperature for 72 h. The resin was washed with 3×[DMF(×1), MeOH(×1)], 3×[MeOH(×1), DCM(×1)] and with DCM(×3).

Preparation P4 (step O)

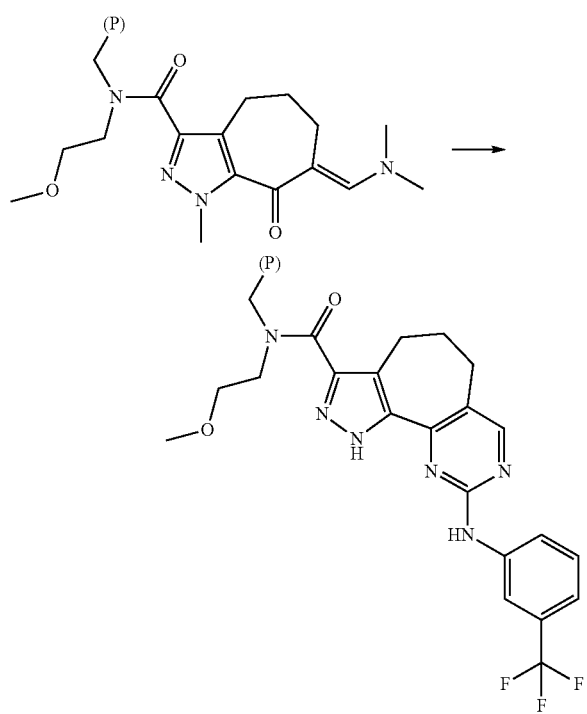

1-[3-(trifluoromethyl)phenyl]guanidine (0.72 mL, 1.15 mmol) was added to resin (0.397 mmol, 1 eq, 0.74 mmol/g) swelling in DMF (1.5 ml) and the suspension was stirred at 120° C. for 72 h.

The resin was washed with 3×[DMF(×1), MeOH(×1)], 3×[MeOH(×1), DCM(×1)] and with DCM(×3).

Example 30

Step P

N-(2-methoxyethyl)-1-methyl-9-{[3-(trifluoromethyl)phenyl]amino}-1,4,5,6-tetrahydropyrazolo[4',3':6,7]cyclohepta[1,2-d]pyrimidine-3-carboxamide (75)

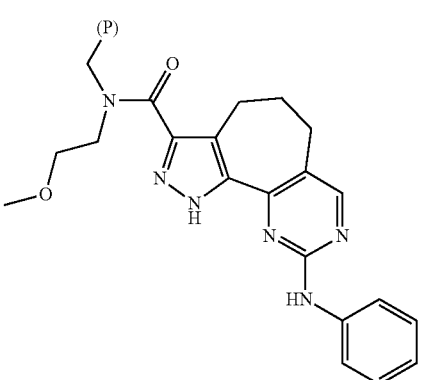

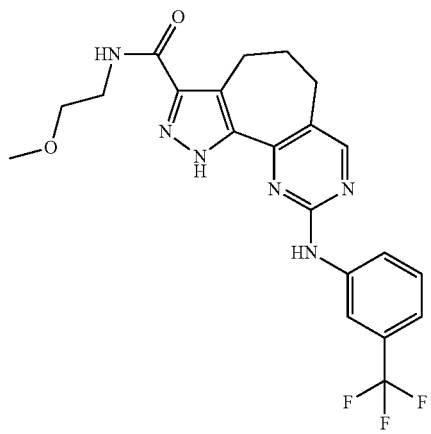

The resin was suspended in a solution of TFA/DCM 1:1 (2 ml) and shaken for 2 h at room temperature. The collected solution was dried under reduced pressure affording a crude which was purified by preparative HPLC.

$^1$H NMR (401 MHz, DMSO-d6) δ ppm 1.89-2.07 (m, 2H) 2.55-2.62 (m, 2H) 3.02 (t, J=7.08 Hz, 2H) 3.27 (s, 3H) 3.37-3.50 (m, 4H) 4.19 (s, 3H) 7.28 (d, J=7.81 Hz, 1H) 7.46-7.57 (m, 1H) 7.92-8.02 (m, 2H) 8.24 (s, 1H) 8.50 (s, 1H) 9.93 (s, 1H)

MS calc: 461.1908; MS found: 461.1898.

According to this same methodology, but employing suitable substituted derivatives, the following compounds were prepared:

N-(2-methoxyethyl)-1-methyl-9-(phenylamino)-1,4,5,6-tetrahydropyrazolo[4',3':6,7]cyclohepta[1,2-d]pyrimidine-3-carboxamide trifluoroacetate (74)

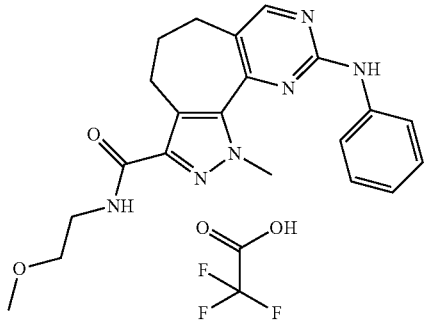

¹H NMR (401 MHz, DMSO-d6) δ ppm 1.88-1.98 (m, 2H) 2.50-2.56 (m, 2H) 2.99 (t, J=7.02 Hz, 2H) 3.24 (s, 3H) 3.34-3.41 (m, 4H) 4.15 (s, 3H) 6.93 (t, J=7.32 Hz, 1H) 7.24-7.30 (m, 2H) 7.69 (d, J=7.69 Hz, 2H) 7.91 (t, J=5.45 Hz, 1H) 8.39 (s, 1H) 9.51 (s, 1H)

MS calc: 393.2034; MS found: 393.2031

1-methyl-N-[2-(morpholin-4-yl)ethyl]-9-{[3-(trifluoromethyl)phenyl]amino}-1,4,5,6-tetrahydropyrazolo[4',3':6,7]cyclohepta[1,2-d]pyrimidine-3-carboxamide trifluoroacetate (76)

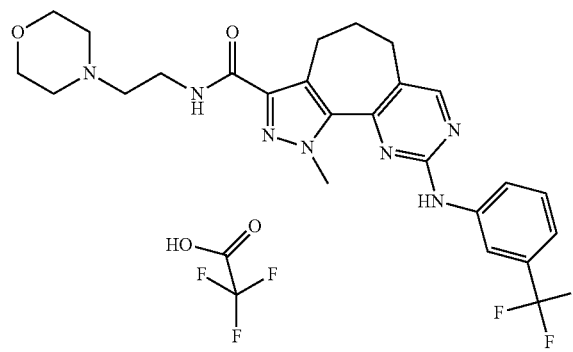

¹H NMR (401 MHz, DMSO-d6) δ ppm 1.89-2.05 (m, 2H) 2.56-2.62 (m, 2H) 3.04 (t, J=7.14 Hz, 2H) 3.13-3.36 (m, 4H) 3.46-3.76 (m, 6H) 3.95-4.08 (m, 2H) 4.20 (s, 3H) 7.29 (d, J=7.95 Hz, 1H) 7.54 (t, J=7.95 Hz, 1H) 7.91 (d, J=7.95 Hz, 1H) 8.27 (s, 1H) 8.49 (t, J=6.10 Hz, 1H) 8.52 (s, 1H) 9.50 (br. s., 1H) 9.96 (s, 1H)

MS calc: 516.2330; MS found: 516.2320

N,N,N-trimethyl-3-{[(1-methyl-9-{[3-(trifluoromethyl)phenyl]amino}-1,4,5,6-tetrahydropyrazolo[4',3':6,7]cyclohepta[1,2-d]pyrimidin-3-yl)carbonyl]amino}propan-1-aminium trifluoroacetate

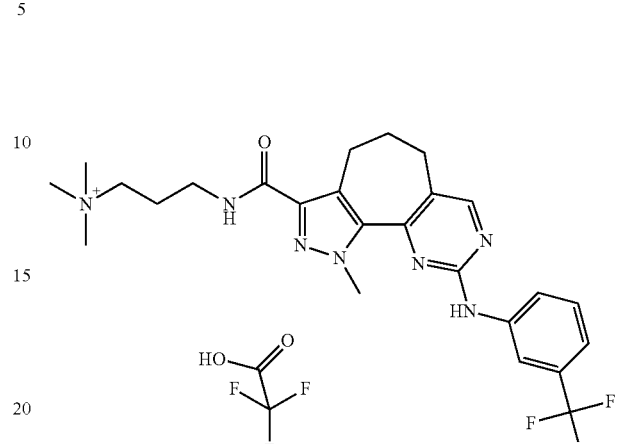

¹H NMR (401 MHz, DMSO-d6) δ ppm 1.87-2.10 (m, 4H) 2.56-2.61 (m, 2H) 3.03 (t, J=7.08 Hz, 2H) 3.05 (s, 9H) 3.26-3.35 (m, 4H) 4.19 (s, 3H) 7.29 (d, J=8.00 Hz, 1H) 7.53 (t, J=8.00 Hz, 1H) 7.92 (d, J=8.00 Hz, 1H) 8.27 (s, 1H) 8.33 (t, J=5.92 Hz, 1H) 8.51 (s, 1H) 9.95 (s, 1H)

MS calc: 502.2537; MS found: 502.2526

1-methyl-9-{[3-(trifluoromethyl)phenyl]amino}-1,4,5,6-tetrahydropyrazolo[4',3':6,7]cyclohepta[1,2-d]pyrimidine-3-carboxamide (77)

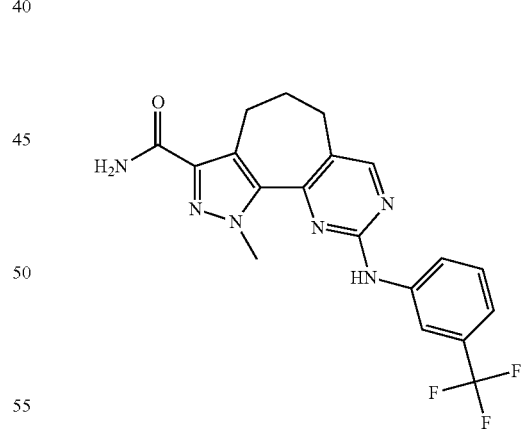

¹H NMR (401 MHz, DMSO-d6) δ ppm 1.93-2.03 (m, 2H) 2.55-2.61 (m, 2H) 3.02 (t, J=7.08 Hz, 2H) 4.18 (s, 3H) 7.20 (br. s., 1H) 7.28 (d, J=8.06 Hz, 1H) 7.45 (br. s., 1H) 7.53 (t, J=8.06 Hz, 1H) 7.96 (d, J=8.06 Hz, 1H) 8.24 (s, 1H) 8.49 (s, 1H) 9.92 (s, 1H)

MS calc: 403.1489; MS found: 403.1480

141

3-({[9-(benzylamino)-1-methyl-1,4,5,6-tetrahydro-pyrazolo[4',3':6,7]cyclohepta[1,2-d]pyrimidin-3-yl]carbonyl}amino)-N,N,N-trimethylpropan-1-aminium trifluoroacetate (78)

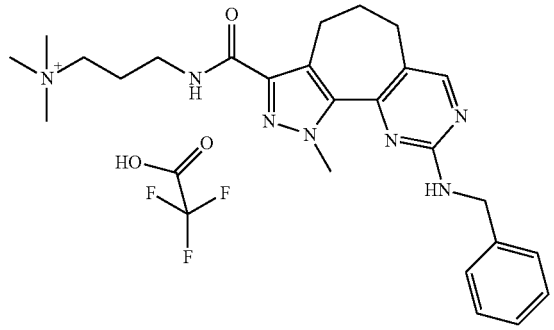

¹H NMR (401 MHz, DMSO-d6) δ ppm 1.84-2.00 (m, 4H) 2.51-2.57 (m, 2H) 2.99 (t, J=7.08 Hz, 2H) 3.04 (s, 9H) 3.22-3.35 (m, 4H) 3.90-4.06 (m, 3H) 4.54 (d, J=6.10 Hz, 2H) 7.17-7.24 (m, 1H) 7.26-7.36 (m, 4H) 7.74 (br. s., 1H) 8.23 (s, 1H) 8.25 (t, J=6.10 Hz, 2H)
MS calc: 448.2819; MS found: 448.2807

N-(2-methoxyethyl)-1-methyl-9-{[4-(4-methylpiperazin-1-yl)phenyl]amino}-1,4,5,6-tetrahydropyrazolo[4',3':6,7]cyclohepta[1,2-d]pyrimidine-3-carboxamide trifluoroacetate (80)

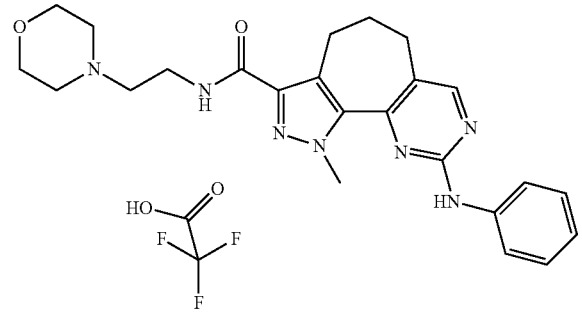 [SMILES: Cn1nc(C(=O)NCCN2CCOCC2)c2c1-c1nc(Nc3ccccc3)ncc1CCC2 ; O=C(O)C(F)(F)F]

¹H NMR (401 MHz, DMSO-d6) δ ppm 1.89-2.03 (m, 2H) 2.51-2.57 (m, 2H) 2.83-2.95 (m, 5H) 3.01 (t, J=7.02 Hz, 2H) 3.10-3.22 (m, 2H) 3.27 (s, 3H) 3.30-3.37 (m, 4H) 3.48-3.63 (m, 2H) 3.68-3.78 (m, 2H) 4.16 (s, 3H) 6.95-7.02 (m, 2H) 7.55-7.64 (m, 2H) 7.90 (t, J=5.49 Hz, 1H) 8.36 (s, 1H) 9.36 (s, 1H) 9.55 (br. s., 1H)
MS calc: 491.2878; MS found: 491.2875

1-methyl-N-[2-(morpholin-4-yl)ethyl]-9-(phenylamino)-1,4,5,6-tetrahydropyrazolo[4',3':6,7]cyclohepta[1,2-d]pyrimidine-3-carboxamide trifluoroacetate (81)

MS calc: 448.2455; MS found: 448.2444

142

9-(benzylamino)-N-(2-methoxyethyl)-1-methyl-1,4,5,6-tetrahydropyrazolo[4',3':6,7]cyclohepta[1,2-d]pyrimidine-3-carboxamide (82)

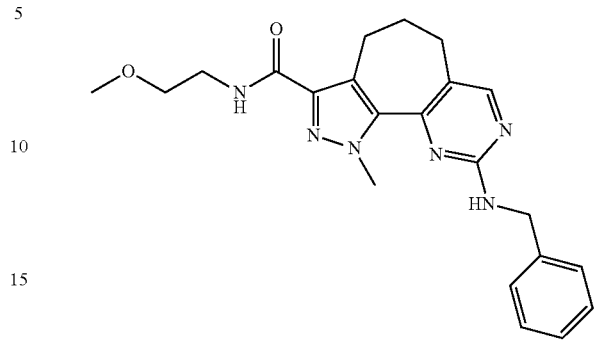

¹H NMR (401 MHz, DMSO-d6) δ ppm 1.84-1.99 (m, 2H) 2.43-2.48 (m, 2H) 2.98 (t, J=7.08 Hz, 2H) 3.26 (s, 3H) 3.98 (br. s., 3H) 4.51-4.57 (m, 2H) 7.17-7.24 (m, 1H) 7.26-7.37 (m, 4H) 7.77 (br. s., 1H) 7.89 (t, J=5.55 Hz, 1H) 8.23 (s, 1H)
MS calc: 407.2190; MS found: 407.2196

1-methyl-9-{[4-(4-methylpiperazin-1-yl)phenyl]amino}-N-[2-(morpholin-4-yl)ethyl]-1,4,5,6-tetrahydropyrazolo[4',3':6,7]cyclohepta[1,2-d]pyrimidine-3-carboxamide trifluoroacetate (83)

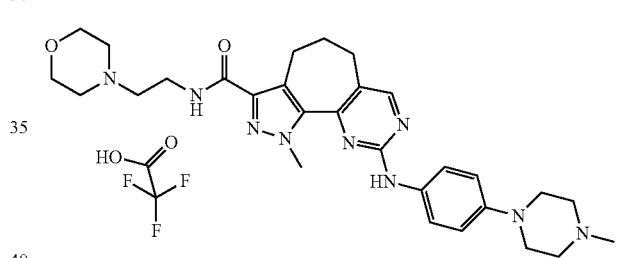

MS calc: 546.3299; MS found: 546.3306

1-methyl-9-{[4-(4-methylpiperazin-1-yl)phenyl]amino}-1,4,5,6-tetrahydropyrazolo[4',3':6,7]cyclohepta[1,2-d]pyrimidine-3-carboxamide trifluoroacetate (67)

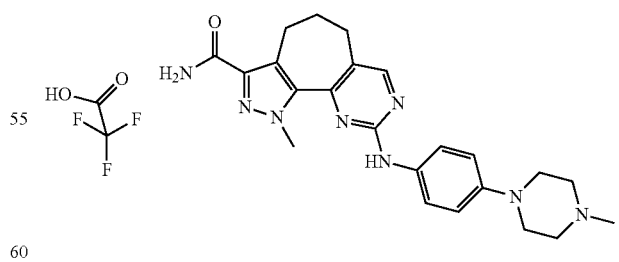

¹H NMR (401 MHz, DMSO-d6) δ ppm 1.82-2.05 (m, 2H) 2.52-2.57 (m, 2H) 2.79-2.96 (m, 5H) 3.01 (t, J=7.02 Hz, 3H) 3.12-3.23 (m, 2H) 3.48-3.61 (m, 2H) 3.68-3.80 (m, 2H) 4.15 (s, 3H) 6.82-7.07 (m, 2H) 7.20 (br. s., 1H) 7.38 (br. s., 1H) 7.53-7.64 (m, 2H) 8.36 (s, 1H) 9.35 (s, 1H) 9.57 (br. s., 1H)
MS calc: 433.2459; MS found: 433.2470

N-(2-methoxyethyl)-1-methyl-9-{[3-(4-methyl piperidin-1-yl)propyl]amino}-1,4,5,6-tetrahydropyrazolo[4',3':6,7]cyclohepta[1,2-d]pyrimidine-3-carboxamide trifluoroacetate (85)

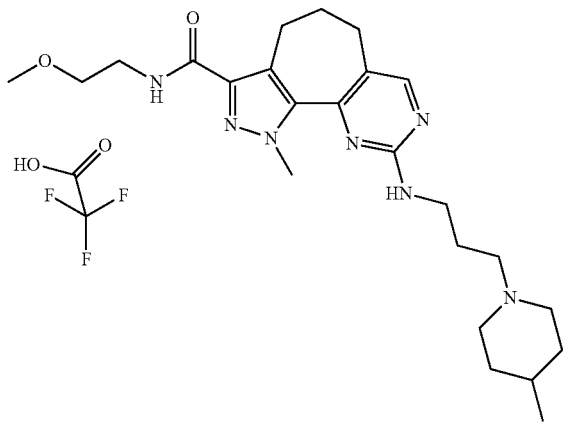 [SMILES: COCCNC(=O)c1nn(C)c2c1CCCc1cnc(NCCCN3CCC(C)CC3)nc1-2 ; O=C(O)C(F)(F)F]

¹H NMR (401 MHz, DMSO-d6) δ ppm 0.91 (d, J=6.47 Hz, 3H) 1.19-1.37 (m, 2H) 1.50-1.67 (m, 1H) 1.67-1.86 (m, 2H) 1.86-2.00 (m, 4H) 2.48-2.51 (m, 2H) 2.82-2.93 (m, 4H) 3.00 (t, J=7.08 Hz, 2H) 3.06-3.14 (m, 4H) 3.27 (s, 3H) 3.45-3.55 (m, 4H) 4.20 (s, 3H) 7.26 (t, J=5.37 Hz, 1H) 7.89 (t, J=5.37 Hz, 1H) 8.23 (s, 1H) 8.93 (br. s., 1H)
MS calc: 456.3081; MS found: 456.3080

1-methyl-9-{[3-(4-methylpiperidin-1-yl)propyl]amino}-1,4,5,6-tetrahydropyrazolo[4',3':6,7]cyclohepta[1,2-d]pyrimidine-3-carboxamide trifluoroacetate (86)

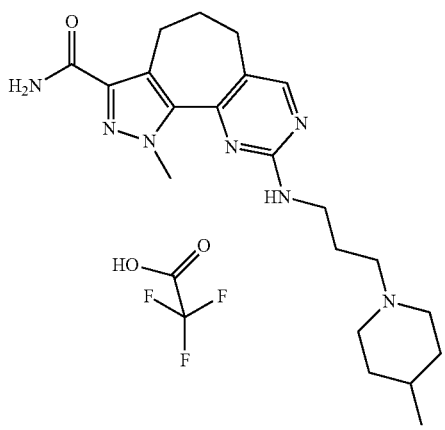 [SMILES: CC1CCN(CCCNc2ncc3c(n2)-c2c(c(C(N)=O)nn2C)CCC3)CC1 ; O=C(O)C(F)(F)F]

¹H NMR (401 MHz, DMSO-d6) δ ppm 0.91 (d, J=6.47 Hz, 3H) 1.17-1.38 (m, 2H) 1.48-1.68 (m, 1H) 1.70-1.85 (m, 2H) 1.85-1.99 (m, 2H) 2.78-2.94 (m, 2H) 3.00 (t, J=7.08 Hz, 2H) 3.06-3.21 (m, 4H) 4.19 (s, 3H) 7.19 (br. s., 1H) 7.25 (t, J=5.49 Hz, 1H) 7.37 (br. s., 1H) 8.23 (s, 1H) 8.77-8.92 (m, 1H)
MS calc: 398.2663; MS found: 398.2657

Pharmacology

The compounds of formula (I) are active as protein kinase inhibitors and are therefore useful, for instance, to restrict the unregulated proliferation of tumour cells.

In therapy, they may be used in the treatment of various tumours, such as those formerly defined, as well as in the treatment of other cell proliferative disorders such as benign prostate hyperplasia, familial adenomatosis polyposis, neurofibromatosis, psoriasis, vascular smooth cell proliferation associated with atherosclerosis, pulmonary fibrosis, arthritis, glomerulonephritis and post-surgical stenosis and restenosis.

The inhibiting activity of putative MPS1 inhibitors and the potency of selected compounds was determined through the assays below described.

The short forms and abbreviations used herein have the following meaning:
Ci Curie
DMSO dimethylsulfoxide
KDa kiloDalton
microCi microCurie
mg milligram
microg microgram
ng nanogram
L liter
mL milliliter
microL microliter
M molar
mM millimolar
microM micromolar
nM nanomolar
Et ethyl Cloning, Expression and Purification of Recombinant MPS1 Full Length Protein.

MPS1 full length (corresponding to residues 2-857 of the full length sequence, see Swiss-Prot accession number P33981) was PCR amplified from the full-length human MPS1 gene present in house as clone pGEX4t_MPS1.

```
Amplification was performed using the forward
oligonucleotide:
5'ggggacaagtttgtacaaaaaagcaggcttactggaagttctgttc caggggcccgaatccgaggatttaagtggcagag3'
and the reverse oligonucleotide:

5'ggggaccactttgtacaagaaagctgggttttattttttttcccctt ttttttttcaaaagtcttggaggatgaag3'].
```

Both the oligonucleotides are described in WO2009/156315 published on 30 Dec. 2009.

For cloning purposes, the oligonucleotides included attB sites in order to obtain an attB-flanked PCR product suitable for cloning using the Gateway® technology (Invitrogen). Furthermore, for purification purposes, forward primer included a protease cleavage site. The resulting PCR product was cloned in the pDONR201 plasmid and then transferred in the baculovirus expression vector pVL1393GST (Invitrogen) Gateway®-modified. Cloning was performed according to the protocols described in the Gateway® manual.

Baculoviruses were generated by cotransfecting Sf9 insect cells with the expression vector and the viral DNA using the BaculoGold® transfection kit (Pharmingen). Viral supernatant was recovered after 5 days and subjected to 3 rounds of amplification to increase viral titer. Recombinant protein was produced by infecting High5 insect cells. After 72 hours of infection at 21° C., cells were recovered, pelletted and freezed at −80° C. For purification of recombinant protein, pellet was thawed, resuspended in lysis buffer (PBS, NaCl 150 mM, Glycerol 10%, CHAPS 0.1%, DTT 20 mM, protease and phosphatase inhibitors) and lysed by Gaulin. Lysate was cleared by centrifugation and loaded on a GST affinity column. After extensive wash, recombinant protein was cleaved by a specific protease and eluted by incubation.

To get a fully activated enzyme, the protein was then subjected to auto-phosphorylation in presence of ATP 1 mM at 25° C. for 2 hours in kinase buffer (Hepes pH7.5 50 mM, MgCl$_2$ 2.5 mM, MnCl$_2$ 1 mM, DTT 1 mM, phosphatase inhibitors); ATP was then removed whit a desalting column.
Biochemical Assay for Inhibitors of MPS1 Kinase Activity The inhibitory activity of putative kinase inhibitors and the potency of selected compounds were determined using a trans-phosphorylation assay.

Specific peptide or protein substrates are trans-phosphorylated by their specific ser-thr or tyr kinase in the presence of ATP traced with $^{33}$P-γ-ATP, and in the presence of their own optimal buffer and cofactors.

At the end of the phosphorylation reaction, more than 98% unlabeled ATP and radioactive ATP is captured by an excess of the ion exchange dowex resin; the resin then settles down to the bottom of the reaction plate by gravity.

Supernatant is subsequently withdrawn and transferred into a counting plate, then evaluated by P-counting.
Reagents/Assay Conditions
i. Dowex Resin Preparation 500 g of wet resin (SIGMA, custom prepared resin DOWEX 1×8 200-400 mesh, 2.5 Kg) are weighed out and diluted to 2 L in 150 mM sodium formate, pH 3.00.

The resin is allowed to settle down (some hours) and then the supernatant is discarded.

After three washes as above over a couple of days, the resin is allowed to settle and two volumes (wrt the resin volume) of 150 mM sodium formate buffer are added.

The pH is then measured and should be around 3.00.

The washed resin is stable for more than a week; the stock resin is kept at 4° C. before use.
ii. Kinase Buffer (KB)

The buffer for MPS1 assay was composed of HEPES 50 mM, at pH 7.5, with 2.5 mM MgCl$_2$, 1 mM MnCl$_2$, 1 mM DTT, 3 microM Na$_3$VO$_4$, 2 mM P-glycerophosphate and 0.2 mg/mL BSA.
iii. Assay Conditions The assay was run with a final concentration MPS1 of 5 nM, in the presence of 15 microM ATP and 1.5 nM $^{33}$P-γ-ATP; the substrate was P38-β-tide, used at 200 microM.
Robotized Dowex Assay The test mix consisted of:
1) 3× Enzyme mix (done in Kinase Buffer 3×), 5 microL/well
2) 3× substrate and ATP mix (done in ddH$_2$O), together with $^{33}$P-γ-ATP, 5 microL/well
3) 3× test compounds (diluted into ddH$_2$O—3% DMSO)—5 microL/well See below for compound dilution and assay scheme
Compound Dilution and Assay Scheme is Defined Below:
i. Dilution of Compounds Test compounds are received as a 1 mM solution in 100% DMSO, distributed into 96 or 384 well plates:
a) for percent inhibition studies (HTS), individual dilution plates at 1 mM are diluted at a 3× concentration (30 microM) in ddH$_2$O (3% DMSO=final concentration) using a Beckman NX automated pipetting platform. The same instrument is used for distributing the diluted mother plates into the test plates.
b) for IC$_{50}$ determination (KSS platform), 100 μl of each compound at 1 mM in 100% DMSO are transferred from the original plate into the first column of another 96 well plate (A1 to G1); well H1 is left empty for the internal standard inhibitor, usually staurosporine.

An automated station for serial dilutions (Biomek FX, Beckman) is used for producing 1:3 dilutions in 100% DMSO, from line A1 to A10, and for all the seven compounds in the column. Moreover, 4-5 copies of daughter plates are prepared by reformatting 5 microL of this first set of 100% DMSO dilution plates into 384 deep well-plates: one copy of the daughter plates with the serial dilutions of test compounds will be thaw the day of the experiments, reconstituted at a 3× concentration with water and used in the IC$_{50}$ determination assays. In a standard experiment, the highest concentration (3×) of all compounds is 30 microM, while the lowest one is 1.5 nM.

Each 384 well-plate will contain reference wells (total enzyme activity vs. no enzymatic activity) for the Z' and signal to background evaluation.
ii. Assay Scheme 384-well plates, V bottom (test plates) are prepared with 5 microL of the compound dilution (3×) and then placed onto a PlateTrak 12 robotized station (Perkin Elmer; the robot has one 384-tips pipetting head for starting the assay plus one 96-tips head for dispensing the resin) together with one reservoir for the Enzyme mix (3×) and one for the ATP mix (3×).

At the start of the run, the robot aspirates 5 microL of ATP mix, makes an air gap inside the tips (2 microL) and aspirates 5 microL of MPS1 mix. The following dispensation into the plates allows the kinase reaction to start upon 3 cycles of mixing, done by the robot itself.

At this point, the correct concentration is restored for all reagents.

The robot incubates the plates for 60 minutes at room temperature, and then stops the reaction by pipetting 70 microL of dowex resin suspension into the reaction mix. Three cycles of mixing are done immediately after the addition of the resin.

The resin suspension is very dense; in order to avoid tip clogging, wide bore tips are used to dispense it.

Another mixing cycle is performed after all the plates are stopped, this time using normal tips: the plates are then allowed to rest for about one hour in order to maximize ATP capture. At this point, 22 microL of the supernatant are transferred into 384-Optiplates (Perkin-Elmer), with 50 microL of Microscint 40 (Perkin-Elmer); after 5 min of orbital shaking the plates are read on a Perkin-Elmer Top Count radioactivity counter.
iii. Data Analysis Data are analysed by an internally customized version of the SW package "Assay Explorer" that provides either % inhibition for primary assays or sigmoidal fittings of the ten-dilutions curves for IC$_{50}$ determination in the secondary assays/hit confirmation routines.
In Vitro Cell Proliferation Assay A2780 human ovarian cancer cells, MCF7 human breast cancer cells and MV-4-11 (biphenotypic B myelomonocytic leukemia) cells (1250 cells/well) were seeded in white 384 well-plates in complete medium (RPMI 1640 or EMEM plus 10% Fetal bovine serum) and treated with compounds dissolved in 0.1% DMSO, 24 h after seeding. The cells were incubated at 37° C. and 5% CO$_2$ and after 72 hours the plates were processed using CellTiter-Glo assay (Promega) following the manufacturer's instruction.

CellTiter-Glo is a homogenous method based on the quantification of the ATP present, an indicator of metabolitically active cells. ATP is quantified using a system based on luciferase and D-luciferin resulting into light generation. The luminescent signal is proportional to the number of cells present in culture.

Briefly, 25 microL/well reagent solution were added to each well and after 5 minutes shacking microplates were read by Envision (PerkinElmer) luminometer. The luminescent signal was proportional to the number of cells present in culture.

Inhibitory activity was evaluated comparing treated versus control data using Assay Explorer (MDL) program. IC$_{50}$ was calculated using sigmoidal interpolation curve.

Given the above inhibition assays, the compounds of formula (I) of the invention resulted to possess a good MPS1 inhibitory activity, typically with an IC$_{50}$ in the range between 0.001 and 5 microM.

Moreover, the compounds of formula (I) of the invention show good cellular proliferation inhibitory activity, typically with an $IC_{50}$ in the range of from 0.010 to 5 microM in A2780 cells.

Biochemical Assay for Inhibitors of PIM-1 Kinase Activity

The inhibitory activity of putative kinase inhibitors and the potency of selected compounds were determined using a trans-phosphorylation assay.

Specific peptide or protein substrates are trans-phosphorylated by their specific ser-thr or tyr kinase in the presence of ATP traced with $^{33}P$-γ-ATP, and in the presence of their own optimal buffer and cofactors.

At the end of the phosphorylation reaction, more than 98% unlabeled ATP and radioactive ATP is captured by an excess of the ion exchange dowex resin; the resin then settles down to the bottom of the reaction plate by gravity.

Supernatant is subsequently withdrawn and transferred into a counting plate, then evaluated by β-counting.

Reagents/Assay Conditions
Dowex Resin Preparation 500 g of wet resin (SIGMA, custom prepared resin DOWEX 1×8 200-400 mesh, 2.5 Kg) are weighed out and diluted to 2 L in 150 mM sodium formate, pH 3.00.

The resin is allowed to settle down (some hours) and then the supernatant is discarded.

After three washes as above over a couple of days, the resin is allowed to settle and two volumes (wrt the resin volume) of 150 mM sodium formate buffer are added.

The pH is then measured and should be around 3.00.

The washed resin is stable for more than a week; the stock resin is kept at 4° C. before use.

Kinase Buffer (KB)

The buffer for PIM-1 assay was composed of HEPES 50 mM, at pH 7.5, with 10 mM $MgCl_2$, 1 mM DTT, 3 microM $NaVO_3$, and 0.2 mg/mL BSA Full-length human PIM-1 was expressed and purified as described in Bullock A N, et al., J. Biol. Chem. 2005, 280, 41675-82.

The enzyme showed a linear kinetic after a step of pre-activation by auto-phosphorylation in the following conditions:

1.7 microM PIM1 was incubated 1 hour RT at 28° C. in the presence of 125 microM ATP Assay Conditions
ATP concentration: 200 microM
$^{33}P$-γ-ATP: 6 nM
Enzyme concentration: 1 nM
Substrate concentration Aktide (Chemical Abstract Service Registry Number 324029-01-8): 25 microM
Robotized dowex assay
The test mix consisted of:
1) 3× Enzyme mix (done in Kinase Buffer 3×), 5 microL/well
2) 3× substrate and ATP mix (done in $ddH_2O$), together with $^{33}P$-γ-ATP, 5 microL/well
3) 3× test compounds (diluted into $ddH_2O$—3% DMSO)—5 microL/well See below for compound dilution and assay scheme
Dilution of Compounds For $IC_{50}$ determination, test compounds are received as a 1 mM solution in 100% DMSO and distributed into 96-well plates: compounds are then plated into the first column of a new 96-well plate (A1 to G1), 100 microL/well.

An automated station (Biomek FX, Beckman) is used for serial dilutions, producing 1:3 dilutions in 100% DMSO, from line A1 to A10, for all the compounds in the column. Moreover, 4-5 copies of daughter plates are prepared by reformatting 5 microL of this first set of 100% DMSO dilution plates into 384-deep well plates: one copy of these serial dilution plates with the test compounds is thawed on the day of study, reconstituted at the working concentration (3-fold the final concentration) with 162 microL/well of water and used for $IC_{50}$ determination assays. In a standard experiment, the highest concentration (3×) of compounds is typically 30 microM, while the lowest one is typically 1.5 nM.

Each 384-well plate generates at least one curve of the standard inhibitor staurosporine and reference wells (total enzyme activity vs. no enzymatic activity) for evaluation of Z' and signal to background (S/B) ratio.

Assay Scheme 384-well plates, V bottom (test plates) are prepared with 5 microL of compound diluted as previously described (3×) and then placed onto a PlateTrak 12 robotized station (Perkin Elmer; the robot has one 384-tip pipetting head for assay start, plus one 96-tip head for dispensing resin) together with one reservoir for Enzyme mix (3×) and one for ATP mix (3×).

Data are analyzed by an internally customized version of the "Assay Explorer" SW package, which provides sigmoidal fitting of the ten-dilution curves for $IC_{50}$ determination in secondary assay/hit confirmation routines.

Method for PIM-2 Kinase Inhibition Assay: Dowex Technique

Kinase Buffer (KB)

The buffer for PIM-2 assay was composed of HEPES 50 mM, at pH 7.5, with 1 mM $MgCl_2$, 1 mM DTT, 3 microM $Na_3VO_4$, and 0.2 mg/mL BSA Full-length human PIM-2 was expressed and purified as described in Fedorov O, et al., PNAS 2007 104, 51, 20523-28.

Assay Conditions (Final Concentrations)
Enzyme concentration=1.5 nM
Aktide substrate (Chemical Abstract Service Registry Number 324029-01-8)=5 microM
ATP=4 microM
$^{33}P$-γ-ATP=1 nM
Robotized Dowex Assay
See above: same procedure as described for PIM-1.

The following Table A reports the experimental data of some representative compounds of the invention of formula (I) being tested on the MPS1, PIM1 and PIM2 enzymes in the specific in vitro kinase assays above described ($IC_{50}$ microM).

TABLE A

| Compound no. | Name | $IC_{50}$ MPS1 (microM) | $IC_{50}$ PIM-1 (microM) | $IC_{50}$ PIM-2 (microM) |
|---|---|---|---|---|
| 1 | 9-[(4-bromo-2-methoxyphenyl)amino]-1-methyl-1,4,5,6-tetrahydropyrazolo[4',3':6,7]cyclohepta[1,2-d]pyrimidine-3-carboxamide | 0.421 | | |
| 3 | 9-{[2-methoxy-4-(4-methylpiperazin-1-yl)phenyl]amino}-1-methyl-1,4,5,6-tetrahydropyrazolo[4',3':6,7]cyclohepta[1,2-d]pyrimidine-3-carboxamide | 0.194 | 1.321 | 5.913 |

TABLE A-continued

| Compound no. | Name | IC$_{50}$ MPS1 (microM) | IC$_{50}$ PIM-1 (microM) | IC$_{50}$ PIM-2 (microM) |
|---|---|---|---|---|
| 4 | N-(2,6-diethylphenyl)-9-{[2-methoxy-4-(4-methylpiperazin-1-yl)phenyl]amino}-1-methyl-1,4,5,6-tetrahydropyrazolo[4',3':6,7]cyclohepta[1,2-d]pyrimidine-3-carboxamide | 0.184 | | |
| 5 | N-[(1S)-2-amino-1-phenylethyl]-9-({2-methoxy-4-[(1-methylpiperidin-4-yl)carbamoyl]phenyl}amino)-1-methyl-1,4,5,6-tetrahydropyrazolo[4',3':6,7]cyclohepta[1,2-d]pyrimidine-3-carboxamide dihydrochloride | 0.469 | 0.497 | 3.761 |
| 8 | 9-{[2-methoxy-4-(4-methylpiperazin-1-yl)phenyl]amino}-1-methyl-N-phenyl-1,4,5,6-tetrahydropyrazolo[4',3':6,7]cyclohepta[1,2-d]pyrimidine-3-carboxamide | 0.353 | | |
| 27 | N-(2-ethyl-6-methylphenyl)-9-{[2-methoxy-4-(4-methylpiperazin-1-yl)phenyl]amino}-1-methyl-1,4,5,6-tetrahydropyrazolo[4',3':6,7]cyclohepta[1,2-d]pyrimidine-3-carboxamide | 0.189 | | |
| 28 | N-cyclohexyl-9-{[2-methoxy-4-(4-methylpiperazin-1-yl)phenyl]amino}-1-methyl-1,4,5,6-tetrahydropyrazolo[4',3':6,7]cyclohepta[1,2-d]pyrimidine-3-carboxamide | 0.249 | | |
| 32 | 9-[(4-bromo-2-methoxyphenyl)amino]-N,1-dimethyl-1,4,5,6-tetrahydropyrazolo[4',3':6,7]cyclohepta[1,2-d]pyrimidine-3-carboxamide | 0.277 | | |
| 35 | N-(2,6-diethylphenyl)-9-({2-methoxy-4-[(1-methylpiperidin-4-yl)carbamoyl]phenyl}amino)-1-methyl-1,4,5,6-tetrahydropyrazolo[4',3':6,7]cyclohepta[1,2-d]pyrimidine-3-carboxamide | 0.066 | | |
| 43 | N-(2,6-diethylphenyl)-1-methyl-9-({4-[(4-methyl-1,4-diazepan-1-yl)carbonyl]-2-(trifluoromethoxy)phenyl}amino)-1,4,5,6-tetrahydropyrazolo[4',3':6,7]cyclohepta[1,2-d]pyrimidine-3-carboxamide | 0.199 | | |
| 56 | N-(2,6-diethylphenyl)-9-{[2-methoxy-4-(4-methyl piperazin-1-yl)phenyl]amino}-1-(2,2,2-trifluoroethyl)-1,4,5,6-tetrahydropyrazolo[4',3':6,7]cyclohepta[1,2-d]pyrimidine-3-carboxamide | 0.862 | | |
| 67 | 1-methyl-9-{[4-(4-methylpiperazin-1-yl)phenyl]amino}-1,4,5,6-tetrahydropyrazolo[4',3':6,7]cyclohepta[1,2-d]pyrimidine-3-carboxamide trifluoroacetate | 1.196 | 2.454 | 3.599 |
| 71 | N-(2,6-diethylphenyl)-9-({4-[4-(dimethylamino)piperidin-1-yl]-2-methoxyphenyl}amino)-1-(2-hydroxyethyl)-1,4,5,6-tetrahydropyrazolo[4',3':6,7]cyclohepta[1,2-d]pyrimidine-3-carboxamide trifluoroacetate | 0.174 | | |
| 97 | N-(2,6-diethylphenyl)-9-{[2-methoxy-4-(4-methylpiperazin-1-yl)phenyl]amino}-2-methyl-2,4,5,6-tetrahydropyrazolo[4',3':6,7]cyclohepta[1,2-d]pyrimidine-3-carboxamide | 0.853 | | |
| 99 | N-(2,6-diethylphenyl)-9-{[2-methoxy-4-(4-methylpiperazin-1-yl)phenyl]amino}-5,6-dihydro-4H-isoxazolo[4',5':6,7]cyclohepta[1,2-d]pyrimidine-3-carboxamide | 0.134 | | |
| 101 | N-(2,6-diethylphenyl)-9-{[2-methoxy-4-(4-methylpiperazin-1-yl)phenyl]amino}-5,6-dihydro-4H-isoxazolo[4',3':6,7]cyclohepta[1,2-d]pyrimidine-3-carboxamide | 0.308 | | |

The invention claimed is:

1. A compound of formula (I)

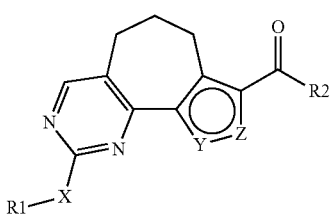

(I)

wherein:

R1 is hydrogen, halogen or an optionally substituted group selected from amino, straight or branched C$_1$-C$_6$ alkyl, C$_3$-C$_7$ cycloalkyl, cycloalkyl-alkyl, aryl, arylalkyl, heterocyclyl and heterocyclylalkyl;

X is a single bond or a divalent radical selected from —NR'—, —CONR'—, —NH—CO—NH—, —O—, —S—, —SO$_2$— and —OSO$_2$—, wherein R' is hydrogen or an optionally substituted group selected from straight or branched C$_1$-C$_6$ alkyl, C$_3$-C$_7$ cycloalkyl, cycloalkyl-alkyl, aryl, arylalkyl, heterocyclyl and heterocyclylalkyl;

one of Y and Z is nitrogen and the other is N—R3, wherein R3 is hydrogen or an optionally substituted group selected from straight or branched $C_1$-$C_6$ alkyl, $C_3$-$C_7$ cycloalkyl, cycloalkyl-alkyl, aryl, arylalkyl, heterocyclyl and heterocyclylalkyl or is a group —(CH$_2$)$_n$—, wherein n is 2 or 3, forming a ring with R2, or Y is oxygen and Z is nitrogen, or Y is nitrogen and Z is oxygen;

R2 is a group selected from —NR"R"', —N(OR"')R" and OR", wherein R" and R"' are, each independently, hydrogen or an optionally substituted group selected from straight or branched $C_1$-$C_6$ alkyl, $C_3$-$C_7$ cycloalkyl, cycloalkyl-alkyl, aryl, arylalkyl, heterocyclyl and heterocyclylalkyl or, together with the nitrogen atom to which they are bonded, R" and R"' may form a 5 to 6 membered heteroaryl or heterocyclyl group, optionally containing one additional heteroatom selected among N, O and S;

or a pharmaceutically acceptable salt thereof.

2. A compound according to claim 1, wherein: X is a group —NH— and R2 is a group selected from —NHR", —N(OR"')R" and —OR", wherein R" is hydrogen or an optionally substituted group selected from straight or branched $C_1$-$C_6$ alkyl, $C_3$-$C_7$ cycloalkyl, cycloalkyl-alkyl, aryl, arylalkyl, heterocyclyl and heterocyclylalkyl.

3. A compound according to claim 1, wherein: X is a group —O— and R2 is a group selected from —NHR", —N(OR"')R" and —OR", wherein R" is hydrogen or an optionally substituted group selected from straight or branched $C_1$-$C_6$ alkyl, $C_3$-$C_7$ cycloalkyl, cycloalkyl-alkyl, aryl, arylalkyl, heterocyclyl and heterocyclylalkyl.

4. A compound according to claim 1, wherein: X is a group —S— and R2 is a group selected from —NHR", —N(OR"')R" and —OR", wherein R" is hydrogen or an optionally substituted group selected from straight or branched $C_1$-$C_6$ alkyl, $C_3$-$C_7$ cycloalkyl, cycloalkyl-alkyl, aryl, arylalkyl, heterocyclyl and heterocyclylalkyl.

5. A compound according to claim 1, wherein: X is a bond and R2 is a group selected from —NHR", —N(OR"')R" and —OR", wherein R" is hydrogen or an optionally substituted group selected from straight or branched $C_1$-$C_6$ alkyl, $C_3$-$C_7$ cycloalkyl, cycloalkyl-alkyl, aryl, arylalkyl, heterocyclyl and heterocyclylalkyl.

6. A compound according to claim 1, wherein: X is a group —NH— and R2 is a group —NHR" or —N(OR"')R" wherein R" is hydrogen or an optionally substituted group selected from straight or branched $C_1$-$C_4$ alkyl and aryl.

7. A compound according to claim 1, wherein: X is a group —O— and $R_2$ is a group —NHR" or —N(OR"')R" wherein R" is hydrogen or an optionally substituted group selected from straight or branched $C_1$-$C_4$ alkyl and aryl.

8. A compound according to claim 1, wherein: X is a group —S— and R2 is a group —NHR" or —N(OR"')R" wherein R" is hydrogen or an optionally substituted group selected from straight or branched $C_1$-$C_4$ alkyl and aryl.

9. A compound according to claim 1, wherein: X is a bond and R2 is a group —NHR" or —N(OR"')R" wherein R" is hydrogen or an optionally substituted group selected from straight or branched $C_1$-$C_4$ alkyl and aryl.

10. A compound according to claim 1, having formula (Ib1) or (Ib2):

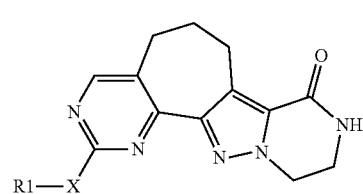

(Ib1)

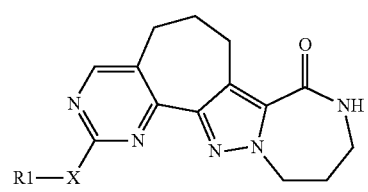

(Ib2)

wherein R1 and X are as defined in claim 1.

11. A compound according to claim 1, having formula (Ib3) or (Ib4):

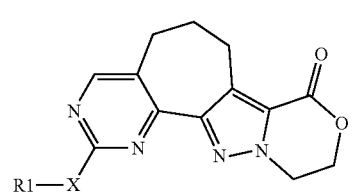

(Ib3)

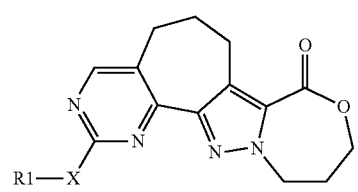

(Ib4)

wherein R1 and X are as defined in claim 1.

12. A compound according to claim 1, selected from:

9-[(4-bromo-2-methoxyphenyl)amino]-1-methyl-1,4,5,6-tetrahydropyrazolo[4',3':6,7]cyclohepta[1,2-d]pyrimidine-3-carboxamide 9-[(4-bromo-2-methoxyphenyl)amino]-N-(2,6-diethylphenyl)-1-methyl-1,4,5,6-tetrahydropyrazolo[4',3':6,7]cyclohepta[1,2-d]pyrimidine-3-carboxamide 9-{[2-methoxy-4-(4-methylpiperazin-1-yl)phenyl]amino}-1-methyl-1,4,5,6-tetrahydropyrazolo[4',3':6,7]cyclohepta[1,2-d]pyrimidine-3-carboxamide N-(2,6-diethylphenyl)-9-{[2-methoxy-4-(4-methylpiperazin-1-yl)phenyl]amino}-1-methyl-1,4,5,6-tetrahydropyrazolo[4',3':6,7]cyclohepta[1,2-d]pyrimidine-3-carboxamide N-[(1S)-2-amino-1-phenylethyl]-9-({2-methoxy-4-[(1-methylpiperidin-4-yl)carbamoyl]phenyl}amino)-1-methyl-1,4,5,6-tetrahydropyrazolo[4',3':6,7]cyclohepta[1,2-d]pyrimidine-3-carboxamide ethyl 9-{[2-methoxy-4-(4-methylpiperazin-1-yl)phenyl]amino}-1,4,5,6-tetrahydropyrazolo[4',3':6,7]cyclohepta[1,2-d]pyrimidine-3-carboxylate N-benzyl-9-{[2-methoxy-4-(4-methylpiperazin-1-yl)phenyl]amino}-1-methyl-1,4,5,6-tetrahydropyrazolo[4',3':6,7]cyclohepta[1,2-d]pyrimidine-3-carboxamide 9-{[2-methoxy-4-(4-methylpiperazin-1-yl)phenyl]amino}-1-methyl-N-phenyl-1,4,5,6-tetrahydropyrazolo[4',3':6,7]cyclohepta[1,2-d]pyrimidine-3-carboxamide N-(2,6-diethylphenyl)-9-({4-[(4-hydroxycyclohexyl)
amino]-2-methoxyphenyl}amino)-1-methyl-1,4,5,6-
tetrahydropyrazolo[4',3':6,7]cyclohepta[1,2-d]pyrimi-
dine-3-carboxamide N-(2,6-diethylphenyl)-9-[(4-{[3-(dimethylamino)propyl]
(methyl)amino}-2-methoxyphenyl)amino]-1-methyl-1,
4,5,6-tetrahydropyrazolo[4',3':6,7]cyclohepta[1,2-d]
pyrimidine-3-carboxamide N-(2,6-diethylphenyl)-9-({2-methoxy-4-[4-(pyrrolidin-1-
yl)piperidin-1-yl]phenyl}amino)-1-methyl-1,4,5,6-tet-
rahydropyrazolo[4',3':6,7]cyclohepta[1,2-d]pyrimi-
dine-3-carboxamide N-(2,6-diethylphenyl)-9-({4-[(3R)-3-(dimethylamino)
pyrrolidin-1-yl]-2-methoxyphenyl}amino)-1-methyl-1,
4,5,6-tetrahydropyrazolo[4',3':6,7]cyclohepta[1,2-d]
pyrimidine-3-carboxamide N-(2,6-diethylphenyl)-9-[(4-{[2-(dimethylamino)ethyl]
(methyl)amino}-2-methoxyphenyl)amino]-1-methyl-1,
4,5,6-tetrahydropyrazolo[4',3':6,7]cyclohepta[1,2-d]
pyrimidine-3-carboxamide N-(2,6-diethylphenyl)-9-({4-[4-(2-hydroxyethyl)piper-
azin-1-yl]-2-methoxyphenyl}amino)-1-methyl-1,4,5,6-
tetrahydropyrazolo[4',3':6,7]cyclohepta[1,2-d]pyrimi-
dine-3-carboxamide N-(2-ethylphenyl)-9-{[2-methoxy-4-(4-methylpiperazin-
1-yl)phenyl]amino}-1-methyl-1,4,5,6-tetrahydropyra-
zolo[4',3':6,7]cyclohepta[1,2-d]pyrimidine-3-carboxa-
mide 9-[(4-bromo-2-methoxyphenyl)amino]-1-methyl-N-
[(1S)-2-(morpholin-4-yl)-1-phenylethyl]-1,4,5,6-tet-
rahydropyrazolo[4',3':6,7]cyclohepta[1,2-d]pyrimi-
dine-3-carboxamide 9-[(4-bromo-2-methoxyphenyl)amino]-N-(2,6-dimeth-
ylphenyl)-1-methyl-1,4,5,6-tetrahydropyrazolo[4',3':6,
7]cyclohepta[1,2-d]pyrimidine-3-carboxamide 9-{[2-methoxy-4-(4-methylpiperazin-1-yl)phenyl]
amino}-1-methyl-N-[(1S)-2-(morpholin-4-yl)-1-phe-
nylethyl]-1,4,5,6-tetrahydropyrazolo[4',3':6,7]cyclo-
hepta[1,2-d]pyrimidine-3-carboxamide 9-[(4-bromo-2-methoxyphenyl)amino]-N-(2-ethyl-6-me-
thylphenyl)-1-methyl-1,4,5,6-tetrahydropyrazolo[4',3':
6,7]cyclohepta[1,2-d]pyrimidine-3-carboxamide N-(2,6-dimethylphenyl)-9-{[2-methoxy-4-(4-methylpip-
erazin-1-yl)phenyl]amino}-1-methyl-1,4,5,6-tetrahy-
dropyrazolo[4',3':6,7]cyclohepta[1,2-d]pyrimidine-3-
carboxamide 9-{[4-(dimethylamino)-2-methoxyphenyl]amino}-N-(2,
6-dimethylphenyl)-1-methyl-1,4,5,6-tetrahydropyra-
zolo[4',3':6,7]cyclohepta[1,2-d]pyrimidine-3-carboxa-
mide N-(2,6-diethylphenyl)-9-({4-[4-(dimethylamino)piperi-
din-1-yl]-2-methoxyphenyl}amino)-1-methyl-1,4,5,6-
tetrahydropyrazolo[4',3':6,7]cyclohepta[1,2-d]pyrimi-
dine-3-carboxamide N-(2,6-diethylphenyl)-9-{[2-methoxy-4-(4-methyl-1,4-
diazepan-1-yl)phenyl]amino}-1-methyl-1,4,5,6-tet-
rahydropyrazolo[4',3':6,7]cyclohepta[1,2-d]pyrimi-
dine-3-carboxamide N-(2,6-diethylphenyl)-9-[(2-methoxyphenyl)amino]-1-
methyl-1,4,5,6-tetrahydropyrazolo[4',3':6,7]cyclohepta
[1,2-d]pyrimidine-3-carboxamide N-(2,6-diethylphenyl)-9-({2-methoxy-4-[(1-methylpip-
eridin-4-yl)amino]phenyl}amino)-1-methyl-1,4,5,6-
tetrahydropyrazolo[4',3':6,7]cyclohepta[1,2-d]pyrimi-
dine-3-carboxamide 9-{[4-(1-azabicyclo[2.2.2]oct-3-ylamino)-2-methox-
yphenyl]amino}-N-(2,6-diethylphenyl)-1-methyl-1,4,
5,6-tetrahydropyrazolo[4',3':6,7]cyclohepta[1,2-d]pyri-
midine-3-carboxamide N-(2-ethyl-6-methylphenyl)-9-{[2-methoxy-4-(4-meth-
ylpiperazin-1-yl)phenyl]amino}-1-methyl-1,4,5,6-tet-
rahydropyrazolo[4',3':6,7]cyclohepta[1,2-d]pyrimi-
dine-3-carboxamide N-cyclohexyl-9-{[2-methoxy-4-(4-methylpiperazin-1-yl)
phenyl]amino}-1-methyl-1,4,5,6-tetrahydropyrazolo
[4',3':6,7]cyclohepta[1,2-d]pyrimidine-3-carboxamide N-(2,6-diethylphenyl)-1-methyl-9-{[4-(4-methylpiper-
azin-1-yl)phenyl]amino}-1,4,5,6-tetrahydropyrazolo
[4',3':6,7]cyclohepta[1,2-d]pyrimidine-3-carboxamide 9-amino-N-(2,6-diethylphenyl)-1-methyl-1,4,5,6-tetrahy-
dropyrazolo[4',3':6,7]cyclohepta[1,2-d]pyrimidine-3-
carboxamide 1-[3-(dimethylamino)propyl]-9-(methylsulfanyl)-1,4,5,6-
tetrahydropyrazolo[4',3':6,7]cyclohepta[1,2-d]pyrimi-
dine-3-carboxamide 9-[(4-bromo-2-methoxyphenyl)amino]-N,1-dimethyl-1,4,
5,6-tetrahydropyrazolo[4',3':6,7]cyclohepta[1,2-d]pyri-
midine-3-carboxamide 4-({3-[(2,6-diethylphenyl)carbamoyl]-1-methyl-1,4,5,6-
tetrahydropyrazolo[4',3':6,7]cyclohepta[1,2-d]pyrimi-
din-9-yl}amino)-3-methoxybenzoic 4-({3-[(2,6-diethylphenyl)carbamoyl]-1-methyl-1,4,5,6-
tetrahydropyrazolo[4',3':6,7]cyclohepta[1,2-d]pyrimi-
din-9-yl}amino)-3-(trifluoromethoxy)benzoic acid N-(2,6-diethylphenyl)-9-({2-methoxy-4-[(1-methylpip-
eridin-4-yl)carbamoyl]phenyl}amino)-1-methyl-1,4,5,
6-tetrahydropyrazolo[4',3':6,7]cyclohepta[1,2-d]pyri-
midine-3-carboxamide N-(2,6-diethylphenyl)-9-[(2-methoxy-4-{[4-(pyrrolidin-
1-yl)piperidin-1-yl]carbonyl}phenyl)amino]-1-methyl-
1,4,5,6-tetrahydropyrazolo[4',3':6,7]cyclohepta[1,2-d]
pyrimidine-3-carboxamide N-(2,6-diethylphenyl)-9-[(4-{[4-(dimethylamino)piperi-
din-1-yl]carbonyl}-2-methoxyphenyl)amino]-1-me-
thyl-1,4,5,6-tetrahydropyrazolo[4',3':6,7]cyclohepta[1,
2-d]pyrimidine-3-carboxamide N-(2,6-diethylphenyl)-9-({2-methoxy-4-[(4-methyl-1,4-
diazepan-1-yl)carbonyl]phenyl}amino)-1-methyl-1,4,
5,6-tetrahydropyrazolo[4',3':6,7]cyclohepta[1,2-d]pyri-
midine-3-carboxamide 9-{[2-methoxy-4-(4-methylpiperazin-1-yl)phenyl]
amino}-N,1-dimethyl-1,4,5,6-tetrahydropyrazolo[4',3':
6,7]cyclohepta[1,2-d]pyrimidine-3-carboxamide N-(2,6-diethylphenyl)-1-methyl-9({4-[(1-methylpiperi-
din-4-yl)carbamoyl]-2-(trifluoromethoxy)
phenyl}amino)-1,4,5,6-tetrahydropyrazolo[4',3':6,7]
cyclohepta[1,2-d]pyrimidine-3-carboxamide N-(2,6-diethylphenyl)-1-methyl-9-{[4-{[4-(pyrrolidin-1-
yl)piperidin-1-yl]carbonyl}-2-(trifluoromethoxy)phe-
nyl]amino}-1,4,5,6-tetrahydropyrazolo[4',3':6,7]cyclo-
hepta[1,2-d]pyrimidine-3-carboxamide N-(2,6-diethylphenyl)-9-{[4-{[4-(dimethylamino)piperi-
din-1-yl]carbonyl}-2-(trifluoromethoxy)phenyl]
amino}-1-methyl-1,4,5,6-tetrahydropyrazolo[4',3':6,7]
cyclohepta[1,2-d]pyrimidine-3-carboxamide N-(2,6-diethylphenyl)-1-methyl-9-({4-[(4-methyl-1,4-di-
azepan-1-yl)carbonyl]-2-(trifluoromethoxy)
phenyl}amino)-1,4,5,6-tetrahydropyrazolo[4',3':6,7]
cyclohepta[1,2-d]pyrimidine-3-carboxamide 9-amino-1-methyl-1,4,5,6-tetrahydropyrazolo[4',3':6,7]
cyclohepta[1,2-d]pyrimidine-3-carboxamide 1-methyl-9-({4-[(4-methylpiperazin-1-yl)sulfonyl]
phenyl}amino)-1,4,5,6-tetrahydropyrazolo[4',3':6,7]
cyclohepta[1,2-d]pyrimidine-3-carboxamide 1-methyl-9-[(4-nitrophenyl)amino]-N-propyl-1,4,5,6-tet-
rahydropyrazolo[4',3':6,7]cyclohepta[1,2-d]pyrimi-
dine-3-carboxamide 1-methyl-9-(methylsulfanyl)-1,4,5,6-tetrahydropyrazolo
[4',3':6,7]cyclohepta[1,2-d]pyrimidine-3-carboxamide N-(2,6-diethylphenyl)-1-(4-methoxybenzyl)-9-{[2-methoxy-4-(4-methylpiperazin-1-yl)phenyl]amino}-1,4,5,6-tetrahydropyrazolo[4',3':6,7]cyclohepta[1,2-d]pyrimidine-3-carboxamide N-(2,6-diethylphenyl)-9-{[2-methoxy-4-(4-methylpiperazin-1-yl)phenyl]amino}-1,4,5,6-tetrahydropyrazolo[4',3':6,7]cyclohepta[1,2-d]pyrimidine-3-carboxamide 1-methyl-9-({4-[(4-methylpiperazin-1-yl)sulfonyl]phenyl}amino)-N-propyl-1,4,5,6-tetrahydropyrazolo[4',3':6,7]cyclohepta[1,2-d]pyrimidine-3-carboxamide 9-[(4-acetylphenyl)amino]-1-methyl-N-propyl-1,4,5,6-tetrahydropyrazolo[4',3':6,7]cyclohepta[1,2-d]pyrimidine-3-carboxamide N-(2,6-diethylphenyl)-1-ethyl-9-{[2-methoxy-4-(4-methylpiperazin-1-yl)phenyl]amino}-1,4,5,6-tetrahydropyrazolo[4',3':6,7]cyclohepta[1,2-d]pyrimidine-3-carboxamide N-(2,6-diethylphenyl)-9-[2-methoxy-4-(4-methylpiperazin-1-yl)phenyl]amino-1-(pyridin-4-ylmethyl)-1,4,5,6-tetrahydropyrazolo[4',3':6,7]cyclohepta[1,2-d]pyrimidine-3-carboxamide N-(2,6-diethylphenyl)-9-{[2-methoxy-4-(4-methylpiperazin-1-yl)phenyl]amino}-1-(tetrahydro-2H-pyran-2-ylmethyl)-1,4,5,6-tetrahydropyrazolo[4',3':6,7]cyclohepta[1,2-d]pyrimidine-3-carboxamide N-(2,6-diethylphenyl)-1-(3-hydroxypropyl)-9-{[2-methoxy-4-(4-methylpiperazin-1-yl)phenyl]amino}-1,4,5,6-tetrahydropyrazolo[4',3':6,7]cyclohepta[1,2-d]pyrimidine-3-carboxamide N-(2,6-diethylphenyl)-9-[2-methoxy-4-(4-methylpiperazin-1-yl)phenyl]amino-1-(2,2,2-trifluoroethyl)-1,4,5,6-tetrahydropyrazolo[4',3':6,7]cyclohepta[1,2-d]pyrimidine-3-carboxamide N-(2,6-diethylphenyl)-1-(3-hydroxybenzyl)-9-[2-methoxy-4-(4-methylpiperazin-1-yl)phenyl]amino 1-1,4,5,6-tetrahydropyrazolo[4',3':6,7]cyclohepta[1,2-d]pyrimidine-3-carboxamide N-(2,6-diethylphenyl)-1-[3-(dimethylamino)propyl]-9-{[2-methoxy-4-(4-methylpiperazin-1-yl)phenyl]amino}-1,4,5,6-tetrahydropyrazolo[4',3':6,7]cyclohepta[1,2-d]pyrimidine-3-carboxamide N-(2,6-diethylphenyl)-9-{[2-methoxy-4-(4-methylpiperazin-1-yl)phenyl]amino}-1-[2-(tetrahydro-2H-pyran-2-yloxy)ethyl]-1,4,5,6-tetrahydropyrazolo[4',3':6,7]cyclohepta[1,2-d]pyrimidine-3-carboxamide N-(2,6-diethylphenyl)-1-(2-hydroxyethyl)-9-{[2-methoxy-4-(4-methylpiperazin-1-yl)phenyl]amino}-1,4,5,6-tetrahydropyrazolo[4',3':6,7]cyclohepta[1,2-d]pyrimidine-3-carboxamide N-(2,6-diethylphenyl)-9-({4-[4-(dimethylamino)piperidin-1-yl]-2-methoxyphenyl}amino)-1-(4-methoxybenzyl)-1,4,5,6-tetrahydropyrazolo[4',3':6,7]cyclohepta[1,2-d]pyrimidine-3-carboxamide N-(2,6-diethylphenyl)-9-({4-[4-(dimethylamino)piperidin-1-yl]-2-methoxyphenyl}amino)-1,4,5,6-tetrahydropyrazolo[4',3':6,7]cyclohepta[1,2-d]pyrimidine-3-carboxamide N-(2,6-diethylphenyl)-9-({4-[4-(dimethylamino)piperidin-1-yl]-2-methoxyphenyl}amino)-1-ethyl-1,4,5,6-tetrahydropyrazolo[4',3':6,7]cyclohepta[1,2-d]pyrimidine-3-carboxamide N-(2,6-diethylphenyl)-1-[2-(dimethylamino)ethyl]-9-({4-[4-(dimethylamino)piperidin-1-yl]-2-methoxyphenyl}amino)-1,4,5,6-tetrahydropyrazolo[4',3':6,7]cyclohepta[1,2-d]pyrimidine-3-carboxamide 9-[(5-bromo-2-methylphenyl)amino]-1-methyl-1,4,5,6-tetrahydropyrazolo[4',3':6,7]cyclohepta[1,2-d]pyrimidine-3-carboxamide 1-methyl-9-[(5-nitro-1H-benzimidazol-2-yl)amino]-1,4,5,6-tetrahydropyrazolo[4',3':6,7]cyclohepta[1,2-d]pyrimidine-3-carboxamide 1-methyl-9-{[4-(4-methylpiperazin-1-yl)phenyl]amino}-1,4,5,6-tetrahydropyrazolo[4',3':6,7]cyclohepta[1,2-d]pyrimidine-3-carboxamide 1-methyl-9-{[5-(4-methylpiperazin-1-yl)-2-(trifluoromethoxy)phenyl]amino}-1,4,5,6-tetrahydropyrazolo[4',3':6,7]cyclohepta[1,2-d]pyrimidine-3-carboxamide N-(2,6-diethylphenyl)-9-({4-[4-(dimethylamino)piperidin-1-yl]-2-methoxyphenyl}amino)-1-[2-(1,3-dioxo-1,3-dihydro-2H-isoindol-2-yl)ethyl]-1,4,5,6-tetrahydropyrazolo[4',3':6,7]cyclohepta[1,2-d]pyrimidine-3-carboxamide 1-(2-aminoethyl)-N-(2,6-diethylphenyl)-9-({4-[4-(dimethylamino)piperidin-1-yl]-2-methoxyphenyl}amino)-1,4,5,6-tetrahydropyrazolo[4',3':6,7]cyclohepta[1,2-d]pyrimidine-3-carboxamide N-(2,6-diethylphenyl)-9-({4-[4-(dimethylamino)piperidin-1-yl]-2-methoxyphenyl}amino)-1-(2-hydroxyethyl)-1,4,5,6-tetrahydropyrazolo[4',3':6,7]cyclohepta[1,2-d]pyrimidine-3-carboxamide N-methoxy-N,1-dimethyl-9-{[3-(trifluoromethyl)phenyl]amino}-1,4,5,6-tetrahydropyrazolo[4',3':6,7]cyclohepta[1,2-d]pyrimidine-3-carboxamide 1-methyl-9-(phenylamino)-1,4,5,6-tetrahydropyrazolo[4',3':6,7]cyclohepta[1,2-d]pyrimidine-3-carboxamide N-(2-methoxyethyl)-1-methyl-9-(phenylamino)-1,4,5,6-tetrahydropyrazolo[4',3':6,7]cyclohepta[1,2-d]pyrimidine-3-carboxamide N-(2-methoxyethyl)-1-methyl-9-{[3-(trifluoromethyl)phenyl]amino}-1,4,5,6-tetrahydropyrazolo[4',3':6,7]cyclohepta[1,2-d]pyrimidine-3-carboxamide 1-methyl-N-[2-(morpholin-4-yl)ethyl]-9-{[3-(trifluoromethyl)phenyl]amino}-1,4,5,6-tetrahydropyrazolo[4',3':6,7]cyclohepta[1,2-d]pyrimidine-3-carboxamide 1-methyl-9-{[3-(trifluoromethyl)phenyl]amino}-1,4,5,6-tetrahydropyrazolo[4',3':6,7]cyclohepta[1,2-d]pyrimidine-3-carboxamide 3-({[9-(benzylamino)-1-methyl-1,4,5,6-tetrahydropyrazolo[4',3':6,7]cyclohepta[1,2-d]pyrimidin-3-yl]carbonyl}amino)-N,N,N-trimethylpropan-1-aminium 9-(benzylamino)-1-methyl-1,4,5,6-tetrahydropyrazolo[4',3':6,7]cyclohepta[1,2-d]pyrimidine-3-carboxamide N-(2-methoxyethyl)-1-methyl-9-{[4-(4-methylpiperazin-1-yl)phenyl]amino}-1,4,5,6-tetrahydropyrazolo[4',3':6,7]cyclohepta[1,2-d]pyrimidine-3-carboxamide 1-methyl-N-[2-(morpholin-4-yl)ethyl]-9-(phenylamino)-1,4,5,6-tetrahydropyrazolo[4',3':6,7]cyclohepta[1,2-d]pyrimidine-3-carboxamide 9-(benzylamino)-N-(2-methoxyethyl)-1-methyl-1,4,5,6-tetrahydropyrazolo[4',3':6,7]cyclohepta[1,2-d]pyrimidine-3-carboxamide 1-methyl-9-{[4-(4-methylpiperazin-1-yl)phenyl]amino}-N-[2-(morpholin-4-yl)ethyl]-1,4,5,6-tetrahydropyrazolo[4',3':6,7]cyclohepta[1,2-d]pyrimidine-3-carboxamide 1-(2-hydroxyethyl)-9-(methylsulfanyl)-1,4,5,6-tetrahydropyrazolo[4',3':6,7]cyclohepta[1,2-d]pyrimidine-3-carboxamide N-(2-methoxyethyl)-1-methyl-9-{[3-(4-methylpiperidin-1-yl)propyl]amino}-1,4,5,6-tetrahydropyrazolo[4',3':6,7]cyclohepta[1,2-d]pyrimidine-3-carboxamide 1-methyl-9-{[3-(4-methylpiperidin-1-yl)propyl]amino}-1,4,5,6-tetrahydropyrazolo[4',3':6,7]cyclohepta[1,2-d]pyrimidine-3-carboxamide ethyl 1-methyl-9-(methylsulfanyl)-1,4,5,6-tetrahydropyrazolo[4',3':6,7]cyclohepta[1,2-d]pyrimidine-3-carboxylate ethyl 1-methyl-9-phenyl-1,4,5,6-tetrahydropyrazolo[4',3':6,7]cyclohepta[1,2-d]pyrimidine-3-carboxylate ethyl 1-methyl-9-[4-(trifluoromethyl)phenyl]-1,4,5,6-tetrahydropyrazolo[4',3':6,7]cyclohepta[1,2-d]pyrimidine-3-carboxylate ethyl 9-(4-methoxyphenyl)-1-methyl-1,4,5,6-tetrahydropyrazolo[4',3':6,7]cyclohepta[1,2-d]pyrimidine-3-carboxylate ethyl 1-methyl-9-[4-(trifluoromethoxy)phenyl]-1,4,5,6-tetrahydropyrazolo[4',3':6,7]cyclohepta[1,2-d]pyrimidine-3-carboxylate 1-methyl-9-(methylsulfanyl)-1,4,5,6-tetrahydropyrazolo[4',3':6,7]cyclohepta[1,2-d]pyrimidine-3-carboxylic acid 2-methyl-9-{[4-(4-methylpiperazin-1-yl)phenyl]amino}-2,4,5,6-tetrahydropyrazolo[4',3':6,7]cyclohepta[1,2-d]pyrimidine-3-carboxamide 9-[(4-bromo-2-methoxyphenyl)amino]-2-methyl-2,4,5,6-tetrahydropyrazolo[4',3':6,7]cyclohepta[1,2-d]pyrimidine-3-carboxamide 9-{[2-methoxy-4-(4-methylpiperazin-1-yl)phenyl]amino}-2-methyl-2,4,5,6-tetrahydropyrazolo[4',3':6,7]cyclohepta[1,2-d]pyrimidine-3-carboxamide 9-[(4-bromo-2-methoxyphenyl)amino]-N-(2,6-diethylphenyl)-2-methyl-2,4,5,6-tetrahydropyrazolo[4',3':6,7]cyclohepta[1,2-d]pyrimidine-3-carboxamide N-(2,6-diethylphenyl)-9-{[2-methoxy-4-(4-methylpiperazin-1-yl)phenyl]amino}-2-methyl-2,4,5,6-tetrahydropyrazolo[4',3':6,7]cyclohepta[1,2-d]pyrimidine-3-carboxamide N-(2,6-diethylphenyl)-9-({4-[4-(dimethylamino)piperidin-1-yl]-2-methoxyphenyl}amino)-5,6-dihydro-4H-isoxazolo[4',5':6,7]cyclohepta[1,2-d]pyrimidine-3-carboxamide N-(2,6-diethylphenyl)-9-{[2-methoxy-4-(4-methylpiperazin-1-yl)phenyl]amino}-5,6-dihydro-4H-isoxazolo[4',5':6,7]cyclohepta[1,2-d]pyrimidine-3-carboxamide N-(2,6-diethylphenyl)-9-({4-[4-(dimethylamino)piperidin-1-yl]-2-methoxyphenyl}amino)-5,6-dihydro-4H-isoxazolo[4',3':6,7]cyclohepta[1,2-d]pyrimidine-3-carboxamide and N-(2,6-diethylphenyl)-9-{[2-methoxy-4-(4-methylpiperazin-1-yl)phenyl]amino}-5,6-dihydro-4H-isoxazolo[4',3':6,7]cyclohepta[1,2-d]pyrimidine-3-carboxamide;

or a pharmaceutically acceptable salt thereof.

13. A pharmaceutical composition comprising a therapeutically effective amount of a compound of formula (I), as defined in claim 1, and one or more pharmaceutically acceptable excipient, carrier and/or diluent.

14. A pharmaceutical composition according to claim 13, in a form selected from solid form, solution, suspension, emulsion.

15. A pharmaceutical composition according to claim 14, in a form selected from tablets, optionally coated capsules, suppositories, parenteral solutions, oral solutions, suspensions or emulsions.

16. A pharmaceutical composition according to claim 13, further comprising one or more agents.

17. A pharmaceutical composition according to claim 16, wherein the agent is one or more among: cytostatic or cytotoxic agents, antibiotic-type agents, alkylating agents, antimetabolite agents, hormonal agents, immunological agents, interferon-type agents, cyclooxygenase inhibitors (e.g. COX-2 inhibitors), matrixmetalloprotease inhibitors, telomerase inhibitors, tyrosine kinase inhibitors, anti-growth factor receptor agents, anti-HER agents, anti-EGFR agents, anti-angiogenesis agents (e.g. angiogenesis inhibitors), farnesyl transferase inhibitors, ras-raf signal transduction pathway inhibitors, cell cycle inhibitors, other cdks inhibitors, tubulin binding agents, topoisomerase I inhibitors and topoisomerase II inhibitors.

18. A product or kit, comprising a compound of formula (I) or a pharmaceutically acceptable salt thereof, as defined in claim 1, or pharmaceutical compositions thereof, said pharmaceutical compositions comprising a therapeutically effective amount of a compound of formula (I) and one or more pharmaceutically acceptable excipient, carrier and/or diluent, and one or more chemotherapeutic agents, as a combined preparation for simultaneous, separate or sequential use in anticancer therapy, the cancer selected from the group consisting of ovarian cancer, melanoma, pancreatic cancer, colon cancer, leukemia, breast cancer, leukemia, lung cancer and astrocytoma.

19. A method for treating a disease that comprises administering to a mammal in need thereof an effective amount of a compound of formula (I), as defined in claim 1, the disease selected from the group consisting of ovarian cancer, melanoma, pancreatic cancer, colon cancer, leukemia, breast cancer, leukemia, lung cancer and astrocytoma.

20. A process to prepare a compound of formula (I) as described in claim 1, comprising the following steps:

st.H) reacting a compound of formula (Vab), (Va), (Vb), or (Vc) or (Vd):

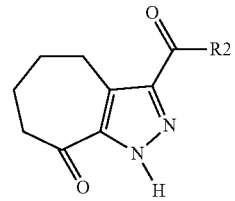

(Vab)

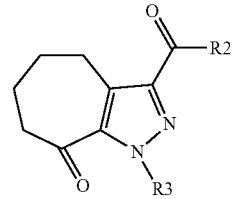

(Va)

(Vb)

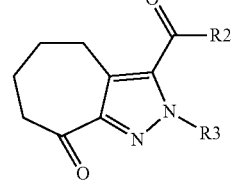

(Vc)

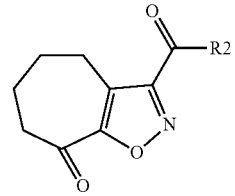

(Vd)

wherein R3 is as defined in claim 1 but not hydrogen and R2 is ethoxy or methoxy or a group NR"R'" or N(OR'")R", wherein R" and R'" are as defined in formula (I), with an N,N-dimethylformamide derivative so as to obtain a compound of formula (VII):

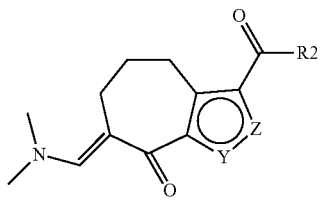

(VII)

wherein R2 is ethoxy or methoxy or a group NR"R'" or N(OR'")R", wherein R" and R'" are as defined in formula (I), and Y and Z are as defined in claim 1;

st.I) the compound of formula (VII) is then reacted according to any one of the alternative steps (st.I1), (st.I2), (st.I3) or (st.I4).

st.I1) with guanidine or a salt thereof so as to obtain a compound of formula (I):

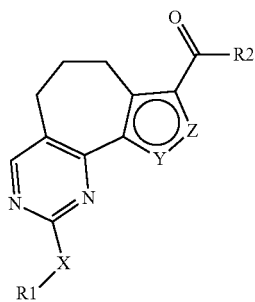

(I)

wherein R1 is hydrogen, X is amino, R2 is ethoxy or methoxy or a group NR"R'" or N(OR'")R", wherein R" and R'" are as defined in formula (I), and Z and Y are as above defined; and optionally converting them into other derivatives of formula (I);

st.I2) with a guanidine derivative or a salt thereof of formula (VIII):

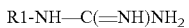

R1-NH—C(=NH)NH$_2$    (VIII)

wherein R1 is as defined in claim 1 but not hydrogen, so as to obtain a compound of formula (I) wherein R1 is as reported in claim 1 but not hydrogen, X is NH, R2 is ethoxy or methoxy or a group NR"R'" or N(OR'")R", wherein R" and R'" are as defined in formula (I), and Y and Z are as defined in claim 1; and optionally converting them into other derivatives of formula (I);

st.I3) with an isothiourea derivative or a salt thereof of formula (IX)

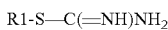

R1-S—C(=NH)NH$_2$    (IX)

wherein R1 is as reported in claim 1 but not hydrogen, so as to obtain a compound of formula (I) wherein R1 is as reported in claim 1 but not hydrogen, X is S, R2 is ethoxy or methoxy or a group NR"R'" or N(OR'")R", wherein R" and R'" are as defined in formula (I), and Y and Z are as defined in claim 1; and optionally converting them into other derivatives of formula (I);

st.I4) with an isourea derivative or a salt thereof of formula (XXV)

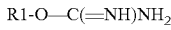

R1-O—C(=NH)NH$_2$    (XXV)

wherein R1 is as reported in claim 1 but not hydrogen, so as to obtain a compound of formula (I) wherein R1 is as reported in claim 1 but not hydrogen, X is O, R2 is ethoxy or methoxy or a group NR"R'" or N(OR'")R", wherein R" and R'" are as defined in formula (I), and Y and Z are as defined in claim 1; and optionally converting them into other derivatives of formula (I).

21. A process according to claim 20, including the use of an R2-containing resin.

\* \* \* \* \*